United States Patent
Gordon-Kamm et al.

(10) Patent No.: US 10,443,064 B2
(45) Date of Patent: Oct. 15, 2019

(54) METHODS AND COMPOSITIONS FOR TARGETED POLYNUCLEOTIDE MODIFICATION

(71) Applicant: PIONEER HI-BRED INTERNATIONAL, INC., Johnston, IA (US)

(72) Inventors: William J. Gordon-Kamm, Urbandale, IA (US); Keith S. Lowe, Johnston, IA (US); David J. Peterson, Ames, IA (US); Christopher J. Scelonge, Ankeny, IA (US); Grace M. St. Clair, Des Moines, IA (US); Bing-Bing Wang, Johnston, IA (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 27 days.

(21) Appl. No.: 15/890,698

(22) Filed: Feb. 7, 2018

(65) Prior Publication Data

US 2018/0171346 A1 Jun. 21, 2018

Related U.S. Application Data

(63) Continuation of application No. 14/215,110, filed on Mar. 17, 2014, now Pat. No. 9,926,571, which is a continuation of application No. 12/982,013, filed on Dec. 30, 2010, now Pat. No. 8,704,041.

(60) Provisional application No. 61/291,207, filed on Dec. 30, 2009.

(51) Int. Cl.
*C12N 15/82* (2006.01)
*C07K 14/415* (2006.01)

(52) U.S. Cl.
CPC ........ *C12N 15/8213* (2013.01); *C07K 14/415* (2013.01)

(58) Field of Classification Search
None
See application file for complete search history.

(56) References Cited

U.S. PATENT DOCUMENTS

| | | | |
|---|---|---|---|
| 5,929,301 A | 7/1999 | Baszcynski et al. |
| 6,093,874 A | 7/2000 | Jofuku et al. |
| 6,140,466 A | 10/2000 | Barbas, III et al. |
| 6,175,056 B1 | 1/2001 | Carlucci et al. |
| 6,331,661 B1 | 12/2001 | Baszczynski et al. |
| 6,453,242 B1 | 9/2002 | Eisenberg et al. |
| 6,458,594 B1 | 10/2002 | Baszczynski et al. |
| 6,511,808 B2 | 1/2003 | Wolffe et al. |
| 6,512,165 B1 | 1/2003 | Ross et al. |
| 6,534,261 B1 | 3/2003 | Cox, III et al. |
| 6,833,252 B1 | 12/2004 | Dujon et al. |
| 7,102,055 B1 | 9/2006 | Baszczynski |
| 7,151,170 B1 | 12/2006 | Boutilier et al. |
| 7,151,201 B2 | 12/2006 | Barbas, III et al. |
| 7,214,536 B2 | 5/2007 | Dujon et al. |
| 7,256,322 B2 | 8/2007 | Lowe et al. |
| 7,262,054 B2 | 8/2007 | Jamieson et al. |
| 7,348,468 B1 | 3/2008 | Cahoon et al. |
| 7,378,510 B2 | 5/2008 | Barbas, III et al. |
| 7,414,172 B2 | 8/2008 | Pages et al. |
| 7,579,529 B2 | 8/2009 | Gordon-Kamm et al. |
| 7,595,434 B2 | 9/2009 | Fischer et al. |
| 7,700,829 B2 | 4/2010 | Zuo et al. |
| 7,816,580 B2 | 10/2010 | Zuo et al. |
| 2003/0049835 A1 | 3/2003 | Helliwell et al. |
| 2003/0059767 A1 | 3/2003 | Barbas, III et al. |
| 2003/0082813 A1 | 5/2003 | Zuo et al. |
| 2003/0108880 A1 | 6/2003 | Rebar et al. |
| 2003/0135889 A1 | 7/2003 | Ross et al. |
| 2004/0101880 A1 | 5/2004 | Rozwadowski et al. |
| 2005/0044595 A1 | 2/2005 | Arias et al. |
| 2005/0257289 A1* | 11/2005 | Gordon-Kamm ........ A01H 1/08 800/281 |
| 2007/0117128 A1 | 5/2007 | Smith et al. |
| 2007/0271628 A1 | 11/2007 | Lowe et al. |
| 2008/0134353 A1 | 6/2008 | Dirks |

FOREIGN PATENT DOCUMENTS

| | | |
|---|---|---|
| EP | 1 033 405 A2 | 9/2000 |
| EP | 1 054 891 A1 | 11/2000 |
| EP | 1 057 891 A | 12/2000 |

(Continued)

OTHER PUBLICATIONS

Al-Abed, D., et al.; "Split-seed: a new tool for maize researchers"; Planta (2006) 223:1355-1360; Springer-Verlag; Germany.

Boutilier, K., et al.; "Ectopic Expression of Baby Boom Triggers a Conversion from Vegetative to Embryonic Growth"; The Plant Cell (2002) 14:1737-1749; American Society of Plant Physiologists; Rockville, MD US.

Bowie, J.U., et al.; "Decipering the Message in Protein Sequences: Tolerance to Amino Acid Substitutions"; Science (1990) 247:1306-1310; American Association for the Advancement of Science; Washington, DC US.

Cai, et al.; "Target transgene integration in plant cells using designed zinc finger nucleases"; Plant Molecular Biology (2009) 69:699-709; Springer; The Netherlands.

(Continued)

*Primary Examiner* — Matthew R Keogh

(57) ABSTRACT

A variety of methods and compositions are provided, including methods and compositions for targeted modification of a specific target site in a cell or organism, methods for integrating polynucleotides of interest, methods to assess promoter activity, directly select transformed organisms, minimize or eliminate expression resulting from random integration into the genome of an organism, such as a plant, remove polynucleotides of interest, combine multiple transfer cassettes, invert or excise a polynucleotide, silence a gene, and identify and/or characterize transcriptional regulating regions. The methods involve the introduction of a cell proliferation factor and a double-strand break-inducing enzyme into an organism.

36 Claims, 17 Drawing Sheets

Specification includes a Sequence Listing.

(56) References Cited

FOREIGN PATENT DOCUMENTS

| | | |
|---|---|---|
| EP | 1 094 112 A2 | 4/2001 |
| EP | 1 185 656 | 3/2002 |
| WO | 199807842 A | 2/1998 |
| WO | 199915178 | 4/1999 |
| WO | 199921574 | 5/1999 |
| WO | 199925821 A1 | 5/1999 |
| WO | 199925840 A1 | 5/1999 |
| WO | 199925841 A1 | 5/1999 |
| WO | 199925855 A1 | 5/1999 |
| WO | 199941974 A1 | 8/1999 |
| WO | 200040694 A1 | 7/2000 |
| WO | 200042219 A1 | 7/2000 |
| WO | 200075330 | 12/2000 |
| WO | 200123545 A1 | 4/2001 |
| WO | 200123575 A2 | 4/2001 |
| WO | 200200900 A2 | 1/2002 |
| WO | 200242459 A2 | 5/2002 |
| WO | 2002097059 A2 | 12/2002 |
| WO | 2002099084 A2 | 12/2002 |
| WO | 2003001902 A2 | 1/2003 |
| WO | 2003002751 A2 | 1/2003 |
| WO | 2003054198 A2 | 7/2003 |
| WO | 2003062455 A2 | 7/2003 |
| WO | 2004067753 A2 | 8/2004 |
| WO | 2005049842 A2 | 6/2005 |
| WO | 2005063990 A2 | 7/2005 |
| WO | 2007047589 A1 | 4/2007 |
| WO | 2008145747 A1 | 12/2008 |
| WO | 2009006297 A2 | 1/2009 |
| WO | 2009154639 A1 | 12/2009 |

OTHER PUBLICATIONS

Cotsaftis, O., et al.; "Enhancing gene targeting efficiency in higher plants: rice is on the move"; Trangenic Research (2005) 14:1-14; Springer Science; The Netherlands.

De Pater, S., et al.; "ZFN-induced mutagenesis and gene-targeting in *Arabidopsis* through Agrobacterium-mediated floral dip transformation"; Plant Biotechnology Journal (2009) 7:821-835; Wiley-Blackwell ; Oxford, UK.

Deng, et al.; "A novel method for induction of plant regeneration via somatic embryogenesis"; Plant Science (2009) 177:43-48; Elsevier; Oxford, UK.

El Ouakfaoui, et al.; "Control of somatic embryogenesis and embryo development by AP2 transcription factors"; Plant Mol Biol published on-line 2010, 14 pages; Springer, The Netherlands.

Feng, Q., et al.; "Sequence and Analysisof Rice Chromosome 4"; Nature (2002) 420:316-320; Nature Publishing Group; London, UK.

Huang, X-Q., et al.; "High-frequency plant regeneration through callus initiation from mature embryos of maize (*Zea mays* L.)"; Plant Cell Reports (2004) 22:793-800; Springer; Germany.

Kizis, D., et al.; "Role of AP2/EREBP Transcription Factors in Gene Regulation During Abiotic Stress"; FEBS Letters (2001) 498:187-189; Blackwell Publishing Ltd; Oxford, UK.

Marsch-Martinez, N., et al.; "BOLITA, an *Arabidopsis* AP2/ERF-Like Transcription Factor that Affects Cell Expansion and Proliferation/Differentiation Pathway"; Plant Molecular Biology (2006) 62:825-843; Springer, The Netherlands.

Mcconnell, J.R., et al.; "Role of PHABULOSA and PHAVOLUTA in determining Radial Patterning in Shoots"; Nature (2001) 411:709-713; Nature Publishing Group; London, UK.

Mizukami, Y. and Fischer, R.L.; "Plant Organ Size Control: AINTEGUMENTA Regulates Growth and Cell Numbers During Organogenesis"; PNAS (2000) 97(2):942-947; National Academy of Sciences; Washington, DC US.

Morcillo, et al.; "EgAP2-1, an AINTEGUMENTA-like (AIL) gene expressed in meristematic and proliferating tissues of embryos in oil palm"; Planta (2007) 226:1353-1362; Springer-Verlag' Germany.

Puchta, Holger; "Gene replacemnt by homologous recombination in plants"; Plant Molecular Biology (2002) 48:173-182; Springer, The Netherlands.

Riechmann, J.L.; "The AP2/EREBP Family of Plant Transcription Factors"; Biological Chemistry (1998) 379:633-646; De Gruyter, Berlin, Germany.

Saskl, T., et al.; "The Genome Sequence and Structure of Rice Chromosome 1"; Nature (2002) 420:312-316; Nature Publishing Group; London, UK.

Sato, S., et al.; "Structural Analysis of *Arabidopsis thaliana* Chromosome 3.I. Sequence Features of the Regions of 4,504,864 bp Covered by Sixty P1 and TAC Clones"; DNA Research (2000) 7:131-135; Oxford University Press; Oxford, UK.

Seligman, et al.; "Mutations altering the cleavage specificity of a homing endonuclease"; Nucleic Acid Research (2002) 30(17):3870-3879; Oxford University Press; Oxford, UK.

Shukla, et al.; "Precise genome modification in the crop species *Zea mays* using zinc-finger nucleases"; Nature (2009) 459:437-443; Nature Publishing Group; London, UK.

Srinivasan, et al.; "Heterologous expression of the Baby Boom AP2/ERF transciption factor enhances the regneration capacity of tobacco (*Nicotiana tabacum* L.)"; Planta (2007) 225:341-351; Springer-Verlag; Berlin/Heidelberg, Germany.

Sussman, et al.; "Isolation andCharacterization of New Homing Endonuclease Specificities at Individual Targe Site Positions"; J. Mol. Biol (2004) 342:31-41; Elsevier Ltd; Amsterdam, The Netherlands.

Theologis, A., et al.; "Sequence and Analysis of Chromosome 1 of the Plant *Arabidopsis thaliana*"; Nature (2000) 408:816-820; Nature Publishing Group; London, UK.

Topfer, R., et al.; "Uptake and Transient Expression of Chimeric Genes in Seed-Derived Embryos"; The Plant Cell (1989) 1:133-139; American Society of Plant Physiologists; Rockville, MD US.

Vilardell, et al.; "Gene sequence, developmental expression, and protein phophorylation of RAB-17 in maize"; Plant Molecular Biology (1990) 14:423-432; Springer; The Netherlands.

Vilardell, et al.; "Regulation of the maize rab17 gene promoter in transgenic heterologous systems"; Plant Molecular Biology (1991) 17:985-993; Springer, The Netherlands.

Wang, A.S.; "Callus induction and plant generation from maize mature embryos"; Plant Cell Reports (1987) 6:360-362; Springer; Berlin/Heidelberg, Germany.

GenBank Report for Accession No. AAD30633, Direct Submission on Oct. 30, 2002.
GenBank Report for Accession No. AAL47205, Direct Submission on May 31, 2002.
GenBank Report for Accession No. AAM33800, Direct Submission on Oct. 10, 2002.
GenBank Report for Accession No. AAM33801, Direct Submission on Oct. 10, 2002.
GenBank Report for Accession No. AAM33803, Direct Submission on Oct. 10, 2002.
GenBank Report for Accession No. AY062108, Direct Submission on Oct. 31, 2001.
GenBank Report for Accession No. AY062180, Direct Submission on Oct. 31, 2001.
GenBank Report for Accession No. BAB02492, Direct Submission on Feb. 14, 2004.
GenBank Report for Accession No. BAB89946, Direct Submission on Aug. 31, 2004.
GenBank Report for Accession No. CAE02944, Direct Submission on Apr. 16, 2005.
GenBank Report for Accession No. CAE05555, Direct Submission on Apr. 16, 2005.
GenBank Report for Accession No. CC603221, 2003.
GenBank Report for Accession No. CC667986, Jun. 20, 2003.
GenBank Report for Accession No. CL960366, Sep. 22, 2004.
GenBank Report for Accession No. F96549, Direct Submission on Mar. 31, 2001.
GenBank Report for Accession No. NP175530, Direct Submission on Feb. 23, 2005.
GenBank Report for Accession No. NP197245, Direct Submission on Feb. 23, 2005.

(56) References Cited

OTHER PUBLICATIONS

Gidoni, D., et al.; "Embryonal Recombination and Germline Inheritance of Recombined FRT Loci Mediated by Constiutitvely Expressed FLP in Tobacco"; Euphytica (2001) 121:145-156; Springer, The Netherlands.

Nardmann, J. and Werr, W., "The Shoot Stem Cell Niche in Angiosperms: Expression Patters of WUS Orthologues in Rice and Maize Imply Major Modifications in the Course of Mono- and Dicot Evolution"; Mol Biol Evol (2006) 23(12):2492-2504; Oxford University Press; Oxford, UK.

Louwerse, J. D. et al., "Stable Recombinase-Mediated Cassette Exchange in *Arabidopsis* Using Agrobacterium tumefaciens"; Plant Physiology (2007) 145:1282-1293.

* cited by examiner

```
              SEQ ID NO:
GmPLT3b       61   ( 221) YEKELEEMKNMTRQEFVASLRRKSSGFSRGA
GmPLT3a       62   ( 217) YEKELEEMKNMTRQEFVASLRRKSSGFSRGA
OsBBM         31   ( 353) YEKELEEMKHMTRQEFVASLRRKSSGFSRGA
VvBBM         27   ( 278) YEKEIEEMKHMTRQEYVASLRRKSSGFSRGA
GmBBM         25   ( 339) YEKELEEMKHMTRQEYVASLRRKSSGFSRGA
ZmPLT3b       63   ( 210) YEKELEEMKSMTRQEFIASLRRKSSGFSRGA
AtBBM         17   ( 280) YEKEVEEMKHMTRQEYVASLRRKSSGFSRGA
OsPLT3        64   ( 214) YEKELEEMKHMTRQEFVASLRRKSSGFSRGA
ZmBBM         2    ( 343) YEKELEDMKHMTRQEFVASLRRKSSGFSRGA
BnBBM2        21   ( 280) YEKEIEEMKHMTRQEYVASLRRKSSGFSRGA
BnBBM1        19   ( 280) YEKEVEEMKHMTRQEYVASLRRKSSGFSRGA
OsBBM1        33   ( 238) YEKELDEMKHMNRQEFVASLRRKSSGFSRGA
AtPLT3/AIL5   65   ( 273) YESELEEMKHMTRQEFVASLRRKSSGFSRGA
AtPLT2        66   ( 260) YEKEVEEMKNMTRQEFVASIRRKSSGFSRGA
SbPLT3b       67   ( 205) YEKELEEMKSMTRQEFIASLRRKSSGFSRGA
OsAIL1        68   ( 323) YEKELEEMKHMTRQEFIAHLRRNSSGFSRGA
SbBBM         39   ( 347) YEKELEDMKHMTRQEFVASLRRKSSGFSRGA
MtBBM         23   ( 329) YEKEVEEMKHMTRQEYVASLRRKSSGFSRGA
SbBBM2        41   ( 356) YEKELEEMKHMTRQEYIAYLRRNSSGFSRGA
ZmBBM2        29   ( 349) YEKELEEMKHMTRQEYIAYLRRNSSGFSRGA
GmPLT2        69   ( 234) YEKELDEMKHMTRQEFVAAIRRKSSGFSRGA
OsBBM3        37   ( 349) YEKELEEMKHMTRQEYIAHLRRNSSGFSRGA
MtPLT3        70   ( 229) YEKEIDDMKNMTRQEFVASLRRKSSGFSRGA
ZmPLT3        71   ( 197) YEKEVEEMKNMTRQEFVASLRRKSSGFSRGA
OsPLT3b       72   ( 200) YETELEEMKSMTRQEFIASLRRKSSGFSRGA
GmPLT1        73   ( 239) YEKELDEMKHMTRQEFVAAIRRKSSGFSRGA
AtPLT1        74   ( 251) YEKEVEEMKHMTRQEFVAAIRRKSSGFSRGA
OsBBM2        35   ( 370) YEKELDEMKHMTRQEYIAYLRRNSSGFSRGA
MtPLT1/2      75   ( 233) YEKEIDEMKHMTRQEFVASIRRKSSGFSRGA
ZmAIL1        76   ( 341) YEKELEEMKHMSRQEFIAHLRRNSSGFSRGA
GmAIL1        77   ( 272) YEKELEEMKHMTRQEFVANLRRKSSGFSRGA
SbPLT3        78   ( 208) YEKELEEMKTMTRQEFVASLRRKSSGFSRGA
GmAIL6        79   ( 291) YSKEVEEMKHVTKQEFIASLRRKSSGFSRGA
AtAIL6        80   ( 323) YSKEVEEMKHMTKQEFIASLRRKSSGFSRGA
MtAIL1        81   ( 318) YDKELEEMKHMTRQEFVANLRRKSSGFSRGA
SbAIL1        82   ( 333) YEKELEEMKHMSRQEFIAHLRRNSSGFSRGA
AtANT         83   ( 353) YQKEIEDMKNMTRQEYVAHLRRKSSGFSRGA
SbANT         84   ( 353) YQEELEEMKNMTRQEYVAHLRRKSSGFSRGA
GmAIL7        85   ( 290) YSKEVEEMKHVTKQEFIASLRRKSSGFSRGA
ZmANT         86   ( 372) YREELEEMKNMTRQEYVAHLRRKSSGFSRGA
OsANT         87   ( 372) YQEELEEMKNMSRQEYVAHLRRKSSGFSRGA
AtAIL7        88   ( 243) YSKELEEMNHMTKQEFIASLRRKSSGFSRGA
ZmANT2        89   ( 354) YRDELEEMKGMTRQEFVAHLRRRSSGFSRGA
MtANT         90   ( 380) YQNQLEEMKNMTRQEYVAHLRRKSSGFSRGA
GmANT         91   ( 334) YQVQLEEMKNMSRQEYVAHLRRKSSGFSRGA
AtAIL1        92   ( 293) YEKEIEELNNMNRQEFVAMLRRNSSGFSRGA
ZmANTr        93   ( 218) YIREIQDMQNMNRRDVVASLRRKSSGFSRGA
AtWRI1        94   ( 135) YTKELEEMQRVTKEEYLASLRRQSSGFSRGV
AtAP2         95   ( 191) YDDDLKQMTNLTKEEFVHVLRRQSTGFPRGS
AtRAP2.7      96   ( 213) YEEDMKQVQNLSKEEFVHILRRQSTGFSRGS
Consensus     3         YEKELEEMK1MTRQE23A4LRRKSSGFSRGA
1= H or N;  2= F or Y;  3= V or I;  4=S or H
```

FIG. 2A

```
             SEQ ID NO:
SbBBM        39        ( 378) SIYRGVTRHHQHGRWQARIGRVAGNKDLYLGTFSTQEEAA
OsBBM        31        ( 384) SIYRGVTRHHQHGRWQARIGRVAGNKDLYLGTFSTQEEAA
ZmBBM         2        ( 374) SIYRGVTRHHQHGRWQARIGRVAGNKDLYLGTFSTQEEAA
GmPLT3b      61        ( 252) SIYRGVTRHHQHGRWQARIGRVAGNKDLYLGTFSTQEEAA
GmPLT3a      62        ( 248) SIYRGVTRHHQHGRWQARIGRVAGNKDLYLGTFSTQEEAA
MtPLT3       70        ( 260) SIYRGVTRHHQHGRWQARIGRVAGNKDLYLGTFSTQEEAA
AtPLT3/AIL5  65        ( 304) SMYRGVTRHHQHGRWQARIGRVAGNKDLYLGTFSTQEEAA
SbBBM2       41        ( 387) SKYRGVTRHHQHGRWQARIGRVAGNKDLYLGTFSTEEEAA
OsBBM2       35        ( 401) SKYRGVTRHHQHGRWQARIGRVAGNKDLYLGTFSTEEEAA
ZmBBM2       29        ( 380) SKYRGVTRHHQHGRWQARIGRVAGNKDLYLGTFSTEEEAA
GmPLT2       69        ( 265) SMYRGVTRHHQHGRWQARIGRVAGNKDLYLGTFSTEEEAA
GmPLT1       73        ( 270) SMYRGVTRHHQHGRWQARIGRVAGNKDLYLGTFSTEEEAA
ZmPLT3b      63        ( 241) SIYRGVTRHHQHGRWQARIGRVAGNKDLYLGTFSTQEEAA
AtAIL1       92        ( 324) SVYRGVTRHHQHGRWQARIGRVAGNKDLYLGTFSTQEEAA
SbPLT3b      67        ( 236) SIYRGVTRHHQHGRWQARIGRVAGNKDLYLGTFSTQEEAA
OsPLT3b      72        ( 231) SIYRGVTRHHQHGRWQARIGRVAGNKDLYLGTFSTQEEAA
OsBBM1       33        ( 269) SIYRGVTRHHQHGRWQARIGRVAGNKDLYLGTFGTQEEAA
MtPLT1/2     75        ( 264) SMYRGVTRHHQHGRWQARIGRVAGNKDLYLGTFSTEEEAA
SbAIL1       82        ( 364) SMYRGVTRHHQHGRWQARIGRVAGNKDLYLGTFSTQEEAA
OsAIL1       68        ( 354) SMYRGVTRHHQHGRWQARIGRVAGNKDLYLGTFSTQEEAA
ZmAIL1       76        ( 372) SMYRGVTRHHQHGRWQARIGRVAGNKDLYLGTFSTQEEAA
AtPLT2       66        ( 291) SMYRGVTRHHQHGRWQARIGRVAGNKDLYLGTFSTEEEAA
AtPLT1       74        ( 282) SMYRGVTRHHQHGRWQARIGRVAGNKDLYLGTFSTEEEAA
OsBBM3       37        ( 380) SKYRGVTRHHQHGRWQARIGRVAGNKDIYLGTFSTEEEAA
VvBBM        27        ( 309) SIYRGVTRHHQHGRWQARIGRVAGNKDLYLGTFSTQEEAA
GmANT        91        ( 365) SIYRGVTRHHQHGRWQARIGRVAGNKDLYLGTFSTQEEAA
GmBBM        25        ( 370) SIYRGVTRHHQHGRWQARIGRVAGNKDLYLGTFSTQEEAA
MtBBM        23        ( 360) SIYRGVTRHHQHGRWQARIGRVAGNKDLYLGTFSTQEEAA
SbANT        84        ( 384) SMYRGVTRHHQHGRWQARIGRVSGNKDLYLGTFSTQEEAA
GmAIL1       77        ( 303) SVYRGVTRHHQHGRWQARIGRVAGNKDLYLGTFSTQEEAA
MtAIL1       81        ( 349) SVYRGVTRHHQHGRWQARIGRVAGNKDLYLGTFSTQEEAA
SbPLT3       78        ( 239) SIYRGVTRHHQHGRWQARIGRVAGNKDLYLGTFSTEEEAA
ZmPLT3       71        ( 228) SIYRGVTRHHQHGRWQARIGRVAGNKDLYLGTFSTEEEAA
AtBBM        17        ( 311) SIYRGVTRHHQHGRWQARIGRVAGNKDLYLGTFGTQEEAA
OsANT        87        ( 403) SIYRGVTRHHQHGRWQARIGRVSGNKDLYLGTFSTQEEAA
BnBBM2       21        ( 311) SIYRGVTRHHQHGRWQARIGRVAGNKDLYLGTFGTQEEAA
BnBBM1       19        ( 311) SIYRGVTRHHQHGRWQARIGRVAGNKDLYLGTFGTQEEAA
MtANT        90        ( 412) SMYRGVTRHHQHGRWQARIGRVAGNKDLYLGTFSTQEEAA
AtANT        83        ( 384) SIYRGVTRHHQHGRWQARIGRVAGNKDLYLGTFGTQEEAA
AtAIL6       80        ( 354) SIYRGVTRHHQQGRWQARIGRVAGNKDLYLGTFATEEEAA
ZmANT        86        ( 403) SIYRGVTRHHQHGRWQARIGRVSGNKDLYLGTFSTQEEAA
OsPLT3       64        ( 245) SIYRGVTRHHQHGRWQARIGRVAGNKDLYLGTFGTEEEAA
GmAIL7       85        ( 321) SIYRGVTRHHQQGRWQARIGRVAGNKDLYLGTFATEEEAA
GmAIL6       79        ( 322) SIYRGVTRHHQQGRWQARIGRVAGNKDLYLGTFATEEEAA
AtAIL7       88        ( 274) SIYRGVTRHHQQGRWQARIGRVAGNKDLYLGTFATEEEAA
ZmANT2       89        ( 385) SIYRGVTRHHQQGRWQSRIGRVAGNKDLYLGTFTTQEEAA
ZmANTr       93        ( 249) SIYRGVTKHHQHGRWQARIGRVAGNKDLYLGTFATEQEAA
AtWRI1       94        ( 166) SKYRGVARHHNGRWEARIGRVFGNKYLYLGTYNTQEEAA
Consensus     4               S1YRGVTRHHQHGRWQARIGRVAGNKDLYLGTFST2EEAA
```

FIG. 2B-1

```
          SEQ ID NO:
SbBBM         39       ( 418)  EAYDIAAIKFRGLNAVTNFDMSR
OsBBM         31       ( 424)  EAYDIAAIKFRGLNAVTNFDMSR
ZmBBM          2       ( 414)  EAYDIAAIKFRGLNAVTNFDMSR
GmPLT3b       61       ( 292)  EAYDIAAIKFRGLNAVTNFDMSR
GmPLT3a       62       ( 288)  EAYDIAAIKFRGLNAVTNFDMSR
MtPLT3        70       ( 300)  EAYDIAAIKFRGLNAVTNFDMSR
AtPLT3/AIL5   65       ( 344)  EAYDIAAIKFRGLNAVTNFDISR
SbBBM2        41       ( 427)  EAYDIAAIKFRGLNAVTNFDMSR
OsBBM2        35       ( 441)  EAYDIAAIKFRGLNAVTNFDMSR
ZmBBM2        29       ( 420)  EAYDIAAIKFRGLNAVTNFDMSR
GmPLT2        69       ( 305)  EAYDIAAIKFRGLNAVTNFDMSR
GmPLT1        73       ( 310)  EAYDIAAIKFRGLNAVTNFDMSR
ZmPLT3b       63       ( 281)  EAYDIAAIKFRGLNAVTNFDMSR
AtAIL1        92       ( 364)  EAYDIAAIKFRGLNAVTNFDINR
SbPLT3b       67       ( 276)  EAYDIAAIKFRGLNAVTNFDMSR
OsPLT3b       72       ( 271)  EAYDIAAIKFRGLNAVTNFDMSR
OsBBM1        33       ( 309)  EAYDIAAIKFRGLNAVTNFDMSR
MtPLT1/2      75       ( 304)  EAYDIAAIKFRGLNAVTNFDMTR
SbAIL1        82       ( 404)  EAYDIAAIKFRGLNAVTNFDISK
OsAIL1        68       ( 394)  EAYDIAAIKFRGLNAVTNFDISK
ZmAIL1        76       ( 412)  EAYDIAAIKFRGLNAVTNFDISK
AtPLT2        66       ( 331)  EAYDIAAIKFRGLNAVTNFEINR
AtPLT1        74       ( 322)  EAYDIAAIKFRGLNAVTNFEINR
OsBBM3        37       ( 420)  EAYDIAAIKFRGLNAVTNFDMSR
VvBBM         27       ( 349)  EAYDIAAIKFRGLNAVTNFDMSR
GmANT         91       ( 405)  EAYDIAAIKFRGANAVTNFDISR
GmBBM         25       ( 410)  EAYDVAAIKFRGLSAVTNFDMSR
MtBBM         23       ( 400)  EAYDVAAIKFRGLSAVTNFDMSR
SbANT         84       ( 424)  EAYDIAAIKFRGLNAVTNFDITR
GmAIL1        77       ( 343)  EAYDIAAIKFRGTSAVTNFDISR
MtAIL1        81       ( 389)  EAYDIAAIKFRGTSAVTNFDISR
SbPLT3        78       ( 279)  EAYDIAAIKFRGLNAVTNFEISR
ZmPLT3        71       ( 268)  EAYDIAAIKFRGLNAVTNFEISR
AtBBM         17       ( 351)  EAYDIAAIKFRGLSAVTNFDMNR
OsANT         87       ( 443)  EAYDVAAIKFRGLNAVTNFDITR
BnBBM2        21       ( 351)  EAYDIAAIKFRGLTAVTNFDMNR
BnBBM1        19       ( 351)  EAYDIAAIKFRGLTAVTNFDMNR
MtANT         90       ( 452)  EAYDIAAIKFRGANAVTNFDIIK
AtANT         83       ( 424)  EAYDVAAIKFRGTNAVTNFDITR
AtAIL6        80       ( 394)  EAYDIAAIKFRGINAVTNFEMNR
ZmANT         86       ( 443)  EAYDVAAIKFRGLSAVTNFDITR
OsPLT3        64       ( 285)  EAYDIAAIKFRGLNAVTNFEIGR
GmAIL7        85       ( 361)  EAYDIAAIKFRGANAVTNFEMNR
GmAIL6        79       ( 362)  EAYDIAAIKFRGANAVTNFEMNR
AtAIL7        88       ( 314)  EAYDIAAIKFRGINAVTNFEMNR
ZmANT2        89       ( 425)  EAYDIAAIKFRGLNAVTNFDIAR
ZmANTr        93       ( 289)  EAYDIAALKFRGENAVTNFEPSR
AtWRI1        94       ( 206)  AAYDMAAIEYRGANAVTNFDISN
Consensus      4              EAYD3AAIKFRGLNAVTNF456R 1= I or M;  2= Q or E;  3= I or V;  4= D or E;  5=M or I;  6= S or N
```

FIG. 2B-2

|  | SEQ ID NO: |  |  |
|---|---|---|---|
| SbBBM | 39 | (276) | SIYRGVTRHRWTGRYEAHLWDNSCRREGQTRK |
| ZmBBM | 2 | (272) | SIYRGVTRHRWTGRYEAHLWDNSCRREGQTRK |
| VvBBM | 27 | (207) | SIYRGVTRHRWTGRYEAHLWDNSCRREGQTRK |
| GmBBM | 25 | (268) | SIYRGVTRHRWTGRYEAHLWDNSCRREGQTRK |
| OsBBM | 31 | (282) | SIYRGVTRHRWTGRYEAHLWDNSCRREGQTRK |
| MtBBM | 23 | (261) | SIYRGVTRHRWTGRYEAHLWDNSCRREGQTRK |
| SbBBM2 | 41 | (285) | SIYRGVTRHRWTGRYEAHLWDNSCRREGQSRK |
| OsBBM3 | 37 | (278) | SIYRGVTRHRWTGRYEAHLWDNSCRREGQSRK |
| OsBBM2 | 35 | (302) | SIYRGVTRHRWTGRYEAHLWDNSCRREGQSRK |
| ZmBBM2 | 29 | (278) | SIYRGVTRHRWTGRYEAHLWDNSCRREGQSRK |
| GmPLT3b | 61 | (150) | SIYRGVTRHRWTGRYEAHLWDNSCRREGQSRK |
| GmPLT3a | 62 | (146) | SIYRGVTRHRWTGRYEAHLWDNSCRREGQSRK |
| MtPLT3 | 70 | (161) | SIYRGVTRHRWTGRYEAHLWDNSCRREGQSRK |
| ZmANT | 86 | (301) | SQYRGVTRHRWTGRYEAHLWDNSCRKEGQTRK |
| GmAIL1 | 77 | (204) | SQYRGVTRHRWTGRYEAHLWDNSCRKEGQTRK |
| MtAIL1 | 81 | (250) | SQYRGVTRHRWTGRYEAHLWDNSCRKEGQTRK |
| SbANT | 84 | (285) | SQYRGVTRHRWTGRYEAHLWDNSCKKEGQTRK |
| OsANT | 87 | (304) | SQYRGVTRHRWTGRYEAHLWDNSCKKEGQTRK |
| GmANT | 91 | (267) | SQYRGVTRHRWTGRYEAHLWDNSCKKEGQTRK |
| GmAIL6 | 79 | (223) | SIYRGVTRHRWTGRYEAHLWDNSCRREGQARK |
| MtANT | 90 | (312) | SQYRGVTRHRWTGRYEAHLWDNSCKKEGQSRK |
| BnBBM2 | 21 | (209) | SIYRGVTRHRWTGRYEAHLWDNSCKREGQTRK |
| BnBBM1 | 19 | (209) | SIYRGVTRHRWTGRYEAHLWDNSCKREGQTRK |
| AtBBM | 17 | (209) | SIYRGVTRHRWTGRYEAHLWDNSCKREGQTRK |
| SbPLT3 | 78 | (140) | SIYRGVTRHRWTGRYEAHLWDNSCRREGQSRK |
| ZmPLT3 | 71 | (126) | SIYRGVTRHRWTGRYEAHLWDNSCRREGQSRK |
| GmPLT2 | 69 | (163) | SIYRGVTRHRWTGRYEAHLWDNSCRREGQSRK |
| GmPLT1 | 73 | (168) | SIYRGVTRHRWTGRYEAHLWDNSCRREGQSRK |
| OsPLT3 | 64 | (143) | SIYRGVTRHRWTGRYEAHLWDNSCRREGQSRK |
| GmAIL7 | 85 | (223) | SIYRGVTRHRWTGRYEAHLWDNSCRREGQARK |
| AtAIL6 | 80 | (253) | SIYRGVTRHRWTGRYEAHLWDNSCRREGQARK |
| AtPLT2 | 66 | (189) | SIYRGVTRHRWTGRYEAHLWDNSCRREGQSRK |
| OsPLT3b | 72 | (129) | SIYRGVTRHRWTGRYEAHLWDNSCRREGQSRK |
| AtPLT1 | 74 | (180) | SIYRGVTRHRWTGRYEAHLWDNSCRREGQSRK |
| AtPLT3/AIL5 | 65 | (202) | SIYRGVTRHRWTGRYEAHLWDNSCRREGQSRK |
| SbPLT3b | 67 | (134) | SIYRGVTRHRWTGRYEAHLWDNSCRREGQSRK |
| ZmPLT3b | 63 | (139) | SIYRGVTRHRWTGRYEAHLWDNSCRREGQSRK |
| ZmANT2 | 89 | (283) | SRYRGVTRHRWTGRYEAHLWDNSCRKDGQTRK |
| AtAIL7 | 88 | (172) | SIYRGVTRHRWTGRYEAHLWDNSCRREGQARK |
| MtPLT1/2 | 75 | (165) | SIYRGVTKHRWTGRYEAHLWDNSCRREGQSRK |
| SbAIL1 | 82 | (265) | SQFRGVTRHRWTGRYEAHLWDNTCRKEGQTRK |
| OsAIL1 | 68 | (252) | SQFRGVTRHRWTGRYEAHLWDNTCRKEGQTRK |
| ZmAIL1 | 76 | (270) | SQFRGVTRHRWTGRYEAHLWDNTCRKEGQTRK |
| OsBBM1 | 33 | (167) | SIYRGVTKHRWTGRYEAHLWDNSCRREGQTRK |
| AtAIL1 | 92 | (222) | SQYRGVTRHRWTGRYEAHLWDNSCKKEGQTRR |
| AtANT | 83 | (282) | SQYRGVTRHRWTGRYEAHLWDNSFKKEGHSRK |
| ZmANTr | 93 | (147) | SIYRGVTRHRWTGRYEAHLWDNTCRKEGQKRK |
| AtWRI1 | 94 | (64) | SIYRGVTRHRWTGRFEAHLWDKSSWNSIQNKK |
| Consensus | 5 |  | S0YRGVTRHRWTGRYEAHLWDNSCR1EGQ2RK |

FIG. 2C-1

```
              SEQ ID NO:
SbBBM        39      ( 308)   GRQGGYDKEEKAARAYDLAALKYWGPTTTTNFPVNN
ZmBBM         2      ( 307)   VYLGGYDKEEKAARAYDLAALKYWGATTTTNFPVSN
VvBBM        27      ( 242)   VYLGGYDKEEKAARAYDLAALKYWGTTTTTNFPISN
GmBBM        25      ( 303)   VYLGGYDKEEKAARAYDLAALKYWGTTTTTNFPISH
OsBBM        31      ( 317)   VYLGGYDKEEKAARAYDLAALKYWGPTTTTNFPVNN
MtBBM        23      ( 293)   GRQGGYDKEEKAARAYDLAALKYWGTTTTTNFPISH
SbBBM2       41      ( 320)   VYLGGYDKEDKAARAYDLAALKYWGTTTTTNFPISN
OsBBM3       37      ( 313)   VYLGGYDKEDKAARAYDLAALKYWGTTTTTNFPMSN
OsBBM2       35      ( 334)   GRQGGYDKEDKAARAYDLAALKYWGTTTTTNFPISN
ZmBBM2       29      ( 313)   VYLGGYDKEDKAARAYDLAALKYWGTTTTTNFPISN
GmPLT3b      61      ( 185)   VYLGGYDKEDKAARAYDLAALKYWGPTTTTNFPISN
GmPLT3a      62      ( 181)   VYLGGYDKEDKAARAYDLAALKYWGPTTTTNFPISN
MtPLT3       70      ( 193)   GRQGGYDKEEKAARAYDLAALKYWGPTTTTNFPISN
ZmANT        86      ( 336)   VYLGGYDVEEKAARAYDLAALKYWGTSTHVNFPVED
GmAIL1       77      ( 236)   GRQGGYDKEEKAAKAYDLAALKYWGPTTHINFPLST
MtAIL1       81      ( 282)   GRQGGYDKEEKAAKAYDLAALKYWGPTTHINFPLST
SbANT        84      ( 317)   GRQGGYDMEEKAARAYDLAALKYWGPSTHINFPLED
OsANT        87      ( 336)   GRQGGYDMEEKAARAYDLAALKYWGPSTHINFPLED
GmANT        91      ( 298)   GRQGGYDMEEKAARAYDLAALKYWGPSTHINFSIEN
GmAIL6       79      ( 255)   GRQGGYDKEEKAARAYDLAALKYWGPTATTNFPVSN
MtANT        90      ( 344)   GRQGGYDMEEKAARAYDQAALKYWGPSTHINFPLEN
BnBBM2       21      ( 244)   VYLGGYDKEEKAARAYDLAALKYWGTTTTTNFPMSE
BnBBM1       19      ( 244)   VYLGGYDKEEKAARAYDLAALKYWGTTTTTNFPMSE
AtBBM        17      ( 244)   VYLGGYDKEEKAARAYDLAALKYWGPTTTTNFPLSE
SbPLT3       78      ( 172)   GRQGGYDKEEKAARAYDLAALKYWGSSTTTNFPVAE
ZmPLT3       71      ( 161)   VYLGGYDKEEKAARAYDLAALKYWGSSTTTNFPVAE
GmPLT2       69      ( 198)   VYLGGYDKEEKAARAYDLAALKYWGTSTTTNFPISN
GmPLT1       73      ( 203)   VYLGGYDKEEKAARSYDLAALKYWGTSTTTNFPISN
OsPLT3       64      ( 178)   VYLGGYDKEEKAARAYDLAALKYWGPSTTTNFPVAE
GmAIL7       85      ( 254)   GRQGGYDKEEKAARSYDLAALKYWGPTATTNFPVSN
AtAIL6       80      ( 287)   VYLGGYDKEDKAARAYDLAALKYWNATATTNFPITN
AtPLT2       66      ( 224)   VYLGGYDKEEKAARAYDLAALKYWGPSTTTNFPITN
OsPLT3b      72      ( 164)   VYLGGYDKEEKAARAYDLAALKYWGPTTTTNFPVAN
AtPLT1       74      ( 215)   VYLGGYDKEDKAARSYDLAALKYWGPSTTTNFPITN
AtPLT3/AIL5  65     ( 237)   VYLGGYDKEDKAARAYDLAALKYWGPTTTTNFPISN
SbPLT3b      67      ( 169)   VYLGGYDKEEKAARAYDLAALKYWGATTTTNFPVSN
ZmPLT3b      63      ( 174)   VYLGGYDKEEKAARAYDLAALKYWGPTTTTNFPVSN
ZmANT2       89      ( 318)   VYLGGYDTEDKAARAYDLAALKYWGPATHVNFPVEN
AtAIL7       88      ( 207)   VYLGGYDKEDRAARAYDLAALKYWGSTATTNFPVSS
MtPLT1/2     75      ( 197)   GRQGGYDKEEKAARSYDLAALKYWGTSTTTNFPVSN
SbAIL1       82      ( 297)   GRQGGYDREEKAARAYDLAALKYWGPSTHINFPLSH
OsAIL1       68      ( 287)   VYLGGYDKEEKAARAYDLAALKYWGPTTHINFPLST
ZmAIL1       76      ( 305)   VYLGGYDREEKAARAYDLAALKYWGPSTHINFPLSH
OsBBM1       33      ( 202)   VYLGGYDKEEKAARAYDLAALKYWGTTTTTNFPVSN
AtAIL1       92      ( 257)   VYLGGYDEEEKAARAYDLAALKYWGPTTHLNFPLSN
AtANT        83      ( 317)   VYLGGYDMEEKAARAYDLAALKYWGPSTHTNFSAEN
ZmANTr       93      ( 182)   VYLGGYDKEDKAARAYDIAALKYWGDNATTNFPREN
AtWRI1       94      (  99)   VYLGAYDSEEAAAHTYDLAALKYWGPDTILNFPAET
Consensus 5                    345GGYDKE6KAARAYDLAALKYWG72T89NFP*SN
0=I or Q; 1=R or K; 2= S or T; 3= V or G; 4= Y or R; 5=L or Q; 6=E or
D; 7= P or T; 8=T or H; 9=T or I; *=I, V, or L
```

FIG. 2C-2

```
           SEQ ID NO:
SbBBM2        41    ( 113)  AVEDSEPKLEDFLGGNSFVSEH
OsBBM2        35    ( 108)  AVEETEPKLEDFLGGNSFVSEQ
ZmBBM2        29    ( 110)  AVEDSEPKLEDFLGGNSFVSDQ
SbBBM         39    (  55)  SALVAEPKLEDFLGGISFSEQH
ZmBBM          2    (  56)  SALVAEPKLEDFLGGISFSEQH
OsBBM         31    (  61)  SALVAEPKLEDFLGGISFSEQQ
GmAIL6        79    (  77)  HVPPPPPKLEDFLGDSSAVMRY
MtBBM         23    ( 106)  NNQQAQPKLENFLGGHSFTDHQ
GmAIL7        85    (  75)  SVSHAPPKLEDFLGDSSAVMRY
MtAIL1        81    (  85)  NSNEEGPKLEDFLGCYSNQNQN
GmANT         91    (  97)  MVPTSSPKLEDFLGGATMGTHE
AtAIL6        80    (  71)  HSQNHIPKLEDFLGDSSSIVRY
VvBBM         27    ( 103)  NLENQEPKLENFLGCRSFADHE
GmBBM         25    ( 107)  QQQQQQPKLENFLGGHSFGEHE
ZmANT2        89    ( 106)  MVPSSPPKLEDFLGGGNGGGQE
BnBBM2        21    (  89)  NDEQDGPKLENFLGRTTTIYNT
BnBBM1        19    (  89)  NDEQDGPKLENFLGRTTTIYNT
OsPLT3        64    (  37)  AGAAPPPKLEDFLGGGCNGGSS
GmAIL1        77    (  50)  NSNEEGPKLEDFLGCYSNSPAK
AtBBM         17    (  91)  NNEQNGPKLENFLGRTTTIYNT
GmPLT2        69    (  54)  HSSNEIPKVADFLGVSKSENQS
MtPLT1/2      75    (  54)  HNSNEVPKVADFLGVCKSENHS
GmPLT3b       61    (  68)  SIFTGGPKFEDFLGSSAATATT
SbPLT3        78    (  35)  AGAAPPPKLEDFLGGGVINGES
ZmPLT3        71    (  36)  AGAAPPPKLEDFLGGGVATGGP
GmPLT3a       62    (  64)  SIFTGAPKFEDFLGGSSATATA
GmPLT1        73    (  54)  HSSSEVPKVADFLGVSKSENES
AtPLT3/AIL5   65    (  95)  SVYPGGPKLENFLGGGASTTTT
AtAIL7        88    (  13)  HSQTQIPKLEDFLGDSFVRYSD
SbAIL1        82    (  72)  AAEANGPKLEDFMSVTCSSNNK
OsBBM1        33    (  47)  GEETAAPKLEDFLGMQVQQETA
AtPLT2        66    (  58)  GEGGEVPKVADFLGVSKSGDHH
ZmAIL1        76    (  76)  AAEAKGPKLEDFMSITCSNKSS
ZmANT         86    ( 123)  VVSSSSPKLEDFLGASASTAMA
OsAIL1        68    (  66)  HAEAKDPKLEDFMSVSYSNKSS
AtPLT1        74    (  52)  DEGGEVPKVADFLGVSKPDENQ
OsBBM3        37    ( 109)  DGVGEAPKLENFLDGNSFSDVH
MtANT         90    ( 110)  MSTTSAPKLENFLGNEAMGTPH
SbANT         84    ( 103)  QPDHHGPKLEDFLGAAAAQSQA
AtANT         83    ( 108)  HHQDSSPKVEDFFGTHHNNTSH
OsANT         87    ( 124)  VVSASPKLEDFLGAGPAMALS
MtPLT3        70    (  79)  SIFTGGHKFEDFLGSSVAPTRT
AtAIL1        92    (  41)  HHDEDVPKVEDLLSNSHQTEYP
OsPLT3b       72    (  42)  GPAEGAPKMEDFLGGLGGGGGA
ZmPLT3b       63    (  44)  AVEESPRTVEDFLGGVGGAGAP
SbPLT3b       67    (  45)  TVEESPKMVEDFLGGVGGAGAP
Consensus      6                  PK123FLG 1= L or V;  2= E or A;  3= D or N
```

FIG. 2D

```
SEQ ID NO:
VvBBM       27      ( 377)  ILESSTLPIGGAAKRL
MtBBM       23      ( 428)  ILESSTLPIGGAAKRL
GmBBM       25      ( 438)  ILESTTLPIGGAAKRL
SbBBM2      41      ( 455)  ILESSTLPVGGAARRL
OsBBM2      35      ( 469)  ILESSTLPVGGAARRL
ZmBBM2      29      ( 448)  ILESSTLPVGGAARRL
AtPLT1      74      ( 350)  ILESSTLPIGGGAAKR
OsBBM3      37      ( 448)  ILDSSTLPVGGAARRL
GmPLT2      69      ( 333)  ILESNTLPIGGGAAKR
GmPLT1      73      ( 338)  ILESNTLPIGGGAAKR
MtPLT1/2    75      ( 332)  ILESNTLPIGGGAAKR
AtPLT2      66      ( 359)  ILESNTLPIGGGAAKR
BnBBM2      21      ( 379)  ILESPSLPIGSAAKRL
BnBBM1      19      ( 379)  ILESPSLPIGSAAKRL
SbBBM       39      ( 446)  ILDSSALPIGSAAKRL
ZmBBM       2       ( 442)  ILDSSALPIGSAAKRL
OsANT       87      ( 471)  ILESSTLLPGELARRK
AtAIL6      80      ( 421)  AIMKSALPIGGAAKRL
AtBBM       17      ( 379)  ILESPSLPIGSSAKRL
GmAIL7      85      ( 388)  AIMKSSLPVGGAAKRL
GmAIL6      79      ( 389)  AIMKSSLPVGGAAKRL
SbANT       84      ( 452)  IMASNTLLPGDLARRR
ZmANT       86      ( 471)  IMESSTLLPGEQVRRR
SbAIL1      82      ( 432)  ICASTHLIGGGDACRR
ZmAIL1      76      ( 440)  ICASTHLIGGGDACRR
OsBBM1      33      ( 337)  IIESSNLPIGTGTTRR
GmAIL1      77      ( 371)  ICSSSTLIAGDLAKRS
OsBBM       31      ( 452)  ILDSAALPVGTAAKRL
OsAIL1      68      ( 422)  ICSSTHLIGGDLACRR
GmANT       91      ( 433)  IMASSNLLAGELARRN
MtAIL1      81      ( 417)  ICSSSTLITGDLAKRS
GmPLT3b     61      ( 319)  SIANSTLPIGGLSGKN
GmPLT3a     62      ( 315)  SIANSTLPIGGLSGKN
AtANT       83      ( 452)  IMSSNTLLSGELARRN
AtAIL7      88      ( 341)  AVMNSSLPVGGAAAKR
SbPLT3b     63      ( 303)  SILNSDLPVGGGAAGR
OsPLT3b     72      ( 298)  SILNSDLPVGGGAATR
ZmANT2      89      ( 453)  IMESSTLLAVEEARKV
MtPLT3      70      ( 327)  SIANCSLPIGGLSNKN
ZmPLT3b     63      ( 308)  SILSSDLPVGGGASGR
OsPLT3      64      ( 312)  SIISSNLPIGSMAGNR
MtANT       90      ( 480)  IMASSNLLNIEQARRN
AtPLT3/AIL5 65      ( 371)  SIASCNLPVGGLMPKP
Consensus    7                      SSTLP1GG2A334
1=I or V; 2= A, L, or G; 3= K or R; 4= L or R
```

FIG. 2E

|           | SEQ ID NO: |      |                  |
|-----------|------------|------|------------------|
| AtBBM     | 17         | ( 4) | MNNWLGFSLSPHDQNH |
| GmANT     | 91         | (15) | NHNWLGFSLSPHMKME |
| BnBBM2    | 21         | ( 2) | NNNWLGFSLSPYEQNH |
| BnBBM1    | 19         | ( 2) | NNNWLGFSLSPYEQNH |
| VvBBM     | 27         | ( 4) | MNNWLGFSLSPRELPP |
| OsBBM     | 31         | ( 4) | MNNWLAFSLSPQDQLP |
| SbBBM     | 39         | ( 4) | VNNWLAFSLSPQELPP |
| ZmBBM     | 2          | ( 4) | VNNWLAFSLSPQELPP |
| MtANT     | 90         | (16) | ENNWLGFSLSPQMNNI |
| OsBBM2    | 35         | ( 4) | ANNWLGFSLSGQENPQ |
| ZmBBM2    | 29         | ( 4) | ANNWLGFSLSGQDNPQ |
| SbBBM2    | 41         | ( 5) | NNHWLGFSLSGQDNPQ |
| GmAIL1    | 77         | ( 1) | MSNWLGFSLTPHLRID |
| MtAIL1    | 81         | ( 1) | MSNWLGFSLTPHLRID |
| ZmANT2    | 89         | ( 4) | GSNWLGFSLSPHTAME |
| GmAIL6    | 79         | ( 4) | ATNWLSFSLSPMEMLR |
| GmPLT2    | 69         | ( 2) | NNNWLSFPLSPTHSSL |
| GmPLT1    | 73         | ( 2) | NNNWLSFPLSPTHSSL |
| MtPLT1/2  | 75         | ( 2) | NNNWLSFPLSPSHSSL |
| GmAIL7    | 85         | ( 5) | STNWLSFSLSPMDMLR |
| AtPLT1    | 74         | ( 3) | SNNWLGFPLSPNNSSL |
| MtBBM     | 23         | ( 3) | SMNLLGFSLSPQEQHP |
| AtPLT2    | 66         | ( 3) | SNNWLAFPLSPTHSSL |
| ZmAIL1    | 76         | ( 4) | NNGWLGFSLSPSAASR |
| OsBBM3    | 37         | ( 4) | ADNWLGFSLSGQGNPQ |
| SbANT     | 84         | (13) | ASSWLGFSLSPHMASA |
| OsANT     | 87         | (20) | VGGWLGFSLSPHMATY |
| SbPLT3b   | 67         | (10) | PHHWLSFSLSNNYHHG |
| OsPLT3b   | 72         | (10) | PHHWLSFSLSNNYHHG |
| ZmPLT3b   | 63         | (10) | PHHWLSFSLSNNYHHG |
| SbAIL1    | 82         | ( 4) | NNGWLGFSLSPSAGRG |
| GmBBM     | 25         | ( 3) | SMNLLGFSLSPQEHPS |
| AtPLT3/AIL5 | 65       | (27) | HQNWLSFSLSNNNNNF |
| GmPLT3b   | 61         | (13) | NNNSLAFSLSNHFPNP |
| GmPLT3a   | 62         | ( 9) | NNNSLAFSLSNHFPNP |
| AtAIL1    | 92         | ( 1) | MKKWLGFSLTPPLRIC |
| ZmANT     | 86         | (23) | GGSWLGFSLSPHMAAT |
| OsPLT3    | 64         | ( 8) | HYPWLNFSLAHHCEME |
| ZmPLT3    | 71         | ( 7) | YHPWLNFSLAHHCDLE |
| SbPLT3    | 78         | ( 6) | HYPWLNFSLAHHGDLE |
| OsAIL1    | 68         | ( 4) | NSGWLGFSLSSSSARG |
| AtANT     | 83         | (15) | TTNLLGFSLSSNMMKM |
| OsBBM1    | 33         | ( 4) | ITNWLGFSSSSFSGAG |
| Consensus | 8          |      | NWLXFSLSP        |
| X=G or S  |            |      |                  |

FIG. 2F

```
         SEQ ID NO:
MtBBM     23    ( 159)  NNSIGLSMIKTWLRNQPPPPE
BnBBM2    21    ( 130)  GGSLGLSMIKTWLRNQPVDNV
BnBBM1    19    ( 130)  GGSLGLSMIKTWLRNQPVDNV
SbBBM     39    ( 156)  SGSIGLSMIKNWLRSQPAPMQ
SbBBM2    41    ( 157)  SNTMELSMIKTWLRNNQVPQP
OsBBM     31    ( 156)  NGGIGLSMIKNWLRSQPAPQP
ZmBBM      2    ( 152)  GGGIGLSMIKNWLRSQPAPMQ
VvBBM     27    ( 131)  YISIGLSMIKTWLRNQPAPTH
ZmBBM2    29    ( 154)  SNTMELSMIKTWLRNNQVAQP
GmBBM     25    ( 164)  SSSIGLSMIKTWLRNQPPHSE
OsBBM3    37    ( 157)  GGTIELSMIKTWLRSNQSQQQ
OsBBM2    35    ( 154)  SNTMELSMIKTWLRNNGQVPA
OsBBM1    33    (  80)  SSVVGLSMIKNWLRSQPPPAV
AtBBM     17    ( 131)  GGSLGLSMIKTWLSNHSVANA
Consensus  9                    1LSMIK2WLR
1= G or E;  2= T or N
```

FIG. 2G

```
         SEQ ID NO:
SbAIL1    82    ( 527)  AGVHQLPVFALWND
OsAIL1    68    ( 536)  TVHHQLPVFALWND
ZmAIL1    76    ( 529)  PGVHQLPMFALWND
ZmANT     86    ( 624)  VSIAHLPVFAAWTD
SbANT     84    ( 664)  VSIAHMPVFAAWTD
OsANT     87    ( 638)  VSIAHLPMFAAWTD
MtANT     90    ( 642)  LSLPQMPVFAAWTD
VvBBM     27    ( 629)  AVCHGTPTFTVWND
GmANT     91    ( 532)  ISLSHLPVFAAWTD
OsBBM     31    ( 681)  GVCHGAQLFSVWND
BnBBM2    21    ( 565)  GGGEVAPTFTVWND
BnBBM1    19    ( 565)  GGGEVAPTFTVWND
GmAIL1    77    ( 499)  GLVNQVPMFALWNE
MtAIL1    81    ( 561)  GLVNQVPMFALWNE
ZmANT2    89    ( 637)  VVVSHRPVFAAWAD
AtBBM     17    ( 570)  GGGEGAPTFSVWND
AtANT     83    ( 541)  LTLPQMPVFAAWAD
SbBBM     39    ( 689)  VGHGGAQLFSVWND
ZmBBM      2    ( 695)  VGHGGAQLFSVWND
GmPLT2    69    ( 540)  MQTSNGGVFTMWND
GmPLT1    73    ( 549)  MQTSNSGVFTMWND
GmPLT3b   61    (  92)  CAPPQLPQFSTDNN
GmPLT3a   62    (  88)  CAPPQLPQFSTDNN
MtPLT3    70    ( 105)  CAPTQLQQFSTDND
AtPLT2    66    ( 555)  QGSNPGGVFTMWNE
AtPLT1    74    ( 561)  QGSNPGGVFTMWNE
MtPLT1/2  75    ( 524)  ENMQTADLFTMWND
Consensus 10                   PXFXXWND
X= any amino acid
```

FIG. 2H

```
SEQ ID NO:
GmANT     91      ( 210)  LQSLSLSMSPGSQSSC
AtANT     83      ( 194)  QQSLSLSMSPGSQSSC
GmPLT2    69      ( 120)  LQSLTLSMGSGKDSTC
GmPLT1    73      ( 121)  LQSLTLSMGSGKDSTC
MtPLT1/2  75      ( 122)  LQSLTLSMGSGKDSTC
MtANT     90      ( 250)  LHSLSLSMSPSSQSSC
MtBBM     23      ( 192)  VQTLSLSMSTGSQSSS
GmBBM     25      ( 202)  QQTLSLSMSTGSQSST
VvBBM     27      ( 174)  AQTLSLSMSTGSHQTG
SbBBM2    29      ( 221)  SQSLALSMSTGSHLPM
OsBBM2    35      ( 234)  SQSLALSMSTGSHSHL
ZmBBM2    29      ( 214)  SQSLALSMSTGSHLPM
SbANT     84      ( 217)  HHALALSMSSGSLSSC
ZmBBM     2       ( 181)  AQGLSLSMNMAGTTQG
GmAIL1    77      ( 150)  FQSLSLTMSPSVQNGV
OsBBM     31      ( 177)  AQALSLSMNMAGTTTA
BnBBM2    21      ( 159)  AKGLSLSMNSSTSCDN
BnBBM1    19      ( 159)  AKGLSLSMNSSTSCDN
SbBBM     39      ( 185)  VQGLSLSMNMAGATQG
OsANT     87      ( 241)  LHPLTLSMSSAGSQSS
MtAIL1    81      ( 191)  FQSLNLTMSPCVQNGV
ZmANT     86      ( 231)  PHPLALSMSSGTGSQS
AtPLT1    74      ( 126)  LQSLTLSMGTTAGNNV
AtPLT2    66      ( 129)  LQSLTLSMGSTGAAAA
AtBBM     17      ( 160)  ARGLSLSMNSSTSDSN
OsBBM3    37      ( 220)  GQGLALSMSTGSVAAA
ZmANT2    89      ( 202)  TRPLSLSMMSPGTQLS
Consensus 11              LXLSM
X = S, T or A
```

FIG. 2I

```
SEQ ID NO:
SbBBM     39      ( 529)  GWCKQEQDHAVIAAAH
OsBBM     31      ( 534)  GWCKQEQDHAVIAAAH
ZmBBM     2       ( 531)  GWCKQEQDHAVIAAAH
SbBBM2    41      ( 536)  GWCKPEQDAAVAAAAH
OsBBM2    35      ( 560)  GWCKPEQDAAVAAAAH
ZmBBM2    29      ( 528)  GWCKPEQDAAAAAAHS
OsBBM3    37      ( 522)  GWCKPEQDAVIAAGHC
MtBBM     23      ( 522)  LWCKQEQDSDDHSTYT
VvBBM     27      ( 454)  VWCKQEQDPDGTHNFQ
OsBBM1    33      ( 416)  AWLKQEQDSSVVTAAQ
GmBBM     25      ( 527)  NWCKQEQDNSDASHSL
Consensus 12              WCKXEQD
X= Q or P
```

FIG. 2J

```
        SEQ ID NO:
OsBBM2     35    ( 529)  HHHGWPTIAFQQPPPLAVHYPY
SbBBM2     41    ( 508)  GHHAWPTIAFQQPSPLSVHYPY
ZmBBM2     29    ( 501)  GHHGWPTIAFQQPSPLSVHYPY
VvBBM      27    ( 425)  HHHGWPTVAFQQAQPFSMHYPY
SbBBM      39    ( 502)  YHGAWPTIAFQPSAATGLYHPY
ZmBBM       2    ( 500)  HGAAWPTIAFQPGAATTGLYHP
OsBBM      31    ( 502)  AAAAWPTIAFQAAAAPPPHAAG
Consensus  13             WPTIAFQ
```

FIG. 2K

```
        SEQ ID NO:
SbBBM      39    ( 572)  MHGLGSMDNASLEHSTGSNSVVYNG
ZmBBM       2    ( 577)  MHGLASIDSASLEHSTGSNSVVYNG
OsBBM      31    ( 576)  QHGLGSIDNASLEHSTGSNSVVYNG
VvBBM      27    ( 487)  LHNLMSMDSSSMDHSSGSNSVIYSG
MtBBM      23    ( 560)  LQNIMSMDSASMDNSSGSNSVVYGG
GmBBM      25    ( 567)  LHPMLSMDSASIDNSSSSNSVVYDG
Consensus  14                    SXGSNSVVYNG
X= S or T
```

FIG. 2L

```
        SEQ ID NO:
SbBBM2     41    (  78)  ETQDWNMRGLDY
ZmBBM2     29    (  75)  ETQDWNMRGLDY
OsBBM2     35    (  76)  EAQDWNMRGLDY
OsBBM3     37    (  74)  ETQDWAMRGLDY
SbBBM      39    (  43)  IPQDWSMRGSEL
OsBBM      31    (  49)  IPQDWSMRGSEL
ZmBBM       2    (  44)  IPQDWSMRGSEL
Consensus  15             QDWXMRG
X= S or N
```

```
              340       *       360       *       380       *       400       *       420       *       440
ZmBBM2  : TFGQRTSIYRGVTRHRWTGRYEAHLWDNSCRREGQSRKGRQVYLGGYDKEKAARAYDLAALKYWGTTTTNFPIQYEKELMKHMRQEYIAYLRRSSGFSRGAS : 380
SbBBM2  : TFGQRTSIYRGVTRHRWTGRYEAHLWDNSCRREGQSRKGRQVYLGGYDKEDKAARAYDLAALKYWGTTTTNFPIQYEKELMKHMRQEYIAYLRRSSGFSRGAS : 387
OsBBM2  : TFGQRTSIYRGVTRHRWTGRYEAHLWDNSCRREGQSRKGRQVYLGGYDKEDKAARAYDLAALKYWGTTTTNFPIQYEKELMKHMRQEYIAYLRRSSGFSRGAS : 404
OsBBM3  : TFGQRTSIYRGVTRHRWTGRYEAHLWDNSCRREGQSRKGRQVYLGGYDKEKAARAYDLAALKYWGTTTTNFPMQYEKELMKHMRQEYIAYLRRSSGFSRGAS : 380
OsBBM1  : TFGQRTSIYRGVTKHRWTGRYEAHLWDNSCRREGQTRKGRQVYLGGYDKEKAARAYDLAALKYWGTTTTNFPVQYEKELMKHMRQEFVAYLRRSSGFSRGAS : 269
ZmBBM   : TFGQRTSIYRGVTRHRWTGRYEAHLWDNSCRREGQTRKGRQVYLGGYDKEKAARAYDLAALKYWGATTTNFPVQYEKELDKHMRQEFVAYLRRSSGFSRGAS : 374
SbBBM   : TFGQRTSIYRGVTRHRWTGRYEAHLWDNSCRREGQTRKGRQVYLGGYDKEKAARAYDLAALKYWGTTTTNFPVNYEKELDKHMRQEFVAYLRRSSGFSRGAS : 378
OsBBM   : TFGQRTSIYRGVTRHRWTGRYEAHLWDNSCRREGQTRKGRQVYLGGYDKEKAARAYDLAALKYWGPTTTNFPVAYEKELMKHMRQEFVAYLRRSSGFSRGAS : 384
BnBBM1  : ESFGQRTSIYRGVTRHRWTGRYEAHLWDNSCKREGQTRKGRQVYLGGYDKEKAARAYDLAALKYWGTTTTNFPMQYEKEVMKHMRQEYVAYLRRSSGFSRGAS : 311
BnBBM2  : SFGQRTSIYRGVTRHRWTGRYEAHLWDNSCKREGQTRKGRQVYLGGYDKEKAARAYDLAALKYWGTTTTNFPMQYEKEIMKHMRQEYVAYLRRSSGFSRGAS : 311
AtBBM   : ESFGQRTSIYRGVTRHRWTGRYEAHLWDNSCKREGQTRKGRQVYLGGYDKEKAARAYDLAALKYWGPTTTNFPLQYEKEVMKHMRQEYVAYLRRSSGFSRGAS : 311
MtBBM   : TFGQRTSIYRGVTRHRWTGRYEAHLWDNSCRREGQTRKGRQVYLGGYDKEKAARAYDLAALKYWGTTTTNFPIQYEKEVMKHMRQEYVAYLRRSSGFSRGAS : 363
GmBBM   : TFGQRTSIYRGVTRHRWTGRYEAHLWDNSCRREGQTRKGRQVYLGGYDKEKAARAYDLAALKYWGTTTTNFPIQYEKELMKHMRQEYVAYLRRSSGFSRGAS : 370
VvBBM   : TFGQRTSIYRGVTRHRWTGRYEAHLWDNSCRREGQTRKGRQVYLGGYDKEKAARAYDLAALKYWGTTTTNFPIQYEKEIMKHMRQEYVAYLRRSSGFSRGAS : 309
          d3FGQRTSIYRGVT4HRWTGRYEAHLWDNSC4REGQ3RKGRQVYLGGYDKE KAARAYDLAALKYWG TTTTNFPGs  YEKE6eeMKHMtRQE56A LRR SSGFSRGAS

*       460       *       480       *       500       *       520       *       540       *
ZmBBM2  : KYRGVTRHHQHGRWQARIGRVAGNKDLYLGTFSTEEEAAEAYDIAAIKFRGLKAVTNFDMSRYDVKILESSTLPVG-GYRRLKQAVDHVEAG-ATIWR-----ADMDGA : 484
SbBBM2  : KYRGVTRHHQHGRWQARIGRVAGNKDLYLGTFSTEEEAAEAYDIAAIKFRGLKAVTNFDMSRYDVKILESSTLPVG-GYRRLKQAVDHVEAG-ATIWR-----ADMDGG : 491
OsBBM2  : KYRGVTRHHQHGRWQARIGRVAGNKDLYLGTFSTEEEAAEAYDIAAIKFRGLKAVTNFDMSRYDVKILESSTLPVG-GYRRLKEAADHAEAGATIWRA-----ADMDGA : 510
OsBBM3  : KYRGVTRHHQHGRWQARIGRVAGNKDIYLGTFSTEEEAAEAYDIAAIKFRGLKAVTNFDMSRYDVKILESSTLPVG-GYRRLKEAEVAAAAA-----------GGG : 476
OsBBM1  : YRGVTRHHQHGRWQARIGRVAGNKDLYLGTFGTQEEAAEAYDIAAIKFRGLKAVTNFDMSRYDVIIESALPIGTGTTRRLKQSSDHTDNVMDINVN---------TEPN : 373
ZmBBM   : YRGVTRHHQHGRWQARIGRVAGNKDLYLGTFSTQEEAAEAYDIAAIKFRGLKAVTNFDMSRYDVILDSSALPIG-SYKRLKEAEAASAQHHHAGV------VSYDVG : 479
SbBBM   : YRGVTRHHQHGRWQARIGRVAGNKDLYLGTFSTQEEAAEAYDIAAIKFRGLKAVTNFDMSRYDVILDSALPIG-SYKRLKEAEAASAQHH-AGV------VSYDVG : 482
OsBBM   : YRGVTRHHQHGRWQARIGRVAGNKDLYLGTFTQEEAAEAYDIAAIKFRGLKAVTNFDMSRYDVILDSAALPVG-TYKRLKQAEAAA--------------AYDVG : 479
BnBBM1  : YRGVTRHHQHGRWQARIGRVAGNKDLYLGTFGTQEEAAEAYDIAAIKFRGLTAVTNFDMRYNVAILESPLPIG-SSKRLKEANRPVPSMMMIS------------ : 408
BnBBM2  : YRGVTRHHQHGRWQARIGRVAGNKDLYLGTFGTQEEAAEAYDIAAIKFRGLTAVTNFDMRYNVAILESPLPIG-SSKRLKEANRPVPSMMMIS------------ : 408
AtBBM   : YRGVTRHHQHGRWQARIGRVAGNKDLYLGTFGTQEEAAEAYDIAAIKFRGLSAVTNFDMRYNVAILESPLPIG-SSKRLKQVNNPVP-AMMIS-------------- : 407
MtBBM   : YRGVTRHHQHGRWQARIGRVAGNKDLYLGTFSTQEEAAEAYDVAAIKFRGLSAVTNFDMSRYDVILESSTLPIG-GYKRLKMEQVELNHVNVDISHRTEGDHSII : 472
GmBBM   : YRGVTRHHQHGRWQARIGRVAGNKDLYLGTFTQEEAAEAYDVAAIKFRGLSAVTNFDMSRYDVILESSTLPIG-SSKRLKMEQVELRVENVHRAD---QEDHSSI : 477
VvBBM   : YRGVTRHHQHGRWQARIGRVAGNKDLYLGTFTQEEAAEAYDIAAIKFRGLSAVTNFDMSRYDVNILESSTLPIG-GYKRLKAEQAEMTID-------GQRTDDEMS-- : 412
          YRGVTRHHQHGRWQARIGRVAGNKD6YLGTF T2EEAAEAYD6AAIKFRGL AVTNFDMsRY1Vk I6 S LP6G  aa4RLK

560       *       580       *       600       *       620       *       640       *       660
ZmBBM2  : -VIQSAEAGMGGYAS------YGHH-GYPTYAF-----QQPSPLSYHYP-YGQP----SRGYPY--AAAAAHSLQYQQL-H------------------SAAHFF : 560
SbBBM2  : -VIQSAEAGMGGYAS------YGHH-AYPTYAF-----QQPSPLSYHYP-YGPP----SRGYPY--AAVAAAHSLQYQQL-H------------------SAAHFF : 569
OsBBM2  : GVIYGADVGMGAAASYHHHH-GYPTYAF-----QQPPPLAYHYP-YGQAPAAPSRGYPY--AAVAAAHSLQYQQL-HS------------------AAAHFF : 597
OsBBM3  : VIVHADGVGGYYYG-----------CGPTYAFGGGGQQPAPLAYHYPSYGQAS--------GYPY--AVIAGHCATYQHL-HSG-----------------GAAATHFF : 558
OsBBM1  : NYVXSHFTNGVGNYGSQH----YGYN-GYSPYSM------QPIPSQYA-NGQPR----AIYLQYSSVVTAAQNLH-HHFSS-------------------YTHFF : 449
ZmBBM   : RIAYHGDGGALAAAYGAHYHGA-AYPTYAFQPGAATT------GLYHPYAQQPMRGG-GYPYQYHAVIAAAHSLQYQHL-NYA-------------------AAGAHFF : 565
SbBBM   : RIAYHGDGGALAAAYGAHYHG----AYPTYAFQP-SAAT------GLYHPYAQ-PMRG----GYPYQ--HAVIAAAHSLQEYHHE-NYA------------------AAGAHFF : 564
OsBBM   : RIAYHGGDGAYAAHYGHHHHSAAAYPTYAFQAAAAPPPHAAGLYHPYAQ-PLRG----GYPYQ--HAVIAAAHSLQYQHHL-NYA-------------------AAAAHFF : 569
BnBBM1  : ----NNYSESENS--------ASGWQNAYVQHHQGVD--------LSLYQHQERYNGY----YYNGGNLSSESARYCFKQYDQHH-FYSNT-----------------QSLMTYID : 484
BnBBM2  : ----NNYSESENN--------ASGWQNAYVQHHQGVD--------LSLYQQHQGERYNGY----YYNGGNLSSESARYCFKQYDQHH-FYSNT----------------QSLMTYID : 484
AtBBM   : ----NNYSESANN--------VSGWQNTYQHHQGMD--------LSLYQQQQERYVG----YYNGGNLSTESTRVCFKQYEEEEQQH-FYNS-------------PSHMTYVD : 482
MtBBM   : NNTYHYTEQAI---YAATNASNWHALSYQHQQPHHHYNANNMQLQNYPYGTQTQK-----LYYQYSODDHSTYTYATYHQEY-QYNN---NNNTHNFFGLQNIMSMDSAS : 573
GmBBM   : MN----YTQGIINNYAAGGTTATHHHNYHNALAFHQPQP---CTTHYPYGQRIN-------VYKQYNSDASHSLYSYSYHQEY-QYNNGTHNFFHTNSGLHPMLSMDSAS : 577
VvBBM   : ----YQYTDGINN-YGAHHHG-WPTVAYQQAGPFS--------HHYPYGHQQRA---VYKQYPDGTHN---FQYSYNT---HNFFQPNV-LHNLMSMDSSS : 497
                  s                                      y                    5 k eqd           Lg
```

FIG. 4B

```
            *       680        *       700        *       720        *       740        *       760        *
ZmBBM2  : QA-SS----------------S T  N-GGAG-----------ASGGY--QGL  GSS-FL  SS-TVVAAADQ HSS-TANGGSTCSYGDDHQEGKLI ----- : 626
SbBBM2  : QA-SS----------------S A  NSGGGG-----------ASGGYHQGL  GSSSFL  SS-TVVAGADQ HSSSTANQGSTCSYGDDHQEGKLI ----- : 639
OsBBM2  : QA-SS----------------S T  N------G----------GGGGY--QGL  --GNAFL AS-TVVA---DQ HSSTATNHGNTCSYGNEEQ-GKLI ----- : 657
OsBBM3  : QQPAS----------------S A  G-----------------NGG  GGNAFM  G-AVVAAADH GGSSAYGGG--------DESGRLV  ----- : 611
OsBBM1  : QQ-SD----------------VPD  TG----------------FVDAPSRSSDSYSFRYNGTNGFHGLP G ISYAMPVATAVDQGQG IHGYGED  ----- : 511
ZmBBM   : SAGQQAAAAAAMHGLASIDSASLEHSTGS  V  NGG--------VGDSNGASAV SG GYM   SAAGATTTSAMVSHEQMHARAY----DEAKQAAQM ----- : 654
SbBBM   : SAGQQ-----AAMHGLGSMDNASLEHSTGS  V  YNG--------VGDSNGSTVV SG -YM   SAATATATTAMVSHEQVHARAQGDHHDEAKQAAQM ----- : 651
OsBBM   : SQAMQ------QQHGLGSIDNASLEHSTGS  V  YN ---------DNGG--- GG GY IM   SAVSATATAVASSHDHG---------GDGGKQVQM ----- : 641
BnBBM1  : HQSSV----------------SD  VTVC NVVG-----------Y  YQ F-AA  --------------NCDAYAASEFD---------------- : 524
BnBBM2  : HQSSV----------------SD  VTVC NVVG-----------Y  YQ F-AA  --------------NCDAYAASEFD---------------- : 524
AtBBM   : HHSS-----------------SD  VTVC NVVS-----------Y  YQ F-A  YG------------TSVNYDPFTAAEIA---------------- : 526
MtBBM   : MDNS-----------------GS  V  YG GDHGG---------Y  NGS Y-M     ---AIAND NQNPRSNNNFGESE IKGFGYENVF TTTD : 638
GmBBM   : IDN S----------------SS  V  YD G-------------Y  GG YNY   GTTTTVVAND DQNPRSNHGFGDNE IKALGYESVY STTD : 643
VvBBM   : MDH SS---------------GS   V  YS GGAADGSAATGGSGSGSFQGVGY NNI F-  S----TVI AHE GHG-QGNGGFGDSEVKAI GYDNMF -STD : 579
                                s                          g      p                                    g

780        *        800        *       820        *
ZmBBM2  : - DAMVATAAGGDPYA----------AARNGYQF -QGSGSTV  IAR----ANGYANNWSSP  NNGMG- : 679
SbBBM2  : - DAMVAATAAGGDPYA---------AARSGYQF SQGSGSTV  IAR----ANGYSNNWSSP  NGGMG- : 693
OsBBM2  : - DAMAMASGAAG-------------GGYQL -QGSASTV  IAR----ANGYSANWSSP  NGAMG- : 703
OsBBM3  : - DGVVDPYAAMR-------------SAYEL SQGSSSSSV  VAKA---ANGYPDNWSSP  N-GMG- : 658
OsBBM1  : -VAGIDTTHDL YG------------SRNVYYL EGSLLADVEKEG---DYGQSVGGNSWVLPTP--- : 559
ZmBBM   : - ESYLVNAENNGGG-----------RMSAWGTVVSAAAAAASSNDNI AADVGHGGAQL  WNDT : 709
SbBBM   : - ESYLVNAEN GGG-----------RMSAAWA VSAPPAAS NDN----MADVGHGGAGL  WNDT : 703
OsBBM   : - SYLVGADA GGGGA----------GRMPSWAM PASAPAAT SSD----MTGVCHG-AQL  WNDT : 695
BnBBM1  : - MR----NHY FAQ-----------QQQTQGSPGGDFPAAMTNNVGSNMYYHGEGGGEVAPT  WNDN : 579
BnBBM2  : - MR----NHY FAQ-----------QQQTQHSPGGDFPAAMTNNVGSNMYHGEGGGEVAPT  WNDN : 579
AtBBM   : - MR----NHY YAQHQ----------QQQQ IQQSPGGDFPVAISNNHSSNMYFHGEGGGEAPT  WNDT : 584
MtBBM   : P  HAGAARNLY QPQQ---------LSVDQG----SNWVPTAIP  LAPR-TTNVSLCP----P  LHE- : 689
GmBBM   : P  HH-ARNLY LTQQQPSSVDAVKASAYDQGSACNTWVPTAIP  HAPRSSTSMALCHGATP  LHE- : 710
VvBBM   : P  HAR----SLY LSQQSSAG-MVKGSSAYDQGSGCNNWVPTAVP  LAPR-TNSLAVCHGTPT  WNDT : 643
             y                                    f
```

METHODS AND COMPOSITIONS FOR TARGETED POLYNUCLEOTIDE MODIFICATION

CROSS-REFERENCE TO RELATED APPLICATIONS

This application is a Continuation of U.S. application Ser. No. 14/215,110 filed 17 Mar. 2014, now U.S. Pat. No. 9,926,571 issued Mar. 27, 2018, which is a Continuation of U.S. application Ser. No. 12/982,013 filed on 30 Dec. 2010, now U.S. Pat. No. 8,704,041 issued 22 Apr. 2014, which claims the benefit of U.S. Provisional Application No. 61/291,207, filed on 30 Dec. 2009, the contents of all of which are hereby incorporated by reference in their entirety.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 3526USCNT2_SeqListing, created on 23 Jan. 2018, and having a size of 442,062 bytes and is filed concurrently with the specification. The sequence listing contained in this ASCII formatted document is part of the specification and is herein incorporated by reference in its entirety.

FIELD OF THE INVENTION

The present invention relates to the field of molecular biology, specifically the targeted modification of polynucleotides, including targeted mutagenesis and recombination events.

BACKGROUND OF THE INVENTION

Random insertion of introduced DNA into the genome of a host cell can be lethal if the foreign DNA disrupts an important native gene or regulatory region. Even if a random insertion event does not impair the functioning of a sequence in a host cell, the expression of an inserted foreign nucleotide sequence may be influenced by position effects caused by the surrounding genomic DNA. In some cases, the nucleotide sequence is inserted into a site where the position effect suppresses the function or regulation of the introduced nucleotide sequence. In other instances, overproduction of the gene product may have deleterious effects on a cell.

For example, in plants, position effects can result in reduced agronomics, additional costs for further research, creation of additional transgenic events, slowing product development. For these reasons, efficient methods are needed to target the insertion of nucleotide sequences into the genome of various organisms, such as plants, at chromosomal positions that allow for the desired function of the sequence of interest.

BRIEF SUMMARY OF THE INVENTION

Methods and compositions for targeted modification of a specific target site in a cell are provided. A variety of compositions and methods that can be used to modify a target site are provided, including methods to recombine polynucleotides, assess promoter activity, directly select transformed organisms, minimize or eliminate expression resulting from random integration into the genome of an organism, such as a plant, remove polynucleotides of interest, combine multiple transfer cassettes, invert or excise a polynucleotide, silence gene(s), and characterize transcriptional regulatory regions. The methods involve the introduction of a cell proliferation factor and a double-strand break-inducing enzyme into an organism, and in some embodiments, the introduction of a transfer cassette. Compositions also include plant cells and plants comprising a heterologous polynucleotide encoding a cell proliferation factor, a double-strand break-inducing enzyme and a transfer cassette comprising a recognition sequence that is recognized by the double-strand break-inducing enzyme.

BRIEF DESCRIPTION OF THE FIGURES

FIGS. 2A-2M show the consensus motif sequences 1-10, 14, 15, and 19, respectively, discovered in the analysis described herein, along with the alignments of the regions of various polypeptides used to generate the consensus motifs.

FIGS. 4A, 4B, and 4C show alignments of the amino acid sequence of various BBM polypeptides: maize babyboom 2 (ZmBBM2; SEQ ID NO: 29), sorghum babyboom 2 (SbBBM2; SEQ ID NO: 41), rice babyboom 2 (OsBBM2; SEQ ID NO: 35), rice babyboom 3 (OsBBM3; SEQ ID NO: 37), rice babyboom 1 (OsBBM1; SEQ ID NO: 33), maize babyboom (ZmBBM; SEQ ID NO: 2), sorghum babyboom (SbBBM; SEQ ID NO: 39), rice babyboom (OsBBM; SEQ ID NO: 31), Brassica babyboom 1 (BnBBM1; SEQ ID NO: 19), Brassica babyboom 2 (BnBBM2; SEQ ID NO: 21), Arabidopsis babyboom (AtBBM; SEQ ID NO: 17), medicago babyboom (MtBBM; SEQ ID NO: 23), soybean babyboom (GmBBM; SEQ ID NO: 25), and grape babyboom (VvBBM; SEQ ID NO: 27).

DETAILED DESCRIPTION OF THE INVENTION

Figure 1:
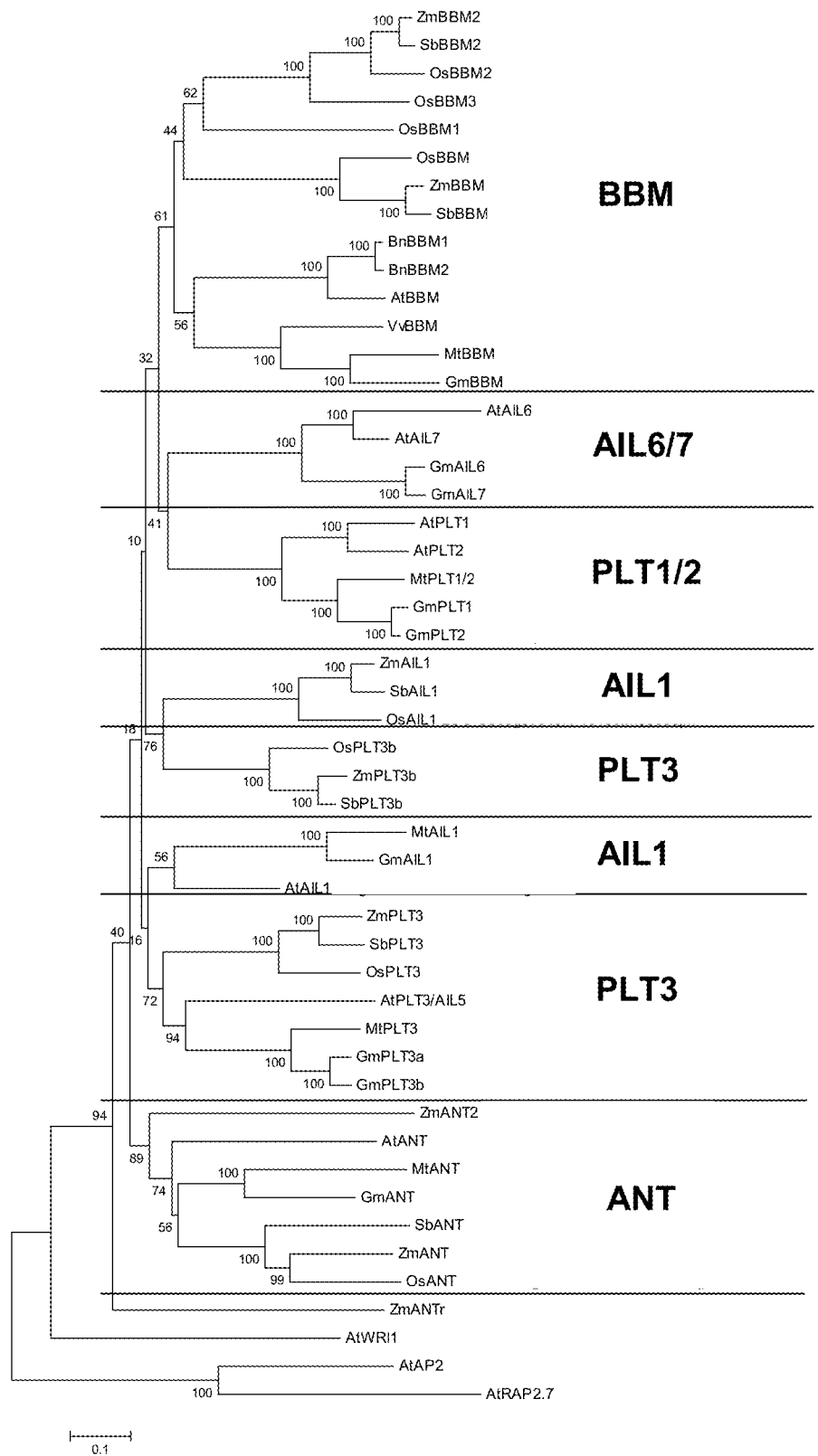
FIG. 1 provides a depiction of a phylogenetic analysis of 50 sequences with homology to maize babyboom (BBM).

Various compositions and methods for modifying a target site in a cell, for example a plant cell, are provided. The modification can include a deletion, mutation, replacement or insertion of a nucleotide sequence. The target site is modified through the activity of a double-strand break-inducing enzyme that recognizes a recognition sequence within the target site. The methods further involve the introduction of a cell proliferation factor, such as a babyboom polypeptide and/or a Wuschel polypeptide, that serves to enhance and promote the modification reaction.

Double-strand breaks induced by double-strand inducing enzymes can result in the induction of DNA repair mechanisms, including the non-homologous end-joining pathway, and homologous recombination. Error-prone DNA repair mechanisms can produce mutations at double-strand break sites. The nonhomologous end-joining (NHEJ) pathways are the most common repair mechanism that serve to bring the broken polynucleotide ends together (Bleuyard et al. (2006) *DNA Repair* 5:1-12). The structural integrity of chromosomes is typically preserved by the repair, but deletions, insertions, or other rearrangements are possible. The two ends of one double-strand break are the most prevalent substrates of NHEJ (Kirik et al. (2000) *EMBO J* 19:5562-6). If two different double-strand breaks occur, however, the free ends from different breaks can be ligated to one another, resulting in chromosomal deletions (Siebert and Puchta (2002) *Plant Cell* 14:1121-31), or chromosomal translocations between different chromosomes (Pacher et al. (2007) *Genetics* 175:21-9).

Episomal DNA molecules, for example T-DNAs, can also be ligated into the double-strand break, resulting in integration of the episomal DNA molecule into the host genome (Chilton and Que (2003) *Plant Physiol* 133:956-65; Salomon and Puchta (1998) *EMBO J* 17:6086-95). Once the sequence around the double-strand breaks is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (S, G2, M phases of a cell cycle) (Molinier et al. (2004) *Plant Cell* 16:342-52). Ectopic and/or epigenic DNA sequences may also serve as a DNA repair template for homologous recombination (Puchta (1999) *Genetics* 152: 1173-81).

DNA double-strand breaks (DSBs) appear to be an effective factor to stimulate homologous recombination pathways in every organism tested to date (Puchta et al. (1995) *Plant Mol Biol* 28:281-92; Tzfira and White (2005) *Trends Biotechnol* 23:567-9; Puchta (2005) *J Exp Bot* 56:1-14). For example, using DNA break-inducing enzymes, a two- to nine-fold increase of homologous recombination was observed between artificially constructed homologous DNA repeats in plants (Puchta et al. (1995) *Plant Mol Biol* 28:281-92). Thus, double-strand break-inducing enzymes can be used for targeted modification of polynucleotides in organisms and the provision of one or more cell proliferation factors enhances the frequency of targeted modification.

Cell proliferation factors can enhance the rate of targeted modification of a target site in a cell of an organism, such as a plant, that has been induced by a double-strand break-inducing enzyme. In these methods, at least one cell proliferation factor and a double-strand break-inducing enzyme are introduced into a cell having a target site with at least one recognition sequence. The double-strand break-inducing enzyme recognizes the recognition sequence and introduces a double-strand break at or near the recognition sequence to produce a modified target site. Modifications to the target site can include a deletion, mutation, replacement, homologous recombination, or insertion of a nucleotide sequence. In certain embodiments, the target site is stably integrated into the genome of the plant. In some of these embodiments, the genomic target site is a native genomic target site. These methods can be used to stimulate recombination at a target site, integrate polynucleotides into a target site, invert or excise a polynucleotide, directly select transformed organisms, minimize or eliminate expression resulting from random integration into the genome of an organism, combine multiple transfer cassettes, silence genes, and characterize transcriptional regulatory regions.

The presently disclosed methods and compositions utilize cell proliferation factors to enhance rates of targeted polynucleotide modification. As used herein, a "cell proliferation factor" is a polypeptide or a polynucleotide capable of stimulating growth of a cell or tissue, including but not limited to promoting progression through the cell cycle, inhibiting cell death, such as apoptosis, stimulating cell division, and/or stimulating embryogenesis. The polynucleotides can fall into several categories, including but not limited to, cell cycle stimulatory polynucleotides, developmental polynucleotides, anti-apoptosis polynucleotides, hormone polynucleotides, or silencing constructs targeted against cell cycle repressors or pro-apoptotic factors. The following are provided as non-limiting examples of each category and are not considered a complete list of useful polynucleotides for each category: 1) cell cycle stimulatory polynucleotides including plant viral replicase genes such as RepA, cyclins, E2F, prolifera, cdc2 and cdc25; 2) developmental polynucleotides such as Lec1, Kn1 family, WUSCHEL, Zwille, BBM, Aintegumenta (ANT), FUS3, and members of the Knotted family, such as Kn1, STM, OSH1, and SbH1; 3) anti-apoptosis polynucleotides such as CED9, Bcl2, Bcl-X(L), Bcl-W, Al, McL-1, Mac1, Boo, and Bax-inhibitors; 4) hormone polynucleotides such as IPT, TZS, and CKI-1; and 5) silencing constructs targeted against cell cycle repressors, such as Rb, CK1, prohibitin, and wee1, or stimulators of apoptosis such as APAF-1, bad, bax, CED-4, and caspase-3, and repressors of plant developmental transitions, such as Pickle and WD polycomb genes including FIE and Medea. The polynucleotides can be silenced by any known method such as antisense, RNA interference, cosuppression, chimerplasty, or transposon insertion.

The cell proliferation factors can be introduced into cells to enhance targeted polynucleotide modification through the introduction of a polynucleotide that encodes the proliferation factor. The use of the term "polynucleotide" is not intended to limit the compositions to polynucleotides comprising DNA. Polynucleotides can comprise ribonucleotides and combinations of ribonucleotides and deoxyribonucleotides. Such deoxyribonucleotides and ribonucleotides include both naturally occurring molecules and synthetic analogues. The polynucleotides also encompass all forms of sequences including, but not limited to, single-, double-, or multi-stranded forms, hairpins, stem-and-loop structures, circular plasmids, and the like. The polynucleotide encoding the cell proliferation factor may be native to the cell or heterologous. A native polypeptide or polynucleotide comprises a naturally occurring amino acid sequence or nucleotide sequence. "Heterologous" in reference to a polypeptide or a nucleotide sequence is a polypeptide or a sequence that originates from a different species, or if from the same species, is substantially modified from its native form in composition and/or genomic locus by deliberate human intervention.

Any of a number of cell proliferation factors can be used. In certain embodiments, those cell proliferation factors that are capable of stimulating embryogenesis are used to enhance targeted polynucleotide modification. Such cell proliferation factors are referred to herein as embryogenesis-stimulating polypeptides and they include, but are not limited to, babyboom polypeptides.

In some embodiments, the cell proliferation factor is a member of the AP2/ERF family of proteins. The AP2/ERF family of proteins is a plant-specific class of putative transcription factors that regulate a wide variety of developmental processes and are characterized by the presence of an AP2 DNA binding domain that is predicted to form an amphipathic alpha helix that binds DNA (PFAM Accession PF00847). The AP2 domain was first identified in APETALA2, an *Arabidopsis* protein that regulates meristem identity, floral organ specification, seed coat development, and floral homeotic gene expression. The AP2/ERF proteins have been subdivided into distinct subfamilies based on the presence of conserved domains. Initially, the family was divided into two subfamilies based on the number of DNA binding domains, with the ERF subfamily having one DNA binding domain, and the AP2 subfamily having 2 DNA binding domains. As more sequences were identified, the family was subsequently subdivided into five subfamilies: AP2, DREB, ERF, RAV, and others. (Sakuma et al. (2002) *Biochem Biophys Res Comm* 290:998-1009).

Members of the APETALA2 (AP2) family of proteins function in a variety of biological events, including but not limited to, development, plant regeneration, cell division, embryogenesis, and cell proliferation (see, e.g., Riechmann and Meyerowitz (1998) *Biol Chem* 379:633-646; Saleh and Pagés (2003) *Genetika* 35:37-50 and Database of *Arabidopsis* Transcription Factors at daft.cbi.pku.edu.cn). The AP2 family includes, but is not limited to, AP2, ANT, Glossy15, AtBBM, BnBBM, and maize ODP2/BBM.

Provided herein is an analysis of fifty sequences with homology to a maize BBM sequence (also referred to as maize ODP2 or ZmODP2, the polynucleotide and amino acid sequence of the maize BBM is set forth in SEQ ID NO: 1 and 2, respectively; the polynucleotide and amino acid sequence of another ZmBBM is set forth in SEQ ID NO: 121 and 122, respectively; and genomic sequences of ZmBBM are set forth in SEQ ID NO: 59 and 101). The analysis identified three motifs (motifs 4-6; set forth in SEQ ID NOs: 6-8), along with the AP2 domains (motifs 2 and 3; SEQ ID NOs: 4 and 5) and linker sequence that bridges the AP2 domains (motif 1; SEQ ID NO: 3), that are found in all of the BBM homologues. Thus, motifs 1-6 distinguish these BBM homologues from other AP2-domain containing proteins (e.g., WRI, AP2, and RAP2.7). Thus, these BBM homologues comprise a subgroup of AP2 family of proteins referred to herein as the BBM/PLT subgroup. In some embodiments, the cell proliferation factor that is used in the methods and compositions is a member of the BBM/PLT group of AP2 domain-containing polypeptides. In these embodiments, the cell proliferation factor comprises two AP2 domains and motifs 4-6 (SEQ ID NOs: 6-8) or a fragment or variant thereof. In some of these embodiments, the AP2 domains have the sequence set forth in SEQ ID NOs: 4 and 5 or a fragment or variant thereof, and in particular embodiments, further comprises the linker sequence of SEQ ID NO: 3 or a fragment or variant thereof. In other embodiments, the cell proliferation factor comprises at least one of motifs 4-6 or a fragment or variant thereof, along with two AP2 domains, which in some embodiments have the sequence set forth in SEQ ID NO: 4 and/or 5 or a fragment or variant thereof, and in particular embodiments have the linker sequence of SEQ ID NO: 3 or a fragment or variant thereof. Based on the phylogenetic analysis provided herein, the subgroup of BBM/PLT polypeptides can be subdivided into the BBM, AIL6/7, PLT1/2, AIL1, PLT3, and ANT groups of polypeptides.

In some embodiments, the cell proliferation factor is a babyboom (BBM) polypeptide, which is a member of the AP2 family of transcription factors. The BBM protein from *Arabidopsis* (AtBBM) is preferentially expressed in the developing embryo and seeds and has been shown to play a central role in regulating embryo-specific pathways. Overexpression of AtBBM has been shown to induce spontaneous formation of somatic embryos and cotyledon-like structures on seedlings. See, Boutiler et al. (2002) *The Plant Cell* 14:1737-1749. The maize BBM protein also induces embryogenesis and promotes transformation (See, U.S. Pat. No. 7,579,529, which is herein incorporated by reference in its entirety). Thus, BBM polypeptides stimulate proliferation, induce embryogenesis, enhance the regenerative capacity of a plant, enhance transformation, and as demonstrated herein, enhance rates of targeted polynucleotide modification. As used herein "regeneration" refers to a morphogenic response that results in the production of new tissues, organs, embryos, whole plants or parts of whole plants that are derived from a single cell or a group of cells. Regeneration may proceed indirectly via a callus phase or directly, without an intervening callus phase. "Regenerative capacity" refers to the ability of a plant cell to undergo regeneration.

In some embodiments, the babyboom polypeptide comprises two AP2 domains and at least one of motifs 7 and 10 (set forth in SEQ ID NO: 9 and 12, respectively) or a variant or fragment thereof. In certain embodiments, the AP2 domains are motifs 3 and 2 (SEQ ID NOs: 5 and 4, respectively) or a fragment or variant thereof, and in particular embodiments, the babyboom polypeptide further comprises a linker sequence between AP2 domain 1 and 2 having motif 1 (SEQ ID NO: 3) or a fragment or variant thereof. In particular embodiments, the BBM polypeptide further comprises motifs 4-6 (SEQ ID NOs 6-8) or a fragment or variant thereof. The BBM polypeptide can further comprise motifs 8 and 9 (SEQ ID NOs: 10 and 11, respectively) or a fragment or variant thereof, and in some embodiments, motif 10 (SEQ ID NO: 12) or a variant or fragment thereof. In some of these embodiments, the BBM polypeptide also comprises at least one of motif 14 (set forth in SEQ ID NO: 13), motif 15 (set forth in SEQ ID NO: 14), and motif 19 (set forth in SEQ ID NO: 15), or variants or fragments thereof. The variant of a particular amino acid motif can be an amino acid sequence having at least about 40%, 50%, 60%, 70%, 75%, 80%, 85%, 90%, 95%, 96%, 97%, 98%, 99%, or greater sequence identity with the motif disclosed herein. Alternatively, variants of a particular amino acid motif can be an amino acid sequence that differs from the amino acid motif by 1, 2, 3, 4, 5, 6, 7, 8, 9, or 10 amino acids.

Non-limiting examples of babyboom polynucleotides or polypeptides that can be used in the methods and compositions include the *Arabidopsis thaliana* AtBBM (SEQ ID NOs: 16 and 17), *Brassica napus* BnBBM1 (SEQ ID NOs: 18 and 19), *Brassica napus* BnBBM2 (SEQ ID NOs: 20 and 21), *Medicago truncatula* MtBBM (SEQ ID NOs: 22 and 23), *Glycine max* GmBBM (SEQ ID NOs: 24 and 25), *Vitis vinifera* VvBBM (SEQ ID NOs: 26 and 27), *Zea mays* ZmBBM (SEQ ID NOs: 1 and 2 and genomic sequence set forth in SEQ ID NO: 59; and SEQ ID NOs: 104 and 105 and genomic sequence set forth in SEQ ID NO: 101) and ZmBBM2 (SEQ ID NOs: 28 and 29), *Oryza sativa* OsBBM (polynucleotide sequences set forth in SEQ ID NOs: 30 and 103 and amino acid sequence set forth in SEQ ID NO: 31; genomic sequence set forth in SEQ ID NO: 102), OsBBM1 (SEQ ID NOs: 32 and 33), OsBBM2 (SEQ ID NOs: 34 and 35), and OsBBM3 (SEQ ID NOs: 36 and 37), *Sorghum bicolor* SbBBM (SEQ ID NOs: 38 and 39 and genomic sequence set forth in SEQ ID NO: 60) and SbBBM2 (SEQ ID NOs: 40 and 41) or active fragments or variants thereof. In particular embodiments, the cell proliferation factor is a maize BBM polypeptide (SEQ ID NO: 2, 29, or 105) or a variant or fragment thereof, or is encoded by a maize BBM polynucleotide (SEQ ID NO: 1, 28, or 104) or a variant or fragment thereof.

In some embodiments, a polynucleotide encoding a cell proliferation factor has a nucleotide sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the nucleotide sequence set forth in SEQ ID NO: 1, 16, 18, 20, 22. 24, 26, 28, 30, 32, 34, 36, 38, 40, 59, 101, 102, 103, 104, or 60 or the cell proliferation factor has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence set forth in SEQ ID NO: 2, 17, 19, 21, 23, 25, 27, 29, 31 33, 35, 37. 39, 105, or 41. in some of these embodiments, the cell proliferation factor has at least one of motifs 7 and 10 (SEQ ID NO: 9 and 12, respectively) or a variant or fragment thereof at the corresponding amino acid residue positions in the babyboom polypeptide. In other embodiments, the cell proliferation factor further comprises at least one of motif 14 (set forth in SEQ ID NO: 13), motif 15 (set forth in SEQ ID NO: 14), and motif 19 (set forth in SEQ ID NO: 15) or a variant or fragment thereof at the corresponding amino acid residue positions in the babyboom polypeptide.

In other embodiments, other cell proliferation factors, such as, Lec1, Kn1 family, WUSCHEL (e.g., WUS1, the polynucleotide and amino acid sequence of which is set forth in SEQ ID NO: 51 and 52; WUS2, the polynucleotide and amino acid sequence of which is set forth in SEQ ID NO: 57 and 58; WUS2 alt, the polynucleotide and amino acid sequence of which is set forth in SEQ ID NO: 99 and 100; WUS3, the polynucleotide and amino acid sequence of which is set forth in SEQ ID NO: 97 and 98), Zwille, and Aintegumeta (ANT), may be used alone, or in combination with a babyboom polypeptide or other cell proliferation factor to enhance targeted polynucleotide modification in plants. See, for example, U.S. Application Publication No. 2003/0135889, International Application Publication No. WO 03/001902, and U.S. Pat. No. 6,512,165, each of which is herein incorporated by reference. When multiple cell proliferation factors are used, or when a babyboom polypeptide is used along with any of the abovementioned polypeptides, the polynucleotides encoding each of the factors can be present on the same expression cassette or on separate expression cassettes. Likewise, the polynucleotide(s) encoding the cell proliferation factor(s) and the polynucleotide encoding the double-strand break-inducing enzyme can be located on the same or different expression cassettes. When two or more factors are coded for by separate expression cassettes, the expression cassettes can be provided to the plant simultaneously or sequentially.

In some embodiments, polynucleotides or polypeptides having homology to a known babyboom polynucleotide or polypeptide and/or sharing conserved functional domains can be identified by screening sequence databases using programs such as BLAST. The databases can be queried using full length sequences, or with fragments including, but not limited to, conserved domains or motifs. In some embodiments, the sequences retrieved from the search can be further characterized by alignment programs to quickly identify and compare conserved functional domains, regions of highest homology, and nucleotide and/or amino differences between sequences, including insertions, deletions, or substitutions, including those programs described in more detail elsewhere herein. The retrieved sequences can also be evaluated using a computer program to analyze and output the phylogenetic relationship between the sequences.

In other embodiments, polynucleotides or polypeptides having homology to a known babyboom polynucleotide or polypeptide and/or sharing conserved functional domains can be identified using standard nucleic acid hybridization techniques, such as those described in more detail elsewhere herein. Extensive guides on nucleic acid hybridization include Tijssen (1993) Laboratory Techniques in Biochemistry and Molecular Biology—Hybridization with Nucleic Acid Probes, Part I, Chapter 2 (Elsevier, NY); Ausubel et al., eds. (1995) Current Protocols in Molecular Biology, Chapter 2 (Greene Publishing and Wiley-Interscience, NY); and, Sambrook et al. (1989) Molecular Cloning: A Laboratory Manual (2d ed., Cold Spring Harbor Laboratory Press, Plainview, N.Y.).

According to the presently disclosed methods, cell proliferation factors are introduced into cells to enhance the modification of a target site within the cell. The terms "target site," and "target sequence," as used interchangeably herein, refer to a polynucleotide sequence present in a cell of an organism, such as a plant, that comprises at least one recognition sequence and/or a nick/cleavage site for a double-strand break-inducing enzyme. The target site may be part of the organism's native genome or integrated therein or may be present on an episomal polynucleotide. The genomic target sequence may be on any region of any chromosome, and may or may not be in a region encoding a protein or RNA. The target site may be native to the cell or heterologous. In some embodiments, the heterologous target sequence may have been transgenically inserted into the organism's genome, and may be on any region of any chromosome, including an artificial or satellite chromosome, and may or may not be in a region encoding a protein or RNA. It is recognized that the cell or the organism may comprise multiple target sites, which may be located at one or multiple loci within or across chromosomes. Multiple independent manipulations of each target site in the organism can be performed using the presently disclosed methods.

The target sites comprise at least one recognition sequence. As used herein, the terms "recognition sequence" or "recognition site," used interchangeably herein, refer to any nucleotide sequence that is specifically recognized and/or bound by a double-strand break-inducing enzyme. The length of the recognition site sequence can vary, and includes, for example, sequences that are at least about 3, 4, 6, 8, 10, 12, 14, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 80, 90, 100, or more nucleotides in length. In some embodiments, the recognition site is of a sufficient length to only be present in a genome of an organism one time. In some embodiments, the recognition site is palindromic, that is, the sequence on one strand reads the same in the opposite direction on the complementary strand. The double-strand break-inducing enzyme recognizes the recognition sequence and introduces a double-strand break at or near the recognition sequence. The nick/cleavage site could be within the sequence that is specifically recognized by the enzyme or the nick/cleavage site could be outside of the sequence that is specifically recognized by the enzyme. In some embodiments, the double-strand break is introduced about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, or more nucleotides away from the recognition sequence.

In some embodiments, the cleavage occurs at nucleotide positions immediately opposite each other to produce a blunt end cut or, in alternative embodiments, the cuts are staggered to produce single-stranded overhangs, also called "sticky ends", which can be either 5' overhangs, or 3' overhangs. The recognition sequence can be endogenous (native) or heterologous to the plant cell. When the recognition site is an endogenous sequence, it may be recognized by a naturally-occurring, or native double-strand break-inducing enzyme. Alternatively, an endogenous recognition sequence may be recognized and/or bound by a modified or engineered double-strand break-inducing enzyme designed or selected to specifically recognize the endogenous recognition sequence to produce a double-strand break.

A double-strand break-inducing enzyme is any enzyme that recognizes and/or binds to a specific recognition sequence to produce a double-strand break at or near the recognition sequence. The double-strand break could be due to the enzymatic activity of the enzyme itself or the enzyme might introduce a single-stranded nick in the DNA that then leads to a double-strand break induced by other cellular machinery (e.g., cellular repair mechanisms). Examples of double-strand break-inducing enzymes include, but are not limited to, endonucleases, site-specific recombinases, transposases, topoisomerases, and zinc finger nucleases, and include modified derivatives, variants, and fragments thereof. A modified double-strand break-inducing enzyme can be derived from a native, naturally-occurring double-strand break-inducing enzyme or it can be artificially created or synthesized. Those modified double-strand break-inducing enzymes that are derived from a native, naturally-occurring double-strand break-inducing enzymes can be modified to recognize a different recognition sequence (at least one nucleotide difference) than its native form. In certain embodiments, the double-strand break-inducing enzyme recognizes recognition sequences that are of a sufficient length to have only one copy in a genome of an organism.

In some embodiments, the double-strand break-inducing enzyme can be provided to an organism through the introduction of a polynucleotide encoding the enzyme. In some of these embodiments, the polynucleotide can be modified to at least partially optimize codon usage in the organism, such as plants. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, WO 99/25841, and Murray et al. (1989) *Nucleic Acids Res.* 17:477-498, herein incorporated by reference. Such polynucleotides wherein the frequency of codon usage has been designed to mimic the frequency of preferred codon usage of the host cell are referred to herein as being "codon-modified", "codon-preferred", or "codon-optimized." The polynucleotide encoding the cell proliferation factor, and in some embodiments, the polynucleotide of interest, can also be at least partially modified to optimized codon usage in the host cell or organism.

In some embodiments, the double-strand break-inducing enzyme is a transposase. Transposases are polypeptides that mediate transposition of a transposon from one location in the genome to another. Transposases typically induce double-strand breaks to excise the transposon, recognize subterminal repeats, and bring together the ends of the excised transposon, in some systems, other proteins are also required to bring together the ends during transposition. Examples of transposons and transposases include, but are not limited to, the Ac/Ds, Dt/rdt, Mu-Ml/Mn, and Spm(En)/dSpm elements from maize, the Tam elements from snapdragon, the Mu transposon from bacteriophage, bacterial transposons (Tn) and insertion sequences (IS), Ty elements of yeast (retrotransposon), Ta1 elements from *Arabidopsis* (retrotransposon), the P element transposon from Drosophila (Gloor et al. (1991) *Science* 253:1110-1117), the Copia, Mariner and Minos elements from *Drosophila*, the Hermes elements from the housefly, the PiggyBack elements from *Trichplusia ni*, Tc1 elements from *C. elegans*, and IAP elements from mice (retrotransposon).

In other embodiments, the double-strand break-inducing enzyme is a DNA topoisomerase. DNA topoisomerases modulate DNA secondary and higher order structures and functions related primarily to replication, transcription, recombination and repair. Topoisomerases share two characteristics: (i) the ability to cleave and reseal the phosphodiester backbone of DNA in two successive transesterification reactions; and (ii) once a topoisomerase cleaved DNA intermediate is formed, the enzyme allows the severed DNA ends to come apart, allowing the passage of another single- or double-stranded DNA segment. DNA topoisomerases can be classified into three evolutionary independent families: type IA, type IB and type II.

Type IA and type IB topoisomerases cleave only a single strand of DNA. The *Escherichia coli* topoisomerase I and topoisomerase III, *Saccharomyces cerevisiae* topoisomerase III and reverse gyrase belong to the type IA or type 1-5' subfamily as the protein link is to a 5' phosphate in the DNA. The prototype of type IB or 1-3' enzymes are found in all eukaryotes and also in vaccinia virus topoisomerase I where the protein is attached to a 3' phosphate. Despite differences in mechanism and specificity between the bacterial and eukaryotic enzymes, yeast DNA topoisomerase I can complement a bacterial DNA topoisomerase I mutant (Bjornsti et al. (1987) *Proc Natl Acad Sci USA* 84:8971-5). Type IA topoisomerases relax negatively supercoiled DNA and require magnesium and a single-stranded region of DNA. Topoisomerases IB relax both positively and negatively supercoiled DNA with equal efficiency and do not require a single-stranded region of DNA or metal ions for function.

The type II family of DNA topoisomerases are homodimeric (eukaryotic topoisomerase II) or tetrameric (gyrase) enzymes that cleave both strands of a DNA duplex. Type II topoisomerases include, but are not limited to, *E. coli* DNA gyrase, *E. coli* topoisomerase IV (par E), eukaryotic type II topoisomerases, and archaic topoisomerase VI. Preferred cutting sites are known for available topoisomerases.

In particular embodiments, the double-strand break-inducing enzyme is an endonuclease. Endonucleases are enzymes that cleave the phosphodiester bond within a polynucleotide chain, and include restriction endonucleases that cleave DNA at specific sites without damaging the bases. Restriction endonucleases include Type I, Type II, Type III, and Type IV endonucleases, which further include various subtypes. In the Type I and Type III systems, a single protein complex has both methylase and restriction activities.

Type I and Type III restriction endonucleases recognize specific recognition sequences, but typically cleave at a variable position from the recognition site, which can be hundreds of base pairs away from the recognition site. In Type II systems, the restriction activity is independent of any methylase activity, and typically cleavage occurs at specific sites within or near to the recognition site. Most Type II enzymes cut palindromic sequences, however Type IIa enzymes recognize non-palindromic recognition sites and cleave outside of the recognition site; Type IIb enzymes cut sequences twice with both sites outside of the recognition site; and Type IIs endonucleases recognize an asymmetric recognition site and cleave on one side and at a defined distance of about 1-20 nucleotides from the recognition site.

Type IV restriction enzymes target methylated DNA. Restriction enzymes are further described and classified, for example in the REBASE database (on the world wide web at rebase.neb.com; Roberts et al. (2003) *Nucleic Acids Res* 31:418-20; Roberts et al. (2003) *Nucleic Acids Res* 31:1805-

12; and Belfort et al. (2002) in Mobile DNA II, pp. 761-783, Eds. Craigie, et al., ASM Press, Washington, D.C., each of which is herein incorporated by reference in its entirety).

Endonucleases that are suitable for use in the presently described methods and compositions include homing endonucleases, which like restriction endonucleases, bind and cut polynucleotides at a specific recognition sequence, however the recognition sequences for homing endonucleases are typically longer, about 18 bp or more. These sequences are predicted to naturally occur infrequently in a genome, typically only one or two sites per genome.

Homing endonucleases, also known as meganucleases, have been classified into four families based on conserved sequence motifs: the LAGLIDADG, GIY-YIG, H-N-H, and His-Cys box families. These motifs participate in the coordination of metal ions and hydrolysis of phosphodiester bonds. Homing endonucleases are notable for their long recognition sites, and for tolerating some sequence polymorphisms in their DNA substrates. The naming convention for homing endonucleases is similar to the convention for other restriction endonucleases. Homing endonucleases are also characterized by a prefix of F-, I-, or PI- for enzymes encoded by free-standing ORFs, introns, and inteins, respectively. For example, the intron-, intein-, and freestanding gene-encoded homing endonucleases from *Saccharomyces cerevisiae* are denoted I-SceI, PI-SceI, and F-SceII (HO endonuclease), respectively. Homing endonuclease domains, structure and function are known (see for example, Guhan and Muniyappa (2003) *Crit Rev Biochem Mol Biol* 38:199-248; Lucas et al. (2001) *Nucleic Acids Res* 29:960-9; Jurica and Stoddard (1999) *Cell Mol Life Sci* 55:1304-26; Stoddard (2006) *Q Rev Biophys* 38:49-95; and Moure et al. (2002) *Nat Struct Biol* 9:764, each of which is herein incorporated by reference). In some embodiments, a naturally occurring variant, and/or an engineered derivative homing endonuclease is used. The cleavage specificity of a homing endonuclease can be changed by rational design of amino acid substitutions at the DNA binding domain and/or combinatorial assembly and selection of mutated monomers (see, for example, Arnould et al. (2006) *J Mol Biol* 355: 443-58; Ashworth et al. (2006) *Nature* 441:656-9; Doyon et al. (2006) *J Am Chem Soc* 128:2477-84; Rosen et al. (2006) *Nucleic Acids Res* 34:4791-800; and Smith et al. (2006) *Nucleic Acids Res* 34:e149, each of which is herein incorporated by reference). Engineered homing endonucleases have been demonstrated that can cleave cognate mutant sites without broadening their specificity. The endonuclease can be a modified endonuclease that binds a non-native or heterologous recognition sequence and does not bind a native or endogenous recognition sequence. An engineered or modified endonuclease can have only a single modified amino acid or many amino acid changes. Methods for modifying the kinetics, cofactor interactions, expression, optimal conditions, and/or recognition site specificity of homing endonucleases, and subsequently screening for activity are known, see for example, Epinat et al. (2003) *Nucleic Acids Res* 31:2952-62; Chevalier et al. (2002) *Mol Cell* 10:895-905; Gimble et al. (2003) *Mol Biol* 334:993-1008; Seligman et al. (2002) *Nucleic Acids Res* 30:3870-9; Sussman et al. (2004) *J Mol Biol* 342:31-41; Rosen et al. (2006) *Nucleic Acids Res* 34:4791-800; Chames et al. (2005) *Nucleic Acids Res* 33:e178; Smith et al. (2006) *Nucleic Acids Res* 34:e149; Gruen et al. (2002) *Nucleic Acids Res* 30:e29; Chen and Zhao, (2005) *Nucleic Acids Res* 33:e154; U.S. Application Publication No. US2007/0117128; and International Application Publication Nos. WO 05/105989, WO 03/078619, WO 06/097854, WO 06/097853, WO 06/097784, WO 04/031346, WO 04/067753, and WO 07/047859, each of which is herein incorporated by reference in its entirety.

Any homing endonuclease can be used as a double-strand break inducing agent including, but not limited to, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any variant or derivative thereof.

In still other embodiments, the double-strand break-inducing enzyme is a zinc finger nuclease. Zinc finger nucleases (ZFNs) are engineered double-strand break inducing agents comprised of a zinc finger DNA binding domain and a double strand break-inducing enzymatic domain. Recognition site specificity is conferred by the zinc finger domain, which typically comprises two, three, four, or more zinc fingers, for example having a C2H2 structure; however other zinc finger structures are known and have been engineered. Zinc finger domains are amenable to the design of polypeptides which specifically bind a selected polynucleotide recognition sequence. ZFNs consist of an engineered DNA-binding zinc finger domain linked to a non-specific endonuclease domain, for example, a nuclease domain from a Type IIs endonuclease such as FokI. Additional functionalities can be fused to the zinc-finger binding domain, including transcriptional activator domains, transcription repressor domains, and methylases. In some examples, dimerization of the nuclease domain is required for cleavage activity. Each zinc finger recognizes three consecutive base pairs in the target DNA. For example, a 3-finger domain recognizes a sequence of nine contiguous nucleotides, with a dimerization requirement of the nuclease. Two sets of zinc finger triplets are used to bind an 18-nucleotide recognition sequence. A recognition sequence of 18 nucleotides is long enough to be unique in a genome ($4^{18}=6.9 \times 10^{10}$).

To date, designer zinc finger modules predominantly recognize GNN and ANN triplets (Dreier et al. (2001) *J Biol Chem* 276:29466-78; Dreier et al. (2000) *J Mol Biol* 303: 489-502; Liu et al. (2002) *J Biol Chem* 277:3850-6, each of which is herein incorporated by reference), but examples using CNN or TNN triplets are also known (Dreier et al. (2005) *J Biol Chem* 280:35588-97; Jamieson et al. (2003) *Nature Rev Drug Discov* 2:361-8). See also, Dural et al. (2005) *Nucleic Acids Res* 33:5978-90; Segal (2002) *Methods* 26:76-83; Porteus and Carroll (2005) *Nat Biotechnol* 23:967-73; Pabo et al. (2001) *Ann Rev Biochem* 70:313-40; Wolfe et al. (2000) *Ann Rev Biophys Biomol Struct* 29:183-212; Segal and Barbas (2001) *Curr Opin Biotechnol* 12:632-7; Segal et al. (2003) *Biochemistry* 42:2137-48; Beerli and Barbas (2002) *Nat Biotechnol* 20:135-41; Mani et al. (2005) *Biochem Biophys Res Comm* 335:447-57; Lloyd et al. (2005) *Proc Natl Acad Sci USA* 102:2232-7; Carroll et al. (2006) *Nature Protocols* 1:1329; Ordiz et al. (2002) *Proc Natl Acad Sci USA* 99:13290-5; Guan et al. (2002) *Proc Natl*

*Acad Sci USA* 99:13296-301; Townsend et al. (2009) *Nature* 459:442-445; Sander et al. (2008) *Nucl Acids Res* 37:509-515; Fu et al. (2009) *Nucl Acids Res* 37:D297-283; Maeder et al. (2008) *Mol Cell* 31:294-301; Wright et al. (2005) *Plant J* 44:693-705; Wright et al. (2006) *Nat Prot* 1:1637-1652; zinc-finger consortium (website at www-dot-zincfinger-dot-org); International Application Publication Nos. WO 02/099084; WO 00/42219; WO 02/42459; WO 03/062455; U.S. Application Publication Nos. 2003/0059767 and 2003/0108880; and U.S. Pat. Nos. 6,534,261, 7,262,054, 7,378,510, 7,151,201, 6,140,466, 6,511,808 and 6,453,242; each of which is herein incorporated by reference in its entirety.

Alternatively, engineered zinc finger DNA binding domains can be fused to other double-strand break-inducing enzymes or derivatives thereof that retain DNA nicking/cleaving activity. For example, this type of fusion can be used to direct the double-strand break-inducing enzyme to a different recognition site, to alter the location of the nick or cleavage site, to direct the inducing agent to a shorter recognition site, or to direct the inducing agent to a longer recognition site. In some embodiments, a zinc finger DNA binding domain is fused to a site-specific recombinase, transposase, topoisomerase, endonuclease, or a derivative thereof that retains DNA nicking and/or cleaving activity.

In some embodiments, a site-specific recombinase is used as the double-strand break-inducing enzyme. A site-specific recombinase, also referred to herein as a recombinase, is a polypeptide that catalyzes conservative site-specific recombination between its compatible recombination sites, and includes native polypeptides as well as derivatives, variants and/or fragments that retain activity, and native polynucleotides, derivatives, variants, and/or fragments that encode a recombinase that retains activity. The recombinase used in the methods and compositions can be a native recombinase or a biologically active fragment or variant of the recombinase. In some embodiments, the site-specific recombinase is a recombinantly produced enzyme or variant thereof, which catalyzes conservative site-specific recombination between specified DNA recombination sites. For reviews of site-specific recombinases and their recognition sites, see Sauer (1994) *Curr Op Biotechnol* 5:521-527; and Sadowski (1993) *FASEB* 7:760-767, each of which is herein incorporated by reference in its entirety.

Any recombinase system can be used in the methods and compositions. A recombinase can be provided via a polynucleotide that encodes the recombinase, a modified polynucleotide encoding the recombinase, or the polypeptide itself. Non-limiting examples of site-specific recombinases that can be used to produce a double-strand break at a recognition sequence include FLP, Cre, SSV1, lambda Int, phi C31 Int, HK022, R, Gin, Tn1721, CinH, ParA, Tn5053, Bxb1, TP907-1, U153, and other site-specific recombinases known in the art, including those described in Thomson and Ow (2006) *Genesis* 44:465-476, which is herein incorporated by reference in its entirety. Examples of site-specific recombination systems used in plants can be found in U.S. Pat. Nos. 5,929,301, 6,175,056, 6,331,661; and International Application Publication Nos. WO 99/25821, WO 99/25855, WO 99/25841, and WO 99/25840, the contents of each are herein incorporated by reference.

In some embodiments, recombinases from the Integrase or Resolvase families are used, including biologically active variants and fragments thereof. The Integrase family of recombinases has over one hundred members and includes, for example, FLP, Cre, lambda integrase, and R. The Integrase family has been grouped into two classes based on the structure of the active sites, serine recombinases and tyrosine recombinases. The tyrosine family, which includes Cre, FLP, SSV1, and lambda integrase, uses the catalytic tyrosine's hydroxyl group for a nucleophilic attack on the phosphodiester bond of the DNA. Typically, members of the tyrosine family initially nick the DNA, which later forms a double strand break. In the serine recombinase family, which includes phiC31 integrase, a conserved serine residue forms a covalent link to the DNA target site (Grindley et al. (2006) *Ann Rev Biochem* 16:16). For other members of the Integrase family, see, for example, Esposito et al. (1997) *Nucleic Acids Res* 25:3605-3614; and Abremski et al. (1992) *Protein Eng* 5:87-91; each of which are herein incorporated by reference in its entirety. Other recombination systems include, for example, the *Streptomycete* bacteriophage phi C31 (Kuhstoss et al. (1991) *J Mol Biol* 20:897-908); the SSV1 site-specific recombination system from *Sulfolobus shibatae* (Maskhelishvili et al. (1993) *Mol Gen Genet* 237:334-342); and a retroviral integrase-based integration system (Tanaka et al. (1998) *Gene* 17:67-76). In some embodiments, the recombinase does not require cofactors or a supercoiled substrate. Such recombinases include Cre, FLP, or active variants or fragments thereof.

The FLP recombinase is a protein that catalyzes a site-specific reaction that is involved in amplifying the copy number of the two-micron plasmid of *S. cerevisiae* during DNA replication. FLP recombinase catalyzes site-specific recombination between two FRT sites. The FLP protein has been cloned and expressed (Cox (1993) *Proc Natl Acad Sci USA* 80:4223-4227). The FLP recombinase for use in the methods and compositions may be derived from the genus *Saccharomyces*. In some embodiments, a recombinase polynucleotide modified to comprise more plant-preferred codons is used. A recombinant FLP enzyme encoded by a nucleotide sequence comprising maize preferred codons (FLPm) that catalyzes site-specific recombination events is known (the polynucleotide and polypeptide sequence of which is set forth in SEQ ID NO: 42 and 43, respectively; see, e.g., U.S. Pat. No. 5,929,301, which is herein incorporated by reference in its entirety). Thus, in some embodiments, the site-specific recombinase used in the methods and compositions has the sequence set forth in SEQ ID NO: 43 (FLP) has at least about 70%, 75%, 80%, 85%, 90%, 95%, 96%, 97%, 98%, 99%, or greater sequence identity to SEQ ID NO: 43. In some of those embodiments wherein the site-specific recombinase is provided to the cell through the introduction of a polynucleotide that encodes the site-specific recombinase, the polynucleotide has the sequence set forth in SEQ ID NO: 42 (FLPm) or has at least about 70%, 75%, 80%, 85%, 90%, 95%, 96%, 97%, 98%, 99%, or greater sequence identity to SEQ ID NO: 42. Additional functional variants and fragments of FLP are known (Buchholz et al. (1998) *Nat Biotechnol* 16:657-662; Hartung et al. (1998) *J Biol Chem* 273:22884-22891; Saxena et al. (1997) *Biochim Biophys Acta* 1340:187-204; Hartley et al. (1980) *Nature* 286:860-864; Voziyanov et al. (2002) *Nucleic Acids Res* 30:1656-1663; Zhu & Sadowski (1995) *J Biol Chem* 270:23044-23054; and U.S. Pat. No. 7,238,854, each of which is herein incorporated by reference in its entirety).

The bacteriophage recombinase Cre catalyzes site-specific recombination between two lox sites. The Cre recombinase is known (Guo et al. (1997) *Nature* 389:40-46; Abremski et al. (1984) *J Biol Chem* 259:1509-1514; Chen et al. (1996) *Somat Cell Mol Genet* 22:477-488; Shaikh et al. (1977) *J Biol Chem* 272:5695-5702; and, Buchholz et al. (1998) *Nat Biotechnol* 16:657-662, each of which is herein incorporated by reference in its entirety). Cre polynucleotide sequences may also be synthesized using plant-preferred codons, for example such sequences (maize optimized Cre (moCre); the polynucleotide and polypeptide sequence of which is set forth in SEQ ID NO: 44 and 45, respectively) are described, for example, in International Application Publication No. WO 99/25840, which is herein incorporated by reference in its entirety. Thus, in some embodiments, the site-specific recombinase used in the methods and compositions has the sequence set forth in SEQ ID NO: 45 (Cre) has at least about 70%, 75%, 80%, 85%, 90%, 95%, 96%, 97%, 98%, 99%, or greater sequence identity to SEQ ID NO: 45. In some of those embodiments wherein the site-specific recombinase is provided to the cell through the introduction of a polynucleotide that encodes the site-specific recombinase, the polynucleotide has the sequence set forth in SEQ ID NO: 44 (moCre) or has at least about 70%, 75%, 80%, 85%, 90%, 95%, 96%, 97%, 98%, 99%, or greater sequence identity to SEQ ID NO: 44. Variants of the Cre recombinase are known (see, for example U.S. Pat. No. 6,890,726; Rufer & Sauer (2002) *Nucleic Acids Res* 30:2764-2772; Wierzbicki et al. (1987) *J Mol Biol* 195:785-794; Petyuk et al. (2004) *J Biol Chem* 279:37040-37048; Hartung & Kisters-Woike (1998) *J Biol Chem* 273:22884-22891; Santoro & Schultz (2002) *Proc Natl Acad Sci USA* 99:4185-4190; Koresawa et al. (2000) *J Biochem* (Tokyo) 127:367-372; and Vergunst et al. (2000) *Science* 290:979-982, each of which are herein incorporated by reference in its entirety).

In some embodiments, a chimeric recombinase is used. A chimeric recombinase is a recombinant fusion protein which is capable of catalyzing site-specific recombination between recombination sites that originate from different recombination systems. For example, if the set of recombination sites comprises a FRT site and a LoxP site, a chimeric FLP/Cre recombinase or active variant or fragment thereof can be used, or both recombinases may be separately provided. Methods for the production and use of such chimeric recombinases or active variants or fragments thereof are described, for example, in International Application Publication No. WO 99/25840; and Shaikh & Sadowski (2000) *J Mol Biol* 302:27-48, each of which are herein incorporated by reference in its entirety.

In other embodiments, a variant recombinase is used. Methods for modifying the kinetics, cofactor interaction and requirements, expression, optimal conditions, and/or recognition site specificity, and screening for activity of recombinases and variants are known, see for example Miller et al. (1980) *Cell* 20:721-9; Lange-Gustafson and Nash (1984) *J Biol Chem* 259:12724-32; Christ et al. (1998) *J Mol Biol* 288:825-36; Lorbach et al. (2000) *J Mol Biol* 296:1175-81; Vergunst et al. (2000) *Science* 290:979-82; Dorgai et al. (1995) *J Mol Biol* 252:178-88; Dorgai et al. (1998) *J Mol Biol* 277:1059-70; Yagu et al. (1995) *J Mol Biol* 252:163-7; Sclimente et al. (2001) *Nucleic Acids Res* 29:5044-51; Santoro and Schultze (2002) *Proc Natl Acad Sci USA* 99:4185-90; Buchholz and Stewart (2001) *Nat Biotechnol* 19:1047-52; Voziyanov et al. (2002) *Nucleic Acids Res* 30:1656-63; Voziyanov et al. (2003) *J Mol Biol* 326:65-76; Klippel et al. (1988) *EMBO J* 7:3983-9; Arnold et al. (1999) *EMBO J* 18:1407-14; and International Application Publication Nos. WO 03/08045, WO 99/25840, and WO 99/25841; each of which is herein incorporated by reference in its entirety. The recognition sites range from about 30 nucleotide minimal sites to a few hundred nucleotides.

By "recombination site" is intended a polynucleotide (native or synthetic/artificial) that is recognized by the recombinase enzyme of interest. As outlined above, many recombination systems are known in the art and one of skill will recognize the appropriate recombination site to be used with the recombinase of interest.

Non-limiting examples of recombination sites include FRT sites including, for example, the native FRT site (FRT1, SEQ ID NO:46), and various functional variants of FRT, including but not limited to, FRT5 (SEQ ID NO:47), FRT6 (SEQ ID NO:48), FRT7 (SEQ ID NO:49), FRT12 (SEQ ID NO: 53), and FRT87 (SEQ ID NO:50). See, for example, International Application Publication Nos. WO 03/054189, WO 02/00900, and WO 01/23545; and Schlake et al. (1994) *Biochemistry* 33:12745-12751, each of which is herein incorporated by reference. Recombination sites from the Cre/Lox site-specific recombination system can be used. Such recombination sites include, for example, native LOX sites and various functional variants of LOX.

In some embodiments, the recombination site is a functional variant of a FRT site or functional variant of a LOX site, any combination thereof, or any other combination of recombinogenic or non-recombinogenic recombination sites known. Functional variants include chimeric recombination sites, such as an FRT site fused to a LOX site (see, for example, Luo et al. (2007) *Plant Biotech J* 5:263-274, which is herein incorporated by reference in its entirety). Functional variants also include minimal sites (FRT and/or LOX alone or in combination). The minimal native FRT recombination site (SEQ ID NO: 46) has been characterized and comprises a series of domains comprising a pair of 11 base pair symmetry elements, which are the FLP binding sites; the 8 base pair core, or spacer, region; and the polypyrimidine tracts. In some embodiments, at least one modified FRT recombination site is used. Modified or variant FRT recombination sites are sites having mutations such as alterations, additions, or deletions in the sequence. The modifications include sequence modification at any position, including but not limited to, a modification in at least one of the 8 base pair spacer domain, a symmetry element, and/or a polypyrimidine tract. FRT variants include minimal sites (see, e.g., Broach et al. (1982) *Cell* 29:227-234; Senecoff et al. (1985) *Proc Natl Acad Sci USA* 82:7270-7274; Gronostajski & Sadowski (1985) *J Biol Chem* 260:12320-12327; Senecoff et al. (1988) *J Mol Biol* 201:405-421; and International Application Publication No. WO99/25821), and sequence variants (see, for example, Schlake & Bode (1994) *Biochemistry* 33:12746-12751; Seibler & Bode (1997) *Biochemistry* 36:1740-1747; Umlauf & Cox (1988) *EMBO J* 7:1845-1852; Senecoff et al. (1988) *J Mol Biol* 201:405-421; Voziyanov et al. (2002) *Nucleic Acids Res* 30:7; International Application Publication Nos. WO 07/011733, WO 99/25854, WO 99/25840, WO 99/25855, WO 99/25853 and WO 99/25821; and U.S. Pat. Nos. 7,060,499 and 7,476,539; each of which are herein incorporated by reference in its entirety).

An analysis of the recombination activity of variant LOX sites is presented in Lee et al. (1998) *Gene* 216:55-65 and in U.S. Pat. No. 6,465,254. Also, see for example, Huang et al. (1991) *Nucleic Acids Res* 19:443-448; Sadowski (1995) In *Progress in Nucleic Acid Research and Molecular Biology* Vol. 51, pp. 53-91; U.S. Pat. No. 6,465,254; Cox (1989) In *Mobile DNA*, Berg and Howe (eds) American Society of Microbiology, Washington D.C., pp. 116-670; Dixon et al. (1995) *Mol Microbiol* 18:449-458; Buchholz et al. (1996) *Nucleic Acids Res* 24:3118-3119; Kilby et al. (1993) *Trends Genet* 9:413-421; Rossant & Geagy (1995) *Nat Med* 1:592-594; Albert et al. (1995) *Plant J* 7:649-659; Bayley et al. (1992) *Plant Mol Biol* 18:353-361; Odell et al. (1990) *Mol Gen Genet* 223:369-378; Dale & Ow (1991) *Proc Natl Acad Sci USA* 88:10558-10562; Qui et al. (1994) *Proc Natl Acad*

Sci USA 91:1706-1710; Stuurman et al. (1996) *Plant Mol Biol* 32:901-913; Dale et al. (1990) *Gene* 91:79-85; and International Application Publication No. WO 01/111058; each of which is herein incorporated by reference in its entirety.

Naturally occurring recombination sites or biologically active variants thereof are of use. Methods to determine if a modified recombination site is recombinogenic are known (see, for example, International Application Publication No. WO 07/011733, which is herein incorporated by reference in its entirety). Variant recognition sites are known, see for example, Hoess et al. (1986) *Nucleic Acids Res* 14:2287-300; Albert et al. (1995) *Plant J* 7:649-59; Thomson et al. (2003) Genesis 36:162-7; Huang et al. (1991) *Nucleic Acids Res* 19:443-8; Siebler and Bode (1997) *Biochemistry* 36:1740-7; Schlake and Bode (1994) *Biochemistry* 33:12746-51; Thygarajan et al. (2001) *Mol Cell Biol* 21:3926-34; Umlauf and Cox (1988) *EMBO J* 7:1845-52; Lee and Saito (1998) *Gene* 216:55-65; International Application Publication Nos. WO 01/23545, WO 99/25851, WO 01/11058, WO 01/07572; and U.S. Pat. No. 5,888,732; each of which is herein incorporated by reference in its entirety.

The recombination sites employed in the methods and compositions can be identical or dissimilar sequences. Recombination sites with dissimilar sequences can be either recombinogenic or non-recombinogenic with respect to one another.

By "recombinogenic" is intended that the set of recombination sites (i.e., dissimilar or corresponding) are capable of recombining with one another. Alternatively, by "non-recombinogenic" is intended the set of recombination sites, in the presence of the appropriate recombinase, will not recombine with one another or recombination between the sites is minimal. Accordingly, it is recognized that any suitable set of non-recombinogenic and/or recombinogenic recombination sites may be utilized, including a FRT site or functional variant thereof, a LOX site or functional variant thereof, any combination thereof, or any other combination of non-recombinogenic and/or recombination sites known in the art.

In some embodiments, the recombination sites are asymmetric, and the orientation of any two sites relative to each other will determine the recombination reaction product. Directly repeated recombination sites are those recombination sites in a set of recombinogenic recombination sites that are arranged in the same orientation, such that recombination between these sites results in excision, rather than inversion, of the intervening DNA sequence. Inverted recombination sites are those recombination sites in a set of recombinogenic recombination sites that are arranged in the opposite orientation, so that recombination between these sites results in inversion, rather than excision, of the intervening DNA sequence.

Fragments and variants of the polynucleotides encoding double-strand break-inducing enzymes and cell proliferation factors and fragments and variants of the double-strand break-inducing enzymes and cell proliferation proteins can be used in the methods and compositions. By "fragment" is intended a portion of the polynucleotide and hence the protein encoded thereby or a portion of the polypeptide. Fragments of a polynucleotide may encode protein fragments that retain the biological activity of the native protein and hence implement a double-strand break (double-strand break-inducing enzyme) or stimulate cell growth (cell proliferation factor). Thus, fragments of a polynucleotide may range from at least about 20 nucleotides, about 50 nucleotides, about 100 nucleotides, about 500 nucleotides, about 1000 nucleotides, and up to the full-length polynucleotide encoding a double-strand break-inducing enzyme or cell proliferation factor.

A fragment of a polynucleotide that encodes a biologically active portion of a double-strand break-inducing enzyme or a cell proliferation protein will encode at least about 15, 25, 30, 50, 100, 150, 200, 250, 300, 320, 350, 375, 400, or 500 contiguous amino acids, or up to the total number of amino acids present in a full-length double-strand break-inducing enzyme or cell proliferation protein used in the methods or compositions.

A biologically active portion of a double-strand break-inducing enzyme or cell proliferation protein can be prepared by isolating a portion of one of the polynucleotides encoding the portion of the double-strand break-inducing enzyme or cell proliferation polypeptide and expressing the encoded portion of the double-strand break-inducing enzyme or cell proliferation protein, and assessing the activity of the portion of the double-strand break-inducing enzyme or cell proliferation factor. Polynucleotides that encode fragments of a double-strand break-inducing enzyme or cell proliferation polypeptide can comprise nucleotide sequence comprising at least about 15, 20, 50, 75, 100, 150, 200, 250, 300, 350, 400, 450, 500, 550, 600, 650, 700, 800, 900, 1,000, 1,100, or 1,500 nucleotides, or up to the number of nucleotides present in a full-length double-strand break-inducing enzyme or cell proliferation factor nucleotide sequence disclosed herein.

"Variant" sequences have a high degree of sequence similarity. For polynucleotides, conservative variants include those sequences that, because of the degeneracy of the genetic code, encode the amino acid sequence of one of the native recombinase polypeptides. Variants such as these can be identified with the use of well-known molecular biology techniques, such as, for example, with polymerase chain reaction (PCR) and hybridization techniques. Variant polynucleotides also include synthetically derived nucleotide sequences, such as those generated, for example, by using site-directed mutagenesis but which still encode a biologically active protein, such as a double-strand break inducing agent or a cell proliferation factor. Generally, variants of a particular polynucleotide will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by known sequence alignment programs and parameters.

Variants of a particular polynucleotide (i.e., the reference polynucleotide) can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the recombinase are known in the art. Percent sequence identity between any two polypeptides can be calculated using sequence alignment programs and parameters described. Where any given pair of polynucleotides is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

A variant protein can be derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins are biologically active, that is they continue to possess the desired biological activity of the native protein, that is, introduce a double-strand break at or near a recognition sequence (double-strand break-inducing enzyme) or stimulate cell growth (cell proliferation factor). Such variants may result from, for example, genetic polymorphism or from human manipulation. Biologically active variants of a native double-strand break-inducing protein or cell proliferation factor will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by known sequence alignment programs and parameters. A biologically active variant of a protein may differ from that protein by as few as 1-15 amino acid residues, as few as 1-10, such as 6-10, as few as 5, as few as 4, 3, 2, or even 1 amino acid residue.

The introduction of a cell proliferation factor into a cell can also enhance the rate of targeted integration of a polynucleotide of interest. In these methods, at least one cell proliferation factor is introduced into a cell and a double-strand break-inducing enzyme is introduced, along with a transfer cassette comprising the polynucleotide of interest. As used herein, a "transfer cassette" refers to a polynucleotide that can be introduced into a cell, wherein the polynucleotide comprises a polynucleotide of interest that is to be inserted into a target site of a cell. The introduction of a double-strand break can result in the integration of the polynucleotide of interest through non-homologous end joining or if the transfer cassette comprises at least one region of homology to the target site, the polynucleotide of interest can be integrated through homologous recombination.

Homology indicates at least two sequences that have structural similarity such that they are recognized as being structurally or functionally related sequences. For example, homology indicates that two polynucleotide sequences have sufficient structural similarity to act as substrates for a homologous recombination reaction. Homology can be described or identified in by any known means. In some examples, homology is described using percent sequence identity or sequence similarity, for example by using computer implemented algorithms to search or measure the sequence identity and similarity. Sequence identity or similarity may exist over the full length of a sequence, or may be less evenly distributed, for example it may be significantly higher in a conserved domain region.

The amount of homology or sequence identity shared by two sequences can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bp. The amount of homology can also be described by percent sequence identity over the full aligned length of the two polynucleotides which includes percent sequence identity of about at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus.

Homology can also be described by the predicted ability of two polynucleotides to specifically hybridize under high stringency conditions, which is described elsewhere herein (see, for example, Sambrook, et al., (1989) Molecular Cloning: A Laboratory Manual, Cold Spring Harbor Laboratory Press, NY; Current Protocols in Molecular Biology, Ausubel, et al., Eds (1994) Current Protocols, a joint venture between Greene Publishing Associates, Inc. and John Wiley & Sons, Inc; and, Tijssen, (1993) Laboratory Techniques in Biochemistry and Molecular Biology—Hybridization with Nucleic Acid Probes, Elsevier, New York).

In those embodiments wherein the transfer cassette comprises at least one region of homology to a region of the target site, there is sufficient homology between the two regions to allow for homologous recombination to occur between the transfer cassette and the target site. In some embodiments, the transfer cassette comprises a first region of homology to the target site, which can be the recognition sequence, and the polynucleotide of interest. In other embodiments, the transfer cassette comprises a first region of homology to the target site, a polynucleotide of interest, and a second region of homology to the target site. In some of these embodiments, the regions of homology are recombination sites and the double-strand break-inducing enzyme is a site-specific recombinase, such as FLP, Cre, SSVI, R, Int, lambda, phiC31, or HK022. The first and the second recombination site can be recombinogenic or non-recombinogenic with respect to one another. In other embodiments, the region(s) of homology of the transfer cassette to the target site are homologous to other regions of the target site, which can comprise genomic sequence.

In specific embodiments wherein the double-strand break-inducing enzyme that is introduced into a cell along with at least one cell proliferation factor is a site-specific recombinase, the target site of the cell comprises a first recombination site, and a transfer cassette is further introduced into the cell that comprises a second site-specific recombination site and a polynucleotide of interest, wherein the first and the second recombination sites are recombinogenic with each other in the presence of the site-specific recombinase, the polynucleotide of interest can be inserted at the target site. The first and the second recombination sites can be identical or dissimilar.

In other specific embodiments, the introduction of at least one cell proliferation factor into a cell can also enhance the rate of insertion of a polynucleotide of interest into a target site in a cell, wherein the target site comprises a first and a second recombination site that are dissimilar and non-recombinogenic with respect to one another, wherein the recombination sites flank a nucleotide sequence, through the further introduction of a site-specific recombinase, and a transfer cassette comprising a third and a fourth recombination site flanking a polynucleotide of interest, wherein the third recombination site is recombinogenic with the first recombination site, and the fourth recombination site is recombinogenic with the second recombination site in the presence of the site-specific recombinase. The nucleotide sequence between the recombination sites of the target site will be exchanged with the polynucleotide of interest between the recombination sites of the transfer cassette.

As used herein, the term "flanked by", when used in reference to the position of the recombination sites or regions of homology of the target site or the transfer cassette, refers to a position immediately adjacent to the sequence intended to be exchanged or inserted.

The recombination sites or regions of homology of the transfer cassette may be directly contiguous with the polynucleotide of interest or there may be one or more intervening sequences present between one or both ends of the polynucleotide of interest and the recombination sites or regions of homology. Intervening sequences of particular interest include linkers, adapters, selectable markers, additional polynucleotides of interest, promoters, and/or other sites that aid in vector construction or analysis. It is further recognized that the recombination sites or regions of homology can be contained within the polynucleotide of interest (i.e., such as within introns, coding sequene, or 5' and 3' untranslated regions).

A method to directly select a transformed cell or an organism (such as a plant or plant cell) is provided. The method comprises providing a cell or organism having a polynucleotide comprising a target site. The polynucleotide comprises, in the following order, a promoter and a target site. A transfer cassette is introduced into the cell or organism, where the transfer cassette comprises, in the following order, a first region of homology with the target site, a polynucleotide comprising a selectable marker not operably linked to a promoter, and a second region of homology with the target site. At least one cell proliferation factor (e.g., babyboom polypeptide) and a double-strand break-inducing enzyme are introduced into the cell or into the organism and the selectable marker is integrated into the target site. The cell or organism is then grown on the appropriate selective agent to recover the organism that has successfully undergone targeted integration of the selectable marker at the target site. In certain embodiments, the target site is stably integrated into the genome of the plant. In some of these embodiments, the genomic target site is a native genomic target site.

In specific embodiments of the method for directly selecting a transformed cell or an organism as described herein, the cell or the organism has a polynucleotide comprising, in the following order, a promoter and a target site that comprises a first and a second recombination site, wherein the first and the second recombination sites are dissimilar and non-recombinogenic with respect to one another. A transfer cassette is introduced into the cell or organism, wherein the transfer cassette comprises, in the following order, a first recombination site, a polynucleotide comprising a selectable marker not operably linked to a promoter, and a second recombination site, wherein the first and the second recombination sites are non-recombinogenic with respect to one another. A cell proliferation factor and a site-specific recombinase is introduced into the cell or organism and the selectable marker is integrated into the target site. The cell or organism is then grown to recover the organism with the targeted integration.

A selectable marker comprises a DNA segment that allows one to identify or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like. Examples of selectable markers include, but are not limited to, DNA segments that comprise restriction enzyme sites; DNA segments that encode products which provide resistance against otherwise toxic compounds (e.g., antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glyphosate, sulfonylureas, glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillen and Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable markers is not meant to be limiting. Any selectable marker can be used in the methods and compositions.

The activity of various promoters at a characterized location in the genome of a cell or an organism can be determined. Thus, the desired activity and/or expression level of a nucleotide sequence of interest can be achieved, as well as, the characterization of promoters for expression in the cell or the organism of interest.

In one embodiment, the method for assessing promoter activity in a cell or an organism comprises providing a cell or an organism comprising (e.g., in its genome) a target site having a first and a second recombination site, wherein the first and the second recombination sites are dissimilar and non-recombinogenic with respect to one another. A transfer cassette is introduced into the cell or the organism, where the transfer cassette comprises a promoter operably linked to a polynucleotide comprising a selectable marker and the transfer cassette is flanked by the first and the second recombination sites. At least one cell proliferation factor and a site-specific recombinase is provided, wherein the recombinase recognizes and implements recombination at the first and second recombination sites. Promoter activity is assessed by monitoring expression of the selectable marker. In this manner, different promoters can be integrated at the same position in the genome and their activity compared.

In some embodiments of the method for assessing promoter activity, the transfer cassette comprises in the following order: the first recombination site, a promoter operably linked to a third recombination site operably linked to a polynucleotide comprising a selectable marker, and the second recombination site, where the first, the second, and the third recombination sites are dissimilar and non-recombinogenic with respect to one another. This transfer cassette can be generically represented as RSa-P1::RSc::S1-RSb. Following the introduction of the transfer cassette at the target site, the activity of the promoter (P1) can be analyzed using methods known in the art. Once the activity of the promoter is characterized, additional transfer cassettes comprising a polynucleotide of interest flanked by the second and the third recombination site can be introduced into the organism. Upon recombination, the expression of the polynucleotide of interest will be regulated by the characterized promoter. Accordingly, organisms, such as plant lines, having promoters that achieve the desired expression levels in the desired tissues can be engineered so that nucleotide sequences of interest can be readily inserted downstream of the promoter and operably linked to the promoter and thereby expressed in a predictable manner.

It is further recognized that multiple promoters can be employed to regulate transcription at a single target site. In this method, the target site comprising the first and the second recombination sites is flanked by two convergent promoters. "Convergent promoters" refers to promoters that are oriented to face one another on either terminus of the target site. The same promoter, or different promoters may be used at the target site. Each of the convergent promoters is operably linked to either the first or the second recombination site. For example, the target site flanked by the convergent promoters can comprise P1→:R1-R2:←P2, where P is a promoter, the arrow indicates the direction of transcription, R is a recombination site, and the colon indicates the components are operably linked.

The transfer cassette employed with the target site having the convergent promoters can comprise, in the following order, the first recombination site, a first polynucleotide of interest orientated in the 5' to 3' direction, a second polynucleotide of interest orientated in the 3' to 5' direction, and a second recombination site. The insertion of the transfer cassette at the target site results in the first polynucleotide of interest operably linked to the first convergent promoter, and the second polynucleotide of interest operably linked to the second convergent promoter. The expression of the first and/or the second polynucleotide of interest may be increased or decreased in the cell or organism. The expression of the first and/or the second polynucleotide of interest may also be independently regulated depending upon which promoters are used. It is recognized that target sites can be flanked by other elements that influence transcription. For example, insulator elements can flank the target site to minimize position effects. See, for example, U.S. Publication No. 2005/144665, herein incorporated by reference.

In further embodiments, methods are provided to identify a cis transcriptional regulatory region in an organism. By "transcriptional regulatory region" is intended any cis acting element that modulates the level of an RNA. Such elements include, but are not limited to, a promoter, an element of a promoter, an enhancer, an intron, or a terminator region that is capable of modulating the level of RNA in a cell. Thus, the methods find use in generating enhancer or promoter traps. In one embodiment, the reporter or marker gene of the target site is expressed only when it inserts close to (enhancer trap) or within (promoter trap) another gene. The expression pattern of the reporter gene will depend on the enhancer elements of the gene near or in which the reporter gene inserts. In this embodiment, the target site introduced into the cell or the organism can comprise a marker gene operably linked to a recombination site. In specific embodiments, the marker gene is flanked by dissimilar and non-recombinogenic recombination sites. The marker gene is either not operably linked to a promoter (promoter trap) or the marker gene is operably linked to a promoter that lacks enhancer elements (enhancer trap). Following insertion of the target site into the genome of the cell or the organism, the expression pattern of the marker gene is determined for each transformant. When a transformant with a marker gene expression pattern of interest is found, the enhancer/promoter trap sequences can be used as a probe to clone the gene that has that expression pattern, or alternatively to identify the promoter or enhancer regulating the expression. In addition, once a target site is integrated and under transcriptional control of a transcriptional regulatory element, methods can further be employed to introduce a transfer cassette having a polynucleotide of interest into that target in the cell or the organism. A recombination event between the target site and the transfer cassette will allow the nucleotide sequence of interest to come under the transcriptional control of the promoter and/or enhancer element. See, for example, Geisler et al. (2002) *Plant Physiol* 130:1747-1753; Topping et al. (1997) *Plant Cell* 10:1713-245; Friedrich et al. (1991) *Genes Dev* 5:1513-23; Dunn et al. (2003) *Appl Environ Microbiol* 1197-1205; and von Melchner et al. (1992) *Genes Dev* 6:919-27; all of which are herein incorporated by reference. In these methods, a cell proliferation factor (e.g., a babyboom polypeptide) is further introduced into the cell or organism to enhance recombination.

Further, methods are provided for locating preferred integration sites within the genome of a plant cell. Such methods comprise introducing into the plant cell a transfer cassette comprising in the following order: a first recombination site, a promoter active in the plant cell operably linked to a polynucleotide, and a second recombination site; wherein the first and second recombination sites are non-recombinogenic with respect to one another. A cell proliferation factor and site-specific recombinase that recognizes and implements recombination at the first and second recombination sites are introduced into the plant cell. The level of expression of the polynucleotide is determined using any method known in the art and the plant cell that is expressing the polynucleotide is selected.

Methods are also provided for the integration of multiple transfer cassettes at a target site in a cell. In some embodiments, the target site is constructed to have multiple sets of dissimilar and non-recombinogenic recombination sites. Thus, multiple genes or polynucleotides can be stacked or ordered. In specific embodiments, this method allows for the stacking of sequences of interest at precise locations in the genome of a cell or an organism. Likewise, once a target site has been established within a cell or an organism (for example, the target site can be stably integrated into the genome of the cell or organism), additional recombination sites may be introduced by incorporating such sites within the transfer cassette. Thus, once a target site has been established, it is possible to subsequently add sites or alter sites through recombination. Such methods are described in detail in International Application Publication No. WO 99/25821, herein incorporated by reference.

In one embodiment, the method comprises introducing into a cell having a target site comprising a first and a second recombination site a first transfer cassette comprising at least the first, a third, and the second recombination sites, wherein the first and the third recombination sites of the first transfer cassette flank a first polynucleotide of interest, and wherein the first, the second, and the third recombination sites are non-recombinogenic with respect to one another. Along with the first transfer cassette, a first site-specific recombinase is introduced into the cell, wherein the first site-specific recombinase recognizes and implements recombination at the first and the second recombination sites. A second transfer cassette is then introduced into the cell, comprising at least the second and the third recombination sites, wherein the second and the third recombination sites of the second transfer cassette flank a second polynucleotide of interest. In some embodiments, a single recombinase can recognize and implement recombination at the first and second recombination sites and at the second and third recombination sites. In other embodiments, along with the second transfer cassette, a second site-specific recombinase is introduced into the cell that recognizes and implements recombination at the second and the third recombination sites. The method further comprises introducing at least one cell proliferation factor to the cell before or during the introduction of the first recombinase, the second recombinase, or both the first and the second recombinase. In a related, alternative method, the target site of the cell has a target site comprising the first, second, and third recombination sites, the first transfer cassette comprises a first polynucleotide of interest flanked by the first and the second recombination sites, and the second transfer cassette comprises a second polynucleotide of interest flanked by at least the second and third recombination sites. A first and a second site-specific recombinase and a cell proliferation factor is introduced similar to the first method for the integration of multiple transfer cassettes described immediately above.

In other embodiments, methods are provided to minimize or eliminate expression resulting from random integration of DNA sequences into the genome of a cell or an organism, such as a plant. This method comprises providing a cell or an organism having stably incorporated into its genome a polynucleotide comprising the following components in the following order: a promoter active in the cell or the organism operably linked to an ATG translational start sequence operably linked to a target site comprising a first and a second functional recombination site, wherein the first and the second recombination sites are dissimilar and non-recombinogenic with respect to one another. A transfer cassette comprising a polynucleotide of interest flanked by the first and the second recombination site is introduced into the cell or the organism. The translational start sequence of the nucleotide sequence of interest in the transfer cassette has been replaced with the first recombination site. A cell proliferation factor (e.g., a babyboom polypeptide) and a recombinase is provided that recognizes and implements recombination at the recombination sites. Recombination with the target site results in the polynucleotide of interest being operably linked to the ATG translational start site of the target site contained in the polynucleotide. By operably linked is intended a fusion between adjacent elements and when used to refer to the linkage between a translational start a promoter and/or a recombination site implies that the sequences are put together to generate an inframe fusion that results in a properly expressed and functional gene product.

Methods for excising or inverting a polynucleotide of interest are provided. Such methods can comprise introducing into a cell having a target site comprising: a polynucleotide of interest flanked by a first and a second recombination site, wherein the first and the second sites are recombinogenic with respect to one another; at least one cell proliferation factor; and a double-strand break-inducing enzyme comprising a site-specific recombinase that recognizes and implements recombination at the first and the second recombination sites, thereby excising or inverting the polynucleotide of interest. Depending on the orientation of the recombination sites, the polynucleotide of interest will be excised or inverted when the appropriate recombinase is provided. For example, directly repeated recombination sites will allow for excision of the polynucleotide of interest and inverted repeats will allow for an inversion of the polynucleotide of interest.

The cell proliferation factor, double-strand break-inducing enzyme or a polynucleotide encoding the same, and in some embodiments, a transfer cassette, is introduced into a cell or an organism according to the presently disclosed methods. "Introducing" is intended to mean presenting to the organism, such as a plant, or the cell the polynucleotide or polypeptide in such a manner that the sequence gains access to the interior of a cell of the organism or to the cell itself. The methods and compositions do not depend on a particular method for introducing a sequence into an organism, only that the polynucleotide or polypeptides gains access to the interior of at least one cell of the organism. Methods for introducing polynucleotides or polypeptides into plants are known in the art including, but not limited to, stable transformation methods, transient transformation methods, virus-mediated methods, and sexual breeding.

"Stable transformation" means that the nucleotide construct introduced into a host cell or an organism integrates into the genome of the host and is capable of being inherited by the progeny thereof. "Transient transformation" is intended to mean that a polynucleotide is introduced and does not integrate into the genome of the host or that a polypeptide is introduced into a host.

Protocols for introducing polypeptides or polynucleotide sequences into plants may vary depending on the type of plant or plant cell being targeted. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. No. 5,886,244; and, U.S. Pat. No. 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice);

Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the sequences can be provided to a plant using a variety of transient transformation methods. Such transient transformation methods include, but are not limited to, the introduction of the double-strand break-inducing enzyme or cell proliferation protein or variants and fragments thereof directly into the plant or the introduction of a double-strand break-inducing enzyme or cell proliferation factor transcript into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107: 775-784, all of which are herein incorporated by reference. Alternatively, the polynucleotide can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

In other embodiments, the polynucleotide may be introduced into plants by contacting plants with a virus or viral nucleic acids. Generally, such methods involve incorporating a nucleotide construct within a viral DNA or RNA molecule. It is recognized that the double-strand break-inducing enzyme or cell proliferation factor may be initially synthesized as part of a viral polyprotein, which later may be processed by proteolysis in vivo or in vitro to produce the desired recombinant protein. Further, it is recognized that promoters also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

The polynucleotides can be provided in a DNA construct. In addition, in specific embodiments, recognition sequences and/or the polynucleotide encoding an appropriate double-strand break-inducing enzyme is also contained in the DNA construct. The construct can include 5' and 3' regulatory sequences operably linked to the polynucleotide of interest. Generally, operably linked means that the nucleic acid sequences being linked are contiguous and, where necessary to join two protein coding regions, contiguous and in the same reading frame. However, it is recognized that intervening sequences can be present between operably linked elements and not disrupt the functional linkage. For example, an operable linkage between a promoter and a polynucleotide of interest comprises a linkage that allows for the promoter sequence to initiate and mediate transcription of the polynucleotide of interest. When used to refer to the linkage between a translational start and a recombination site, the term operably linked implies that the sequences are put together to generate an inframe fusion that results in a properly expressed and functional gene product. Similarly, when used to refer to the linkage between a promoter and a recombination site, the linkage will allow for the promoter to transcribe a downstream nucleotide sequence. The cassette may additionally contain at least one additional gene to be introduced into the organism. Alternatively, the additional gene(s) can be provided on multiple DNA constructs.

Such a DNA construct may be provided with a plurality of restriction sites, recognition sequences, or recombination sites for insertion of the polynucleotide to be under the transcriptional regulation of the regulatory regions. The expression cassette may additionally contain selectable marker genes.

In some embodiments, the DNA construct can include in the 5' to 3' direction of transcription, a transcriptional and translational initiation region, a polynucleotide of interest, and a transcriptional and translational termination region functional in the organism of interest.

The transcriptional initiation region, the promoter, may be native, analogous, foreign, or heterologous to the host organism, and/or to the polynucleotide of interest. Additionally, the promoter may be the natural sequence or alternatively a synthetic sequence. Such constructs may change expression levels of the polynucleotide of interest in the organism.

The termination region may be native or heterologous with the transcriptional initiation region, it may be native or heterologous with the operably linked polynucleotide of interest, or it may be native or heterologous with the host organism. Convenient termination regions are available from the Ti-plasmid of A. tumefaciens, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. The polynucleotide of interest can also be native or analogous or foreign or heterologous to the host organism.

Sequence modifications in addition to codon optimization are known to enhance gene expression in a cellular host. These include elimination of spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The DNA construct may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods or sequences known to enhance translation can also be utilized, for example, introns, and the like.

In preparing the DNA construct, the various DNA fragments may be manipulated, so as to place the sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the DNA construct will comprise a selectable marker gene for the selection of transformed cells. Selectable marker genes are utilized for the selection of transformed cells or tissues and have been discussed in detail elsewhere herein.

A number of promoters can be used. As used herein "promoter" includes reference to a region of DNA involved in recognition and binding of RNA polymerase and other proteins to initiate transcription. A "plant promoter" is a promoter capable of initiating transcription in a plant cell. Any promoter can be used, and is typically selected based on the desired outcome (for a review of plant promoters, see Potenza et al. (2004) *In Vitro Cell Dev Biol* 40:1-22).

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), the *Agrobacterium* nopaline synthase (NOS) promoter (Bevan et al. (1983) *Nucl. Acids Res.* 11:369-385), and the like. Other constitutive promoters are described in, for example, U.S. Pat. Nos. 5,608,149; 5,608,144; 5,604,121; 5,569,597; 5,466,785; 5,399,680; 5,268,463; 5,608,142; and 6,177,611.

In some embodiments, an inducible promoter can be used, such as from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference. Promoters that are expressed locally at or near the site of pathogen infection include, for example, Marineau et al. (1987) *Plant Mol. Biol.* 9:335-342; Matton et al. (1989) *Mol Plant-Microbe Interact* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Additional promoters include the inducible promoter for the maize PRms gene, whose expression is induced by the pathogen Fusarium moniliforme (see, for example, Cordero et al. (1992) *Physiol. Mol. Plant Path.* 41:189-200). Wound-inducible promoters include potato proteinase inhibitor (pin II) gene (Ryan (1990) *Ann. Rev. Phytopath.* 28:425-449; Duan et al. (1996) *Nat Biotechnol* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Lett* 323:73-76); MPI gene (Corderok et al. (1994) *Plant J.* 6:141-150); and the like, herein incorporated by reference. Another inducible promoter is the maize In2-2 promoter (deVeylder et al. (2007) *Plant Cell Physiol* 38:568-577, herein incorporated by reference).

Chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners (De Veylder et al. (1997) *Plant Cell Physiol.* 38:568-77), the maize GST promoter (GST-II-27, WO 93/01294), which is activated by hydrophobic electrophilic compounds that are used as pre-emergent herbicides, the PR-1 promoter (Cao et al. (2006) *Plant Cell Reports* 6:554-60), which is activated by BTH or benxo(1,2,3)thiaidazole-7-carbothioic acid s-methyl ester, the tobacco PR-1a promoter (Ono et al. (2004) *Biosci. Biotechnol. Biochem.* 68:803-7), which is activated by salicylic acid, the copper inducible ACE1 promoter (Mett et al. (1993) *PNAS* 90:4567-4571), the ethanol-inducible promoter AlcA (Caddick et al. (1988) *Nature Biotechnol* 16:177-80), an estradiol-inducible promoter (Bruce et al. (2000) *Plant Cell* 12:65-79), the XVE estradiol-inducible promoter (Zao et al. (2000) *Plant J* 24:265-273), the VGE methoxyfenozide inducible promoter (Padidam et al. (2003) *Transgenic Res* 12:101-109), and the TGV dexamethasone-inducible promoter (Bohner et al. (1999) *Plant J* 19:87-95). Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237; Gatz et al. (1992) *Plant J* 2:397-404; and U.S. Pat. Nos. 5,814,618 and 5,789,156), herein incorporated by reference.

Tissue-preferred promoters can be utilized to target enhanced expression of a sequence of interest within a particular plant tissue. Tissue-preferred promoters include Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et (1996) *Plant Physiol.* 112(2):513-524; Lam (1994) *Results Probl. Cell Differ.* 20:181-196; and Guevara-Garcia et al. (1993) *Plant J.* 4(3):495-505.

Leaf-preferred promoters are known in the art. See, for example, Yamamoto et al. (1997) *Plant J.* 12:255-265; Kwon et al. (1994) *Plant Physiol.* 105:357-67; Yamamoto et al. (1994) *Plant Cell Physiol.* 35:773-778; Gotor et al. (1993) *Plant J.* 3:509-18; Orozco et al. (1993) *Plant Mol. Biol.* 23:1129-1138; and Matsuoka et al. (1993) *Proc. Natl. Acad. Sci. USA* 90:9586-9590. In addition, promoter of cab and rubisco can also be used. See, for example, Simpson et al. (1958) *EMBO J* 4:2723-2729 and Timko et al. (1988) *Nature* 318:57-58.

Root-preferred promoters are known and can be selected from the many available. See, for example, Hire et al. (1992) *Plant Mol. Biol.* 20:207-218 (soybean root-specific glutamine synthase gene); Keller and Baumgartner (1991) *Plant Cell* 3:1051-1061 (root-specific control element in the GRP 1.8 gene of French bean); Sanger et al. (1990) *Plant Mol. Biol.* 14:433-443 (root-specific promoter of the mannopine synthase (MAS) gene of *Agrobacterium tumefaciens*); and Miao et al. (1991) *Plant Cell* 3:11-22 (full-length cDNA clone encoding cytosolic glutamine synthase (GS), which is expressed in roots and root nodules of soybean). See also Bogusz et al. (1990) *Plant Cell* 2:633-641, where two root-specific promoters isolated from hemoglobin genes from the nitrogen-fixing nonlegume *Parasponia andersonii* and the related non-nitrogen-fixing nonlegume *Trema tomentosa* are described. Leach and Aoyagi (1991) describe their analysis of the promoters of the highly expressed rolC and rolD root-inducing genes of *Agrobacterium rhizogenes* (see *Plant Sci* (Limerick) 79:69-76). Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue (see *EMBO J.* 8:343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29:759-772); and rolB promoter (Capana et al. (1994) *Plant Mol. Biol.* 25:681-691. See also U.S. Pat. Nos. 5,837,876; 5,750,386; 5,633,363; 5,459,252; 5,401,836; 5,110,732; and 5,023,179. Another root-preferred promoter includes the promoter of the phaseolin gene (Mural et al. (1983) *Science* 23:476-482 and Sengopta-Gopalen et al. (1988) *Proc. Natl. Acad. Sci. USA* 82:3320-3324.

Seed-preferred promoters include both those promoters active during seed development as well as promoters active during seed germination. See Thompson et al. (1989) *Bio-Essays* 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase); (see WO 00/11177 and U.S. Pat. No. 6,225,529; herein incorporated by reference). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, nuc1, etc. See also WO 00/12733, where seed-preferred promoters from end1 and end2 genes are disclosed; herein incorporated by reference. In particular embodiments, the maize oleosin promoter set forth in SEQ ID NO: 55 or a variant or fragment thereof is used.

Where low-level expression is desired, weak promoters will be used. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels. Such weak constitutive promoters include, for example, the core promoter of the Rsyn7 promoter (WO 99/43838 and U.S. Pat. No. 6,072,050), the core 35S CaMV promoter, and the like.

Other promoters of interest include the Rab16 promoter (Mundy et al. (1990) *PNAS* 87: 1406-1410), the *Brassica* LEA3-1 promoter (U.S. Application Publication No. US 2008/0244793), the HVA1s, Dhn8s, and Dhn4s from barley and the wsi18j, rab16Bj from rice (Xiao and Xue (2001) *Plant Cell Rep* 20:667-73), and D113 from cotton (Luo et al. (2008) *Plant Cell Rep* 27:707-717).

In some embodiments, the polynucleotide encoding a cell proliferation factor (e.g., babyboom polypeptide) is operably linked to a maize ubiquitin promoter or a maize oleosin promoter (e.g., SEQ ID NO: 65 or a variant or fragment thereof).

In some embodiments, the methods further comprise identifying cells comprising the modified target locus and recovering plants comprising the modified target locus. In some examples, recovering a plant having the modifed target locus occurs at a higher frequency as compared to a control method without a cell proliferation factor.

Any method can be used to identify a plant cell or plant comprising a modified target locus. In some examples, plant cell or plants having a modified target locus are identified using one or more of the following techniques, including but not limited to PCR methods, hybridization methods such as Southern or Northern blots, restriction digest analyses, or DNA sequencing.

The cells having the introduced sequence may be grown into plants in accordance with conventional methods, see, for example, McCormick et al. (1986) *Plant Cell Rep* 5:81-84. These plants may then be grown, and either pollinated with the same transformed strain or with a different strain, and the resulting progeny expressing the desired phenotypic characteristic and/or comprising the introduced polynucleotide or polypeptide identified. Two or more generations may be grown to ensure that the polynucleotide is stably maintained and inherited, and seeds harvested. In this manner, transformed seed, also referred to as transgenic seed, having a polynucleotide, for example, comprising a modified target site, stably incorporated into their genome are provided.

In some embodiments, the activity and/or level of the cell proliferation factor (e.g., a babyboom polypeptide, Wuschel) is reduced prior to regenerating a plant from the plant cell having the modified target site. In some of these embodiments, the polynucleotide encoding the cell proliferation factor, and in particular embodiments, the polynucleotide encoding the double-strand break-inducing enzyme, as well, are excised prior to the regeneration of a plant. In some of these embodiments, the promoter and other regulatory elements that are operably linked to each of the heterologous polynucleotides are excised along with the heterologous polynucleotides. In certain embodiments, the polynucleotide encoding the cell proliferation factor (and in particular embodiments, the double-strand break-inducing enzyme) are flanked by recombination sites and an appropriate site-specific recombinase is introduced into the plant cell to excise the polynucleotide encoding the cell proliferation factor, and in some embodiments, the double-strand break-inducing enzyme, prior to regeneration of the plant cell into a plant. In some of those embodiments wherein both a babyboom polypeptide and a Wuschel polypeptide are provided to the plant cell, both the polynucleotide encoding the babyboom polypeptide and the polynucleotide encoding the Wuschel polypeptide are excised. The two polynucleotides can be present on the same or on different expression cassettes and, therefore, can be excised in one or two different excision reactions. In some of these embodiments, the polynucleotide encoding the site-specific recombinase for excising the babyboom and Wuschel polynucleotides can be located on the same expression cassette as the babyboom and Wuschel polynucleotides and all three polynucleotides can be excised through the activity of the site-specific recombinase.

In order to control the excision of the cell proliferation factor(s) (and in some embodiments, the double-strand break-inducing enzyme), the expression of the site-specific recombinase that is responsible for the excision can be controlled by a late embryo promoter or an inducible promoter. In some embodiments, the late embryo promoter is GZ (Uead et al. (1994) *Mol Cell Biol* 14:4350-4359), gamma-kafarin promoter (Mishra et al. (2008) *Mol Biol Rep* 35:81-88), Glb1 promoter (Liu et al. (1998) *Plant Cell Reports* 17:650-655), ZM-LEG1 (U.S. Pat. No. 7,211,712), EEP1 (U.S. Patent Application No. US 2007/0169226), B22E (Klemsdal et al. (1991) *Mol Gen Genet* 228:9-16), or EAP1 (U.S. Pat. No. 7,321,031). In some embodiments, the inducible promoter that regulates the expression of the site-specific recombinase is a heat-shock, light-induced promoter, a drought-inducible promoter, including but not limited to Hva1 (Straub et al. (1994) *Plant Mol Biol* 26:617-630), Dhn, and WSI18 (Xiao & Xue (2001) *Plant Cell Rep* 20:667-673). In other embodiments, expression of the site-specific recombinase is regulated by the maize rab17 promoter (nucleotides 1-558 or 51-558 of GenBank Acc. No. X1554 or active fragments or variants thereof; Vilardell et al. (1990) *Plant Mol Biol* 14:423-432; Vilardell et al. (1991) *Plant Mol Biol* 17:985-993; and U.S. Pat. Nos. 7,253,000 and 7,491,813; each of which is herein incorporated in its entirety), or a variant rab17 promoter (for example, the variant rab17 promoter set forth in SEQ ID NO: 54; see U.S. Provisional Application No. 61/291,257 and U.S. Utility Application entitled "Methods and compositions for the introduction and regulated expression of genes in plants," filed concurrently herewith and herein incorporated by reference in its entirety). The wild type or modified rab17 promoter can be induced through exposure of the plant cell, callus, or plant to abscisic acid, sucrose, or dessication. In some embodiments, the site-specific recombinase that excises the polynucleotide encoding the cell proliferation factor is FLP.

Also provided are compositions comprising plant cells or plants comprising a heterologous polynucleotide encoding a cell proliferation factor, wherein the plant cell or plant comprises a target site comprising a recognition sequence; a double-strand break-inducing enzyme that recognizes the recognition sequence; and a transfer cassette comprising a polynucleotide of interest and at least one region of homology with the target site. In some embodiments, the region of homology is a recognition sequence. In these embodiments, the double-strand break-inducing enzyme is a site-specific recombinase capable of recognizing and implementing recombination at the recombination sites within the target site and the transfer cassette. In certain embodiments, the target site is stably integrated into the plant genome.

In some embodiments, the cell proliferation factor is a member of the AP2 family of polypeptides. In some of these embodiments, the cell proliferation factor is a babyboom polypeptide, and in particular embodiments, the babyboom polypeptide comprises two AP2 domains and at least one of: SEQ ID NO: 9 or a sequence having at least about 70%, 75%, 80%, 85%, 90%, 95%, 96%, 97%, 98%, 99%, or greater sequence identity to SEQ ID NO: 9; or SEQ ID NO: 12 or a sequence having at least about 70%, 75%, 80%, 85%, 90%, 95%, 96%, 97%, 98%, 99%, or greater sequence identity to SEQ ID NO: 12. In particular embodiments, the cell proliferation factor has the sequence set forth in SEQ ID NO: 2, 17, 19, 21, 23, 25, 27.29, 31, 33, 35, 37. 39, 105, or 41 or has at least about 70%, 75%, 80%, 85%, 90%, 95%, 96%, 97%, 98%, 99%, or greater sequence identity to SEQ ID NO: 2, 17, 19, 21, 23, 25, 27, 29, 31, 33, 35, 37, 39, 105, or 41. In some of these embodiments, both a babyboom polypeptide and a Wuschel polypeptide are provided to the plant cell.

In certain embodiments, the cell proliferation factor (e.g., babyboom polypeptide, Wuschel polypeptide) and/or the double-strand break-inducing enzyme is provided to the cell through the introduction of a polynucleotide encoding the cell proliferation factor and/or the double-strand break-inducing enzyme. In some of these embodiments, the polynucleotide encoding the cell proliferation factor has the sequence set forth in SEQ ID NO: 1, 16, 18, 20, 22, 24, 26, 28, 30, 32, 34, 36, 38, 40, 59, 101, 102, 103, 104, or 60 or has at least about 70%, 75%, 80%, 85%, 90%, 95%, 96%, 97%, 98%, 99%, or greater sequence identity to SEQ ID NO: 1, 16, 18, 20, 22, 24, 26, 28, 30, 32, 34, 36, 38, 40, 59, 101, 102, 103, 104, or 60. In some of these embodiments, the polynucleotide encoding the cell proliferation factor is operably linked to an oleosin or ubiquitin promoter. In some of those embodiments wherein a Wuschel polynucleotide is also introduced into the plant cell, expression of Wuschel is regulated by the NOS or In2-2 promoter.

The double-strand break-inducing enzyme can be an endonuclease, a zinc finger nuclease, a transposase, a topoisomerase, or a site-specific recombinase. In some embodiments, the double-strand break-inducing enzyme is an endonuclease or a modified endonuclease, such as a meganuclease. In other embodiments, the double-strand break-inducing enzyme is a site-specific recombinase such as FLP or Cre and the recognition sequence comprises a recombination site (e.g., FRT1, FRT87, lox). In some of these embodiments, the site-specific recombinase has the sequence set forth in SEQ ID NO: 43 (FLP) or 45 (Cre) or has at least about 70%, 75%, 80%, 85%, 90%, 95%, 96%, 97%, 98%, 99%, or greater sequence identity to SEQ ID NO: 43 or 45. In some of those embodiments wherein the site-specific recombinase is provided to the cell through the introduction of a polynucleotide that encodes the site-specific recombinase, the polynucleotide has the sequence set forth in SEQ ID NO: 42 (FLPm) or 44 (moCre) or has at least about 70%, 75%, 80%, 85%, 90%, 95%, 96%, 97%, 98%, 99%, or greater sequence identity to SEQ ID NO: 42 or 44.

In particular embodiments, the plant cell or plant comprises a heterologous polynucleotide of interest encoding a cell proliferation factor, wherein the plant cell or plant comprises a target site comprising a first recombination site, a nucleotide sequence, and a second recombination site; a transfer cassette comprising a third recombination site, a polynucleotide of interest, and a fourth recombination site, wherein the first and the third recombination sites are recombinogenic with respect to one another, and the second and fourth recombination sites are recombinogenic with respect to one another; and a site-specific recombinase capable of recognizing and implementing recombination at the first and third and second and fourth recombination sites.

The plant cell or plant can comprise more than one cell proliferation factor. For example, along with a babyboom polypeptide, the plant or plant cell can comprise a Wuschel polypeptide.

In particular embodiments, the heterologous polynucleotide encoding the cell proliferation factor comprises flanking recombination sites to facilitate its excision. In these embodiments, the plant further comprises a site-specific recombinase that recognizes the recombination sites flanking the heterologous polynucleotide encoding the cell proliferation factor. In some embodiments, this site-specific recombinase comprises FLPm or an active variant or fragment thereof. In some of those embodiments wherein the plant cell or plant further comprise a Wuschel polypeptide, the polynucleotide encoding the Wuschel polypeptide and the heterologous polynucleotide encoding the cell proliferation factor are flanked by recombination sites to facilitate the excision of both polynucleotides.

Any plant species can be transformed, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats (*Avena*), barley (*Hordeum*), *Arabidopsis,* switchgrass, vegetables, ornamentals, grasses, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean and sugarcane plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, *sorghum*, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

As used herein, the term plant also includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

In some of those embodiments wherein the organism to which the cell proliferation factor, double-strand break-inducing enzyme, and in certain embodiments, a transfer cassette, is a plant, these elements can be introduced into a plant cell. In particular embodiments, the plant cell is a cell of a recalcitrant tissue or plant, such as an elite maize inbred. As used herein, a "recalcitrant tissue" or "recalcitrant plant" is a tissue or a plant that has a low rate of transformation using traditional methods of transformation, such as those disclosed elsewhere herein. In some embodiments, the recalcitrant tissue or plant is unable to be transformed in the absence of the cell proliferation factor. In other embodiments, the recalcitrant tissue or plant has a rate of successful transformation of less than about 20%, less than about 15%, less than about 10%, less than about 5%, less than about 1%, less than about 0.1%, less than about 0.01%, less than about 0.001%, or less. Non-limiting examples of recalcitrant tissues include mature seed or mature seed tissue, a leaf or leaf tissue, a stem or stem tissue.

In some embodiments, the cell proliferation factor, double-strand break-inducing enzyme, and in certain embodiments, a transfer cassette, are introduced into a mature seed, mature seed tissue, or leaf tissue using the methods described in U.S. Provisional Application entitled "Methods and compositions for the introduction and regulated expression of genes in plants," filed concurrently herewith.

Some embodiments of the methods provide for the targeted insertion of a polynucleotide of interest. If the polynucleotide of interest is introduced into an organism, it may impart various changes in the organism, particularly plants, including, but not limited to, modification of the fatty acid composition in the plant, altering the amino acid content of the plant, altering pathogen resistance, and the like. These results can be achieved by providing expression of heterologous products, increased expression of endogenous products in plants, or suppressed expression of endogenous produces in plants.

General categories of polynucleotides of interest include, for example, those genes involved in information, such as zinc fingers, those involved in communication, such as kinases, those involved in biosynthetic pathways, and those involved in housekeeping, such as heat shock proteins. More specific categories of transgenes, for example, include sequences encoding important traits for agronomics, insect resistance, disease resistance, herbicide resistance, sterility, grain characteristics, oil, starch, carbohydrate, phytate, protein, nutrient, metabolism, digestability, kernel size, sucrose loading, and commercial products.

Traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Protein modifications to alter amino acid levels are described in U.S. Pat. Nos. 5,703,049, 5,885,801, 5,885,802, and 5,990,389 and WO 98/20122, herein incorporated by reference.

Insect resistance genes may encode resistance to pests such as rootworm, cutworm, European Corn Borer, and the like. Such genes include, for example, *Bacillus thuringiensis* toxic protein genes (U.S. Pat. Nos. 5,366,892; 5,747,450; 5,737,514; 5,723,756; 5,593,881; and Geiser et al. (1986) *Gene* 48:109); lectins (Van Damme et al. (1994) *Plant Mol. Biol.* 24:825); and the like.

Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the S4 and/or Hra mutations in ALS), genes coding for resistance to herbicides that act to inhibit action of glutamine synthase, such as phosphinothricin or basta (e.g., the bar gene), genes providing resistance to glyphosate, such as GAT (glyphosate N-acetyltransferase; U.S. Pat. No. 6,395,485), EPSPS (enolpyruvylshikimate-3-phosphate synthase; U.S. Pat. Nos. 6,867,293, 5,188,642, 5,627,061), or GOX (glyphosate oxidoreductase; U.S. Pat. No. 5,463,175), or other such genes known in the art. The nptII gene encodes resistance to the antibiotics kanamycin and geneticin.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

Commercial traits can also be encoded on a gene or genes that could, for example increase starch for ethanol production, or provide expression of proteins.

Reduction of the activity of specific genes (also known as gene silencing, or gene suppression) is desirable for several aspects of genetic engineering in plants. Many techniques for gene silencing are well known to one of skill in the art, including but not limited to antisense technology (see, e.g., Sheehy et al. (1988) *Proc. Natl. Acad. Sci. USA* 85:8805-8809; and U.S. Pat. Nos. 5,107,065; 5,453,566; and 5,759,829); cosuppression (e.g., Taylor (1997) *Plant Cell* 9:1245; Jorgensen (1990) *Trends Biotech.* 8(12):340-344; Flavell (1994) *Proc. Natl. Acad. Sci. USA* 91:3490-3496; Finnegan et al. (1994) *Bio/Technology* 12: 883-888; and Neuhuber et al. (1994) *Mol. Gen. Genet.* 244:230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; Javier (2003) *Nature* 425:257-263; and, Montgomery et al. (1998) *Proc. Natl. Acad. Sci. USA* 95:15502-15507), virus-induced gene silencing (Burton, et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; WO 02/00904; and WO 98/53083); ribozymes (Steinecke et al. (1992) *EMBO J.* 11:1525; U.S. Pat. No. 4,987,071; and, Perriman et al. (1993) *Antisense Res. Dev.* 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Nall. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the babyboom polynucleotide. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire babyboom polynucleotide, or one or more portions thereof, may be used as a probe capable of specifically hybridizing to corresponding babyboom polynucleotide and messenger RNAs. To achieve specific hybridization under a variety of conditions, such probes include sequences that are unique among babyboom polynucleotide sequences and are optimally at least about 10 nucleotides in length, and most optimally at least about 20 nucleotides in length. Such probes may be used to amplify corresponding babyboom polynucleotide from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions.

By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

It is to be noted that the term "a" or "an" entity refers to one or more of that entity; for example, "a polypeptide" is understood to represent one or more polypeptides. As such, the terms "a" (or "an"), "one or more," and "at least one" can be used interchangeably herein.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments±50%, in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods or employ the disclosed compositions.

Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the presently disclosed subject matter be limited to the specific values recited when defining a range.

The following examples are offered by way of illustration and not by way of limitation.

EXPERIMENTAL

Example 1. Vector Construction

Maize recombination targets (RTL) were created using *Agrobacterium* transformation of immature maize embryos (Ishida et al. (1996) *Nat Biotechnol* 14:745-750). The LBA4404 *Agrobacterium* strain was used, which carried a specialized binary T-DNA plasmid system (Komari et al. (1996) *Plant J* 10:165-174) developed for high efficiency maize transformation. The binary *Agrobacterium* plasmid PHP21199 (similar to pSB124, Komari et al. (1996)), which is a T-DNA containing derivative of plasmid PHP10523 (similar to pSB1, Komari et al. (1996)) was constructed as follows. Visual and selectable marker genes were built into the T-DNA region of the intermediate construct, PHP21198 (similar to pSB12, Komari et al. (1996)), and then introduced into *Agrobacterium* to create the co-integrated binary plasmid, PHP21199. The selectable marker expression cassette in the PHP21199 plasmid consisted of the maize ubiquitin1 (UBI) promoter (Christensen & Quail (1996) Transgenic Res 5:213-218), 5' untranslated region (5'utr), and intron (UBI PRO), a sequence encoding glyphosate n-acetyltransferase (GAT4602) (Siehl et al. (2007) *J Biol Chem* 282:11446-11455), and a 3' region from the protease inhibitor 2 (PINII) gene of potato. The visual marker expression cassette in the PHP21199 plasmid consisted of the yellow fluorescent protein (YFP) gene (zs-yellow1 n1) (Clontech, Palo Alto, Calif.) expressed by the same promoter and terminator elements as the gat gene (UBI PRO, PINII). The wild-type FRT was inserted between the maize ubiquitin promoter and the YFP gene. The selectable and visual marker expression cassettes, as well as the properly positioned FRT sites, were assembled with the multi-site Gateway® (Invitrogen, Carlsbad, Calif.) system. The plasmid backbone of PHP21198 served as the destination plasmid (pDEST) with the destination site between the RB and LB in the T-DNA region and three Gateway® entry vectors (pDONR) were provided; one for each marker gene and one for the downstream FRT87 recombinase site. The FRT87 recombinase site is located 3' of the final PINII 3' region. The PHP21199 plasmid therefore comprised RB-UBI PRO::FRT1::YFP+UBI PRO::GAT4602::FRT87-LB.

Site-specific integration (SSI) donor plasmids PHP22297 and PHP27064 were built using the multi-site Gateway® (Invitrogen) system using methods similar to those used to construct the PHP21198 vector, except that an *Agrobacterium* vector was not used since the donor plasmids were introduced into plant cells by particle bombardment. Instead, the destination site was provided by the commercially available pDEST R4-R3 vector (Invitrogen). The entry vector for the first position of PHP22297 consisted of a promoterless bar gene with the PINII terminator. In place of the promoter is a copy of the 35S cauliflower mosaic virus (CaMV 35S) termination region. This feature was included for the purpose of reducing potential bar gene expression due to random promoter trapping following donor integration into the plant genome outside the target site. The FRT1 site was placed between the CaMV 35S terminator and the bar gene to match the FRT1 in the target constructs and integrations. The second entry vector contained a cyan fluorescent protein (CFP) visual marker (am-cyan 1) (Clontech) operably linked to maize UBI PRO and PINII 3' regions as described above. The FRT87 site was placed in the third and final entry vector in order to position the site downstream of all the genes in the donor construct and to match the FRT87 position in the target construct. PHP22297 comprises FRT1::BAR+UBI PRO::CFP::FRT87. Donor construct PHP27064 was also constructed using pDEST R4-R3 (Invitrogen). The first entry vector was nearly identical to that for PHP22297 except that the bar gene was replaced by GAT4621, a GAT gene variant with similar but improved function to GAT4602. This entry vector did not include the 35S CaMV terminator region upstream of the promoterless gat gene. The second entry vector for PHP27064 had YFP in place of CFP, along with the same expression elements as the second entry vector used in the construction of PHP22297. The third entry vector included only FRT87 and was the same as that used for PHP22297. PHP27064 comprises FRT1::GAT4621+UBI PRO::YFP::FRT87.

Example 2. Recombinant Target Lines (RTL)

*Zea mays* immature embryos were transformed by a modified *Agrobacterium*-mediated transformation procedure (Djukanovic et al. (2006) *Plant Biotechnol J* 4:345-357) to introduce the T-DNA from PHP21199. Briefly, 10-12 days after pollination (DAP) embryos were dissected from sterile kernels and placed into liquid medium. After embryo collection, the medium was replaced with 1 ml of *Agrobacterium* suspension at a concentration of 0.35-0.45 OD at 550 nm, wherein the *Agrobacterium* comprised the T-DNA. After a five minute incubation at room temperature, the embryo suspension was poured onto a media plate. Embryos were incubated in the dark for 3 days at 20° C., followed by a 4 day incubation in the dark at 28° C. and a subsequent transfer onto new media plates containing 0.1778 mg/L glyphosate and 100 mg/L carbenicillin. Embryos were subcultured every three weeks until transgenic events were identified. Regeneration was induced by transferring small sectors of tissue onto maturation media containing 0.1 μM ABA, 0.5 ml/L zeatin, 0.1778 mg/L glyphosate, and 100 mg/L carbenicillin. The plates were incubated in the dark for two weeks at 28° C. Somatic embryos were transferred onto media containing 2.15 g/L MS salts (Gibco 11117: Gibco, Grand Island, N.Y.), 2.5 ml/L MS Vitamins Stock Solution, 50 mg/L myo-inositol, 15.0 g/L sucrose, 0.1778 mg/L glyphosate, and 3.0 g/L Gelrite, pH 5.6 and incubated under artificial light at 28° C. One week later, plantlets were moved into glass tubes containing the same medium and grown until they were sampled and/or transplanted to soil. Target lines were screened by qPCR to assess the copy number of the transgenes and only single copy integration events were used as targets.

Example 3. Transformation and Regeneration of Recombinase-mediated Cassette Exchange (RMCE) Events Two plasmids were typically co-bombarded with SSI donor plasmids to facilitate recombination in PHWWE: PHP5096 and PHP21875. PHP5096 included a maize codon-optimized flp recombinase gene (SEQ ID NO: 42) under the control of maize UBI PRO and a pinII 3' sequence. The second co-bombarded plasmid, PHP21875, contained a maize odp2 gene (also referred to herein as maize BBM; see WO 2005/075655, which is herein incorporated by reference in its entirety) controlled by the maize UBI PRO and pinII terminator. Three plasmids were typically co-bombarded with SSI donor plasmids to facilitate recombination in PHI581. The FLP plasmid was PHP5096 as above, but the second plasmid with BBM is either PHP21875 or PHP31729 with BBM expression regulated by the maize oleosin promoter (OLE). The third plasmid introduced into PHI581 is PHP21139, which has an auxin-inducible promoter IN2-2 controlling the expression of the maize wuschel gene (Zm-WUS2). Experiments were performed with or without the BBM expression cassette to assess its impact on the recovery of RMCE events.

i) Delivery of Donor Vector

The donor plasmid was delivered via biolistic-mediated transformation into hemizygous immature embryos containing the recombinant target site created by the integration of PHP21199. 9 toll DAP immature embryos (1-1.5 mm in size) dissected from sterilized kernels were plated with their axis down onto media comprising 4.0 g/L N6 Basal salts (Sigma C-1416), 1.0 ml/L Eriksson's Vitamin Mix (Sigma E-1511), 1.0 mg/L thiamine HCl, 1.5 mg/L 2,4-D, 0.690 g/L L-proline, 30 g/L sucrose, 0.85 mg/L silver nitrate, and 3.0 g/L Gelrite, pH 5.8 and incubated in the dark at 28° C. for 3 to 5 days before the introduction of DNA. Two to four hours prior to bombardment, the embryos were plasmolyzed by placing them on the above media containing 120 gm/L of sucrose.

Plasmid DNA was associated with gold particles in preparation for biolistic-mediated transformation by mixing 100 μg of the donor plasmid, 10 μg of PHP5096 (encoding for mFLP), and in some bombardments, 10 μg of the helper plasmid PHP21875 (UBI:ODP2) (the volume of the DNA solution was adjusted to 40 μl), 50 μl of 1-μm gold particles at 0.01 mg/μl, and 5 μl TFX-50 (Promega E181112). The solution was allowed to gently mix for 10 minutes. The particles and attached DNA were spun down for 1 minute at 10,000 rpm and then the supernatant was removed and replaced with 120 μl of 100% ethanol. The particles were then re-suspended by gentle sonication. 10 μl of the particle solution was spotted on each carrier disc and the ethanol was allowed to evaporate. The macro carrier was placed 2.5 cm from a 450 psi rupture disc with the immature embryos placed on a shelf 7.5 cm below the launch assembly.

ii) Selection of RMCE Events

After bombardment, the embryos were removed from the high sucrose media and placed back on the same medium containing 30 g/L sucrose. The embryos were incubated in the dark at 28° C. for 7 days, at which time the embryos were moved to selection plates of the above media containing either 3.0 mg/L bialaphos (selection of first round RMCE events) or 0.1778 mg/L glypho sate (selection of second round RMCE events). Embryos were subcultured to fresh medium after 3 weeks and transgenic events were identified 4 weeks later. Transgenic events growing under selection were then observed for their fluorescent phenotype. Those that exhibited a fluorescent phenotype indicative of RMCE were regenerated under the appropriate selective agent (bialophos or glyphosate) using the above protocol. Plantlets were sampled and/or transplanted to soil.

iii) Regeneration

Plant regeneration medium (288J) comprised 4.3 g/L MS salts (GIBCO 11117-074), 5.0 ml/L MS vitamins stock solution (0.100 g/L nicotinic acid, 0.02 g/L thiamine HCl, 0.10 g/L pyridoxine HCl, and 0.40 g/L *glycine* brought to volume with polished D-I H2O) (Murashige & Skoog (1962) *Physiol Plant* 15:473), 100 mg/L myo-inositol, 0.5 mg/L zeatin, 60 g/L sucrose and 1.0 ml/L of 0.1 mM abscisic acid (brought to volume with polished D-I H2O after adjusting to pH 5.6), 3.0 g/L Gelrite™ (added after bringing to volume with D-I H2O), and 1.0 mg/L indoleacetic acid and 3.0 mg/L bialaphos (added after sterilizing the medium and cooling to 60° C.). Hormone-free medium (272V) comprised 4.3 g/L MS salts (GIBCO 11117-074), 5.0 ml/L MS vitamins stock solution (0.100 g/L nicotinic acid, 0.02 g/L thiamine HCl, 0.10 g/L pyridoxine HCl, and 0.40 g/L *glycine* (brought to volume with polished D-I H2O), 0.1 g/L myo-inositol, 40.0 g/L sucrose (brought to volume with polished D-I H2O after adjusting pH to 5.6); and 6 g/L bacto-agar (added after bringing to volume with polished D-I H2O), and was sterilized and cooled to 60° C.

iv) Polymerase Chain Reaction

DNA was extracted via a modified alkaline lysis method using 1 punch (200 ng) of fresh leaf tissue (Truett et al. (2000) *Biotechniques* 29:52-54). For quantitative PCR (qPCR), each gene was quantitated using specific forward and reverse primers along with a corresponding FAM based MGB (Applied Biosystems, Foster City, Calif.) fluorogenic multiplexed probe. Each assay was primer titrated and normalized to an amplification signal from an endogenous gene which utilized a VIC®-based sequence specific probe and primer set. The amplification reactions for the bar and CFP genes were run simultaneously with the normalizing gene in a single tube reaction. Upon completion of the qPCR, all raw data were used to calculate the dCT values. Copy number determination was computed with the $\Delta\Delta CT$ method as described in the ABI User Bulletin #2 (Applied Biosystems, Foster City, Calif.). Endpoint positive and negative qPCR calls were made for flp, ubi:odp2, ubi:frt1:bar and the FrtX junctions according to the dCT estimates. A PCR reaction requiring 5 additional cycles than the normalizing gene was considered negative for the transcript.

v) Sequencing

QPCR samples identified as positive for recombinant junctions (UBI-FRT1-BAR, donor-FRT87-target) were further characterized by agarose gel electrophoresis (FIG. 5) and sequencing. Each qPCR reaction was run as an individual lane on a 2% agarose gel and visualized by ethidium bromide staining under UV light. DNA bands of the expected size were independently cut from each lane of the gel and extracted from the agarose using the QiaQUICK gel extraction kit (Qiagen, Valencia, Calif.). Samples of these extractions were submitted directly for DNA sequencing. Replicate DNA samples were submitted for sequencing with both forward and reverse sequencing primers.

vi) Southern Blots

Leaf tissue (2-10 grams fresh weight) was freeze-dried and ground to a fine powder. Ground tissue (350 mg) was re-suspended in 9 ml CTAB extraction buffer with β-mercaptoethanol (10 μl/ml). This solution was incubated at 65° C. for 1 hour. Every 20 minutes, tubes were inverted several times to mix the material and solution. Tubes were removed from the incubator and allowed to cool 10 minutes prior to adding 5 ml chloroform/octanol (24:1). Tubes were mixed by gently inverting for 5 minutes, and then centrifuged at 2500-3000 rpm (1100×G) for 30 minutes. The aqueous top layer was transferred to a fresh tube containing 11 ml precipitation buffer, and inverted several times gently. The tubes were allowed to stand at 25° C. (room temperature) for 30 minutes to 2 hours, were centrifuged at 2000 rpm for 20 minutes, and the supernatant was discarded. The tubes were inverted to dry the pellet. The dried pellet was completely dissolved in 2 ml of 100 mM Tris (pH 7.5), 10 mM EDTA (pH 7.5), 0.7 M NaCl, and precipitated in 5 ml of 95-100% ethanol. DNA was pipetted into a tube containing 1 ml of 76% ethanol, 0.2 M sodium acetate for 20 minutes, transferred to a fresh tube containing 1ml 76% EtOH, 10 mM ammonium acetate for 1 minute, and then transferred again into a third tube and re-suspended.

Example 4. Transient Expression of ZmBBM and Recovery of RMCE Events in Maize

Recombinant Target Loci (RTL) were created by *Agrobacterium*-mediated transformation of immature maize embryos. The target sequence was flanked on the 5' side by the wild-type FLP recognition target site (FRT1) paired on the 3' side with a heterospecific FRT87. The integration copy number was determined by real-time quantitative PCR (qPCR) and transgenic events containing only a single RTL with a single copy of each gene were used. The RTL contained a yellow fluorescent protein gene (YFP) driven by the maize ubiquitin promoter. The wild-type FRT was inserted between the maize ubiquitin promoter and the YFP gene to act as a promoter trap for activation of a promoterless marker gene in the donor vector following FLP-mediated recombination at the FRT site. The target vectors also contained the selectable marker gene glyphosate acetyltransferase (GAT) driven by the maize ubiquitin promoter.

Immature embryos containing the RTL were re-transformed by particle bombardment, wherein the donor vector was co-delivered with the vector PHP5096 (UBI PRO:: FLPm::pinII) in all experiments along with the helper plasmid PHP21875 (UBI PRO::ZmBBM::pinII) in the majority of experiments, both at 1/10 of the concentration of the donor vector. In this instance, transient expression of FLP and BBM was achieved through a reduction in the titer of both the FLP and BBM-containing plasmids, while effectively eliminating random integration and subsequent stable expression of both cassettes. Other means of promoting transient expression can also be used, such as delivery of FLP and/or BBM RNA or protein, in addition to the standard amount of donor plasmid as the substrate for RMCE.

In the first round of RMCE, the donor sequence, flanked by FRT1 and FRT87 sites, contained a promoterless bar gene and the gene encoding the cyan fluorescent protein (CFP) controlled by the maize ubiquitin promoter. RMCE resulted in the exchange of the YFP and GAT genes located at the RTL with bar and CFP from the donor plasmid. To demonstrate the ability to reuse a target site with the FLP/FRT recombination system, a second round of RMCE was performed. Two RTLs were chosen that contained the FRT1-FRT87 pair. The product of the first round of RMCE at the RTL became the target for a new round of RMCE. The next round of RMCE was initiated by delivering the PHP27064 donor vector by particle bombardment. The donor vector contained the wild type FRT1, a promoterless GAT gene for selection and Ubi:YFP flanked by the heterospecific FRT87. RMCE resulted in the exchange of the bar and CFP genes located at the RTL with GAT and YFP from the donor plasmid. The FLP protein used to mediate the recombination was again transiently expressed by co-delivery of the vector PHP5096.

In the first round of RMCE, replacement of the target sequence at the RTL by the donor sequence led to expression of the otherwise promoterless bar gene. Putative RMCE events were initially selected by placing bombarded embryos on bialaphos-containing media (Table 1, column 2). Growth of callus on bialaphos-containing media was indicative of site-specific integration, but some random integrations of the donor vector also resulted in expression of the promoterless bar gene. In fact, random integration of the donor plasmid and growth on bialaphos-containing media was more frequent than RMCE. On average, under our experimental conditions, 9 bialaphos-resistant calli were routinely recovered for every 1 RMCE event identified. Nevertheless, use of the promoter trap and selection on bialaphos-containing media enriched the population of selected calli for RMCE events.

Calli growing on bialaphos-containing media were further characterized by phenotypic loss and gain of expression of fluorescence marker genes. In the first round of RMCE, the excision of the YFP gene resulted in calli which were negative for the YFP phenotype, while integration (targeted or random) of CFP contained in the donor vector, resulted in expression of CFP. In contrast, random integration of the donor vector did not result in replacement and calli were positive for YFP.

In the second round of RMCE, activation of a promoterless GAT gene (in the donor cassette) was used to chemically select for RMCE prior to monitoring of the fluorescent phenotype. In this case, putative RMCE events were YFP positive due to the integration of the donor cassette and CFP negative due to the exchange and excision of the FRT flanked sequence at the RTL. Callus sectors showing the expected fluorescence pattern were transferred to plant regeneration media.

Molecular confirmation of RMCE was performed on DNA extracted from regenerated plantlets. Putative RMCE events were characterized with a series of six PCR reactions. PCR primers unique to the target and donor sequences were used in combination to amplify DNA fragments bridging the recombined FRT junctions. PCR amplification was observed only when recombination between FRT sites at the RTL and donor occurred. Routinely, real-time quantitative PCR was used for this analysis. To verify that the PCR product was generated across the recombinant junction, a sample of the qPCR products were run out on a gel to demonstrate size and sequenced to demonstrate the presence of target sequence, the FRT site, and donor sequence. The predicted fragment sizes of the recombinant products were confirmed by Southern blot hybridization. Putative RMCE events were analyzed by real-time quantitative PCR for copy number of genes in the donor cassette. Excision of the target sequence was verified by qPCR for the fluorescent marker gene initially at the RTL. QPCR was also used to determine if the FLPm or ODP2 genes had integrated.

As can be seen in Table 1, RMCE events were identified through a sieving process, first by activation of a promoterless selectable marker, then by phenotyping of fluorescence and finally by molecular analysis of regenerated plants. Samples found to have both recombinant FRT junctions and excision of the target sequence were considered to be the result of RMCE.

As another means of confirming recombination, genomic DNA was extracted from several of the SSI events and sequenced across the FRT junctions to demonstrate the presence of both target and donor sequence and conservation of the FRT site itself. In one of the recombinant events, sequencing of the FRT87 site revealed a mutation in the 8 bp core region of the FRT site. The number of copies of integrated donor genes was determined by qPCR. Excision of the target sequence was verified by qPCR for the fluorescent marker gene initially at the RTL. qPCR was also used to determine if the FLPm gene had integrated. Random integrants growing under selection and not expressing the target fluorescent marker were identified and eliminated based on the lack of PCR products for the FRT junctions (Table 1, column 3). Precise RMCE was identified by the pattern of the PCR results (Table 1, columns 4 and 5). Only those events containing both the 5' and 3' FRT junctions, a single copy of the donor cassette and the absence of the target sequence and FLPm were considered precise RMCE events (Table 2). An RMCE event was considered imprecise if it contained more then a single copy of either of the donor genes even though both FRT junctions were present. Of the events found to have recombined at both FRT sites, about 10% also contained a random integration locus which segregated independently in the next generation. Various other types of imprecise RMCE and site-specific integrations were also identified by molecular characterization. In all, forty precise RMCE events were identified in the first round of RMCE.

precise RMCE events based on molecular characterization, while about 70% of the regenerated events were eliminated. In ~60% of the discarded events, the FRT junctions were not found. These events may be the result of random integration of the donor plasmid. The remaining 40% of the discarded events appeared to have undergone site-specific integration at the target locus, but resulted in integration patterns reflecting either recombination at only the FRT1 site or an imprecise RMCE (Table 2). In a few events, FLPm was found to be integrated, but these events generally had other abnormalities.

In the second round of RMCE, activation of a promoter-less GAT gene in the donor sequence was used to select for RMCE. In this case, about 62.5% of the regenerated events

TABLE 1

Identification of RMCE events in re-transformed embryos.

| Target embryos bombarded | Bialaphos resistant calli | Regenerable, bialaphos resistant, CFP+/YFP− | Random integration (No recombinant FRT junction) | Site-specific integration (Recombinant FRT1 junction only) | RMCE (Both recombinant and FRT junctions) |
|---|---|---|---|---|---|
| 14,945 | 560 3.75%* | 129 0.86% | 56 0.37% | 21 0.14% | 52 0.35% |

*Percent of bombarded embryos

Although events were identified in which FRT sites in the donor cassette recombined with those at the RTL, not all resulted in clean RMCE events (Table 2). Of the 52 events that had recombination of both FRT sites and loss of the target sequence (RMCE), 12 were found to have additional integrations of the donor cassette or integration of FLP or ZmBBM. Recombination was observed to occur at only the FRT1 site resulting in the separation of YFP from the ubiqutin promoter with and without the excision of the entire target sequence. Random integration of the donor cassette, as observed previously, would result in growth under selection with loss of YFP expression due to excision of the target sequence by illegitimate recombination between heterospecific FRT sites or silencing of YFP.

selected by phenotype were precise RMCE events based on molecular characterization. 96% of the putative RMCE events selected based on phenotype that reached the plant stage were found to have recombined at least at FRT1. The frequency of single recombination events at FRT1 and imprecise RMCE was 45% in the first round of RMCE and 38% in the second round.

The PCR reactions crossing the FRT junctions that were used to identify RMCE events were verified by both sequencing the PCR products and by Southern blot hybridization. The PCR products derived from several events were sequenced to demonstrate the contribution of sequence from the target and donor flanking the FRT site. RMCE was also

TABLE 2

Genotyping of putative RMCE plantlets by real time quantitative PCR.

| Integration | FRT1 junction | FRT87 junction | bar (est. copy) | CFP (est. copy) | YFP | FLPm | # events |
|---|---|---|---|---|---|---|---|
| Desired recombination product (Clean RMCE) | + | + | 1 | 1 | − | − | 40 |
| Other patterns of integration observed | | | | | | | |
| RMCE - with additional donor cassette and/or integrated FLP or ZmBBM plasmid | + | + | ≥1 | ≥1 | − | +/− | 12 |
| FRT1 recombination only - target sequence excised | + | − | ≥1 | ≥1 | − | +/− | 16 |
| FRT1 recombination only - target sequence not excised | + | − | ≥1 | ≥1 | + | +/− | 5 |
| Random integration - target sequence excised | − | − | ≥1 | ≥1 | − | +/− | 12 |
| Random integration - target sequence not excised | − | − | ≥1 | ≥1 | + | +/− | 31 |
| Unknown - Complex integration | +/− | +/− | ≥1 | ≥1 | +/− | +/− | 13 |

About 30% of the regenerated events selected by phenotype (bialaphos resistant, CFP positive, YFP negative) were verified by Southern blot hybridization of genomic DNA extracted from 30 putative RMCE events.

In the above experiments, an equal number of non-ZmBBM and ZmBBM treatments were not analyzed, but embryos from many ears were evaluated from both treatments. Overall, inclusion of ZmBBM resulted in a general 2-3 fold improvement in RMCE recovery in maize as compared to experiments in which the ZmBBM expression cassette was not used.

Example 5. Controlled Expression of ZmBBM

Any method can be used to control the timing and or location of expression of a cell proliferation factor, for example, ZmBBM. Molecular cloning and vector construction methods are well known and any such methods can be used to generate constructs with various elements or systems to regulate the timing or location of expression.

A. Transient Expression of ZmBBM

A particle gun was used to deliver the donor plasmid PHP22297 and PHP5096 plus or minus a UBI PRO::ZmBBM::pinII containing plasmid (PHP21875). During the TFX-mediated precipitation, 100 ng of PHP22297 and 10 ng of PHP5096 and PHP21875 (in the ZmBBM-containing treatment) were mixed. These plasmids, attached to gold particles as described in Example 3, were shot into immature embryos containing a single integrated copy of the T-DNA from PHP21199 (the target locus for RMCE). For this comparison (plus or minus ZmBBM), equal numbers of embryos from each ear, for a total of 176 ears, were used for side-by-side testing. For the control treatment (minus ZmBBM), 4551 bombarded embryos were taken through the selection protocol, and 13 RMCE events were recovered for an overall frequency of 0.29%. When ZmBBM was included in the bombardment, 4719 embryos produced 29 RMCE events for an overall frequency of 0.61%. This represented a consistent 2-fold increase in RCME recovery when the ZmBBM gene was included.

B. Tissue-Preferred Expression of ZmBBM

The ZmBBM gene was placed under the control of a maize oleosin promoter (SEQ ID NO: 55), which is a seed-preferred promoter expressed only in the scutella of developing embryos. The resulting expression plasmid containing OLE PRO::ZmBBM::pinII (PHP31729) was co-delivered along with the donor vector PHP22297, into immature embryos containing a single copy of the recombination target locus. Following selection on bialaphos and screening for loss of YFP and gain of CFP, RMCE events have been recovered. Expression of ZmBBM in callus cells increases the frequency of RMCE.

C. Excision of ZmBBM

An excisable ZmBBM plasmid comprising two expression cassettes (loxP-Ubi::ZmBBM::pinII+Rab17::Cre-loxP) is created. These two expression cassettes are co-delivered, along with the donor vector PHP22297, into immature embryos containing a single copy of the Recombination Target Locus. Expression of ZmBBM in callus cells increases the frequency of RMCE. In these experiments, the promoter controlling the expression of Cre is inactive during callus growth and chemical selection of RMCE events. Upon mild desiccation of the callus, for example, by placing the callus on high osmoticum such as 18% sucrose or onto dry filter papers for 1-3 days, expression of Cre recombinase is stimulated and both the BBM and Cre expression cassettes, being flanked by loxP recombinase target sites, are excised. Regeneration of fertile RMCE events is performed as described elsewhere herein.

D. Inducible Expression of ZmBBM for Recovery of RMCE Events in Maize

The ZmBBM gene can be placed under the control of an inducible expression system, such as that described in U.S. Application Publication No. 2008/0201806 A1, which is herein incorporated by reference in its entirety. Expression cassettes comprising a Triple-Op 35S promoter (Gatz et al. (1992) Plant J 2:397-404) and a pinII 3' sequence operably linked to the ZmBBM gene and a UBI PRO-driven maize-codon modified Tet repressor are constructed. These expression cassettes are co-delivered, along with the donor vector PHP22297, into immature embryos containing a single copy of the Recombination Target Locus. The addition of 1 mg/L tetracycline to the culture medium resulting in BBM expression stimulates cell division and results in an increased recovery of RMCE events in maize.

E. Co-expression of BBM and Wuschel

Developmental and inducible promoters were combined to control the expression of ZmBBM and ZmWUS2, respectively, in order to accomplish site specific integration (SSI) in maize inbred PH581. The experiments involved a different SSI target plasmid, PHP17797, although the basic function was identical to PHP21199 as described above. PHP17797 has the maize ubiquitin promoter driving FLP recombinase as the first gene that included the wild type FRT (FRT1) recombinase site. The second gene was CAMV35S PRO:BAR: pinII to provide bialaphos resistance in tissue culture. After the BAR gene, the FRT5 recombinase site was used instead of the FRT87 in PHP21199. Target immature embryos (PH581, 13 DAP) were bombarded using the particle gun for the co-delivery of donor constructs and developmental gene constructs. The ultimate goal was to recover normal fertile plants and then to segregate BBM and WUS2 from the transformation construct in the progeny. SSI donor vector, PHP33552, was bombarded with and without developmental gene constructs to compare the effect of including BBM and WUS2. PHP33552 included a promoter-less gene encoding the yellow fluorescent protein (YFP, ZS-Yellowl N1, Clontech, Palo Alto, Calif., USA). The genes in PHP33552 were flanked by FRT1 and FRT5 to facilitate recombinase-mediated cassette exchange (RMCE) in the presence of FLP recombinase. Correct site-specific integration activates YFP from a captured promoter in the target locus.

Using a particle gun for transformation, both SSI and standard transformation was attempted in SSI target lines without added BBM and/or WUS2 constructs. PH581 was capable of developing a low frequency of callus using standard transformation methods (0.3%) and a few events were regenerated. The regenerated plants were recovered to the greenhouse and set seed. When SSI methods were used, the numbers of transformed calli with the correct phenotype were lower than with standard transformation methods and no plants could be regenerated. PH581 plant regeneration from tissue culture occurs at a relatively low frequency compared to model maize lines for transformation, such as the public line Hi-II.

Constitutively expressed BBM and WUS2 were co-bombarded with donor vectors for SSI. In these experiments, the maize Ubi promoter controlled the expression of ZmBBM and the *Agrobacterium* nopaline synthase (NOS) promoter regulated ZmWUS2 expression. These treatments provided a higher frequency of callus with the SSI phenotype (10-30%). SSI was confirmed by real-time quantitative PCR (QPCR) analysis in callus that demonstrated continued growth in culture and exhibited the expected phenotype. Importantly, plants were able to be regenerated from the SSI positive callus. However, the plants demonstrated abnormal morphology, suspected to be due at least in part to the uncontrolled expression of BBM and WUS2. Roots showed the thickened phenotype attributable to BBM expression. As in past experiments with these developmental genes, regeneration frequency is negatively impacted by BBM and WUS2 expressed in this manner.

In another set of particle gun transformation experiments using immature PH581 embryos from SSI target lines, standard transformation and SSI were tested with the controlled expression of ZmBBM and ZmWUS2. The maize embryo-preferred promoter, oleosin (Ole Pro) was employed to regulate ZmBBM expression. This promoter is active in developing embryos during callus growth and kernel development. The maize IN2-2 PRO (deVeylder et al. (2007) *Plant Cell Physiol* 38:568-77) was used to express ZmWUS2. The IN2-2 PRO promoter has a low level constitutive activity, which can be further activated in the presence of auxin that can be provided in the tissue culture medium. This expression strategy allowed for the recovery of a number of callus events having the SSI phenotype. It also provided for the recovery of young T0 plants that were characterized with multiple qPCR assays to demonstrate SSI and to confirm the presence or absence of target genes, extra copies of genes from PHP33552, and integrated copies of the BBM and WUS2 plasmids. Young plants with the correct qPCR profile and YFP phenotype were advanced to the greenhouse where they developed into late-stage plants. In most cases, these plants were fertile. In some instances, plants exhibited delayed development or a stunted phenotype. During the flowering stage, the segregation of the cell proliferation transgenes was promoted by crossing tissue cultured plants with conventional PH581. Ears were harvested at about 13-15 DAP and immature embryos were plated on basic culture medium for embryo rescue. YFP positive kernels segregated 1:1 with null kernels as predicted when accounting for single, unlinked transgenic loci, one of which carries OLE PRO-ZmBBM and the second a recombined target locus. QPCR analysis of progeny plants confirmed that the YFP positive plants contained a recombinant SSI target locus. The kernels that were negative for YFP expression were the SSI null segregants.

By controlling the expression of ZmBBM and ZmWUS2 with developmental and inducible promoters, these developmental genes have been used to facilitate RMCE at numerous different target loci.

Example 6: Gene Targeting Using Homing Endonucleases

Molecular cloning and vector construction methods are well known and any such methods can be used to generate constructs to provide elements such as double-strand break-inducing enzymes, artificial target sites, targeting vectors, cell proliferation factors, or any other useful element. Vector construction is performed using standard molecular biology techniques. Any method of transformation can be used, and vector construction and/or insert preparation can be modified accordingly.

DNA double-strand break-inducing enzymes, such as an endonuclease, create double-strand breaks in the genome. Subsequent repair of the break can produce a mutation, DNA insertion, and homologous recombination products. In this manner, a double-strand break-inducing enzyme can be used for targeted modification of the genome to introduce a mutation, targeted insertion, or homologous recombination at a target locus. It is expected that the provision of one or more cell proliferation factors will enhance the targeted modification rates with double-strand break methods. Increased modification rates are expected at both artificial and endogenous target locus sites. Similarly, cell proliferation factors may also increase the rate of recovery of events in which a modification has occurred at the target locus. For example, one or more cell proliferation factors can be provided by introducing expression cassettes (e.g., Ubi Pro::Ubi intron::ZmBBM::pinII+nos Pro::ZmWUS2::pinII), resulting in enhanced gene targeting rates.

A. Artificial Target Site

An artificial target site (ATS) construct (ATS2) was constructed using a MDTP tetra-peptide linker to create a translational fusion between the selectable markers MoPAT (U.S. Pat. No. 6,096,947) and YFP (PHP21829). An in-frame insertion of the I-SceI recognition sequence in front of the MDTP-linker sequence of PHP21829 resulted in PHP22710. Upon delivery of the PHP21829 or PHP22710 construct into Hi-II maize immature embryos for functional evaluation, spots of yellow fluorescence were observed, confirming expression of the marker. Three stop codons were added to the PHP22710 fusion construct in front of the YFP coding sequence to create the artificial target site 2 (ATS2, PHP22709) construct. PHP22709 comprises the following operably linked components: Ubi pro::FLPm-rice actin pro::moPAT/I-Scel site/YFP::pin II-gAt. As expected, no visible yellow fluorescence was observed in Hi-II embryos bombarded with PHP22709.

ATS2 was designed with a minimal amount of sequences derived from maize to facilitate the interpretation of results. moPAT and YFP provide 5' and 3' homologous regions (~1kb and ~4.1 kb, respectively) for targeting in homologous recombination experiments. Homology of the 3' region was increased through the addition of 1578 bp of non-coding genomic sequence from *Arabidopsis* (gAt) following the pinII terminator. A FLP expression cassette was included in some experiments in order to test certain targeting vectors and other experimental design strategies.

B. Targeting Vectors

Several versions of targeting vectors were generated for delivery into maize embryos. Targeting vectors were designed that comprise a maize codon-modified I-SceI (moI-SceI) meganuclease expression vector derived from PHP22603 (U.S. Patent Application Publication No. 2009/0133152, which is herein incorporated by reference) and a positive selectable GAT4621 marker gene, flanked by two DNA segments homologous to the ATS2 target site. The homologous segments are 3019 bp (HR1) and 924 bp (HR2), respectively, in length. The GAT4621 gene is asymmetrically positioned within the homologous region to facilitate the identification of homologous recombinants by PCR. The basic vector was named TV-ATS2 (Targeting Vector for Artificial Target Site #2) and comprises the following operably linked components:
Ubi pro::ubi 5' UTR::moI-SceI::pinII-HR1-ubi pro::ubi 5' UTR::GAT4621::pinII-HR2

A second targeting vector, named TV-ATS2Eraser, has two FRT sites directly flanking the TV-ATS2 elements, and was designed to provide a method to eliminate random integration events from selected material and to enrich the recovery of targeted events. TV-ATS2Eraser comprises the following operably linked components: FRT-ubi pro::ubi 5'UTR::moI-SceI::pinII-HR1-ubi pro::ubi 5' UTR::GAT4621::pinII-HR2-FRT A third targeting vector (TV-ATS2Turbo) carries a T-DNA replication cassette. Replicating T-DNAs are expected to persist longer in the transformed cells, providing more substrate and time for DNA recombination, including homologous recombination. Replication activity is provided by a modified version of the wheat dwarf virus replication-associated protein (Rep) lacking the intron sequences between the two open reading frames RepA and RepB, along with its cognate origin of replication (LIR). The replicase function of Rep is provided by the longer transcript encompassing two open reading frames (RepAB). Testing confirmed replication activity in BMS cells upon the delivery of the TV-ATS2Turbo cassette. It is possible that strong expression of RepAB may negatively impact the growth of transformed tissues. If this is the case, the Rep cassette may also act as a form of negative selection against random integrations, thus helping to identify potential target modification events. TV-ATS2Turbo comprises the following operably linked components: Ubi pro::ubi 5' UTR::moI-SceI::pinII-WDV SIR::RepAB::WDV LIR-HR1-ubi pro::ubi 5' UTR::GAT4621::pinII-HR2.

A fourth targeting vector, TV-ATS2TurboEraser, combines all the elements of the TV-ATS2Turbo vector, including the moI-SceI expression cassette, the GAT4621 marker for selection of all transformation events, the RepAB gene for amplification of T-DNAs, and FRT sites to reduce the number of randomly integrated T-DNAs in selected material. TV-ATS2TurboEraser comprises the following operably linked components: FRT-Ubi pro::ubi 5' UTR::moI-SceI:pinII-WDV SIR::RepAB::WDV LIR-HR1-ubi pro::ubi 5' UTR::GAT4621::pinII-HR2-FRT.

A fifth targeting vector (TV-PHP30662) was constructed using the same elements as TV-ATS2, but the vector lacks the regions of homology to the target site. TV-PHP30662 comprises the following operably linked components: Ubi pro::ubi 5' UTR::moI-SceI::pinII-ubi pro::ubi 5' UTR::GAT4621::pinII.

C. Maize Lines Comprising a Target Site

Maize lines comprising an artificial target site stably integrated into the genome were produced by *Agrobacterium*-mediated transformation. *Zea mays* Hi-II immature embryos were transformed using *Agrobacterium*-mediated transformation essentially as described in Djukanovic et al. (2006) *Plant Biotech J* 4:345-57. Briefly, 10-12 DAP immature embryos (1-1.5 mm in size) were dissected from sterilized kernels and placed into liquid medium. After embryo collection, the medium was replaced with 1 ml *Agrobacterium* (at a concentration of 0.35-0.45 OD550) containing a T-DNA comprising an artificial target site, e.g, ATS2 (PHP22709). Maize embryos were incubated with *Agrobacterium* for 5 minutes at room temperature, and then the mixture was poured onto a media plate. Embryos were incubated axis down, in the dark for 3 days at 20° C., then incubated 4 days in the dark at 28° C., followed by a transfer to new media plates containing 3.0 mg/L Bialaphos and 100 mg/L carbenicillin. Embryos were subcultured every three weeks until transgenic events were identified. Somatic embryogenesis was induced by transferring a small amount of tissue onto regeneration medium (containing 0.1 µM ABA, 1 mg/L IAA, 0.5 mg/L zeatin, 1.5 mg/L Bialaphos, and 100 mg/L carbenicillin) and incubated in the dark for two weeks at 28° C. All material with visible shoots and roots was transferred onto media containing 4.3 g/L MS salts (Gibco 11117), 5.0 ml/L MS Vitamins Stock Solution, 100 mg/L myo-inositol, 40.0 g/L sucrose, and 1.5 g/L Gelrite, pH 5.6, and incubated under artificial light at 28° C. One week later, plantlets were moved into glass tubes containing the same medium and grown until they were sampled and/or transplanted into soil.

Results

A total of 20 T0 transgenic plants were generated. Nineteen T0 plants survived to maturity. Leaf samples from these plants were collected for Southern analysis. Only single copy events that produced greater than 10 T1 kernels were used for further experiments. Twelve T0 events were identified from this process. T1 seeds produced by T0 self pollinations were planted for further characterization to confirm single copy ATS2 events by T1 segregation analysis. PAT activity was determined using a PAT protein detection kit. Four events (59, 60, 99, and 102) showed 1:2:1 Mendelian segregation for the target site. Events 99 and 102 also showed a 3:1 segregation of PAT expression, which also verified that the selected events were transcriptionally active. A total of 68 homozygous plants were produced from six selected single copy events and moved to the greenhouse for seed amplification and embryo production for transformation. Of the six selected events, events 59 and 99 showed a good tassel/ear developmental coordination. Embryos from these two events were used for a FLP activity assay to further confirm that the target site was transcriptionally active and to verify FLP function. FLP activity was assessed with the PHP10968 construct, in which the uidA coding sequence and the maize ubiquitin sequence is separated by the GFP coding sequence flanked by two FRT sites. FLP-mediated excision of this fragment is expected to reconstitute GUS expression. Every embryo from these events had GUS activity, indicating that ATS2 target sites in the two independent events were transcriptionally active. Six homozygous, single copy transgenic maize lines containing the ATS2 fragment were produced. Hemizygous embryos can be produced for re-transformation experiments by back-crossing or outcrossing. An ATS homozygous line is crossed to non-transgenic parental plants in order to produce the ATS hemizygous embryos for re-transformation experiments. All dissected embryos contained one copy of the artificial target site.

D. Target Site Modification

*Agrobacterium*-mediated transformation, as described elsewhere herein, is used to re-transform 9-12 DAP immature target line embryos comprising the ATS2 target site. The target line embryos are transformed with an I-SceI expression vector, and/or a targeting vector, with or without the following cassette: Ole Pro::ZmBBM::pinII+nos Pro::Zm-WUS2::pinII+ALS Pro::Zm-ALS (HRA)::pinII. Zm-ALS (HRA) is the maize acetolactase synthase with two mutated amino acids, making it resistant to sulfonylurea herbicides. Transgenic embryos containing the artificial target site (ATS2) are re-transformed with the targeting vectors delivered on T-DNA molecules. The target sites contain the I-SceI restriction site and the targeting vectors provide the I-SceI meganuclease activity. Re-transformation of transgenic embryos containing ATS2 with an I-SceI expression cassette produces double-strand breaks at the target site. As a result, targeted modifications including short deletions and other rearrangements are introduced at the target site. A GAT expression cassestte is used to confirm construct delivery, therefore embryo co-cultivation is followed by callus selection on media containing 1 mM glyphosate. Transgenic callus events are resistant to glyphosate and exhibit blue fluorescence. In the re-transformation experiments for targeting, the selection protocol does not rely on activation/inactivation of moPAT::YFP; instead, all glyphosate-resistant, CFP+events are screened by PCR for modifications of ATS indicative of targeting events.

For high-throughput PCR screening of large numbers of samples, DNA is extracted by a HotSHOT protocol (Truett et al. (2000) Biotechniques 29:53-54). Briefly, one leaf punch, or a sample of equivalent size, 400 µl of extraction buffer (25 mM NaOH, 0.2 mM EDTA), and two stainless steel beads are placed in each tube of a Mega titer rack. The samples are ground and extracted by shaking in a Genogrinder at 1650 rpm for 30-60 seconds, then incubating for 60-90 minutes at 95° C. The extracts are cooled to room temperature, 400 µl neutralization buffer (40 mM Tris-HCl, pH 5.0) is added, and the extracts are shaken at 500 rpm for 20-30 minutes. The samples are centrifuged at 4000 rpm for 5-10 minutes, followed by the collection of the supernatant. Two µl of the supernatant from each sample is used for PCR.

For further evaluation of putative transformation events, DNA extraction is performed using the Qiagen Dneasy Plant Mini kit according to the provided protocol (Qiagen Inc., Valencia, N. Mex., USA). PCR reactions contain 2 µl of DNA extract (100-200 ng), 10 µl of RedExtractandAmpPCR mix (R4775, Sigma, St. Louis, Mo.), 0.05 µl of each primer at a 100 µM concentration, and 7.9 µl water. The Expanded Long Template PCR amplification system (Roche Molecular Biochemicals, Indianapolis, Ind.) is used to amplify products of about 3 kb or larger. The Eppendorf Mastercycler Gradient cycler (Eppendorf North America, Westbury, N.Y.) is used with a PCR program specific for the particular primer annealing temperature and length of the desired PCR product. PCR products are evaluated and purified by agarose gel electrophoresis, by loading 15 µl of each PCR reaction on a 1% agarose gel. PCR products are purified using a Qiagen PCR purification kit (Qiagen Inc., Valencia, N. Mex.). Products less than 4 kb are directly sequenced, or cloned into the pCR4-TOPO vector (InVitrogen, Carlsbad, Calif., USA). Longer PCR products are first cloned into a vector and then sequenced.

Three PCR primer pairs are used to identify and characterize the transformation events: an ATS primer pair, an I-SceI primer pair, and an HR primer pair. Selected putative targeting events are further characterized by DNA sequencing using BigDye Terminator chemistry on an ABI 3700 capillary sequencing machine (Applied Biosystems, Foster City, Calif.). Each sequencing sample contains either 0.4-0.5 µg plasmid DNA or about 10 ng of the PCR product, and 6.4 pmole primer. Sequences are analyzed using the Sequencher program.

Selected events are further analyzed by Southern blots. Leaf tissue (about 1-2 grams fresh weight) is ground into a fine powder with liquid nitrogen. Twenty ml Puregene® Cell Lysis Solution is added to each sample and incubated 1 hour at 64° C., while shaking at 750 rpm. Samples are centrifuged 10 minutes at 4,000 rpm. DNA extract supernatants are transferred to new tubes, mixed with 5 ml of phenol/chloroform (1:1) solution, and centrifuged 10 minutes at 4000 rpm. The upper phase is removed, and mixed with an equal volume of isopropanol to precipitate the DNA. The solutions are centrifuged for 10 min at 4000 rpm, followed by removal of the supernatant and the resuspension of pellets in 5 ml of TE buffer, pH 8.0, 0.4 ml of ethidium bromide (10 mg/ml), and 5 g of cesium chloride. The mixture is centrifuged overnight (12-17 hrs) at 390,000 g. The DNA extraction and ethidium bromide removal are performed essentially as described in Sambrook et al. (1989) Molecular Cloning: A Laboratory Manual, Cold Spring Harbor Laboratory Press, NY. The final DNA preparations are dissolved in TE buffer to yield 1.0 µg/µl DNA solutions. Tenn DNA from each sample is digested overnight with 50 units of selected restriction enzyme(s) and the resultant digestion product(s) are separated on a 0.7% agarose gel run at 35 mV overnight. The TurboBlotter and Blotting Stack (Schleicher & Schuell, Keene, N.H.) are used to transfer DNA onto a nylon membrane as described in the manufacturer's manual. The DNA fragments are linked to the membrane by UV irradiation at 1.2 kjoules/m$^2$ in a UV Stratalinker (Stratagene, Cedar Creek, Tex.). The blots are prehybridized 2-3 hrs in 20 ml of ExpressHyb hybridization solution (Clontech, Palo Alto, Calif.) at 65° C. The random prime labeling system (Amersham Pharmacia Biotech, Piscataway, N.J.) is used with Redivue [$^{32}$P]dCTP to produce radioactively labeled DNA fragments according to the supplied protocol. Hybridizations are incubated overnight at 65° C. Blots are washed twice with 1% SSCE/0.1% SDS solution for 15 min at 65° C. and then two additional washes are done with 0.1% SSCE/0.1% SDS under the same conditions.

E. Homing Endonuclease Activity in Plant Cells

It is beneficial to be able to evaluate the relative DNA cleavage activity in plant cells of any native, modified, or custom-designed double-strand break inducing agent, for example a meganuclease or zinc-finger nuclease. Modifications include changes to meganuclease polynucleotide or amino acids sequences, such as codon optimization, UTRs, amino acid substitutions, or fusions. The meganuclease and target sequence can be provided to the plant cell using any appropriate delivery method. Any meganucleases and target sequences can be tested in any plant cells in this manner.

Briefly, a sequence encoding the homing endonuclease (EN) with its cognate target site sequence (TS) is integrated into a DNA construct, for example a T-DNA, and delivered to the plant cells. This construct also includes a recombinase, recombinase sites for excision, and viral replication elements. After a specified period of time, or at defined time points in a series, total DNA is extracted from the treated plant cells and used to transform E. coli. Only circular DNAs containing the target sites will be capable of transforming and propagating in E. coli. These DNA molecules are recovered from E. coli and at least a subset of these samples are analyzed for mutations produced by double-strand breaks at the target site. Mutated target sites can be identified by sequencing of PCR products, real-time PCR using fluorescent probes, PCR-based melting curve analysis, or other suitable methods.

For example, a T-DNA construct containing the following operably linked components is constructed: RB-FRT-cole1 ori-F1 ori-AMP-TS-WDV LIR-REP Exon1-REP Intron-REP Exon1-WDV SIR-FRT-UBI pro-UBI intronl-FLPm Exon1-ST LS1 Intron2-FLPm Exon2-pinII term-35S Enh-MN/ST_LS Intron2-Ubi Intronl-Ubi Pro-LB-SPC-cole1 ori-COS. SPC is a bacterial gene conferring resistance to spectinomycin.

The coding regions for both the homing endonuclease (EN) and the recombinase (FLPm) contain an intron (e.g., ST-LS Intron 2) to suppress the expression of the proteins in bacterial cells (*Agrobacterium* or *E. coli*). This vector can be constructed using FLP-mediated recombination between a WDV replicase expression vector containing the target site sequence and an acceptor T-DNA vector containing FLP and the MN.

*Agrobacterium* containing a plasmid with the above components is used to transform BMS cells. In BMS cells, the meganuclease is expressed and can act upon the target site sequence. FLP recombinase is also expressed, excising the TS-containing WDV replicase expression vector, which circularizes and replicates. The acceptor T-DNA vector may also circularize, but cannot replicate. Replication amplifies the quantity of circular TS-containing WDV replicon, which will be the predominant DNA provided to *E. coli*. Six days after transformation, total DNA is isolated from the BMS cells and used to transform *E. coli*. *E. coli* colonies are screened sequentially for resistance to ampicillin and resistance to spectinomycin to identify colonies containing Ti plasmid DNA. Ampicillin-resistant colonies are selected and screened for mutations at the target site. The target sites can be recovered either by extraction of plasmid DNA from the E. coli, or by PCR amplification. PCR amplification reactions allow more efficient analysis of a large number of samples. Mutated target sites can be identified by sequencing of PCR products, real-time PCR using fluorescent probes, PCR-based melting curve analysis, or other suitable methods.

A summary of homing endonuclease and target site assay results are summarized in Table 3, wherein the I-SceI, I-CreI, Lig3-4, Lig3-4+, Lig3-4++ homing endonucleases are combined with the corresponding target site (single or double copy).

TABLE 3

A summary of homing endonuclease and target site assay results.

| Target Site | Homing endonuclease | # clones sequenced | # mutations | Mutation rate |
| --- | --- | --- | --- | --- |
| I-SceI | None | 34 | 0 | 0% |
| I-SceI | I-SceI | 58 | 49 | 84% |
| Double I-SceI | I-SceI | 63 | 57 | 90% |
| I-CreI | None | 34 | 0 | 0% |
| I-CreI | I-CreI | 904 | 318 | 35% |
| Double I-CreI | I-CreI | 66 | 50 | 76% |
| LIG-1 | Lig3-4 | 637 | 3 | 0.5% |
| LIG-1 | Lig3-4+ | 353 | 1 | 0.3% |
| LIG-1 | Lig3-4++ | 237 | 56 | 24% |

Example 7. Targeted Modification of an Endogenous Genomic Locus

A genomic sequence near the liguleless1 locus on chromosome 2 was characterized for use as an endogenous targeting locus. The targeting construct comprised a UBI::moPAT::pinII expression cassette flanked by 3150 bp and 1255 bp of sequence homologous to that of the endogenous genomic locus, in addition to a UBI PRO::I-CRE SC (LIG3/4)::pinII expression cassette encoding a homing endonuclease specific for the endogenous sequence ATATACCTCACACGTACGCGTA (SEQ ID NO: 56).

The targeting plasmid was delivered at 100 ng plasmid/bombardment to scutellar cells of PHWWE immature embryos either alone, or with 25 ng each of PHP21875 (UBI::ZmBBM::pinII) and PHP21139 (In2-2 PRO::Zm-WUS2::In2-1 TERM). After particle bombardment of 569 embryos with all three plasmids, 74 callus events were selected for resistance to bialaphos, and one of these events produced a positive band after PCR screening across the newly formed hybrid junction identifying a putative homologous recombination event . All eight plants regenerated from this event produced a positive PCR signal. Long range PCR, produing longer bands across the newly formed junctions were then used to further confirm successful introduction of the UBI::moPAT::pinII fragment into the endogenous LIG locus. Subsequent Southern analysis demonstrated that after cutting genomic DNA with either PstI or BamHI for probing with Probe 1, or cutting with SpeI or DraI for probing with Probe 2, the expected band sizes were observed which were indicative of perfect integration. Finally, PCR was used to verify that moPAT had integrated as a single copy, and that the I CREI (LIG), ODP2 and WUS2 transgenic expression cassettes had not integrated into the genome. To date, two homologous recombination events have been identified and verified when ODP2 and WUS2 were co-delivered with the donor plasmid, after analyzing approximately 310 events to recover the first perfect homologous recombination (HR) and 74 events to recover the second perfect HR. In separate testing without ODP2 and WUS2, approximately 280 transgenic events were analyzed and no perfect homologous recombination events have been recovered.

Additionally, the developmental genes ZmBBM and ZmWUS2 have also been used to facilitate integration of transgenes at two different endogenous target sites on chromosome 1.

Example 8. Identification of BBM Motifs

Fifty genes from different plant species were identified through a homology search using the maize BBM amino acid sequence (SEQ ID NO: 2) queried against annotated protein sequences (see FIG. 1). The gene structure and sequences of these BBM homologs were manually inspected and compared with EST/cDNA alignments whenever possible. The fifty polypeptides are set forth in SEQ ID NOs: 2, 17, 19, 21, 23, 25, 27, 29, 31, 33, 35, 37, 39, 41, and 61-96. To systematically identify possible motifs within the BBM homologs, protein sequences of these fifty homologs were submitted to the MEME web server, available on the world wide web at meme.nbcr.net/meme4_1/cgi-bin/meme.cgi, with the following specific parameters:
Number of different motifs: 20
Minimum motif width: 5
Maximum motif width: 300
Minimum number of sites: 5

Default values were applied for all other parameters. The raw results from MEME were manually compared with multiple sequence alignments generated by clustalw. Only those candidates showing good consensus with the sequence alignments were considered as motifs for further analysis.

Figure 3:
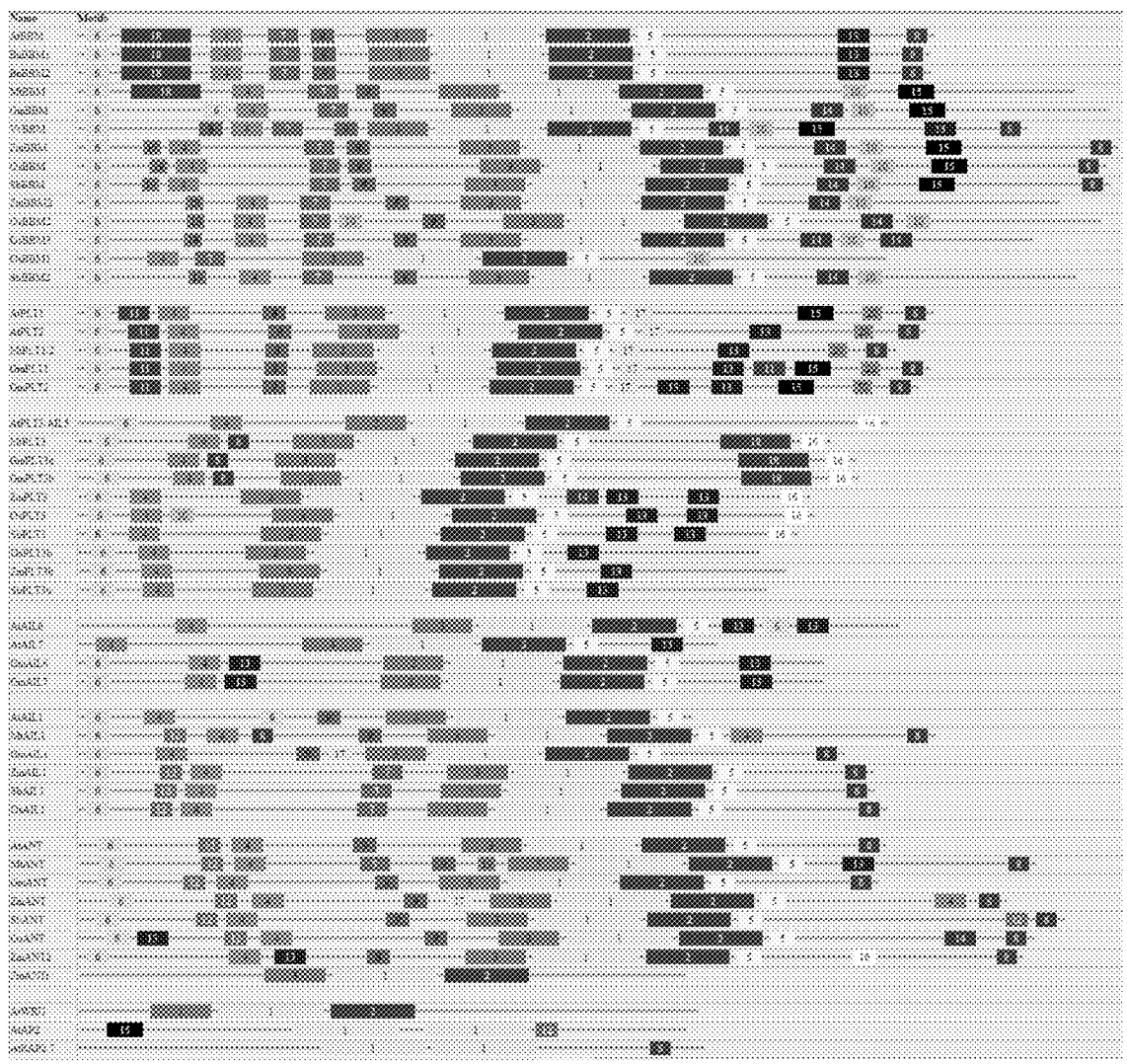
FIG. 3 depicts the motifs found within 50 sequences with homology to maize BBM (ZmBBM).

The fifty genes were subjected to a phylogenetic analysis and a total of six subgroups were identified, including BBM, PLT3, PLT1/2, AIL6/7, AIL1, and ANT (see FIG. 1). FIG. 3 depicts all 50 sequences with each of the motifs that were identified using the MEME web server. FIG. 2 provides the motif consensus sequences along with alignments of the various polypeptides used by the MEME web server to generate the consensus motif. With a few exceptions, motifs 1-6, as defined immediately hereinbelow, are present in all 50 genes. This includes motifs 1-3 (SEQ ID NOs 3-5, respectively), which represent the two AP2 domains and a sequence linking the two domains (linker sequence). Motif 4, with the consensus sequence of PK[L/V][E/A][D/N]FLG (SEQ ID NO: 6) is amino-terminal to the two AP2 domains. Motif 5 (SEQ ID NO: 7) flanks the two AP2 domains on the carboxy terminal end of the polypeptides. Near the amino terminus of the polypeptides is motif 6, with the consensus sequence of NWL[G/S]FSLSP (SEQ ID NO: 8).

Figure 4A:
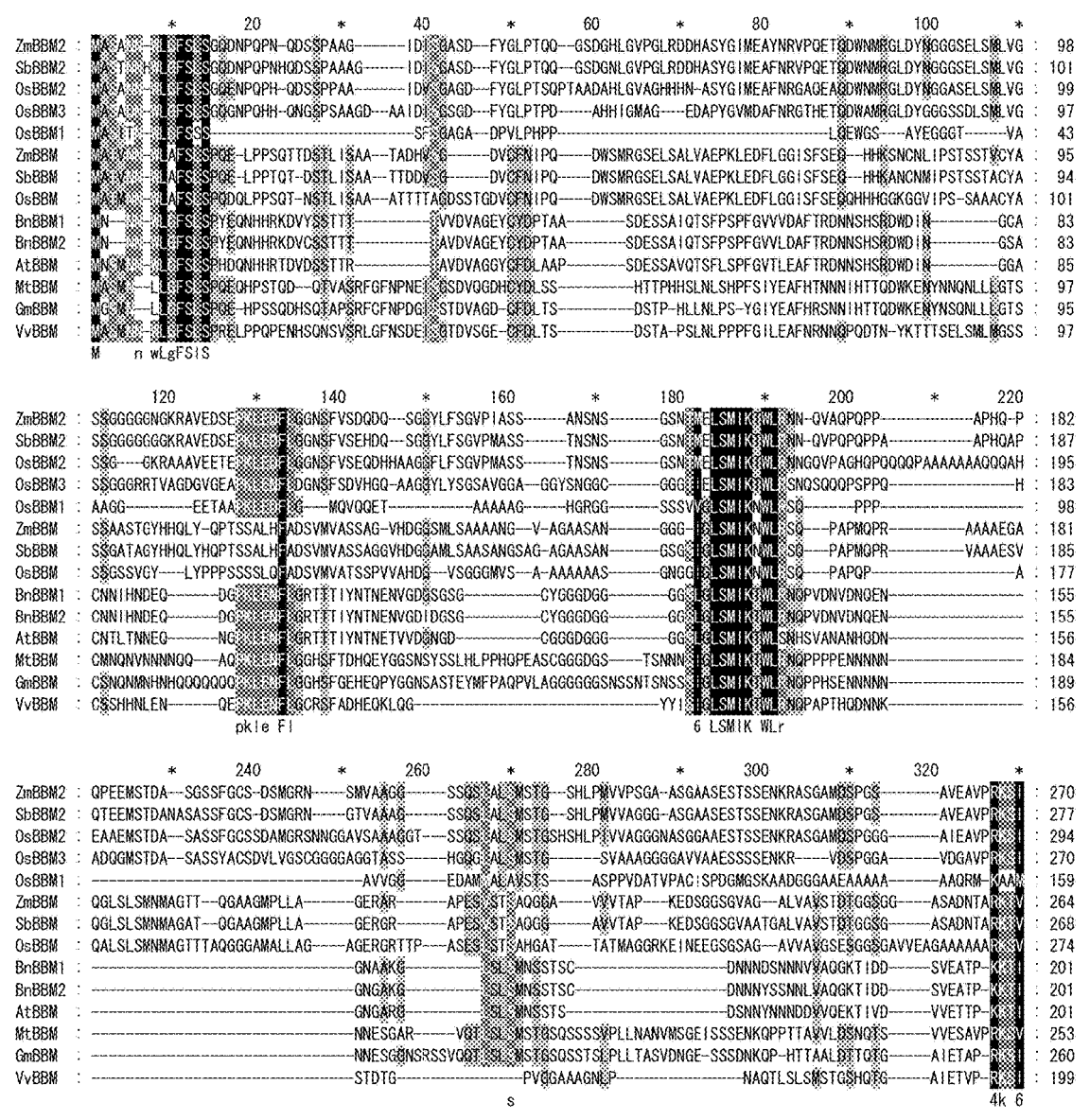

There were motifs that were relatively specific for the BBM subgroup of the homologous sequences (referred to herein as BBM polypeptides). An alignment of the BBM polypeptides can be found in FIG. 4. Motif 7 is found in all BBM polypeptides at the amino terminus of the polypeptide and has the consensus sequence of [G/E]LSMIK[T/N]WLR (SEQ ID NO: 9). Another motif that is present in all of the BBM polypeptides except for the polypeptides from Brassica and from Arabidopsis is Motif 10. Motif 10 has the consensus sequence of WCK[Q/P]EQD (SEQ ID NO: 12) and is located downstream of the AP2 domains.

There are three more motifs specific to the BBM group of polypeptides, including Motif 15 (SEQ ID NO: 14) which appears only in BBM orthologs, but not in the monocot BBM2 polypeptides; a monocot specific motif (Motif 19; SEQ ID NO: 15); and a general BBM specific motif (Motif 14; SEQ ID NO: 13), which appears in BBM homologs except for the *Brassica* and legume branch.

Figure 5:
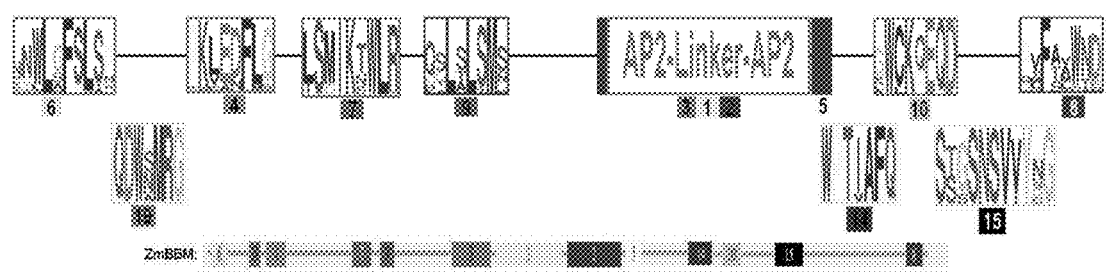
FIG. 5 provides a depiction of the motifs found in babyboom polypeptides.

FIG. 5 provides a summary of the motif structure of the BBM homologs. The amino terminal motifs 4 and 6 and the AP2 flanking motif 5 distinguish the BBM homologous sequences from other two AP2 domain-containing homologs, such as WRI, AP2, and RAP2.7. Therefore, motifs 1-6 can be considered as core BBM/PLT family motifs. Many subgroups of the BBM/PLT family (BBM, PLT1/2, AIL1, and ANT) also have a carboxy-terminal motif (motif 8; SEQ ID NO: 10) and the third amino terminal motif (motif 9; SEQ ID NO: 11).

The BBM polypeptides all have one additional motif (motif 7; SEQ ID NO: 9) in the amino terminus, and all but the *Brassica* and *Arabidopsis* BBM homologs have an AP2 downstream motif (motif 10; SEQ ID NO: 12). Some other BBM/PLT family members (e.g., monocot AIL1) may have a similar motif as motif 7, but none of them also have motif 9. Motif 10 appears only in BBM polypeptides. In summary, the MEME predicted motifs 1-10 can be regarded as BBM polypeptide motifs. All monocot BBM polypeptides (corn, *sorghum*, and rice) also have motif 14, 15, and 19 (see FIG. 3). Some dicot BBM polypeptides and the second monocot BBM group (BBM2) have one or two of these motifs, but none have all three motifs.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for modifying a target site of a plant cell, wherein said target site of said plant cell comprises a recognition sequence, and wherein said method comprises:
  a) introducing into said plant cell at least one heterologous polynucleotide encoding a Babyboom polypeptide at least 90% identical to SEQ ID NO:39 and expressing said heterologous polynucleotide; wherein said heterologous polynucleotide encoding said Babyboom polypeptide at least 90% identical to SEQ ID NO:39 is operably linked to a promoter active in said plant; and
  b) introducing a heterologous polynucleotide encoding a double-strand break-inducing enzyme and expressing said heterologous polynucleotide encoding said double-strand break-inducing enzyme, wherein said double-strand break-inducing enzyme recognizes said recognition sequence and introduces a double-strand break at or near the recognition sequence to produce a modified target site.

2. The method of claim 1, wherein said promoter operably linked to said heterologous polynucleotide encoding said Babyboom polypeptide at least 90% identical to SEQ ID NO:39 is an oleosin promoter, a ubiquitin promoter, a nopaline synthase promoter, or a In2promoter.

3. The method of claim 1, wherein said modified target site comprises a deletion, a mutation, a replacement, or an integration of a nucleotide sequence when compared to said target site.

4. The method of claim 1, wherein said double-strand break-inducing enzyme is selected from the group consisting of an endonuclease, a zinc finger nuclease, a transposase, a topoisomerase, and a site-specific recombinase.

5. The method of claim 4, wherein said endonuclease comprises a homing endonuclease.

6. The method of claim 5, wherein said homing endonuclease comprises a modified endonuclease that has been modified to specifically bind said recognition sequence.

7. The method of claim 6, wherein said modified homing endonuclease is derived from a homing endonuclease selected from the group consisting of I-Sce1, I-Sce11, I-Sce111, I-SceIV, 1-SceV, 1-SceVI, 1-SceVII, I-Ceu1, 1-CeuAIIP, I-Cre1, 1-Crepsb1P, I-Crepsb1, 1P,I-Crepsb111P,1-Crepsb1VP, I-Tlil, I-Ppol, P1-Psp1, F-Sce1, F-Sce11, F-Suv1, F-Tev1, F-Tev11, I-Ama1, I-Ani1, I-Chu1, I-Cmoe1, I-Cpa1, I-Cpa11, I-Csm1, I-Cvu1, 1-CvuAIP, I-Ddi1, I-Ddi11, I-Dir1, I-Dmo1, I-Hmu1, I-Hmu11, I- HsNIP, I-L1a1, I-Msol, I-Naa1, I-Nan1, 1-Nc11P,1-Ngr1P, I-Nit1, I-Nja1, I-Nsp236IP, I-Pak1, 1-PbolP, 1-PculP, 1 -PcuAI, 1 -PcuVI, 1-Pgr1P, 1-Pob1P, I-Por1, 1-Por11P, 1-Pbp1P, 1-SpBeta1P, I-Sca1, 1-Sex1P, 1-Sne1P, I-Spom1, I- SpomCP,1-Spom1P,1-Spom11P,11-Squ1P, 1- Ssp 68031, 1-SthPhiJP, I- SthPhiST3P, 1-SthPhiSTe 3bP, 1-Tde1P, I-Tev1, I-Tev11, I-Tev111, 1-UarAP, I- UarHGPAIP, 1-UarHGPA 13P, 1-Vin1P, 1-Zbi1P, Pl-Mtu1, PI-MtuHIP P1-MtuHIIP, P1-Pfu1, P1-Pfu11, P1-Pko1, P1Pko11, PI-Rma43812IP, PI-SpBeta1P, P1-Sce1, P1-Tfu1, P1-Tfu11, P1-Thy1, PI-TIiI, and PI-TiiII.

8. The method of claim 1, wherein said double-strand break-inducing enzyme is a site-specific recombinase and said recognition sequence comprises a first recombination site.

9. The method of claim 8, wherein said site-specific recombinase is selected from the group consisting of FLP recombinase, Cre, SSV1, R, Gin, lambda Int, phiC31 Int, Tn1721, CinH, ParA, Tn5053, Bxbl, TP907-1, U153, and HK022 Int.

10. The method of claim 8, wherein said target site further comprises a second recombination site, wherein said target site comprises the following operably linked components: said first recombination site, a nucleic acid sequence, and a second recombination site.

11. The method of claim 10, wherein said first recombination site is recombinogenic with the second recombination site in the presence of said site-specific recombinase.

12. The method of claim 11, wherein said nucleic acid sequence is excised or inverted to produce the modified target site.

13. The method of claim 1, wherein said modified target site comprises an integrated polynucleotide of interest, and wherein said method further comprises introducing into said plant cell a transfer cassette comprising said polynucleotide of interest.

14. The method of claim 13, wherein said transfer cassette comprises at least a first region having homology to said target site.

15. The method of claim 14, wherein said transfer cassette comprises in the following order: said first region of homology to said target site, said polynucleotide of interest, and a second region of homology to said target site.

16. The method of claim 1, said method further comprising selecting cells comprising the modified target site and regenerating a plant having the modified target site.

17. The method of claim 16, wherein said method further comprises reducing the activity of said Babyboom polypeptide at least 90% identical to SEQ ID NO:39 prior to regenerating a plant having the modified target site.

18. The method of claim 17, wherein reducing the activity of said Babyboom polypeptide at least 90% identical to SEQ ID NO:39 comprises excising said heterologous polynucleotide encoding said Babyboom polypeptide at least 90% identical to SEQ ID NO:39.

19. The method of claim 18, wherein said heterologous polynucleotide encoding said Babyboom polypeptide at least 90% identical to SEQ ID NO:39 is flanked by recombination sites, and wherein said method further comprises introducing into said plant cell a site-specific recombinase capable of recognizing and implementing recombination at the recombination sites flanking said heterologous polynucleotide encoding said Babyboom polypeptide at least 90% identical to SEQ ID NO:39, whereby said heterologous polynucleotide encoding said Babyboom polypeptide at least 90% identical to SEQ ID NO:39is excised in the presence of said site-specific recombinase.

20. The method of claim 19, wherein said introducing said site-specific recombinase capable of recognizing and implementing recombination at the recombination sites flanking said heterologous polynucleotide encoding said Babyboom polypeptide at least 90% identical to SEQ ID NO:39 comprises introducing a heterologous polynucleotide encoding said site-specific recombinase capable of recognizing and implementing recombination at the recombination sites flanking said heterologous polynucleotide encoding said Babyboom polypeptide at least 90% identical to SEQ ID NO:39 and expressing said heterologous polynucleotide encoding said site-specific recombinase capable of recognizing and implementing recombination at the recombination sites flanking said heterologous polynucleotide encoding said Babyboom polypeptide at least 90% identical to SEQ ID NO:39.

21. The method of claim 20, wherein said heterologous polynucleotide encoding said site-specific recombinase capable of recognizing and implementing recombination at the recombination sites flanking said heterologous polynucleotide encoding said Babyboom polypeptide at least 90% identical to SEQ ID NO:39 is operably linked to an inducible promoter.

22. The method of claim 20, wherein said heterologous polynucleotide encoding said Babyboom polypeptide at least 90% identical to SEQ ID NO:39 and said heterologous polynucleotide encoding said site-specific recombinase capable of recognizing and implementing recombination at the recombination sites flanking said heterologous polynucleotide encoding said Babyboom polypeptide at least 90% identical to SEQ ID NO:39 are flanked by said recombination sites, whereby said heterologous polynucleotide encoding said Babyboom polypeptide at least 90% identical to SEQ ID NO:39 and said heterologous polynucleotide encoding said site-specific recombinase capable of recognizing and implementing recombination at the recombination sites flanking said heterologous polynucleotide encoding said Babyboom polypeptide at least 90% identical to SEQ ID NO:39 is excised in the presence of said site-specific recombinase.

23. The method of claim 1, further comprising introducing into said plant cell a heterologous polynucleotide encoding a Wuschel polypeptide.

24. The method of claim 23, wherein said heterologous polynucleotide encoding said Wuschel polypeptide is operably linked to a nopaline synthase promoter or an In2-2 promoter.

25. The method of claim 23, wherein said heterologous polynucleotide encoding said Wuschel polypeptide is stably integrated into the genome of said plant cell.

26. The method of claim 23, wherein said heterologous polynucleotide encoding said Wuschel polypeptide is transiently expressed.

27. The method of claim 23, wherein said heterologous polynucleotide encoding said Wuschel polypeptide has a nucleotide sequence selected from the group consisting of:
 a) the nucleotide sequence set forth in SEQ ID NO: 51, 57, 99, or 97;
 b) a nucleotide sequence having at least 70% sequence identity to SEQ ID NO: 51, 57, 99, or 97;
 c) a nucleotide sequence encoding the amino acid sequence set forth in SEQ ID NO: 52, 58, 100, or 98; and
 d) a nucleotide sequence encoding an amino acid sequence having at least 70% sequence identity to SEQ ID NO: 52, 58, 100, or 98.

28. The method of claim 23, wherein said method further comprises reducing the activity of said Wuschel polypeptide prior to the regeneration of a plant having the modified target site.

29. The method of claim 1, wherein said plant cell is a dicot plant cell.

30. The method of claim 1, wherein said plant cell is a monocot plant cell.

31. The method of claim 30, wherein said monocot plant is selected from the group consisting of maize, rice, sorghum, barley, wheat, millet, oats, sugarcane, turfgrass, and switch grass.

32. A method for targeting the insertion of a polynucleotide of interest to a target site in a plant cell, wherein said target site comprises a first recombination site, said method comprising:
 a) introducing into said plant cell at least one heterologous polynucleotide encoding a Babyboom polypeptide at least 90% identical to SEQ ID NO:39 and expressing said heterologous polynucleotide encoding said Babyboom polypeptide at least 90% identical to SEQ ID NO:39, wherein said heterologous polynucleotide encoding said Babyboom polypeptide at least 90% identical to SEQ ID NO:39 is operably linked to a promoter active in said plant;
b) introducing into said plant cell a transfer cassette comprising a second recombination site and said polynucleotide of interest, wherein the first and said second recombination sites are recombinogenic with respect to one another; and
c) introducing into said plant cell a site-specific recombinase that recognizes and implements recombination at said first and said second recombination sites, thereby inserting said polynucleotide of interest at the target site.

33. A method for targeting the insertion of a polynucleotide of interest to a target site in a plant cell, wherein said target site comprises a first and a second recombination site, wherein said first and said second recombination sites flank a nucleotide sequence and are non-recombinogenic with respect to one another, said method comprising:
a) introducing into said plant cell at least one heterologous polynucleotide encoding a Babyboom polypeptide at least 90% identical to SEQ ID NO:39 and expressing said heterologous polynucleotide encoding said Babyboom polypeptide at least 90% identical to SEQ ID NO:39; wherein said heterologous polynucleotide encoding said Babyboom polypeptide at least 90% identical to SEQ ID NO:39 is operably linked to a promoter active in said plant;
b) introducing into said plant cell a transfer cassette comprising a third and a fourth recombination site flanking said polynucleotide of interest, wherein the third recombination site is recombinogenic with the first recombination site, and wherein the fourth recombination site is recombinogenic with the second recombination site; and
c) introducing into said plant cell a site-specific recombinase that recognizes and implements recombination at the first, second, third, and fourth recombination sites;
thereby replacing the nucleic acid sequence of the target site with the polynucleotide of interest from the transfer cassette.

34. A method to integrate multiple transfer cassettes at a target site in a plant cell, wherein said target site comprises at least a first and a second recombination site, said method comprising:
a) introducing into said plant cell a first transfer cassette comprising in the following order: at least the first, a third, and the second recombination sites, wherein the first and the third recombination sites of the first transfer cassette flank a first polynucleotide of interest, and wherein said first, said second, and said third recombination sites are non-recombinogenic with respect to one another;
b) introducing into said plant cell a first site-specific recombinase, wherein said site-specific recombinase recognizes and implements recombination at the first and the second recombination sites;
c) introducing a second transfer cassette comprising at least the second and the third recombination sites, wherein the second and the third recombination sites of the second transfer cassette flank a second polynucleotide of interest; and
d) introducing into said plant cell a second site-specific recombinase, wherein said second site-specific recombinase recognizes and implements recombination at the second and third recombination sites;
whereby the first and the second transfer cassettes are integrated at the target site of the plant cell, and wherein said method further comprises introducing at least one heterologous polynucleotide encoding a Babyboom polypeptide at least 90% identical to SEQ ID NO:39 into said plant cell and expressing said heterologous polynucleotide encoding Babyboom polypeptide at least 90% identical to SEQ ID NO:39 before or during the introduction of the first site-specific recombinase, the second site-specific recombinase, or both the first and the second site-specific recombinase; wherein said heterologous polynucleotide encoding said Babyboom polypeptide at least 90% identical to SEQ ID NO:39 is operably linked to a promoter active in said plant.

35. A method to integrate multiple transfer cassettes at a target site in a plant cell, wherein said target site comprises in the following order at least a first, a second, and a third recombination site, wherein said first, said second, and said third recombination sites are non-recombinogenic with respect to one another, said method comprising:
a) introducing into said plant cell a first transfer cassette comprising a first polynucleotide of interest flanked by the first and the second recombination sites;
b) introducing into said plant cell a first site-specific recombinase, wherein said first site-specific recombinase recognizes and implements recombination at the first and the second recombination sites;
c) introducing a second transfer cassette comprising a second polynucleotide of interest flanked by at least the second and the third recombination sites; and
d) introducing into said plant cell a second site-specific recombinase, wherein said second site-specific recombinase recognizes and implements recombination at the second and third recombination sites;
whereby the first and the second transfer cassettes are integrated at the target site of the plant cell, and wherein said method further comprises introducing at least one heterologous polynucleotide encoding a polypeptide at least 90% identical to SEQ ID NO:39 into said plant cell and expressing said heterologous polynucleotide encoding said polypeptide at least 90% identical to SEQ ID NO:39 before or during the introduction of the first site-specific recombinase, the second site-specific recombinase, or both the first and the second site-specific recombinase; wherein said heterologous polynucleotide encoding said Babyboom polypeptide at least 90% identical to SEQ ID NO:39 is operably linked to a promoter active in said plant.

36. A plant cell comprising a target site, wherein said target site of said plant cell comprises a recognition sequence, and wherein said plant cell further comprises at least one heterologous polynucleotide encoding a Babyboom polypeptide at least 90% identical to SEQ ID NO:39 operably linked to a promoter active in said plant, a double-strand break-inducing enzyme capable of recognizing said recognition sequence and introducing a double-strand break at or near the recognition sequence, and a transfer cassette comprising a polynucleotide of interest, wherein said transfer cassette comprises a first region of homology with said target site.

* * * * *

SEQUENCE LISTING

```
<160> NUMBER OF SEQ ID NOS: 105

<210> SEQ ID NO 1
<211> LENGTH: 2130
<212> TYPE: DNA
<213> ORGANISM: Zea mays
<220> FEATURE:
<221> NAME/KEY: CDS
<222> LOCATION: (1)...(2130)

<400> SEQUENCE: 1 atg gcc act gtg aac aac tgg ctc gct ttc tcc ctc tcc ccg cag gag      48
Met Ala Thr Val Asn Asn Trp Leu Ala Phe Ser Leu Ser Pro Gln Glu
 1               5                  10                  15 ctg ccg ccc tcc cag acg acg gac tcc acg ctc atc tcg gcc gcc acc      96
Leu Pro Pro Ser Gln Thr Thr Asp Ser Thr Leu Ile Ser Ala Ala Thr
             20                  25                  30 gcc gac cat gtc tcc ggc gat gtc tgc ttc aac atc ccc caa gat tgg     144
Ala Asp His Val Ser Gly Asp Val Cys Phe Asn Ile Pro Gln Asp Trp
         35                  40                  45 agc atg agg gga tca gag ctt tcg gcg ctc gtc gcg gag ccg aag ctg     192
Ser Met Arg Gly Ser Glu Leu Ser Ala Leu Val Ala Glu Pro Lys Leu
     50                  55                  60 gag gac ttc ctc ggc ggc atc tcc ttc tcc gag cag cat cac aag tcc     240
Glu Asp Phe Leu Gly Gly Ile Ser Phe Ser Glu Gln His His Lys Ser
 65                  70                  75                  80 aac tgc aac ttg ata ccc agc act agc agc aca gtt tgc tac gcg agc     288
Asn Cys Asn Leu Ile Pro Ser Thr Ser Ser Thr Val Cys Tyr Ala Ser
                 85                  90                  95 tca gct gct agc acc ggc tac cat cac cag ctg tac cag ccc acc agc     336
Ser Ala Ala Ser Thr Gly Tyr His His Gln Leu Tyr Gln Pro Thr Ser
            100                 105                 110 tcc gcg ctc cac ttc gcg gac tcc gtc atg gtg gcc tcc tcg gcc ggt     384
Ser Ala Leu His Phe Ala Asp Ser Val Met Val Ala Ser Ser Ala Gly
        115                 120                 125 gtc cac gac ggc ggt tcc atg ctc agc gcg gcc gct aac ggt gtc         432
Val His Asp Gly Gly Ser Met Leu Ser Ala Ala Ala Ala Asn Gly Val
    130                 135                 140
```

```
gct ggc gct gcc agt gcc aac ggc ggc ggc atc ggg ctg tcc atg atc          480
Ala Gly Ala Ala Ser Ala Asn Gly Gly Gly Ile Gly Leu Ser Met Ile
145                 150                 155                 160 aag aac tgg ctg cgg agc caa ccg gcg ccc atg cag ccg agg gcg gcg          528
Lys Asn Trp Leu Arg Ser Gln Pro Ala Pro Met Gln Pro Arg Ala Ala
                165                 170                 175 gcg gct gag ggc gcg cag ggg ctc tct ttg tcc atg aac atg gcg ggg          576
Ala Ala Glu Gly Ala Gln Gly Leu Ser Leu Ser Met Asn Met Ala Gly
            180                 185                 190 acg acc caa ggc gct gct ggc atg cca ctt ctc gct gga gag cgc gca          624
Thr Thr Gln Gly Ala Ala Gly Met Pro Leu Leu Ala Gly Glu Arg Ala
        195                 200                 205 cgg gcg ccc gag agt gta tcg acg tca gca cag ggt ggt gcc gtc gtc          672
Arg Ala Pro Glu Ser Val Ser Thr Ser Ala Gln Gly Gly Ala Val Val
    210                 215                 220 gtc acg gcg ccg aag gag gat agc ggt ggc agc ggt gtt gcc ggt gct          720
Val Thr Ala Pro Lys Glu Asp Ser Gly Gly Ser Gly Val Ala Gly Ala
225                 230                 235                 240 cta gta gcc gtg agc acg gac acg ggt ggc agc ggc ggc gcg tcg gct          768
Leu Val Ala Val Ser Thr Asp Thr Gly Gly Ser Gly Gly Ala Ser Ala
                245                 250                 255 gac aac acg gca agg aag acg gtg gac acg ttc ggg cag cgc acg tcg          816
Asp Asn Thr Ala Arg Lys Thr Val Asp Thr Phe Gly Gln Arg Thr Ser
                260                 265                 270 att tac cgt ggc gtg aca agg cat aga tgg act ggg aga tat gag gca          864
Ile Tyr Arg Gly Val Thr Arg His Arg Trp Thr Gly Arg Tyr Glu Ala
            275                 280                 285 cat ctt tgg gat aac agt tgc aga agg gaa gga caa act cgt aag ggt          912
His Leu Trp Asp Asn Ser Cys Arg Arg Glu Gly Gln Thr Arg Lys Gly
        290                 295                 300 cgt caa gtc tat tta ggt ggc tat gat aaa gag gag aaa gct gct agg          960
Arg Gln Val Tyr Leu Gly Gly Tyr Asp Lys Glu Glu Lys Ala Ala Arg
305                 310                 315                 320 gct tat gat ctt gct gct ctg aag tac tgg ggt gcc aca aca aca aca         1008
Ala Tyr Asp Leu Ala Ala Leu Lys Tyr Trp Gly Ala Thr Thr Thr Thr
                325                 330                 335 aat ttt cca gtg agt aac tac gaa aag gag ctc gag gac atg aag cac         1056
Asn Phe Pro Val Ser Asn Tyr Glu Lys Glu Leu Glu Asp Met Lys His
                340                 345                 350 atg aca agg cag gag ttt gta gcg tct ctg aga agg aag agc agt ggt         1104
Met Thr Arg Gln Glu Phe Val Ala Ser Leu Arg Arg Lys Ser Ser Gly
            355                 360                 365 ttc tcc aga ggt gca tcc att tac agg gga gtg act agg cat cac caa         1152
Phe Ser Arg Gly Ala Ser Ile Tyr Arg Gly Val Thr Arg His His Gln
370                 375                 380 cat gga aga tgg caa gca cgg att gga cga gtt gca ggg aac aag gat         1200
His Gly Arg Trp Gln Ala Arg Ile Gly Arg Val Ala Gly Asn Lys Asp
385                 390                 395                 400 ctt tac ttg ggc acc ttc agc acc cag gag gag gca gcg gag gcg tac         1248
Leu Tyr Leu Gly Thr Phe Ser Thr Gln Glu Glu Ala Ala Glu Ala Tyr
                405                 410                 415 gac atc gcg gcg atc aag ttc cgc ggc ctc aac gcc gtc acc aac ttc         1296
Asp Ile Ala Ala Ile Lys Phe Arg Gly Leu Asn Ala Val Thr Asn Phe
                420                 425                 430 gac atg agc cgc tac gac gtg aag agc atc ctg gac agc agc gcc ctc         1344
Asp Met Ser Arg Tyr Asp Val Lys Ser Ile Leu Asp Ser Ser Ala Leu
            435                 440                 445 ccc atc ggc agc gcc gcc aag cgt ctc aag gag gcc gag gcc gca gcg         1392
Pro Ile Gly Ser Ala Ala Lys Arg Leu Lys Glu Ala Glu Ala Ala Ala
        450                 455                 460
```

```
tcc gcg cag cac cac cac gcc ggc gtg gtg agc tac gac gtc ggc cgc    1440
Ser Ala Gln His His His Ala Gly Val Val Ser Tyr Asp Val Gly Arg
465                 470                 475                 480 atc gcc tcg cag ctc ggc gac ggc gga gcc cta gcg gcg gcg tac ggc    1488
Ile Ala Ser Gln Leu Gly Asp Gly Gly Ala Leu Ala Ala Ala Tyr Gly
                485                 490                 495 gcg cac tac cac ggc gcc gcc tgg ccg acc atc gcg ttc cag ccg ggc    1536
Ala His Tyr His Gly Ala Ala Trp Pro Thr Ile Ala Phe Gln Pro Gly
            500                 505                 510 gcc gcc acc aca ggc ctg tac cac ccg tac gcg cag cag cca atg cgc    1584
Ala Ala Thr Thr Gly Leu Tyr His Pro Tyr Ala Gln Gln Pro Met Arg
        515                 520                 525 ggc ggc ggg tgg tgc aag cag gag cag gac cac gcg gtg atc gcg gcc    1632
Gly Gly Gly Trp Cys Lys Gln Glu Gln Asp His Ala Val Ile Ala Ala
    530                 535                 540 gcg cac agc ctg cag gac ctc cac cac ttg aac ctg ggc gcg gcc ggc    1680
Ala His Ser Leu Gln Asp Leu His His Leu Asn Leu Gly Ala Ala Gly
545                 550                 555                 560 gcg cac gac ttt ttc tcg gca ggg cag cag gcc gcc gcc gca gct gcg    1728
Ala His Asp Phe Phe Ser Ala Gly Gln Gln Ala Ala Ala Ala Ala Ala
                565                 570                 575 atg cac ggc ctg gct agc atc gac agt gcg tcg ctc gag cac agc acc    1776
Met His Gly Leu Ala Ser Ile Asp Ser Ala Ser Leu Glu His Ser Thr
            580                 585                 590 ggc tcc aac tcc gtc gtc tac aac ggc ggg gtc ggc gat agc aac ggc    1824
Gly Ser Asn Ser Val Val Tyr Asn Gly Gly Val Gly Asp Ser Asn Gly
        595                 600                 605 gcc agc gcc gtt ggc agc ggc ggt ggc tac atg atg ccg atg agc gct    1872
Ala Ser Ala Val Gly Ser Gly Gly Tyr Met Met Pro Met Ser Ala
    610                 615                 620 gcc gga gca acc act aca tcg gca atg gtg agc cac gag cag atg cat    1920
Ala Gly Ala Thr Thr Thr Ser Ala Met Val Ser His Glu Gln Met His
625                 630                 635                 640 gca cgg gcc tac gac gaa gcc aag cag gct gct cag atg ggg tac gag    1968
Ala Arg Ala Tyr Asp Glu Ala Lys Gln Ala Ala Gln Met Gly Tyr Glu
                645                 650                 655 agc tac ctg gtg aac gcg gag aac aat ggt ggc gga agg atg tct gca    2016
Ser Tyr Leu Val Asn Ala Glu Asn Asn Gly Gly Gly Arg Met Ser Ala
            660                 665                 670 tgg ggg acc gtc gtc tct gca gcc gcg gcg gca gca agc agc aac       2064
Trp Gly Thr Val Val Ser Ala Ala Ala Ala Ala Ala Ser Ser Asn
        675                 680                 685 gac aac att gcc gcc gac gtc ggc cat ggc ggc gcg cag ctc ttc agt    2112
Asp Asn Ile Ala Ala Asp Val Gly His Gly Gly Ala Gln Leu Phe Ser
    690                 695                 700 gtc tgg aac gac act taa                                            2130
Val Trp Asn Asp Thr
705

<210> SEQ ID NO 2
<211> LENGTH: 709
<212> TYPE: PRT
<213> ORGANISM: Zea mays

<400> SEQUENCE: 2

Met Ala Thr Val Asn Asn Trp Leu Ala Phe Ser Leu Ser Pro Gln Glu
1               5                   10                  15

Leu Pro Pro Ser Gln Thr Thr Asp Ser Thr Leu Ile Ser Ala Ala Thr
            20                  25                  30
```

-continued

Ala Asp His Val Ser Gly Asp Val Cys Phe Asn Ile Pro Gln Asp Trp
         35                  40                  45

Ser Met Arg Gly Ser Glu Leu Ser Ala Leu Val Ala Glu Pro Lys Leu
 50                  55                  60

Glu Asp Phe Leu Gly Gly Ile Ser Phe Ser Glu Gln His His Lys Ser
 65                  70                  75                  80

Asn Cys Asn Leu Ile Pro Ser Thr Ser Ser Thr Val Cys Tyr Ala Ser
                 85                  90                  95

Ser Ala Ala Ser Thr Gly Tyr His His Gln Leu Tyr Gln Pro Thr Ser
            100                 105                 110

Ser Ala Leu His Phe Ala Asp Ser Val Met Val Ala Ser Ser Ala Gly
            115                 120                 125

Val His Asp Gly Gly Ser Met Leu Ser Ala Ala Ala Asn Gly Val
130                 135                 140

Ala Gly Ala Ala Ser Ala Asn Gly Gly Gly Ile Gly Leu Ser Met Ile
145                 150                 155                 160

Lys Asn Trp Leu Arg Ser Gln Pro Ala Pro Met Gln Pro Arg Ala Ala
                165                 170                 175

Ala Ala Glu Gly Ala Gln Gly Leu Ser Leu Ser Met Asn Met Ala Gly
            180                 185                 190

Thr Thr Gln Gly Ala Ala Gly Met Pro Leu Leu Ala Gly Glu Arg Ala
            195                 200                 205

Arg Ala Pro Glu Ser Val Ser Thr Ser Ala Gln Gly Gly Ala Val Val
            210                 215                 220

Val Thr Ala Pro Lys Glu Asp Ser Gly Gly Ser Gly Val Ala Gly Ala
225                 230                 235                 240

Leu Val Ala Val Ser Thr Asp Thr Gly Gly Ser Gly Gly Ala Ser Ala
                245                 250                 255

Asp Asn Thr Ala Arg Lys Thr Val Asp Thr Phe Gly Gln Arg Thr Ser
            260                 265                 270

Ile Tyr Arg Gly Val Thr Arg His Arg Trp Thr Gly Arg Tyr Glu Ala
            275                 280                 285

His Leu Trp Asp Asn Ser Cys Arg Arg Glu Gly Gln Thr Arg Lys Gly
            290                 295                 300

Arg Gln Val Tyr Leu Gly Gly Tyr Asp Lys Glu Glu Lys Ala Ala Arg
305                 310                 315                 320

Ala Tyr Asp Leu Ala Ala Leu Lys Tyr Trp Gly Ala Thr Thr Thr Thr
                325                 330                 335

Asn Phe Pro Val Ser Asn Tyr Glu Lys Glu Leu Glu Asp Met Lys His
            340                 345                 350

Met Thr Arg Gln Glu Phe Val Ala Ser Leu Arg Arg Lys Ser Ser Gly
            355                 360                 365

Phe Ser Arg Gly Ala Ser Ile Tyr Arg Gly Val Thr Arg His His Gln
370                 375                 380

His Gly Arg Trp Gln Ala Arg Ile Gly Arg Val Ala Gly Asn Lys Asp
385                 390                 395                 400

Leu Tyr Leu Gly Thr Phe Ser Thr Gln Glu Glu Ala Ala Glu Ala Tyr
                405                 410                 415

Asp Ile Ala Ala Ile Lys Phe Arg Gly Leu Asn Ala Val Thr Asn Phe
            420                 425                 430

Asp Met Ser Arg Tyr Asp Val Lys Ser Ile Leu Asp Ser Ser Ala Leu
            435                 440                 445

Pro Ile Gly Ser Ala Ala Lys Arg Leu Lys Glu Ala Glu Ala Ala Ala

```
                450                 455                 460
Ser Ala Gln His His Ala Gly Val Val Ser Tyr Asp Val Gly Arg
465                 470                 475                 480

Ile Ala Ser Gln Leu Gly Asp Gly Gly Ala Leu Ala Ala Tyr Gly
                485                 490                 495

Ala His Tyr His Gly Ala Ala Trp Pro Thr Ile Ala Phe Gln Pro Gly
                500                 505                 510

Ala Ala Thr Thr Gly Leu Tyr His Pro Tyr Ala Gln Gln Pro Met Arg
                515                 520                 525

Gly Gly Gly Trp Cys Lys Gln Glu Gln Asp His Ala Val Ile Ala Ala
530                 535                 540

Ala His Ser Leu Gln Asp Leu His His Leu Asn Leu Gly Ala Ala Gly
545                 550                 555                 560

Ala His Asp Phe Phe Ser Ala Gly Gln Gln Ala Ala Ala Ala Ala
                565                 570                 575

Met His Gly Leu Ala Ser Ile Asp Ser Ala Ser Leu Glu His Ser Thr
                580                 585                 590

Gly Ser Asn Ser Val Val Tyr Asn Gly Gly Val Gly Asp Ser Asn Gly
                595                 600                 605

Ala Ser Ala Val Gly Ser Gly Gly Tyr Met Met Pro Met Ser Ala
610                 615                 620

Ala Gly Ala Thr Thr Thr Ser Ala Met Val Ser His Glu Gln Met His
625                 630                 635                 640

Ala Arg Ala Tyr Asp Glu Ala Lys Gln Ala Gln Met Gly Tyr Glu
                645                 650                 655

Ser Tyr Leu Val Asn Ala Glu Asn Asn Gly Gly Arg Met Ser Ala
                660                 665                 670

Trp Gly Thr Val Val Ser Ala Ala Ala Ala Ala Ser Ser Asn
                675                 680                 685

Asp Asn Ile Ala Ala Asp Val Gly His Gly Gly Ala Gln Leu Phe Ser
                690                 695                 700

Val Trp Asn Asp Thr
705

<210> SEQ ID NO 3
<211> LENGTH: 31
<212> TYPE: PRT
<213> ORGANISM: Artificial Sequence
<220> FEATURE:
<223> OTHER INFORMATION: Consensus sequence motif 1
<220> FEATURE:
<221> NAME/KEY: VARIANT
<222> LOCATION: 10
<223> OTHER INFORMATION: Xaa = His or Asn
<220> FEATURE:
<221> NAME/KEY: VARIANT
<222> LOCATION: 16
<223> OTHER INFORMATION: Xaa = Phe or Tyr
<220> FEATURE:
<221> NAME/KEY: VARIANT
<222> LOCATION: 17
<223> OTHER INFORMATION: Xaa = Val or Ile
<220> FEATURE:
<221> NAME/KEY: VARIANT
<222> LOCATION: 19
<223> OTHER INFORMATION: Xaa = Ser or His

<400> SEQUENCE: 3

Tyr Glu Lys Glu Leu Glu Glu Met Lys Xaa Met Thr Arg Gln Glu Xaa
1               5                   10                  15
```

Xaa Ala Xaa Leu Arg Arg Lys Ser Ser Gly Phe Ser Arg Gly Ala
            20                  25                  30

<210> SEQ ID NO 4
<211> LENGTH: 63
<212> TYPE: PRT
<213> ORGANISM: Artificial Sequence
<220> FEATURE:
<223> OTHER INFORMATION: Consensus sequence motif 2
<220> FEATURE:
<221> NAME/KEY: VARIANT
<222> LOCATION: 2
<223> OTHER INFORMATION: Xaa = Ile or Met
<220> FEATURE:
<221> NAME/KEY: VARIANT
<222> LOCATION: 36
<223> OTHER INFORMATION: Xaa = Gln or Glu
<220> FEATURE:
<221> NAME/KEY: VARIANT
<222> LOCATION: 45
<223> OTHER INFORMATION: Xaa = Ile or Val
<220> FEATURE:
<221> NAME/KEY: VARIANT
<222> LOCATION: 60
<223> OTHER INFORMATION: Xaa = Asp or Glu
<220> FEATURE:
<221> NAME/KEY: VARIANT
<222> LOCATION: 61
<223> OTHER INFORMATION: Xaa = Met or Ile
<220> FEATURE:
<221> NAME/KEY: VARIANT
<222> LOCATION: (62)...(62)
<223> OTHER INFORMATION: Xaa = Ser or Asn

<400> SEQUENCE: 4

Ser Xaa Tyr Arg Gly Val Thr Arg His His Gln His Gly Arg Trp Gln
1               5                   10                  15

Ala Arg Ile Gly Arg Val Ala Gly Asn Lys Asp Leu Tyr Leu Gly Thr
            20                  25                  30

Phe Ser Thr Xaa Glu Glu Ala Ala Glu Ala Tyr Asp Xaa Ala Ala Ile
        35                  40                  45

Lys Phe Arg Gly Leu Asn Ala Val Thr Asn Phe Xaa Xaa Xaa Arg
    50                  55                  60

<210> SEQ ID NO 5
<211> LENGTH: 68
<212> TYPE: PRT
<213> ORGANISM: Artificial Sequence
<220> FEATURE:
<223> OTHER INFORMATION: Consensus sequence motif 3
<220> FEATURE:
<221> NAME/KEY: VARIANT
<222> LOCATION: 2
<223> OTHER INFORMATION: Xaa = Ile or Gln
<220> FEATURE:
<221> NAME/KEY: VARIANT
<222> LOCATION: 26
<223> OTHER INFORMATION: Xaa = Arg or Lys
<220> FEATURE:
<221> NAME/KEY: VARIANT
<222> LOCATION: 30, 59
<223> OTHER INFORMATION: Xaa = Ser or Thr
<220> FEATURE:
<221> NAME/KEY: VARIANT
<222> LOCATION: 33
<223> OTHER INFORMATION: Xaa = Val or Gly
<220> FEATURE:
<221> NAME/KEY: VARIANT
<222> LOCATION: 34
<223> OTHER INFORMATION: Xaa = Tyr or Arg
<220> FEATURE:
<221> NAME/KEY: VARIANT
<222> LOCATION: (35)...(35)

```
<223> OTHER INFORMATION: Xaa = Leu or Gln
<220> FEATURE:
<221> NAME/KEY: VARIANT
<222> LOCATION: (42)...(42)
<223> OTHER INFORMATION: Xaa = Glu or Asp
<220> FEATURE:
<221> NAME/KEY: VARIANT
<222> LOCATION: (58)...(58)
<223> OTHER INFORMATION: Xaa = Pro or Thr
<220> FEATURE:
<221> NAME/KEY: VARIANT
<222> LOCATION: (61)...(61)
<223> OTHER INFORMATION: Xaa = Thr or His
<220> FEATURE:
<221> NAME/KEY: VARIANT
<222> LOCATION: (62)...(62)
<223> OTHER INFORMATION: Xaa = Thr or Ile
<220> FEATURE:
<221> NAME/KEY: VARIANT
<222> LOCATION: (66)...(66)
<223> OTHER INFORMATION: Xaa = Ile, Val, or Leu

<400> SEQUENCE: 5

Ser Xaa Tyr Arg Gly Val Thr Arg His Arg Trp Thr Gly Arg Tyr Glu
1               5                   10                  15

Ala His Leu Trp Asp Asn Ser Cys Arg Xaa Glu Gly Gln Xaa Arg Lys
            20                  25                  30

Xaa Xaa Xaa Gly Gly Tyr Asp Lys Glu Xaa Lys Ala Ala Arg Ala Tyr
        35                  40                  45

Asp Leu Ala Ala Leu Lys Tyr Trp Gly Xaa Xaa Thr Xaa Xaa Asn Phe
    50                  55                  60

Pro Xaa Ser Asn
65

<210> SEQ ID NO 6
<211> LENGTH: 8
<212> TYPE: PRT
<213> ORGANISM: Artificial Sequence
<220> FEATURE:
<223> OTHER INFORMATION: Consensus sequence motif 4
<220> FEATURE:
<221> NAME/KEY: VARIANT
<222> LOCATION: 3
<223> OTHER INFORMATION: Xaa = Leu or Val
<220> FEATURE:
<221> NAME/KEY: VARIANT
<222> LOCATION: 4
<223> OTHER INFORMATION: Xaa = Glu or Ala
<220> FEATURE:
<221> NAME/KEY: VARIANT
<222> LOCATION: 5
<223> OTHER INFORMATION: Xaa = Asp or Asn

<400> SEQUENCE: 6

Pro Lys Xaa Xaa Xaa Phe Leu Gly
1               5

<210> SEQ ID NO 7
<211> LENGTH: 13
<212> TYPE: PRT
<213> ORGANISM: Artificial Sequence
<220> FEATURE:
<223> OTHER INFORMATION: Consensus sequence motif 5
<220> FEATURE:
<221> NAME/KEY: VARIANT
<222> LOCATION: 6
<223> OTHER INFORMATION: Xaa = Ile or Val
<220> FEATURE:
<221> NAME/KEY: VARIANT
<222> LOCATION: 9
<223> OTHER INFORMATION: Xaa = Ala or Leu
```

```
<220> FEATURE:
<221> NAME/KEY: VARIANT
<222> LOCATION: 11, 12
<223> OTHER INFORMATION: Xaa = Lys or Arg
<220> FEATURE:
<221> NAME/KEY: VARIANT
<222> LOCATION: 13
<223> OTHER INFORMATION: Xaa = Leu or Arg

<400> SEQUENCE: 7

Ser Ser Thr Leu Pro Xaa Gly Gly Xaa Ala Xaa Xaa Xaa
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Consensus sequence motif 6
<220> FEATURE:
<221> NAME/KEY: VARIANT
<222> LOCATION: 4
<223> OTHER INFORMATION: Xaa = Gly or Ser

<400> SEQUENCE: 8

Asn Trp Leu Xaa Phe Ser Leu Ser Pro
1               5

<210> SEQ ID NO 9
<211> LENGTH: 10
<212> TYPE: PRT
<213> ORGANISM: Artificial Sequence
<220> FEATURE:
<223> OTHER INFORMATION: Consensus sequence motif 7
<220> FEATURE:
<221> NAME/KEY: VARIANT
<222> LOCATION: 1
<223> OTHER INFORMATION: Xaa = Gly or Glu
<220> FEATURE:
<221> NAME/KEY: VARIANT
<222> LOCATION: 7
<223> OTHER INFORMATION: Xaa = Thr or Asn

<400> SEQUENCE: 9

Xaa Leu Ser Met Ile Lys Xaa Trp Leu Arg
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Consensus sequence motif 8
<220> FEATURE:
<221> NAME/KEY: VARIANT
<222> LOCATION: 2, 4, 5
<223> OTHER INFORMATION: Xaa = Any Amino Acid

<400> SEQUENCE: 10

Pro Xaa Phe Xaa Xaa Trp Asn Asp
1               5

<210> SEQ ID NO 11
<211> LENGTH: 5
<212> TYPE: PRT
<213> ORGANISM: Artificial Sequence
<220> FEATURE:
<223> OTHER INFORMATION: Consensus sequence motif 9
<220> FEATURE:
<221> NAME/KEY: VARIANT
<222> LOCATION: 2
```

```
<223> OTHER INFORMATION: Xaa = Ser, Thr, or Ala

<400> SEQUENCE: 11

Leu Xaa Leu Ser Met
1               5

<210> SEQ ID NO 12
<211> LENGTH: 7
<212> TYPE: PRT
<213> ORGANISM: Artificial Sequence
<220> FEATURE:
<223> OTHER INFORMATION: Consensus sequence motif 10
<220> FEATURE:
<221> NAME/KEY: VARIANT
<222> LOCATION: 4
<223> OTHER INFORMATION: Xaa = Gln or Pro

<400> SEQUENCE: 12

Trp Cys Lys Xaa Glu Gln Asp
1               5

<210> SEQ ID NO 13
<211> LENGTH: 7
<212> TYPE: PRT
<213> ORGANISM: Artificial Sequence
<220> FEATURE:
<223> OTHER INFORMATION: Consensus sequence motif 14

<400> SEQUENCE: 13

Trp Pro Thr Ile Ala Phe Gln
1               5

<210> SEQ ID NO 14
<211> LENGTH: 11
<212> TYPE: PRT
<213> ORGANISM: Artificial Sequence
<220> FEATURE:
<223> OTHER INFORMATION: Consensus sequence motif 15
<220> FEATURE:
<221> NAME/KEY: VARIANT
<222> LOCATION: 2
<223> OTHER INFORMATION: Xaa = Ser or Thr

<400> SEQUENCE: 14

Ser Xaa Gly Ser Asn Ser Val Val Tyr Asn Gly
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Consensus sequence motif 19
<220> FEATURE:
<221> NAME/KEY: VARIANT
<222> LOCATION: 4
<223> OTHER INFORMATION: Xaa = Ser or Asn

<400> SEQUENCE: 15

Gln Asp Trp Xaa Met Arg Gly
1               5

<210> SEQ ID NO 16
<211> LENGTH: 1755
<212> TYPE: DNA
<213> ORGANISM: Arabidopsis thaliana
<220> FEATURE:
<221> NAME/KEY: CDS
<222> LOCATION: (1)...(1755)
```

<400> SEQUENCE: 16

```
atg aac tcg atg aat aac tgg tta ggc ttc tct ctc tct cct cat gat      48
Met Asn Ser Met Asn Asn Trp Leu Gly Phe Ser Leu Ser Pro His Asp
 1               5                  10                  15 caa aat cat cac cgt acg gat gtt gac tcc tcc acc acc aga acc gcc      96
Gln Asn His His Arg Thr Asp Val Asp Ser Ser Thr Thr Arg Thr Ala
             20                  25                  30 gta gat gtt gcc gga ggg tac tgt ttt gat ctg gcc gct ccc tcc gat     144
Val Asp Val Ala Gly Gly Tyr Cys Phe Asp Leu Ala Ala Pro Ser Asp
         35                  40                  45 gaa tct tct gcc gtt caa aca tct ttt ctt tct cct ttc ggt gtc acc     192
Glu Ser Ser Ala Val Gln Thr Ser Phe Leu Ser Pro Phe Gly Val Thr
 50                  55                  60 ctc gaa gct ttc acc aga gac aat aat agt cac tcc cga gat tgg gac     240
Leu Glu Ala Phe Thr Arg Asp Asn Asn Ser His Ser Arg Asp Trp Asp
 65                  70                  75                  80 atc aat ggt ggt gca tgc aat aca tta acc aat aac gaa caa aat gga     288
Ile Asn Gly Gly Ala Cys Asn Thr Leu Thr Asn Asn Glu Gln Asn Gly
                 85                  90                  95 cca aag ctt gag aat ttc ctc ggc cgc acc acc acg att tac aat acc     336
Pro Lys Leu Glu Asn Phe Leu Gly Arg Thr Thr Thr Ile Tyr Asn Thr
            100                 105                 110 aac gag acc gtt gta gat gga aat ggc gat tgt gga gga gga gac ggt     384
Asn Glu Thr Val Val Asp Gly Asn Gly Asp Cys Gly Gly Gly Asp Gly
        115                 120                 125 ggt ggc ggc tca cta ggc ctt tcg atg ata aaa aca tgg ctg agt         432
Gly Gly Gly Ser Leu Gly Leu Ser Met Ile Lys Thr Trp Leu Ser
    130                 135                 140 aat cat tcg gtt gct aat gct aat cat caa gac aat ggt aac ggt gca     480
Asn His Ser Val Ala Asn Ala Asn His Gln Asp Asn Gly Asn Gly Ala
145                 150                 155                 160 cga ggc ttg tcc ctc tct atg aat tca tct act agt gat agc aac aac     528
Arg Gly Leu Ser Leu Ser Met Asn Ser Ser Thr Ser Asp Ser Asn Asn
                165                 170                 175 tac aac aac aat gat gat gtc gtc caa gag aag act att gtt gat gtc     576
Tyr Asn Asn Asn Asp Asp Val Val Gln Glu Lys Thr Ile Val Asp Val
            180                 185                 190 gta gaa act aca ccg aag aaa act att gag agt ttt gga caa agg acg     624
Val Glu Thr Thr Pro Lys Lys Thr Ile Glu Ser Phe Gly Gln Arg Thr
        195                 200                 205 tct ata tac cgc ggt gtt aca agg cat cgg tgg aca ggt aga tac gag     672
Ser Ile Tyr Arg Gly Val Thr Arg His Arg Trp Thr Gly Arg Tyr Glu
    210                 215                 220 gca cat tta tgg gac aat agt tgc aaa aga gaa ggc cag act cgc aaa     720
Ala His Leu Trp Asp Asn Ser Cys Lys Arg Glu Gly Gln Thr Arg Lys
225                 230                 235                 240 gga aga caa gtt tat ctg gga ggt tat gac aaa gaa gaa aaa gca gct     768
Gly Arg Gln Val Tyr Leu Gly Gly Tyr Asp Lys Glu Glu Lys Ala Ala
                245                 250                 255 agg gct tac gat tta gcc gca cta aag tat tgg gga ccc acc act act     816
Arg Ala Tyr Asp Leu Ala Ala Leu Lys Tyr Trp Gly Pro Thr Thr Thr
            260                 265                 270 act aac ttc ccc ttg agt gaa tat gag aaa gag gta gaa gag atg aag     864
Thr Asn Phe Pro Leu Ser Glu Tyr Glu Lys Glu Val Glu Glu Met Lys
        275                 280                 285 cac atg acg agg caa gag tat gtt gcc tct ctg cgc agg aaa agt agt     912
His Met Thr Arg Gln Glu Tyr Val Ala Ser Leu Arg Arg Lys Ser Ser
    290                 295                 300
```

```
ggt ttc tct cgt ggt gca tcg att tat cga gga gta aca agg cat cac    960
Gly Phe Ser Arg Gly Ala Ser Ile Tyr Arg Gly Val Thr Arg His His
305                 310                 315                 320 caa cat gga agg tgg caa gct agg atc gga aga gtc gcc ggt aac aaa   1008
Gln His Gly Arg Trp Gln Ala Arg Ile Gly Arg Val Ala Gly Asn Lys
                325                 330                 335 gac ctc tac ttg gga act ttc ggc aca cag gaa gag gct gct gag gct   1056
Asp Leu Tyr Leu Gly Thr Phe Gly Thr Gln Glu Glu Ala Ala Glu Ala
            340                 345                 350 tat gac att gca gcc att aaa ttc aga gga tta agc gca gtg act aac   1104
Tyr Asp Ile Ala Ala Ile Lys Phe Arg Gly Leu Ser Ala Val Thr Asn
        355                 360                 365 ttc gac atg aac aga tac aat gtt aaa gca atc ctc gag agc ccg agt   1152
Phe Asp Met Asn Arg Tyr Asn Val Lys Ala Ile Leu Glu Ser Pro Ser
    370                 375                 380 cta cct att ggt agt tct gcg aaa cgt ctc aag gac gtt aac aat ccg   1200
Leu Pro Ile Gly Ser Ser Ala Lys Arg Leu Lys Asp Val Asn Asn Pro
385                 390                 395                 400 gtt cca gct atg atg att agt aat aac gtt tca gag agt gca aat aat   1248
Val Pro Ala Met Met Ile Ser Asn Asn Val Ser Glu Ser Ala Asn Asn
                405                 410                 415 gtt agc ggt tgg caa aac act gcg ttt cag cat cat cag gga atg gat   1296
Val Ser Gly Trp Gln Asn Thr Ala Phe Gln His His Gln Gly Met Asp
            420                 425                 430 ttg agc tta ttg cag caa cag cag gag agg tac gtt ggt tat tac aat   1344
Leu Ser Leu Leu Gln Gln Gln Gln Glu Arg Tyr Val Gly Tyr Tyr Asn
        435                 440                 445 gga gga aac ttg tct acc gag agt act agg gtt tgt ttc aaa caa gag   1392
Gly Gly Asn Leu Ser Thr Glu Ser Thr Arg Val Cys Phe Lys Gln Glu
    450                 455                 460 gag gaa caa caa cac ttc ttg aga aac tcg ccg agt cac atg act aat   1440
Glu Glu Gln Gln His Phe Leu Arg Asn Ser Pro Ser His Met Thr Asn
465                 470                 475                 480 gtt gat cat cat agc tcg acc tct gat gat tct gtt acc gtt tgt gga   1488
Val Asp His His Ser Ser Thr Ser Asp Asp Ser Val Thr Val Cys Gly
                485                 490                 495 aat gtt gtt agt tat ggt ggt tat caa gga ttc gca atc cct gtt gga   1536
Asn Val Val Ser Tyr Gly Gly Tyr Gln Gly Phe Ala Ile Pro Val Gly
            500                 505                 510 aca tcg gtt aat tac gat ccc ttt act gct gct gag att gct tac aac   1584
Thr Ser Val Asn Tyr Asp Pro Phe Thr Ala Ala Glu Ile Ala Tyr Asn
        515                 520                 525 gca aga aat cat tat tac tat gct cag cat cag caa caa cag cag att   1632
Ala Arg Asn His Tyr Tyr Tyr Ala Gln His Gln Gln Gln Gln Gln Ile
    530                 535                 540 cag cag tcg ccg gga gga gat ttt ccg gtg gcg att tcg aat aac cat   1680
Gln Gln Ser Pro Gly Gly Asp Phe Pro Val Ala Ile Ser Asn Asn His
545                 550                 555                 560 agc tct aac atg tac ttt cac ggg gaa ggt ggt gga gaa ggg gct cca   1728
Ser Ser Asn Met Tyr Phe His Gly Glu Gly Gly Gly Glu Gly Ala Pro
                565                 570                 575 acg ttt tca gtt tgg aac gac act tag                               1755
Thr Phe Ser Val Trp Asn Asp Thr
            580
```

<210> SEQ ID NO 17
<211> LENGTH: 584
<212> TYPE: PRT
<213> ORGANISM: Arabidopsis thaliana

<400> SEQUENCE: 17

```
Met Asn Ser Met Asn Asn Trp Leu Gly Phe Ser Leu Ser Pro His Asp
1               5                   10                  15

Gln Asn His His Arg Thr Asp Val Asp Ser Ser Thr Thr Arg Thr Ala
            20                  25                  30

Val Asp Val Ala Gly Gly Tyr Cys Phe Asp Leu Ala Ala Pro Ser Asp
        35                  40                  45

Glu Ser Ser Ala Val Gln Thr Ser Phe Leu Ser Pro Phe Gly Val Thr
    50                  55                  60

Leu Glu Ala Phe Thr Arg Asp Asn Asn Ser His Ser Arg Asp Trp Asp
65                  70                  75                  80

Ile Asn Gly Gly Ala Cys Asn Thr Leu Thr Asn Asn Glu Gln Asn Gly
                85                  90                  95

Pro Lys Leu Glu Asn Phe Leu Gly Arg Thr Thr Thr Ile Tyr Asn Thr
            100                 105                 110

Asn Glu Thr Val Val Asp Gly Asn Gly Asp Cys Gly Gly Gly Asp Gly
            115                 120                 125

Gly Gly Gly Gly Ser Leu Gly Leu Ser Met Ile Lys Thr Trp Leu Ser
        130                 135                 140

Asn His Ser Val Ala Asn Ala Asn His Gln Asp Asn Gly Asn Gly Ala
145                 150                 155                 160

Arg Gly Leu Ser Leu Ser Met Asn Ser Ser Thr Ser Asp Ser Asn Asn
                165                 170                 175

Tyr Asn Asn Asn Asp Asp Val Val Gln Glu Lys Thr Ile Val Asp Val
            180                 185                 190

Val Glu Thr Thr Pro Lys Lys Thr Ile Glu Ser Phe Gly Gln Arg Thr
            195                 200                 205

Ser Ile Tyr Arg Gly Val Thr Arg His Arg Trp Thr Gly Arg Tyr Glu
210                 215                 220

Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Lys Ala Ala
                245                 250                 255

Arg Ala Tyr Asp Leu Ala Ala Leu Lys Tyr Trp Gly Pro Thr Thr Thr
            260                 265                 270

Thr Asn Phe Pro Leu Ser Glu Tyr Glu Lys Glu Val Glu Glu Met Lys
            275                 280                 285

His Met Thr Arg Gln Glu Tyr Val Ala Ser Leu Arg Arg Lys Ser Ser
            290                 295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
            325                 330                 335

Asp Leu Tyr Leu Gly Thr Phe Gly Thr Gln Glu Glu Ala Ala Glu Ala
            340                 345                 350

Tyr Asp Ile Ala Ala Ile Lys Phe Arg Gly Leu Ser Ala Val Thr Asn
            355                 360                 365

Phe Asp Met Asn Arg Tyr Asn Val Lys Ala Ile Leu Glu Ser Pro Ser
            370                 375                 380

Leu Pro Ile Gly Ser Ser Ala Lys Arg Leu Lys Asp Val Asn Asn Pro
385                 390                 395                 400

Val Pro Ala Met Met Ile Ser Asn Asn Val Ser Glu Ser Ala Asn Asn
                405                 410                 415
```

-continued

```
Val Ser Gly Trp Gln Asn Thr Ala Phe Gln His His Gln Gly Met Asp
            420                 425                 430

Leu Ser Leu Leu Gln Gln Gln Gln Glu Arg Tyr Val Gly Tyr Tyr Asn
        435                 440                 445

Gly Gly Asn Leu Ser Thr Glu Ser Thr Arg Val Cys Phe Lys Gln Glu
    450                 455                 460

Glu Glu Gln Gln His Phe Leu Arg Asn Ser Pro Ser His Met Thr Asn
465                 470                 475                 480

Val Asp His His Ser Thr Ser Asp Asp Ser Val Thr Val Cys Gly
                485                 490                 495

Asn Val Val Ser Tyr Gly Gly Tyr Gln Gly Phe Ala Ile Pro Val Gly
            500                 505                 510

Thr Ser Val Asn Tyr Asp Pro Phe Thr Ala Ala Glu Ile Ala Tyr Asn
        515                 520                 525

Ala Arg Asn His Tyr Tyr Tyr Ala Gln His Gln Gln Gln Gln Gln Ile
    530                 535                 540

Gln Gln Ser Pro Gly Gly Asp Phe Pro Val Ala Ile Ser Asn Asn His
545                 550                 555                 560

Ser Ser Asn Met Tyr Phe His Gly Glu Gly Gly Gly Glu Gly Ala Pro
                565                 570                 575

Thr Phe Ser Val Trp Asn Asp Thr
            580
```

<210> SEQ ID NO 18
<211> LENGTH: 1740
<212> TYPE: DNA
<213> ORGANISM: Brassica napus
<220> FEATURE:
<221> NAME/KEY: CDS
<222> LOCATION: (1)...(1740)

<400> SEQUENCE: 18

```
atg aat aat aac tgg tta ggc ttt tct ctc tct cct tat gaa caa aat    48
Met Asn Asn Asn Trp Leu Gly Phe Ser Leu Ser Pro Tyr Glu Gln Asn
1               5                   10                  15 cac cat cgt aag gac gtc tac tct tcc acc acc aca acc gtc gta gat    96
His His Arg Lys Asp Val Tyr Ser Ser Thr Thr Thr Thr Val Val Asp
                20                  25                  30 gtc gcc gga gag tac tgt tac gat ccg acc gct gcc tcc gat gag tct    144
Val Ala Gly Glu Tyr Cys Tyr Asp Pro Thr Ala Ala Ser Asp Glu Ser
            35                  40                  45 tca gcc atc caa aca tcg ttt cct tct ccc ttt ggt gtc gtc gtc gat    192
Ser Ala Ile Gln Thr Ser Phe Pro Ser Pro Phe Gly Val Val Val Asp
        50                  55                  60 gct ttc acc aga gac aac aat agt cac tcc cga gat tgg gac atc aat    240
Ala Phe Thr Arg Asp Asn Asn Ser His Ser Arg Asp Trp Asp Ile Asn
65                  70                  75                  80 ggt tgt gca tgc aat aac atc cac aac gat gag caa gat gga cca aag    288
Gly Cys Ala Cys Asn Asn Ile His Asn Asp Glu Gln Asp Gly Pro Lys
                85                  90                  95 ctt gag aat ttc ctt ggc cgc acc acc acg att tac aac acc aac gaa    336
Leu Glu Asn Phe Leu Gly Arg Thr Thr Thr Ile Tyr Asn Thr Asn Glu
                100                 105                 110 aac gtt gga gat gga agt gga agt ggc tgt tat gga gga gga gac ggt    384
Asn Val Gly Asp Gly Ser Gly Ser Gly Cys Tyr Gly Gly Gly Asp Gly
            115                 120                 125 ggt ggt ggc tca cta gga ctt tcg atg ata aag aca tgg ctg aga aat    432
Gly Gly Gly Ser Leu Gly Leu Ser Met Ile Lys Thr Trp Leu Arg Asn
        130                 135                 140
```

-continued

| | |
|---|---|
| caa ccc gtg gat aat gtt gat aat caa gaa aat ggc aat gct gca aaa<br>Gln Pro Val Asp Asn Val Asp Asn Gln Glu Asn Gly Asn Ala Ala Lys<br>145                   150                   155                   160 | 480 |
| ggc ctg tcc ctc tca atg aac tca tct act tct tgt gat aac aac aac<br>Gly Leu Ser Leu Ser Met Asn Ser Ser Thr Ser Cys Asp Asn Asn Asn<br>                  165                   170                   175 | 528 |
| gac agc aat aac aac gtt gtt gcc caa ggg aag act att gat gat agc<br>Asp Ser Asn Asn Asn Val Val Ala Gln Gly Lys Thr Ile Asp Asp Ser<br>         180                   185                   190 | 576 |
| gtt gaa gct aca ccg aag aaa act att gag agt ttt gga cag agg acg<br>Val Glu Ala Thr Pro Lys Lys Thr Ile Glu Ser Phe Gly Gln Arg Thr<br>195                   200                   205 | 624 |
| tct ata tac cgc ggt gtt aca agg cat cgg tgg aca gga aga tat gag<br>Ser Ile Tyr Arg Gly Val Thr Arg His Arg Trp Thr Gly Arg Tyr Glu<br>         210                   215                   220 | 672 |
| gca cat tta tgg gat aat agt tgt aaa aga gaa ggc caa acg cgc aaa<br>Ala His Leu Trp Asp Asn Ser Cys Lys Arg Glu Gly Gln Thr Arg Lys<br>225                   230                   235                   240 | 720 |
| gga aga caa gtt tat ttg gga ggt tat gac aaa gaa gaa aaa gca gct<br>Gly Arg Gln Val Tyr Leu Gly Gly Tyr Asp Lys Glu Glu Lys Ala Ala<br>                  245                   250                   255 | 768 |
| agg gct tat gat tta gcc gca ctc aag tat tgg gga acc acc act act<br>Arg Ala Tyr Asp Leu Ala Ala Leu Lys Tyr Trp Gly Thr Thr Thr Thr<br>         260                   265                   270 | 816 |
| act aac ttc ccc atg agc gaa tat gaa aaa gag gta gaa gag atg aag<br>Thr Asn Phe Pro Met Ser Glu Tyr Glu Lys Glu Val Glu Glu Met Lys<br>275                   280                   285 | 864 |
| cac atg aca agg caa gag tat gtt gcc tca ctg cgc agg aaa agt agt<br>His Met Thr Arg Gln Glu Tyr Val Ala Ser Leu Arg Arg Lys Ser Ser<br>         290                   295                   300 | 912 |
| ggt ttc tct cgt ggt gca tcg att tat cgt gga gta aca aga cat cac<br>Gly Phe Ser Arg Gly Ala Ser Ile Tyr Arg Gly Val Thr Arg His His<br>305                   310                   315                   320 | 960 |
| caa cat gga aga tgg caa gct agg ata gga aga gtc gcc ggt aac aaa<br>Gln His Gly Arg Trp Gln Ala Arg Ile Gly Arg Val Ala Gly Asn Lys<br>                  325                   330                   335 | 1008 |
| gac ctc tac ttg gga act ttt ggc aca caa gaa gaa gct gca gag gca<br>Asp Leu Tyr Leu Gly Thr Phe Gly Thr Gln Glu Glu Ala Ala Glu Ala<br>         340                   345                   350 | 1056 |
| tac gac att gcg gcc atc aaa ttc aga gga tta acc gca gtg act aac<br>Tyr Asp Ile Ala Ala Ile Lys Phe Arg Gly Leu Thr Ala Val Thr Asn<br>                  355                   360                   365 | 1104 |
| ttc gac atg aac aga tac aac gtt aaa gca atc ctc gaa agc cct agt<br>Phe Asp Met Asn Arg Tyr Asn Val Lys Ala Ile Leu Glu Ser Pro Ser<br>370                   375                   380 | 1152 |
| ctt cct att ggt agc gcc gca aaa cgt ctc aag gag gct aac cgt ccg<br>Leu Pro Ile Gly Ser Ala Ala Lys Arg Leu Lys Glu Ala Asn Arg Pro<br>385                   390                   395                   400 | 1200 |
| gtt cca agt atg atg atg atc agt aat aac gtt tca gag agt gag aat<br>Val Pro Ser Met Met Met Ile Ser Asn Asn Val Ser Glu Ser Glu Asn<br>                  405                   410                   415 | 1248 |
| agt gct agc ggt tgg caa aac gct gcg gtt cag cat cat cag gga gta<br>Ser Ala Ser Gly Trp Gln Asn Ala Ala Val Gln His His Gln Gly Val<br>         420                   425                   430 | 1296 |
| gat ttg agc tta ttg cac caa cat caa gag agg tac aat ggt tat tat<br>Asp Leu Ser Leu Leu His Gln His Gln Glu Arg Tyr Asn Gly Tyr Tyr<br>                  435                   440                   445 | 1344 |
| tac aat gga gga aac ttg tct tcg gag agt gct agg gct tgt ttc aaa<br>Tyr Asn Gly Gly Asn Leu Ser Ser Glu Ser Ala Arg Ala Cys Phe Lys | 1392 |

```
                    450                 455                 460
caa gag gat gat caa cac cat ttc ttg agc aac acg cag agc ctc atg      1440
Gln Glu Asp Asp Gln His His Phe Leu Ser Asn Thr Gln Ser Leu Met
465                 470                 475                 480 act aat atc gat cat caa agt tct gtt tcg gat gat tcg gtt act gtt      1488
Thr Asn Ile Asp His Gln Ser Ser Val Ser Asp Asp Ser Val Thr Val
                485                 490                 495 tgt gga aat gtt gtt ggt tat ggt ggt tat caa gga ttt gca gcc ccg      1536
Cys Gly Asn Val Val Gly Tyr Gly Gly Tyr Gln Gly Phe Ala Ala Pro
            500                 505                 510 gtt aac tgc gat gcc tac gct gct agt gag ttt gat tat aac gca aga      1584
Val Asn Cys Asp Ala Tyr Ala Ala Ser Glu Phe Asp Tyr Asn Ala Arg
        515                 520                 525 aac cat tat tac ttt gct cag cag cag cag acc cag cag tcg cca ggt      1632
Asn His Tyr Tyr Phe Ala Gln Gln Gln Gln Thr Gln Gln Ser Pro Gly
    530                 535                 540 gga gat ttt ccc gcg gca atg acg aat aat gtt ggc tct aat atg tat      1680
Gly Asp Phe Pro Ala Ala Met Thr Asn Asn Val Gly Ser Asn Met Tyr
545                 550                 555                 560 tac cat ggg gaa ggt ggt gga gaa gtt gct cca aca ttt aca gtt tgg      1728
Tyr His Gly Glu Gly Gly Gly Glu Val Ala Pro Thr Phe Thr Val Trp
                565                 570                 575 aac gac aat tag                                                      1740
Asn Asp Asn <210> SEQ ID NO 19
<211> LENGTH: 579
<212> TYPE: PRT
<213> ORGANISM: Brassica napus

<400> SEQUENCE: 19

Met Asn Asn Asn Trp Leu Gly Phe Ser Leu Ser Pro Tyr Glu Gln Asn
1               5                   10                  15

His His Arg Lys Asp Val Tyr Ser Ser Thr Thr Thr Val Val Asp
            20                  25                  30

Val Ala Gly Glu Tyr Cys Tyr Asp Pro Thr Ala Ala Ser Asp Glu Ser
        35                  40                  45

Ser Ala Ile Gln Thr Ser Phe Pro Ser Pro Phe Gly Val Val Val Asp
    50                  55                  60

Ala Phe Thr Arg Asp Asn Asn Ser His Ser Arg Asp Trp Asp Ile Asn
65                  70                  75                  80

Gly Cys Ala Cys Asn Asn Ile His Asn Asp Glu Gln Asp Gly Pro Lys
                85                  90                  95

Leu Glu Asn Phe Leu Gly Arg Thr Thr Thr Ile Tyr Asn Thr Asn Glu
            100                 105                 110

Asn Val Gly Asp Gly Ser Gly Ser Gly Cys Tyr Gly Gly Asp Gly
        115                 120                 125

Gly Gly Gly Ser Leu Gly Leu Ser Met Ile Lys Thr Trp Leu Arg Asn
    130                 135                 140

Gln Pro Val Asp Asn Val Asp Asn Gln Glu Asn Gly Asn Ala Ala Lys
145                 150                 155                 160

Gly Leu Ser Leu Ser Met Asn Ser Ser Thr Ser Cys Asp Asn Asn
                165                 170                 175

Asp Ser Asn Asn Asn Val Val Ala Gln Gly Lys Thr Ile Asp Asp Ser
            180                 185                 190

Val Glu Ala Thr Pro Lys Lys Thr Ile Glu Ser Phe Gly Gln Arg Thr
        195                 200                 205
```

```
Ser Ile Tyr Arg Gly Val Thr Arg His Arg Trp Thr Gly Arg Tyr Glu
    210                 215                 220

Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Glu Lys Ala Ala
                245                 250                 255

Arg Ala Tyr Asp Leu Ala Ala Leu Lys Tyr Trp Gly Thr Thr Thr Thr
                260                 265                 270

Thr Asn Phe Pro Met Ser Glu Tyr Glu Lys Glu Val Glu Glu Met Lys
            275                 280                 285

His Met Thr Arg Gln Glu Tyr Val Ala Ser Leu Arg Arg Lys Ser Ser
    290                 295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
                325                 330                 335

Asp Leu Tyr Leu Gly Thr Phe Gly Thr Gln Glu Ala Ala Glu Ala
                340                 345                 350

Tyr Asp Ile Ala Ala Ile Lys Phe Arg Gly Leu Thr Ala Val Thr Asn
                355                 360                 365

Phe Asp Met Asn Arg Tyr Asn Val Lys Ala Ile Leu Glu Ser Pro Ser
370                 375                 380

Leu Pro Ile Gly Ser Ala Ala Lys Arg Leu Lys Glu Ala Asn Arg Pro
385                 390                 395                 400

Val Pro Ser Met Met Met Ile Ser Asn Asn Val Ser Glu Ser Glu Asn
                405                 410                 415

Ser Ala Ser Gly Trp Gln Asn Ala Ala Val Gln His Gln Gly Val
                420                 425                 430

Asp Leu Ser Leu Leu His Gln His Gln Glu Arg Tyr Asn Gly Tyr Tyr
                435                 440                 445

Tyr Asn Gly Gly Asn Leu Ser Ser Glu Ser Ala Arg Ala Cys Phe Lys
    450                 455                 460

Gln Glu Asp Asp Gln His His Phe Leu Ser Asn Thr Gln Ser Leu Met
465                 470                 475                 480

Thr Asn Ile Asp His Gln Ser Ser Val Ser Asp Asp Ser Val Thr Val
                485                 490                 495

Cys Gly Asn Val Val Gly Tyr Gly Gly Tyr Gln Gly Phe Ala Ala Pro
                500                 505                 510

Val Asn Cys Asp Ala Tyr Ala Ala Ser Glu Phe Asp Tyr Asn Ala Arg
                515                 520                 525

Asn His Tyr Tyr Phe Ala Gln Gln Gln Gln Thr Gln Gln Ser Pro Gly
    530                 535                 540

Gly Asp Phe Pro Ala Ala Met Thr Asn Asn Val Gly Ser Asn Met Tyr
545                 550                 555                 560

Tyr His Gly Glu Gly Gly Gly Glu Val Ala Pro Thr Phe Thr Val Trp
                565                 570                 575

Asn Asp Asn

<210> SEQ ID NO 20
<211> LENGTH: 1740
<212> TYPE: DNA
<213> ORGANISM: Brassica napus
<220> FEATURE:
<221> NAME/KEY: CDS
```

<222> LOCATION: (1)...(1740)

<400> SEQUENCE: 20

```
atg aat aat aac tgg tta ggc ttt tct ctc tct cct tat gaa caa aat      48
Met Asn Asn Asn Trp Leu Gly Phe Ser Leu Ser Pro Tyr Glu Gln Asn
 1               5                  10                  15 cac cat cgt aag gac gtc tgc tct tcc acc acc aca acc gcc gta gat      96
His His Arg Lys Asp Val Cys Ser Ser Thr Thr Thr Thr Ala Val Asp
             20                  25                  30 gtc gcc gga gag tac tgt tac gat ccg acc gct gcc tcc gat gag tct     144
Val Ala Gly Glu Tyr Cys Tyr Asp Pro Thr Ala Ala Ser Asp Glu Ser
         35                  40                  45 tca gcc atc caa aca tcg ttt cct tct ccc ttt ggt gtc gtc ctc gat     192
Ser Ala Ile Gln Thr Ser Phe Pro Ser Pro Phe Gly Val Val Leu Asp
     50                  55                  60 gct ttc acc aga gac aac aat agt cac tcc cga gat tgg gac atc aat     240
Ala Phe Thr Arg Asp Asn Asn Ser His Ser Arg Asp Trp Asp Ile Asn
 65                  70                  75                  80 ggt agt gca tgt aat aac atc cac aat gat gag caa gat gga cca aaa     288
Gly Ser Ala Cys Asn Asn Ile His Asn Asp Glu Gln Asp Gly Pro Lys
                 85                  90                  95 ctt gag aat ttc ctt ggc cgc acc acc acg att tac aac acc aac gaa     336
Leu Glu Asn Phe Leu Gly Arg Thr Thr Thr Ile Tyr Asn Thr Asn Glu
            100                 105                 110 aac gtt gga gat atc gat gga agt ggg tgt tat gga gga gga gac ggt     384
Asn Val Gly Asp Ile Asp Gly Ser Gly Cys Tyr Gly Gly Gly Asp Gly
        115                 120                 125 ggt ggt ggc tca cta gga ctt tcg atg ata aag aca tgg ctg aga aat     432
Gly Gly Gly Ser Leu Gly Leu Ser Met Ile Lys Thr Trp Leu Arg Asn
    130                 135                 140 caa ccc gtg gat aat gtt gat aat caa gaa aat ggc aat ggt gca aaa     480
Gln Pro Val Asp Asn Val Asp Asn Gln Glu Asn Gly Asn Gly Ala Lys
145                 150                 155                 160 ggc ctg tcc ctc tca atg aac tca tct act tct tgt gat aac aac aac     528
Gly Leu Ser Leu Ser Met Asn Ser Ser Thr Ser Cys Asp Asn Asn Asn
                165                 170                 175 tac agc agt aac aac ctt gtt gcc caa ggg aag act att gat gat agc     576
Tyr Ser Ser Asn Asn Leu Val Ala Gln Gly Lys Thr Ile Asp Asp Ser
            180                 185                 190 gtt gaa gct aca ccg aag aaa act att gag agt ttt gga cag agg acg     624
Val Glu Ala Thr Pro Lys Lys Thr Ile Glu Ser Phe Gly Gln Arg Thr
        195                 200                 205 tct ata tac cgc ggt gtt aca agg cat cgg tgg aca gga aga tat gag     672
Ser Ile Tyr Arg Gly Val Thr Arg His Arg Trp Thr Gly Arg Tyr Glu
    210                 215                 220 gca cat tta tgg gat aat agt tgt aaa cga gaa ggc caa acg cgc aaa     720
Ala His Leu Trp Asp Asn Ser Cys Lys Arg Glu Gly Gln Thr Arg Lys
225                 230                 235                 240 gga aga caa gtt tat ttg gga ggt tat gac aaa gaa gaa aaa gca gct     768
Gly Arg Gln Val Tyr Leu Gly Gly Tyr Asp Lys Glu Glu Lys Ala Ala
                245                 250                 255 agg gct tat gat tta gcc gca ctc aag tat tgg gga acc acc act act     816
Arg Ala Tyr Asp Leu Ala Ala Leu Lys Tyr Trp Gly Thr Thr Thr Thr
            260                 265                 270 act aac ttc ccc atg agc gaa tat gag aaa gag ata gaa gag atg aag     864
Thr Asn Phe Pro Met Ser Glu Tyr Glu Lys Glu Ile Glu Glu Met Lys
        275                 280                 285 cac atg aca agg caa gag tat gtt gcc tca ctt cgc agg aaa agt agt     912
His Met Thr Arg Gln Glu Tyr Val Ala Ser Leu Arg Arg Lys Ser Ser
    290                 295                 300
```

```
ggt ttc tct cgt ggt gca tcg att tat cgt gga gta aca aga cat cac    960
Gly Phe Ser Arg Gly Ala Ser Ile Tyr Arg Gly Val Thr Arg His His
305                 310                 315                 320 caa cat gga aga tgg caa gct agg ata gga aga gtc gcc ggt aac aaa   1008
Gln His Gly Arg Trp Gln Ala Arg Ile Gly Arg Val Ala Gly Asn Lys
                325                 330                 335 gac ctc tac ttg gga act ttt ggc aca caa gaa gaa gct gca gag gca   1056
Asp Leu Tyr Leu Gly Thr Phe Gly Thr Gln Glu Glu Ala Ala Glu Ala
            340                 345                 350 tac gac att gcg gcc atc aaa ttc aga gga tta acc gca gtg act aac   1104
Tyr Asp Ile Ala Ala Ile Lys Phe Arg Gly Leu Thr Ala Val Thr Asn
        355                 360                 365 ttc gac atg aac aga tac aac gtt aaa gca atc ctc gaa agc cct agt   1152
Phe Asp Met Asn Arg Tyr Asn Val Lys Ala Ile Leu Glu Ser Pro Ser
    370                 375                 380 ctt cct att ggt agc gcc gca aaa cgt ctc aag gag gct aac cgt ccg   1200
Leu Pro Ile Gly Ser Ala Ala Lys Arg Leu Lys Glu Ala Asn Arg Pro
385                 390                 395                 400 gtt cca agt atg atg atg atc agt aat aac gtt tca gag agt gag aat   1248
Val Pro Ser Met Met Met Ile Ser Asn Asn Val Ser Glu Ser Glu Asn
                405                 410                 415 aat gct agc ggt tgg caa aac gct gcg gtt cag cat cat cag gga gta   1296
Asn Ala Ser Gly Trp Gln Asn Ala Ala Val Gln His His Gln Gly Val
            420                 425                 430 gat ttg agc tta ttg cag caa cat caa gag agg tac aat ggt tat tat   1344
Asp Leu Ser Leu Leu Gln Gln His Gln Glu Arg Tyr Asn Gly Tyr Tyr
        435                 440                 445 tac aat gga gga aac ttg tct tcg gag agt gct agg gct tgt ttc aaa   1392
Tyr Asn Gly Gly Asn Leu Ser Ser Glu Ser Ala Arg Ala Cys Phe Lys
    450                 455                 460 caa gag gat gat caa cac cat ttc ttg agc aac acg cag agc ctc atg   1440
Gln Glu Asp Asp Gln His His Phe Leu Ser Asn Thr Gln Ser Leu Met
465                 470                 475                 480 act aat atc gat cat caa agt tct gtt tca gat gat tcg gtt act gtt   1488
Thr Asn Ile Asp His Gln Ser Ser Val Ser Asp Asp Ser Val Thr Val
                485                 490                 495 tgt gga aat gtt gtt ggt tat ggt ggt tat caa gga ttt gca gcc ccg   1536
Cys Gly Asn Val Val Gly Tyr Gly Gly Tyr Gln Gly Phe Ala Ala Pro
            500                 505                 510 gtt aac tgc gat gcc tac gct gct agt gag ttt gac tat aac gca aga   1584
Val Asn Cys Asp Ala Tyr Ala Ala Ser Glu Phe Asp Tyr Asn Ala Arg
        515                 520                 525 aac cat tat tac ttt gct cag cag cag cag acc cag cat tcg cca gga   1632
Asn His Tyr Tyr Phe Ala Gln Gln Gln Gln Thr Gln His Ser Pro Gly
    530                 535                 540 gga gat ttt ccc gcg gca atg acg aat aat gtt ggc tct aat atg tat   1680
Gly Asp Phe Pro Ala Ala Met Thr Asn Asn Val Gly Ser Asn Met Tyr
545                 550                 555                 560 tac cat ggg gaa ggt ggt gga gaa gtt gct cca aca ttt aca gtt tgg   1728
Tyr His Gly Glu Gly Gly Gly Glu Val Ala Pro Thr Phe Thr Val Trp
                565                 570                 575 aac gac aat tag                                                   1740
Asn Asp Asn <210> SEQ ID NO 21
<211> LENGTH: 579
<212> TYPE: PRT
<213> ORGANISM: Brassica napus

<400> SEQUENCE: 21
```

```
Met Asn Asn Asn Trp Leu Gly Phe Ser Leu Ser Pro Tyr Glu Gln Asn
1               5                   10                  15

His His Arg Lys Asp Val Cys Ser Ser Thr Thr Thr Ala Val Asp
            20                  25                  30

Val Ala Gly Glu Tyr Cys Tyr Asp Pro Thr Ala Ala Ser Asp Glu Ser
        35                  40                  45

Ser Ala Ile Gln Thr Ser Phe Pro Ser Pro Phe Gly Val Val Leu Asp
50                      55                  60

Ala Phe Thr Arg Asp Asn Asn Ser His Ser Arg Asp Trp Asp Ile Asn
65                      70                  75                  80

Gly Ser Ala Cys Asn Asn Ile His Asn Asp Glu Gln Asp Gly Pro Lys
                85                  90                  95

Leu Glu Asn Phe Leu Gly Arg Thr Thr Thr Ile Tyr Asn Thr Asn Glu
                100                 105                 110

Asn Val Gly Asp Ile Asp Gly Ser Gly Cys Tyr Gly Gly Gly Asp Gly
            115                 120                 125

Gly Gly Gly Ser Leu Gly Leu Ser Met Ile Lys Thr Trp Leu Arg Asn
130                 135                 140

Gln Pro Val Asp Asn Val Asp Asn Gln Glu Asn Gly Asn Gly Ala Lys
145                 150                 155                 160

Gly Leu Ser Leu Ser Met Asn Ser Ser Thr Ser Cys Asp Asn Asn
                165                 170                 175

Tyr Ser Ser Asn Asn Leu Val Ala Gln Gly Lys Thr Ile Asp Asp Ser
                180                 185                 190

Val Glu Ala Thr Pro Lys Lys Thr Ile Glu Ser Phe Gly Gln Arg Thr
            195                 200                 205

Ser Ile Tyr Arg Gly Val Thr Arg His Arg Trp Thr Gly Arg Tyr Glu
210                 215                 220

Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Lys Ala Ala
                245                 250                 255

Arg Ala Tyr Asp Leu Ala Ala Leu Lys Tyr Trp Gly Thr Thr Thr Thr
            260                 265                 270

Thr Asn Phe Pro Met Ser Glu Tyr Glu Lys Glu Ile Glu Glu Met Lys
            275                 280                 285

His Met Thr Arg Gln Glu Tyr Val Ala Ser Leu Arg Arg Lys Ser Ser
        290                 295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
                325                 330                 335

Asp Leu Tyr Leu Gly Thr Phe Gly Thr Gln Glu Glu Ala Ala Glu Ala
            340                 345                 350

Tyr Asp Ile Ala Ala Ile Lys Phe Arg Gly Leu Thr Ala Val Thr Asn
        355                 360                 365

Phe Asp Met Asn Arg Tyr Asn Val Lys Ala Ile Leu Glu Ser Pro Ser
        370                 375                 380

Leu Pro Ile Gly Ser Ala Ala Lys Arg Leu Lys Glu Ala Asn Arg Pro
385                 390                 395                 400

Val Pro Ser Met Met Met Ile Ser Asn Asn Val Ser Glu Ser Glu Asn
                405                 410                 415
```

-continued

```
Asn Ala Ser Gly Trp Gln Asn Ala Ala Val Gln His His Gln Gly Val
            420                 425                 430
Asp Leu Ser Leu Leu Gln His Gln Glu Arg Tyr Asn Gly Tyr Tyr
        435                 440                 445
Tyr Asn Gly Gly Asn Leu Ser Ser Glu Ser Ala Arg Ala Cys Phe Lys
    450                 455                 460
Gln Glu Asp Asp Gln His His Phe Leu Ser Asn Thr Gln Ser Leu Met
465                 470                 475                 480
Thr Asn Ile Asp His Gln Ser Ser Val Ser Asp Asp Ser Val Thr Val
                485                 490                 495
Cys Gly Asn Val Val Gly Tyr Gly Tyr Gln Gly Phe Ala Ala Pro
            500                 505                 510
Val Asn Cys Asp Ala Tyr Ala Ala Ser Glu Phe Asp Tyr Asn Ala Arg
        515                 520                 525
Asn His Tyr Tyr Phe Ala Gln Gln Gln Thr Gln His Ser Pro Gly
    530                 535                 540
Gly Asp Phe Pro Ala Ala Met Thr Asn Asn Val Gly Ser Asn Met Tyr
545                 550                 555                 560
Tyr His Gly Glu Gly Gly Gly Glu Val Ala Pro Thr Phe Thr Val Trp
                565                 570                 575
Asn Asp Asn
```

<210> SEQ ID NO 22
<211> LENGTH: 2070
<212> TYPE: DNA
<213> ORGANISM: Medicago truncatula
<220> FEATURE:
<221> NAME/KEY: CDS
<222> LOCATION: (1)...(2070)

<400> SEQUENCE: 22

```
atg gcc tct atg aac ttg tta ggt ttc tct cta tct cca caa gaa caa      48
Met Ala Ser Met Asn Leu Leu Gly Phe Ser Leu Ser Pro Gln Glu Gln
  1               5                  10                  15 cat cca tca aca caa gat caa acg gtg gct tcc cgt ttt ggg ttc aac      96
His Pro Ser Thr Gln Asp Gln Thr Val Ala Ser Arg Phe Gly Phe Asn
              20                  25                  30 cct aat gaa atc tca ggc tct gat gtt caa gga gat cac tgc tat gat     144
Pro Asn Glu Ile Ser Gly Ser Asp Val Gln Gly Asp His Cys Tyr Asp
          35                  40                  45 ctc tct tct cac aca act cct cat cat tca ctc aac ctt tct cat cct     192
Leu Ser Ser His Thr Thr Pro His His Ser Leu Asn Leu Ser His Pro
      50                  55                  60 ttt tcc att tat gaa gct ttc cac aca aat aac aac att cac acc act     240
Phe Ser Ile Tyr Glu Ala Phe His Thr Asn Asn Asn Ile His Thr Thr
 65                  70                  75                  80 caa gat tgg aag gag aac tac aac aac caa aac cta cta ttg gga aca     288
Gln Asp Trp Lys Glu Asn Tyr Asn Asn Gln Asn Leu Leu Leu Gly Thr
                  85                  90                  95 tca tgc atg aac caa aat gtg aac aac aac aac caa caa gca caa cca     336
Ser Cys Met Asn Gln Asn Val Asn Asn Asn Asn Gln Gln Ala Gln Pro
             100                 105                 110 aag cta gaa aac ttc ctc ggt gga cac tct ttc acc gac cat caa gaa     384
Lys Leu Glu Asn Phe Leu Gly Gly His Ser Phe Thr Asp His Gln Glu
         115                 120                 125 tac ggt ggt agc aac tca tac tct tca tta cac ctc cca cct cat cag     432
Tyr Gly Gly Ser Asn Ser Tyr Ser Ser Leu His Leu Pro Pro His Gln
     130                 135                 140
```

-continued

| | |
|---|---|
| ccg gaa gca tcc tgt ggc ggt ggt gat ggt agt aca agt aac aat aac<br>Pro Glu Ala Ser Cys Gly Gly Gly Asp Gly Ser Thr Ser Asn Asn Asn<br>145                           150                        155                      160 | 480 |
| tca ata ggt tta tct atg ata aaa aca tgg ctc aga aac caa cca cca<br>Ser Ile Gly Leu Ser Met Ile Lys Thr Trp Leu Arg Asn Gln Pro Pro<br>                   165                       170                       175 | 528 |
| cca cca gaa aac aac aac aat aac aac aat gaa agt ggt gca cgt gtg<br>Pro Pro Glu Asn Asn Asn Asn Asn Asn Asn Glu Ser Gly Ala Arg Val<br>              180                       185                       190 | 576 |
| cag aca cta tca ctt tct atg agt act ggc tca cag tca agt tca tct<br>Gln Thr Leu Ser Leu Ser Met Ser Thr Gly Ser Gln Ser Ser Ser Ser<br>195                          200                      205 | 624 |
| gtg cct ctt ctc aat gca aat gtg atg agt ggt gag att tcc tca tcg<br>Val Pro Leu Leu Asn Ala Asn Val Met Ser Gly Glu Ile Ser Ser Ser<br>210                         215                      220 | 672 |
| gaa aac aaa caa cca ccc aca act gca gtt gta ctt gat agc aac caa<br>Glu Asn Lys Gln Pro Pro Thr Thr Ala Val Val Leu Asp Ser Asn Gln<br>225                          230                      235                      240 | 720 |
| aca agt gtc gtt gaa agt gct gtg cct aga aaa tcc gtt gat aca ttt<br>Thr Ser Val Val Glu Ser Ala Val Pro Arg Lys Ser Val Asp Thr Phe<br>                   245                       250                       255 | 768 |
| gga caa aga act tcc att tac cgt ggt gta aca agg cat aga tgg aca<br>Gly Gln Arg Thr Ser Ile Tyr Arg Gly Val Thr Arg His Arg Trp Thr<br>              260                       265                       270 | 816 |
| ggg aga tat gaa gct cac ctt tgg gat aat agt tgt aga aga gag ggg<br>Gly Arg Tyr Glu Ala His Leu Trp Asp Asn Ser Cys Arg Arg Glu Gly<br>                   275                       280                       285 | 864 |
| cag act cgc aaa gga agg caa gtt tac ttg gga ggt tat gac aaa gaa<br>Gln Thr Arg Lys Gly Arg Gln Val Tyr Leu Gly Gly Tyr Asp Lys Glu<br>290                          295                      300 | 912 |
| gaa aaa gca gct aga gcc tat gat ttg gca gca cta aaa tat tgg gga<br>Glu Lys Ala Ala Arg Ala Tyr Asp Leu Ala Ala Leu Lys Tyr Trp Gly<br>305                          310                      315                      320 | 960 |
| aca act act aca aca aat ttt cca att agc cat tat gaa aaa gaa gtg<br>Thr Thr Thr Thr Thr Asn Phe Pro Ile Ser His Tyr Glu Lys Glu Val<br>                       325                       330                      335 | 1008 |
| gaa gaa atg aag cat atg aca agg caa gag tac gtt gcg tca ttg aga<br>Glu Glu Met Lys His Met Thr Arg Gln Glu Tyr Val Ala Ser Leu Arg<br>             340                       345                      350 | 1056 |
| agg aaa agt agt ggt ttt tca cga ggt gca tcc att tac cga gga gta<br>Arg Lys Ser Ser Gly Phe Ser Arg Gly Ala Ser Ile Tyr Arg Gly Val<br>                   355                       360                       365 | 1104 |
| aca aga cat cat caa cat ggt aga tgg caa gct agg att gga aga gtt<br>Thr Arg His His Gln His Gly Arg Trp Gln Ala Arg Ile Gly Arg Val<br>370                          375                      380 | 1152 |
| gca ggc aac aaa gat ctc tac cta gga act ttc agc act caa gaa gag<br>Ala Gly Asn Lys Asp Leu Tyr Leu Gly Thr Phe Ser Thr Gln Glu Glu<br>385                          390                      395                      400 | 1200 |
| gca gca gag gca tat gat gtg gca gca ata aaa ttc aga gga ctg agt<br>Ala Ala Glu Ala Tyr Asp Val Ala Ala Ile Lys Phe Arg Gly Leu Ser<br>                   405                       410                      415 | 1248 |
| gca gtt aca aac ttt gac atg agc aga tat gat gtc aaa acc ata ctt<br>Ala Val Thr Asn Phe Asp Met Ser Arg Tyr Asp Val Lys Thr Ile Leu<br>              420                       425                      430 | 1296 |
| gag agc agc aca tta cca att ggt ggt gct gca aag cgt tta aaa gac<br>Glu Ser Ser Thr Leu Pro Ile Gly Gly Ala Ala Lys Arg Leu Lys Asp<br>             435                       440                      445 | 1344 |
| atg gag caa gtt gaa ttg aat cat gtg aat gtt gat att agc cat aga<br>Met Glu Gln Val Glu Leu Asn His Val Asn Val Asp Ile Ser His Arg<br>450                          455                      460 | 1392 |

```
act gaa caa gat cat agc atc atc aac aac act tcc cat tta aca gaa    1440
Thr Glu Gln Asp His Ser Ile Ile Asn Asn Thr Ser His Leu Thr Glu
465                 470                 475                 480 caa gcc atc tat gca gca aca aat gca tct aat tgg cat gca ctt tca    1488
Gln Ala Ile Tyr Ala Ala Thr Asn Ala Ser Asn Trp His Ala Leu Ser
            485                 490                 495 ttc caa cat caa caa cca cat cat cat tac aat gcc aac aac atg cag    1536
Phe Gln His Gln Gln Pro His His His Tyr Asn Ala Asn Asn Met Gln
        500                 505                 510 tta cag aat tat cct tat gga act caa act caa aag ctt tgg tgc aaa    1584
Leu Gln Asn Tyr Pro Tyr Gly Thr Gln Thr Gln Lys Leu Trp Cys Lys
    515                 520                 525 caa gaa caa gat tct gat gat cat agt act tat act act gct act gat    1632
Gln Glu Gln Asp Ser Asp Asp His Ser Thr Tyr Thr Thr Ala Thr Asp
530                 535                 540 att cat caa cta cag tta ggg aat aat aat aac aat act cac aat ttc    1680
Ile His Gln Leu Gln Leu Gly Asn Asn Asn Asn Asn Thr His Asn Phe
545                 550                 555                 560 ttt ggt tta caa aat atc atg agt atg gat tct gct tcc atg gat aat    1728
Phe Gly Leu Gln Asn Ile Met Ser Met Asp Ser Ala Ser Met Asp Asn
            565                 570                 575 agt tct gga tct aat tct gtt gtt tat ggt ggt gga gat cat ggt ggt    1776
Ser Ser Gly Ser Asn Ser Val Val Tyr Gly Gly Gly Asp His Gly Gly
        580                 585                 590 tat gga gga aat ggt gga tat atg att cca atg gct att gca aat gat    1824
Tyr Gly Gly Asn Gly Gly Tyr Met Ile Pro Met Ala Ile Ala Asn Asp
    595                 600                 605 ggt aac caa aat cca aga agc aac aac aat ttt ggt gag agt gag att    1872
Gly Asn Gln Asn Pro Arg Ser Asn Asn Asn Phe Gly Glu Ser Glu Ile
610                 615                 620 aaa gga ttt ggt tat gaa aat gtt ttt ggg act act act gat cct tat    1920
Lys Gly Phe Gly Tyr Glu Asn Val Phe Gly Thr Thr Thr Asp Pro Tyr
625                 630                 635                 640 cat gca cag gca gca agg aac ttg tac tat cag cca caa caa tta tct    1968
His Ala Gln Ala Ala Arg Asn Leu Tyr Tyr Gln Pro Gln Gln Leu Ser
            645                 650                 655 gtt gat caa gga tca aat tgg gtt cca act gct att cca aca ctt gct    2016
Val Asp Gln Gly Ser Asn Trp Val Pro Thr Ala Ile Pro Thr Leu Ala
        660                 665                 670 cca agg act acc aat gtc tct cta tgt cct cct ttc act ttg ttg cat    2064
Pro Arg Thr Thr Asn Val Ser Leu Cys Pro Pro Phe Thr Leu Leu His
    675                 680                 685 gaa tag                                                            2070
Glu

<210> SEQ ID NO 23
<211> LENGTH: 689
<212> TYPE: PRT
<213> ORGANISM: Medicago truncatula

<400> SEQUENCE: 23

Met Ala Ser Met Asn Leu Leu Gly Phe Ser Leu Ser Pro Gln Glu Gln
1               5                   10                  15

His Pro Ser Thr Gln Asp Gln Thr Val Ala Ser Arg Phe Gly Phe Asn
            20                  25                  30

Pro Asn Glu Ile Ser Gly Ser Asp Val Gln Gly Asp His Cys Tyr Asp
        35                  40                  45

Leu Ser Ser His Thr Thr Pro His His Ser Leu Asn Leu Ser His Pro
    50                  55                  60
```

-continued

```
Phe Ser Ile Tyr Glu Ala Phe His Thr Asn Asn Ile His Thr Thr
 65                  70                  75                  80

Gln Asp Trp Lys Glu Asn Tyr Asn Asn Gln Asn Leu Leu Leu Gly Thr
                 85                  90                  95

Ser Cys Met Asn Gln Asn Val Asn Asn Asn Gln Gln Ala Gln Pro
            100                 105                 110

Lys Leu Glu Asn Phe Leu Gly Gly His Ser Phe Thr Asp His Gln Glu
            115                 120                 125

Tyr Gly Gly Ser Asn Ser Tyr Ser Ser Leu His Leu Pro Pro His Gln
            130                 135                 140

Pro Glu Ala Ser Cys Gly Gly Asp Gly Ser Thr Ser Asn Asn Asn
145                 150                 155                 160

Ser Ile Gly Leu Ser Met Ile Lys Thr Trp Leu Arg Asn Gln Pro Pro
                165                 170                 175

Pro Pro Glu Asn Asn Asn Asn Asn Asn Glu Ser Gly Ala Arg Val
            180                 185                 190

Gln Thr Leu Ser Leu Ser Met Ser Thr Gly Ser Gln Ser Ser Ser Ser
            195                 200                 205

Val Pro Leu Leu Asn Ala Asn Val Met Ser Gly Glu Ile Ser Ser Ser
210                 215                 220

Glu Asn Lys Gln Pro Pro Thr Thr Ala Val Val Leu Asp Ser Asn Gln
225                 230                 235                 240

Thr Ser Val Val Glu Ser Ala Val Pro Arg Lys Ser Val Asp Thr Phe
                245                 250                 255

Gly Gln Arg Thr Ser Ile Tyr Arg Gly Val Thr Arg His Arg Trp Thr
            260                 265                 270

Gly Arg Tyr Glu Ala His Leu Trp Asp Asn Ser Cys Arg Arg Glu Gly
            275                 280                 285

Gln Thr Arg Lys Gly Arg Gln Val Tyr Leu Gly Gly Tyr Asp Lys Glu
            290                 295                 300

Glu Lys Ala Ala Arg Ala Tyr Asp Leu Ala Ala Leu Lys Tyr Trp Gly
305                 310                 315                 320

Thr Thr Thr Thr Thr Asn Phe Pro Ile Ser His Tyr Glu Lys Glu Val
                325                 330                 335

Glu Glu Met Lys His Met Thr Arg Gln Glu Tyr Val Ala Ser Leu Arg
            340                 345                 350

Arg Lys Ser Ser Gly Phe Ser Arg Gly Ala Ser Ile Tyr Arg Gly Val
            355                 360                 365

Thr Arg His His Gln His Gly Arg Trp Gln Ala Arg Ile Gly Arg Val
            370                 375                 380

Ala Gly Asn Lys Asp Leu Tyr Leu Gly Thr Phe Ser Thr Gln Glu Glu
385                 390                 395                 400

Ala Ala Glu Ala Tyr Asp Val Ala Ala Ile Lys Phe Arg Gly Leu Ser
                405                 410                 415

Ala Val Thr Asn Phe Asp Met Ser Arg Tyr Asp Val Lys Thr Ile Leu
            420                 425                 430

Glu Ser Ser Thr Leu Pro Ile Gly Gly Ala Ala Lys Arg Leu Lys Asp
            435                 440                 445

Met Glu Gln Val Glu Leu Asn His Val Asn Val Asp Ile Ser His Arg
            450                 455                 460

Thr Glu Gln Asp His Ser Ile Ile Asn Asn Thr Ser His Leu Thr Glu
465                 470                 475                 480
```

```
Gln Ala Ile Tyr Ala Ala Thr Asn Ala Ser Asn Trp His Ala Leu Ser
                485                 490                 495

Phe Gln His Gln Gln Pro His His Tyr Asn Ala Asn Asn Met Gln
        500                 505                 510

Leu Gln Asn Tyr Pro Tyr Gly Thr Gln Thr Gln Lys Leu Trp Cys Lys
        515                 520                 525

Gln Glu Gln Asp Ser Asp His Ser Thr Tyr Thr Ala Thr Asp
    530                 535                 540

Ile His Gln Leu Gln Leu Gly Asn Asn Asn Asn Thr His Asn Phe
545                 550                 555                 560

Phe Gly Leu Gln Asn Ile Met Ser Met Asp Ser Ala Ser Met Asp Asn
                565                 570                 575

Ser Ser Gly Ser Asn Ser Val Val Tyr Gly Gly Gly Asp His Gly Gly
            580                 585                 590

Tyr Gly Gly Asn Gly Gly Tyr Met Ile Pro Met Ala Ile Ala Asn Asp
            595                 600                 605

Gly Asn Gln Asn Pro Arg Ser Asn Asn Asn Phe Gly Glu Ser Glu Ile
    610                 615                 620

Lys Gly Phe Gly Tyr Glu Asn Val Phe Gly Thr Thr Thr Asp Pro Tyr
625                 630                 635                 640

His Ala Gln Ala Ala Arg Asn Leu Tyr Tyr Gln Pro Gln Gln Leu Ser
                645                 650                 655

Val Asp Gln Gly Ser Asn Trp Val Pro Thr Ala Ile Pro Thr Leu Ala
            660                 665                 670

Pro Arg Thr Thr Asn Val Ser Leu Cys Pro Pro Phe Thr Leu Leu His
        675                 680                 685

Glu

<210> SEQ ID NO 24
<211> LENGTH: 2133
<212> TYPE: DNA
<213> ORGANISM: Glycine max
<220> FEATURE:
<221> NAME/KEY: CDS
<222> LOCATION: (1)...(2133)

<400> SEQUENCE: 24 atg ggg tct atg aat ttg tta ggt ttt tct ctc tct cct caa gaa cac      48
Met Gly Ser Met Asn Leu Leu Gly Phe Ser Leu Ser Pro Gln Glu His
 1               5                  10                  15 cct tct agt caa gat cac tct caa acg gca cct tct cgt ttt tgc ttc      96
Pro Ser Ser Gln Asp His Ser Gln Thr Ala Pro Ser Arg Phe Cys Phe
            20                  25                  30 aac cct gat gga atc tca agc act gat gta gca gga gac tgc ttt gat     144
Asn Pro Asp Gly Ile Ser Ser Thr Asp Val Ala Gly Asp Cys Phe Asp
        35                  40                  45 ctc act tct gac tca act cct cat tta ctc aac ctt ccc tct tac ggc     192
Leu Thr Ser Asp Ser Thr Pro His Leu Leu Asn Leu Pro Ser Tyr Gly
    50                  55                  60 ata tac gaa gct ttt cat agg agc aac aat att cac acc act caa gat     240
Ile Tyr Glu Ala Phe His Arg Ser Asn Asn Ile His Thr Thr Gln Asp
65                  70                  75                  80 tgg aag gag aac tac aac agc caa aac ttg cta ttg gga act tca tgc     288
Trp Lys Glu Asn Tyr Asn Ser Gln Asn Leu Leu Leu Gly Thr Ser Cys
                85                  90                  95 agc aac caa aac atg aac cac aac cat cag caa caa caa caa caa cag     336
Ser Asn Gln Asn Met Asn His Asn His Gln Gln Gln Gln Gln Gln Gln
            100                 105                 110
```

```
cca aag ctt gaa aac ttc ctc ggt gga cac tca ttt ggt gaa cat gag    384
Pro Lys Leu Glu Asn Phe Leu Gly Gly His Ser Phe Gly Glu His Glu
            115                 120                 125 caa ccc tac ggt ggt aac tca gcc tct aca gaa tac atg ttc ccg gct    432
Gln Pro Tyr Gly Gly Asn Ser Ala Ser Thr Glu Tyr Met Phe Pro Ala
    130                 135                 140 cag ccg gta ttg gcc ggt ggc ggc ggt ggt agc aat agc agc aac        480
Gln Pro Val Leu Ala Gly Gly Gly Gly Gly Ser Asn Ser Ser Asn
145                 150                 155                 160 aca agc aac agt agc tcc ata ggg tta tcc atg ata aag aca tgg ttg    528
Thr Ser Asn Ser Ser Ser Ile Gly Leu Ser Met Ile Lys Thr Trp Leu
            165                 170                 175 agg aac caa cca cca cac tca gaa aac aac aat aac aac aat gaa        576
Arg Asn Gln Pro Pro His Ser Glu Asn Asn Asn Asn Asn Asn Glu
    180                 185                 190 agt ggt ggc aat agt aga agc agt gtg cag cag act cta tca ctt tcc    624
Ser Gly Gly Asn Ser Arg Ser Ser Val Gln Gln Thr Leu Ser Leu Ser
            195                 200                 205 atg agt act ggt tca caa tca agc aca tca cta ccc ctt ctc act gct    672
Met Ser Thr Gly Ser Gln Ser Ser Thr Ser Leu Pro Leu Leu Thr Ala
    210                 215                 220 agt gtg gat aat gga gag agt tct tct gat aac aaa caa cca cat acc    720
Ser Val Asp Asn Gly Glu Ser Ser Ser Asp Asn Lys Gln Pro His Thr
225                 230                 235                 240 acg gct gca ctt gat aca acc caa acc gga gcc att gaa act gca ccc    768
Thr Ala Ala Leu Asp Thr Thr Gln Thr Gly Ala Ile Glu Thr Ala Pro
            245                 250                 255 aga aag tcc att gac act ttt gga cag aga act tct atc tac cgt ggt    816
Arg Lys Ser Ile Asp Thr Phe Gly Gln Arg Thr Ser Ile Tyr Arg Gly
    260                 265                 270 gta aca agg cat agg tgg acg ggg agg tat gag gct cac ctg tgg gat    864
Val Thr Arg His Arg Trp Thr Gly Arg Tyr Glu Ala His Leu Trp Asp
            275                 280                 285 aat agt tgt aga aga gag gga caa act cgc aaa gga agg caa gtt tac    912
Asn Ser Cys Arg Arg Glu Gly Gln Thr Arg Lys Gly Arg Gln Val Tyr
    290                 295                 300 ttg gga ggt tat gac aaa gaa gaa aag gca gct aga gcc tac gat ttg    960
Leu Gly Gly Tyr Asp Lys Glu Glu Lys Ala Ala Arg Ala Tyr Asp Leu
305                 310                 315                 320 gca gca cta aaa tac tgg gga aca act acg aca aca aat ttt cca att    1008
Ala Ala Leu Lys Tyr Trp Gly Thr Thr Thr Thr Thr Asn Phe Pro Ile
            325                 330                 335 agc cac tat gag aaa gag ttg gaa gaa atg aag cac atg act agg caa    1056
Ser His Tyr Glu Lys Glu Leu Glu Glu Met Lys His Met Thr Arg Gln
    340                 345                 350 gag tac gtt gcg tca ttg aga agg aag agt agt ggg ttt tct cgc ggg    1104
Glu Tyr Val Ala Ser Leu Arg Arg Lys Ser Ser Gly Phe Ser Arg Gly
            355                 360                 365 gca tcc att tat cga ggt gtg acg aga cac cat caa cat gga aga tgg    1152
Ala Ser Ile Tyr Arg Gly Val Thr Arg His His Gln His Gly Arg Trp
    370                 375                 380 caa gcg agg att gga aga gtt gct ggc aac aag gat ctc tac ttg gga    1200
Gln Ala Arg Ile Gly Arg Val Ala Gly Asn Lys Asp Leu Tyr Leu Gly
385                 390                 395                 400 act ttc agc acc caa gag gag gca gca gaa gca tat gat gta gca gca    1248
Thr Phe Ser Thr Gln Glu Glu Ala Ala Glu Ala Tyr Asp Val Ala Ala
            405                 410                 415 atc aaa ttc aga gga cta agt gct gtt aca aac ttt gac atg agc aga    1296
Ile Lys Phe Arg Gly Leu Ser Ala Val Thr Asn Phe Asp Met Ser Arg
```

```
                420              425              430
tat gac gtg aaa agc ata ctt gag agc acc act ttg cca att ggt ggt      1344
Tyr Asp Val Lys Ser Ile Leu Glu Ser Thr Thr Leu Pro Ile Gly Gly
            435              440              445 gct gca aag cgt ttg aag gat atg gag cag gtg gaa ctg agg gtg gag      1392
Ala Ala Lys Arg Leu Lys Asp Met Glu Gln Val Glu Leu Arg Val Glu
    450              455              460 aat gtt cat aga gca gat caa gaa gat cat agt agc atc atg aac tct      1440
Asn Val His Arg Ala Asp Gln Glu Asp His Ser Ser Ile Met Asn Ser
465              470              475              480 cac tta act caa gga atc att aac aac tat gca gca gga gga aca aca      1488
His Leu Thr Gln Gly Ile Ile Asn Asn Tyr Ala Ala Gly Gly Thr Thr
                485              490              495 gcg act cat cat cat aac tgg cac aat gct ctt gca ttc cac caa cct      1536
Ala Thr His His His Asn Trp His Asn Ala Leu Ala Phe His Gln Pro
            500              505              510 caa cct tgc acc acc ata cac tac cct tat gga caa aga att aat tgg      1584
Gln Pro Cys Thr Thr Ile His Tyr Pro Tyr Gly Gln Arg Ile Asn Trp
    515              520              525 tgc aag caa gaa caa gac aac tct gat gcc tct cac tct ttg tct tat      1632
Cys Lys Gln Glu Gln Asp Asn Ser Asp Ala Ser His Ser Leu Ser Tyr
530              535              540 tca gat att cat caa cta cag cta ggg aac aat ggc aca cac aac ttc      1680
Ser Asp Ile His Gln Leu Gln Leu Gly Asn Asn Gly Thr His Asn Phe
545              550              555              560 ttt cac aca aat tca ggg ttg cac cct atg tta agc atg gat tct gct      1728
Phe His Thr Asn Ser Gly Leu His Pro Met Leu Ser Met Asp Ser Ala
                565              570              575 tcc att gac aat agc tct tca tct aac tct gtt gtt tat gat ggt tat      1776
Ser Ile Asp Asn Ser Ser Ser Ser Asn Ser Val Val Tyr Asp Gly Tyr
            580              585              590 gga ggt ggt ggg ggc tat aat gtg att cct atg ggg act act act act      1824
Gly Gly Gly Gly Gly Tyr Asn Val Ile Pro Met Gly Thr Thr Thr Thr
    595              600              605 gtt gtt gca aat gat ggt gat caa aat cca aga agc aat cat ggt ttt      1872
Val Val Ala Asn Asp Gly Asp Gln Asn Pro Arg Ser Asn His Gly Phe
610              615              620 ggt gat aat gag ata aag gca ctt ggt tat gaa agt gtg tat ggt tct      1920
Gly Asp Asn Glu Ile Lys Ala Leu Gly Tyr Glu Ser Val Tyr Gly Ser
625              630              635              640 aca act gat cct tat cat gca cat gca agg aac ttg tat tat ctt act      1968
Thr Thr Asp Pro Tyr His Ala His Ala Arg Asn Leu Tyr Tyr Leu Thr
                645              650              655 caa cag caa cca tct tct gtt gat gca gtg aag gct agt gca tat gat      2016
Gln Gln Gln Pro Ser Ser Val Asp Ala Val Lys Ala Ser Ala Tyr Asp
            660              665              670 caa gga tct gca tgc aat act tgg gtt cca act gct att cca act cat      2064
Gln Gly Ser Ala Cys Asn Thr Trp Val Pro Thr Ala Ile Pro Thr His
    675              680              685 gca cca agg tct agt act agt atg gct ctc tgc cat ggt gct acg ccc      2112
Ala Pro Arg Ser Ser Thr Ser Met Ala Leu Cys His Gly Ala Thr Pro
690              695              700 ttc tct tta ttg cat gaa tag                                          2133
Phe Ser Leu Leu His Glu
705              710

<210> SEQ ID NO 25
<211> LENGTH: 710
<212> TYPE: PRT
<213> ORGANISM: Glycine max
```

<400> SEQUENCE: 25

```
Met Gly Ser Met Asn Leu Leu Gly Phe Ser Leu Ser Pro Gln Glu His
1               5                   10                  15

Pro Ser Ser Gln Asp His Ser Gln Thr Ala Pro Ser Arg Phe Cys Phe
            20                  25                  30

Asn Pro Asp Gly Ile Ser Ser Thr Asp Val Ala Gly Asp Cys Phe Asp
        35                  40                  45

Leu Thr Ser Asp Ser Thr Pro His Leu Leu Asn Leu Pro Ser Tyr Gly
    50                  55                  60

Ile Tyr Glu Ala Phe His Arg Ser Asn Asn Ile His Thr Thr Gln Asp
65                  70                  75                  80

Trp Lys Glu Asn Tyr Asn Ser Gln Asn Leu Leu Leu Gly Thr Ser Cys
                85                  90                  95

Ser Asn Gln Asn Met Asn His Asn His Gln Gln Gln Gln Gln Gln Gln
            100                 105                 110

Pro Lys Leu Glu Asn Phe Leu Gly Gly His Ser Phe Gly Glu His Glu
            115                 120                 125

Gln Pro Tyr Gly Gly Asn Ser Ala Ser Thr Glu Tyr Met Phe Pro Ala
    130                 135                 140

Gln Pro Val Leu Ala Gly Gly Gly Gly Gly Ser Asn Ser Ser Asn
145                 150                 155                 160

Thr Ser Asn Ser Ser Ile Gly Leu Ser Met Ile Lys Thr Trp Leu
                165                 170                 175

Arg Asn Gln Pro Pro His Ser Glu Asn Asn Asn Asn Asn Asn Glu
            180                 185                 190

Ser Gly Gly Asn Ser Arg Ser Ser Val Gln Gln Thr Leu Ser Leu Ser
    195                 200                 205

Met Ser Thr Gly Ser Gln Ser Ser Thr Ser Leu Pro Leu Leu Thr Ala
    210                 215                 220

Ser Val Asp Asn Gly Glu Ser Ser Asp Asn Lys Gln Pro His Thr
225                 230                 235                 240

Thr Ala Ala Leu Asp Thr Thr Gln Thr Gly Ala Ile Glu Thr Ala Pro
                245                 250                 255

Arg Lys Ser Ile Asp Thr Phe Gly Gln Arg Thr Ser Ile Tyr Arg Gly
            260                 265                 270

Val Thr Arg His Arg Trp Thr Gly Arg Tyr Glu Ala His Leu Trp Asp
    275                 280                 285

Asn Ser Cys Arg Arg Glu Gly Gln Thr Arg Lys Gly Arg Gln Val Tyr
    290                 295                 300

Leu Gly Gly Tyr Asp Lys Glu Glu Lys Ala Ala Arg Ala Tyr Asp Leu
305                 310                 315                 320

Ala Ala Leu Lys Tyr Trp Gly Thr Thr Thr Thr Asn Phe Pro Ile
                325                 330                 335

Ser His Tyr Glu Lys Glu Leu Glu Met Lys His Met Thr Arg Gln
            340                 345                 350

Glu Tyr Val Ala Ser Leu Arg Arg Lys Ser Ser Gly Phe Ser Arg Gly
    355                 360                 365

Ala Ser Ile Tyr Arg Gly Val Thr Arg His His Gln His Gly Arg Trp
    370                 375                 380

Gln Ala Arg Ile Gly Arg Val Ala Gly Asn Lys Asp Leu Tyr Leu Gly
385                 390                 395                 400

Thr Phe Ser Thr Gln Glu Glu Ala Ala Glu Ala Tyr Asp Val Ala Ala
```

```
                        405                 410                 415
Ile Lys Phe Arg Gly Leu Ser Ala Val Thr Asn Phe Asp Met Ser Arg
        420                 425                 430

Tyr Asp Val Lys Ser Ile Leu Glu Ser Thr Thr Leu Pro Ile Gly Gly
            435                 440                 445

Ala Ala Lys Arg Leu Lys Asp Met Glu Gln Val Glu Leu Arg Val Glu
    450                 455                 460

Asn Val His Arg Ala Asp Gln Glu Asp His Ser Ser Ile Met Asn Ser
465                 470                 475                 480

His Leu Thr Gln Gly Ile Ile Asn Asn Tyr Ala Ala Gly Gly Thr Thr
                485                 490                 495

Ala Thr His His His Asn Trp His Asn Ala Leu Ala Phe His Gln Pro
            500                 505                 510

Gln Pro Cys Thr Thr Ile His Tyr Pro Tyr Gly Gln Arg Ile Asn Trp
        515                 520                 525

Cys Lys Gln Glu Gln Asp Asn Ser Asp Ala Ser His Ser Leu Ser Tyr
    530                 535                 540

Ser Asp Ile His Gln Leu Gln Leu Gly Asn Asn Gly Thr His Asn Phe
545                 550                 555                 560

Phe His Thr Asn Ser Gly Leu His Pro Met Leu Ser Met Asp Ser Ala
                565                 570                 575

Ser Ile Asp Asn Ser Ser Ser Ser Asn Ser Val Val Tyr Asp Gly Tyr
            580                 585                 590

Gly Gly Gly Gly Gly Tyr Asn Val Ile Pro Met Gly Thr Thr Thr Thr
        595                 600                 605

Val Val Ala Asn Asp Gly Asp Gln Asn Pro Arg Ser Asn His Gly Phe
    610                 615                 620

Gly Asp Asn Glu Ile Lys Ala Leu Gly Tyr Glu Ser Val Tyr Gly Ser
625                 630                 635                 640

Thr Thr Asp Pro Tyr His Ala His Ala Arg Asn Leu Tyr Tyr Leu Thr
                645                 650                 655

Gln Gln Gln Pro Ser Ser Val Asp Ala Val Lys Ala Ser Ala Tyr Asp
            660                 665                 670

Gln Gly Ser Ala Cys Asn Thr Trp Val Pro Thr Ala Ile Pro Thr His
        675                 680                 685

Ala Pro Arg Ser Ser Thr Ser Met Ala Leu Cys His Gly Ala Thr Pro
    690                 695                 700

Phe Ser Leu Leu His Glu
705                 710

<210> SEQ ID NO 26
<211> LENGTH: 1932
<212> TYPE: DNA
<213> ORGANISM: Vitis vinifera
<220> FEATURE:
<221> NAME/KEY: CDS
<222> LOCATION: (1)...(1932)

<400> SEQUENCE: 26 atg gct tcc atg aac aac tgg ttg ggt ttc tct ttg tcc cct cga gaa      48
Met Ala Ser Met Asn Asn Trp Leu Gly Phe Ser Leu Ser Pro Arg Glu
 1               5                  10                  15 ctt cca cca cag cct gaa aat cac tca cag aac agt gtc tct aga ctt      96
Leu Pro Pro Gln Pro Glu Asn His Ser Gln Asn Ser Val Ser Arg Leu
                20                  25                  30 ggt ttc aac tct gat gaa atc tct ggg act gat gtg tca ggt gag tgt     144
```

```
                    Gly Phe Asn Ser Asp Glu Ile Ser Gly Thr Asp Val Ser Gly Glu Cys
                                 35                  40                  45 ttt gat ctc act tca gat tcc act gct ccc tct ctc aac ctc cct ccc              192
Phe Asp Leu Thr Ser Asp Ser Thr Ala Pro Ser Leu Asn Leu Pro Pro
         50                  55                  60 cct ttt ggg ata ctt gaa gca ttc aac agg aat aat cag ccc caa gat              240
Pro Phe Gly Ile Leu Glu Ala Phe Asn Arg Asn Asn Gln Pro Gln Asp
 65                  70                  75                  80 act aac tac aaa acc acc act tct gag ctc tcc atg ctc atg ggt agt              288
Thr Asn Tyr Lys Thr Thr Thr Ser Glu Leu Ser Met Leu Met Gly Ser
                 85                  90                  95 tca tgc agt agt cat cat aac ctc gaa aac caa gaa ccc aaa ctt gaa              336
Ser Cys Ser Ser His His Asn Leu Glu Asn Gln Glu Pro Lys Leu Glu
            100                 105                 110 aat ttc ctg ggc tgc cgc tct ttt gct gat cat gag cag aaa ctt caa              384
Asn Phe Leu Gly Cys Arg Ser Phe Ala Asp His Glu Gln Lys Leu Gln
        115                 120                 125 ggg tac tac att tcc att ggt tta tcc atg atc aag aca tgg ctg cgg              432
Gly Tyr Tyr Ile Ser Ile Gly Leu Ser Met Ile Lys Thr Trp Leu Arg
    130                 135                 140 aac caa cct gca ccc acc cat cag gat aac aac aag agt act gat act              480
Asn Gln Pro Ala Pro Thr His Gln Asp Asn Asn Lys Ser Thr Asp Thr
145                 150                 155                 160 ggg cct gtc ggt gga gcc gcc gct ggg aac cta ccc aat gca cag acc              528
Gly Pro Val Gly Gly Ala Ala Ala Gly Asn Leu Pro Asn Ala Gln Thr
                165                 170                 175 tta tcg ttg tcc atg agc acc ggc tcg cac cag acc ggt gcc att gaa              576
Leu Ser Leu Ser Met Ser Thr Gly Ser His Gln Thr Gly Ala Ile Glu
            180                 185                 190 acg gtg cca agg aag tcc att gat aca ttt gga cag agg aca tcc ata              624
Thr Val Pro Arg Lys Ser Ile Asp Thr Phe Gly Gln Arg Thr Ser Ile
        195                 200                 205 tac cgt ggt gta aca agg cat aga tgg acg ggt aga tat gag gct cat              672
Tyr Arg Gly Val Thr Arg His Arg Trp Thr Gly Arg Tyr Glu Ala His
    210                 215                 220 cta tgg gac aac agt tgc aga aga gaa gga caa act cga aag gga agg              720
Leu Trp Asp Asn Ser Cys Arg Arg Glu Gly Gln Thr Arg Lys Gly Arg
225                 230                 235                 240 caa gtt tat tta ggt ggt tat gac aaa gaa gaa aag gca gct agg gct              768
Gln Val Tyr Leu Gly Gly Tyr Asp Lys Glu Glu Lys Ala Ala Arg Ala
                245                 250                 255 tac gat tta gca gca ctg aag tat tgg ggt acc acc aca aca aat              816
Tyr Asp Leu Ala Ala Leu Lys Tyr Trp Gly Thr Thr Thr Thr Asn
            260                 265                 270 ttc cct att agc aac tat gaa aaa gag ata gag gag atg aag cac atg              864
Phe Pro Ile Ser Asn Tyr Glu Lys Glu Ile Glu Glu Met Lys His Met
        275                 280                 285 aca agg cag gag tac gta gca tct ctg cga agg aag agt agc ggg ttt              912
Thr Arg Gln Glu Tyr Val Ala Ser Leu Arg Arg Lys Ser Ser Gly Phe
    290                 295                 300 tct cgt gga gca tcc ata tat aga gga gtg acc aga cac cat cag cat              960
Ser Arg Gly Ala Ser Ile Tyr Arg Gly Val Thr Arg His His Gln His
305                 310                 315                 320 ggg aga tgg cag gca agg att gga aga gtc gca ggc aac aaa gat ctt             1008
Gly Arg Trp Gln Ala Arg Ile Gly Arg Val Ala Gly Asn Lys Asp Leu
                325                 330                 335 tac ttg gga act ttc agc acc caa gag gaa gca gca gag gcc tat gac             1056
Tyr Leu Gly Thr Phe Ser Thr Gln Glu Glu Ala Ala Glu Ala Tyr Asp
            340                 345                 350
```

-continued

| | |
|---|---|
| att gct gcc att aag ttt cga gga ttg aat gcg gtg acc aac ttt gat<br>Ile Ala Ala Ile Lys Phe Arg Gly Leu Asn Ala Val Thr Asn Phe Asp<br>355                    360                    365 | 1104 |
| atg agt aga tat gat gtt aat agc att cta gag agc agt acc ttg ccg<br>Met Ser Arg Tyr Asp Val Asn Ser Ile Leu Glu Ser Ser Thr Leu Pro<br>370                    375                  380 | 1152 |
| att ggt gga gct gca aag cgg ttg aaa gat gct gag cag gct gaa atg<br>Ile Gly Gly Ala Ala Lys Arg Leu Lys Asp Ala Glu Gln Ala Glu Met<br>385                    390                    395                  400 | 1200 |
| act ata gat gga cag agg aca gac gat gag atg agc tca cag ctg act<br>Thr Ile Asp Gly Gln Arg Thr Asp Asp Glu Met Ser Ser Gln Leu Thr<br>405                    410                  415 | 1248 |
| gat gga atc aac aac tat gga gca cac cat ggc tgg cct act gtt<br>Asp Gly Ile Asn Asn Tyr Gly Ala His His Gly Trp Pro Thr Val<br>420                    425                  430 | 1296 |
| gca ttc caa caa gct cag cca ttt agc atg cac tac cct tat ggc cat<br>Ala Phe Gln Gln Ala Gln Pro Phe Ser Met His Tyr Pro Tyr Gly His<br>435                    440                  445 | 1344 |
| cag cag agg gct gtt tgg tgt aag caa gag caa gac cct gat ggc aca<br>Gln Gln Arg Ala Val Trp Cys Lys Gln Glu Gln Asp Pro Asp Gly Thr<br>450                    455                  460 | 1392 |
| cac aac ttt caa gat ctt cac caa cta caa ttg gga aac act cac aac<br>His Asn Phe Gln Asp Leu His Gln Leu Gln Leu Gly Asn Thr His Asn<br>465                    470                    475                  480 | 1440 |
| ttc ttc cag cct aat gtt ctg cac aac ctc atg agc atg gac tct tct<br>Phe Phe Gln Pro Asn Val Leu His Asn Leu Met Ser Met Asp Ser Ser<br>                      485                    490                  495 | 1488 |
| tca atg gac cat agc tca ggc tcc aat tca gtc atc tat agc ggt ggt<br>Ser Met Asp His Ser Ser Gly Ser Asn Ser Val Ile Tyr Ser Gly Gly<br>500                    505                  510 | 1536 |
| gga gcc gct gat ggc agc gct gca act ggc ggc agt ggc agt ggg agc<br>Gly Ala Ala Asp Gly Ser Ala Ala Thr Gly Gly Ser Gly Ser Gly Ser<br>515                    520                  525 | 1584 |
| ttc caa ggg gta ggt tat ggg aac aac att ggc ttt gtg atg ccc ata<br>Phe Gln Gly Val Gly Tyr Gly Asn Asn Ile Gly Phe Val Met Pro Ile<br>530                    535                  540 | 1632 |
| agc acc gtc atc gct cat gaa ggc ggc cat ggc cag gga aat ggt ggc<br>Ser Thr Val Ile Ala His Glu Gly Gly His Gly Gln Gly Asn Gly Gly<br>545                    550                    555                  560 | 1680 |
| ttt gga gat agc gaa gtg aag gcg att ggt tac gac aac atg ttt gga<br>Phe Gly Asp Ser Glu Val Lys Ala Ile Gly Tyr Asp Asn Met Phe Gly<br>                      565                    570                  575 | 1728 |
| tcg aca gat cct tac cat gct agg agc ttg tac tat ctt tca cag caa<br>Ser Thr Asp Pro Tyr His Ala Arg Ser Leu Tyr Tyr Leu Ser Gln Gln<br>580                    585                  590 | 1776 |
| tca tct gca ggc atg gtg aag ggc agt agt gca tat gat cag ggg tca<br>Ser Ser Ala Gly Met Val Lys Gly Ser Ser Ala Tyr Asp Gln Gly Ser<br>595                    600                  605 | 1824 |
| ggg tgt aac aac tgg gtt cca act gca gtt cca acc cta gct cca agg<br>Gly Cys Asn Asn Trp Val Pro Thr Ala Val Pro Thr Leu Ala Pro Arg<br>610                    615                  620 | 1872 |
| act aac agc ttg gca gta tgc cat gga aca cct aca ttc aca gta tgg<br>Thr Asn Ser Leu Ala Val Cys His Gly Thr Pro Thr Phe Thr Val Trp<br>625                    630                    635                  640 | 1920 |
| aat gat aca taa<br>Asn Asp Thr | 1932 |

<210> SEQ ID NO 27
<211> LENGTH: 643
<212> TYPE: PRT

<213> ORGANISM: Vitis vinifera

<400> SEQUENCE: 27

```
Met Ala Ser Met Asn Asn Trp Leu Gly Phe Ser Leu Ser Pro Arg Glu
1               5                   10                  15

Leu Pro Pro Gln Pro Glu Asn His Ser Gln Asn Ser Val Ser Arg Leu
            20                  25                  30

Gly Phe Asn Ser Asp Glu Ile Ser Gly Thr Asp Val Ser Gly Glu Cys
        35                  40                  45

Phe Asp Leu Thr Ser Asp Ser Thr Ala Pro Ser Leu Asn Leu Pro Pro
    50                  55                  60

Pro Phe Gly Ile Leu Glu Ala Phe Asn Arg Asn Asn Gln Pro Gln Asp
65                  70                  75                  80

Thr Asn Tyr Lys Thr Thr Thr Ser Glu Leu Ser Met Leu Met Gly Ser
                85                  90                  95

Ser Cys Ser Ser His His Asn Leu Glu Asn Gln Glu Pro Lys Leu Glu
            100                 105                 110

Asn Phe Leu Gly Cys Arg Ser Phe Ala Asp His Glu Gln Lys Leu Gln
        115                 120                 125

Gly Tyr Tyr Ile Ser Ile Gly Leu Ser Met Ile Lys Thr Trp Leu Arg
    130                 135                 140

Asn Gln Pro Ala Pro Thr His Gln Asp Asn Asn Lys Ser Thr Asp Thr
145                 150                 155                 160

Gly Pro Val Gly Gly Ala Ala Gly Asn Leu Pro Asn Ala Gln Thr
                165                 170                 175

Leu Ser Leu Ser Met Ser Thr Gly Ser His Gln Thr Gly Ala Ile Glu
            180                 185                 190

Thr Val Pro Arg Lys Ser Ile Asp Thr Phe Gly Gln Arg Thr Ser Ile
        195                 200                 205

Tyr Arg Gly Val Thr Arg His Arg Trp Thr Gly Arg Tyr Glu Ala His
    210                 215                 220

Leu Trp Asp Asn Ser Cys Arg Arg Glu Gly Gln Thr Arg Lys Gly Arg
225                 230                 235                 240

Gln Val Tyr Leu Gly Gly Tyr Asp Lys Glu Lys Ala Ala Arg Ala
                245                 250                 255

Tyr Asp Leu Ala Ala Leu Lys Tyr Trp Gly Thr Thr Thr Thr Thr Asn
            260                 265                 270

Phe Pro Ile Ser Asn Tyr Glu Lys Glu Ile Glu Glu Met Lys His Met
        275                 280                 285

Thr Arg Gln Glu Tyr Val Ala Ser Leu Arg Arg Lys Ser Ser Gly Phe
    290                 295                 300

Ser Arg Gly Ala Ser Ile Tyr Arg Gly Val Thr Arg His His Gln His
305                 310                 315                 320

Gly Arg Trp Gln Ala Arg Ile Gly Arg Val Ala Gly Asn Lys Asp Leu
                325                 330                 335

Tyr Leu Gly Thr Phe Ser Thr Gln Glu Glu Ala Ala Glu Ala Tyr Asp
            340                 345                 350

Ile Ala Ala Ile Lys Phe Arg Gly Leu Asn Ala Val Thr Asn Phe Asp
        355                 360                 365

Met Ser Arg Tyr Asp Val Asn Ser Ile Leu Glu Ser Ser Thr Leu Pro
    370                 375                 380

Ile Gly Gly Ala Ala Lys Arg Leu Lys Asp Ala Glu Gln Ala Glu Met
385                 390                 395                 400
```

Thr Ile Asp Gly Gln Arg Thr Asp Asp Glu Met Ser Ser Gln Leu Thr
            405                 410                 415

Asp Gly Ile Asn Asn Tyr Gly Ala His His Gly Trp Pro Thr Val
        420                 425                 430

Ala Phe Gln Gln Ala Gln Pro Phe Ser Met His Tyr Pro Tyr Gly His
        435                 440                 445

Gln Gln Arg Ala Val Trp Cys Lys Gln Glu Gln Asp Pro Asp Gly Thr
    450                 455                 460

His Asn Phe Gln Asp Leu His Gln Leu Gln Leu Gly Asn Thr His Asn
465                 470                 475                 480

Phe Phe Gln Pro Asn Val Leu His Asn Leu Met Ser Met Asp Ser Ser
                485                 490                 495

Ser Met Asp His Ser Ser Gly Ser Asn Ser Val Ile Tyr Ser Gly Gly
            500                 505                 510

Gly Ala Ala Asp Gly Ser Ala Ala Thr Gly Gly Ser Gly Ser Gly Ser
        515                 520                 525

Phe Gln Gly Val Gly Tyr Gly Asn Asn Ile Gly Phe Val Met Pro Ile
    530                 535                 540

Ser Thr Val Ile Ala His Glu Gly Gly His Gly Gln Gly Asn Gly Gly
545                 550                 555                 560

Phe Gly Asp Ser Glu Val Lys Ala Ile Gly Tyr Asp Asn Met Phe Gly
                565                 570                 575

Ser Thr Asp Pro Tyr His Ala Arg Ser Leu Tyr Tyr Leu Ser Gln Gln
            580                 585                 590

Ser Ser Ala Gly Met Val Lys Gly Ser Ser Ala Tyr Asp Gln Gly Ser
        595                 600                 605

Gly Cys Asn Asn Trp Val Pro Thr Ala Val Pro Thr Leu Ala Pro Arg
    610                 615                 620

Thr Asn Ser Leu Ala Val Cys His Gly Thr Pro Thr Phe Thr Val Trp
625                 630                 635                 640

Asn Asp Thr

<210> SEQ ID NO 28
<211> LENGTH: 2040
<212> TYPE: DNA
<213> ORGANISM: Zea mays
<220> FEATURE:
<221> NAME/KEY: CDS
<222> LOCATION: (1)...(2040)

<400> SEQUENCE: 28

| | | | | | | | | | | | | | | | | |
|---|---|---|---|---|---|---|---|---|---|---|---|---|---|---|---|---|---|
| atg | gct | tca | gcg | aac | aac | tgg | ctg | ggc | ttc | tcg | ctc | tcg | ggc | cag | gat | | 48 |
| Met | Ala | Ser | Ala | Asn | Asn | Trp | Leu | Gly | Phe | Ser | Leu | Ser | Gly | Gln | Asp | | |
| 1 | | | | 5 | | | | | 10 | | | | | 15 | | | |
| aac | ccg | cag | cct | aac | cag | gat | agc | tcg | cct | gcc | gcc | ggt | atc | gac | atc | | 96 |
| Asn | Pro | Gln | Pro | Asn | Gln | Asp | Ser | Ser | Pro | Ala | Ala | Gly | Ile | Asp | Ile | | |
| | | | 20 | | | | | 25 | | | | | 30 | | | | |
| tcc | ggc | gcc | agc | gac | ttc | tat | ggc | ctg | ccc | acg | cag | cag | ggc | tcc | gac | | 144 |
| Ser | Gly | Ala | Ser | Asp | Phe | Tyr | Gly | Leu | Pro | Thr | Gln | Gln | Gly | Ser | Asp | | |
| | | 35 | | | | | 40 | | | | | 45 | | | | | |
| ggg | cat | ctc | ggc | gtg | ccg | ggc | ctg | cgg | gac | gat | cac | gct | tct | tat | ggt | | 192 |
| Gly | His | Leu | Gly | Val | Pro | Gly | Leu | Arg | Asp | Asp | His | Ala | Ser | Tyr | Gly | | |
| | 50 | | | | | 55 | | | | | 60 | | | | | | |
| atc | atg | gag | gcc | tac | aac | agg | gtt | cct | caa | gaa | acc | caa | gat | tgg | aac | | 240 |
| Ile | Met | Glu | Ala | Tyr | Asn | Arg | Val | Pro | Gln | Glu | Thr | Gln | Asp | Trp | Asn | | |
| 65 | | | | 70 | | | | | 75 | | | | | 80 | | | |
| atg | agg | ggc | ttg | gac | tac | aac | ggc | ggt | ggc | tcg | gag | ctc | tcg | atg | ctt | | 288 |

```
       Met Arg Gly Leu Asp Tyr Asn Gly Gly Gly Ser Glu Leu Ser Met Leu
                    85                  90                  95 gtg ggg tcc agc ggc ggc ggg ggc aac ggc aag agg gcc gtg gaa              336
Val Gly Ser Ser Gly Gly Gly Gly Asn Gly Lys Arg Ala Val Glu
            100                 105                 110 gac agc gag ccc aag ctc gaa gat ttc ctc ggc ggc aac tcg ttc gtc          384
Asp Ser Glu Pro Lys Leu Glu Asp Phe Leu Gly Gly Asn Ser Phe Val
                115                 120                 125 tcc gat caa gat cag tcc ggc ggt tac ctg ttc tct gga gtc ccg ata          432
Ser Asp Gln Asp Gln Ser Gly Gly Tyr Leu Phe Ser Gly Val Pro Ile
            130                 135                 140 gcc agc agc gcc aat agc aac agc ggg agc aac acc atg gag ctc tcc          480
Ala Ser Ser Ala Asn Ser Asn Ser Gly Ser Asn Thr Met Glu Leu Ser
145                 150                 155                 160 atg atc aag acc tgg cta cgg aac aac cag gtg gcc cag ccc cag ccg          528
Met Ile Lys Thr Trp Leu Arg Asn Asn Gln Val Ala Gln Pro Gln Pro
                165                 170                 175 cca gct cca cat cag ccg cag cct gag gaa atg agc acc gac gcc agc          576
Pro Ala Pro His Gln Pro Gln Pro Glu Glu Met Ser Thr Asp Ala Ser
            180                 185                 190 ggc agc agc ttt gga tgc tcg gat tcg atg gga agg aac agc atg gtg          624
Gly Ser Ser Phe Gly Cys Ser Asp Ser Met Gly Arg Asn Ser Met Val
                195                 200                 205 gcg gct ggt ggg agc tcg cag agc ctg gcg ctc tcg atg agc acg ggc          672
Ala Ala Gly Gly Ser Ser Gln Ser Leu Ala Leu Ser Met Ser Thr Gly
            210                 215                 220 tcg cac ctg ccc atg gtt gtg ccc agc ggc gcc gcc agc gga gcg gcc          720
Ser His Leu Pro Met Val Val Pro Ser Gly Ala Ala Ser Gly Ala Ala
225                 230                 235                 240 tcg gag agc aca tcg tcg gag aac aag cga gcg agc ggt gcc atg gat          768
Ser Glu Ser Thr Ser Ser Glu Asn Lys Arg Ala Ser Gly Ala Met Asp
                245                 250                 255 tcg ccc ggc agc gcg gta gaa gcc gta ccg agg aag tcc atc gac acg          816
Ser Pro Gly Ser Ala Val Glu Ala Val Pro Arg Lys Ser Ile Asp Thr
            260                 265                 270 ttc ggg caa agg acc tct ata tat cga ggt gta aca agg cat aga tgg          864
Phe Gly Gln Arg Thr Ser Ile Tyr Arg Gly Val Thr Arg His Arg Trp
                275                 280                 285 aca ggg cgg tat gag gct cat cta tgg gat aat agt tgt aga agg gaa          912
Thr Gly Arg Tyr Glu Ala His Leu Trp Asp Asn Ser Cys Arg Arg Glu
            290                 295                 300 ggg cag agt cgc aag ggt agg caa gtt tac ctt ggt ggc tat gac aag          960
Gly Gln Ser Arg Lys Gly Arg Gln Val Tyr Leu Gly Gly Tyr Asp Lys
305                 310                 315                 320 gag gac aag gca gca agg gct tat gat ttg gca gct ctc aag tat tgg          1008
Glu Asp Lys Ala Ala Arg Ala Tyr Asp Leu Ala Ala Leu Lys Tyr Trp
                325                 330                 335 ggc act acg aca aca aca aat ttc cct ata agc aac tac gaa aag gag          1056
Gly Thr Thr Thr Thr Thr Asn Phe Pro Ile Ser Asn Tyr Glu Lys Glu
            340                 345                 350 cta gaa gaa atg aaa cat atg act aga cag gag tac att gca tac cta          1104
Leu Glu Glu Met Lys His Met Thr Arg Gln Glu Tyr Ile Ala Tyr Leu
                355                 360                 365 aga aga aat agc agt gga ttt tct cgt ggg gcg tca aag tat cgt gga          1152
Arg Arg Asn Ser Ser Gly Phe Ser Arg Gly Ala Ser Lys Tyr Arg Gly
            370                 375                 380 gta act aga cat cat cag cat ggg aga tgg caa gca agg ata ggg aga          1200
Val Thr Arg His His Gln His Gly Arg Trp Gln Ala Arg Ile Gly Arg
385                 390                 395                 400
```

```
gtt gca gga aac aag gat ctc tac ttg ggc aca ttc agc acc gag gag    1248
Val Ala Gly Asn Lys Asp Leu Tyr Leu Gly Thr Phe Ser Thr Glu Glu
            405                 410                 415 gag gcg gcg gag gcc tac gac atc gcc gcg atc aag ttc cgc ggt ctc    1296
Glu Ala Ala Glu Ala Tyr Asp Ile Ala Ala Ile Lys Phe Arg Gly Leu
        420                 425                 430 aac gcc gtc acc aac ttc gac atg agc cgc tac gac gtg aag agc atc    1344
Asn Ala Val Thr Asn Phe Asp Met Ser Arg Tyr Asp Val Lys Ser Ile
                435                 440                 445 ctc gag agc agc aca ctg cct gtc ggc ggt gcg gcc agg cgc ctc aag    1392
Leu Glu Ser Ser Thr Leu Pro Val Gly Gly Ala Ala Arg Arg Leu Lys
    450                 455                 460 gac gcc gtg gac cac gtg gag gcc ggc gcc acc atc tgg cgc gcc gac    1440
Asp Ala Val Asp His Val Glu Ala Gly Ala Thr Ile Trp Arg Ala Asp
465                 470                 475                 480 atg gac ggc gcc gtg atc tcc cag ctg gcc gaa gcc ggg atg ggc ggc    1488
Met Asp Gly Ala Val Ile Ser Gln Leu Ala Glu Ala Gly Met Gly Gly
                485                 490                 495 tac gcc tcg tac ggc cac cac ggc tgg ccg acc atc gcg ttc cag cag    1536
Tyr Ala Ser Tyr Gly His His Gly Trp Pro Thr Ile Ala Phe Gln Gln
            500                 505                 510 ccg tcg ccg ctc tcc gtc cac tac ccg tac ggc cag ccg tcc cgc ggg    1584
Pro Ser Pro Leu Ser Val His Tyr Pro Tyr Gly Gln Pro Ser Arg Gly
        515                 520                 525 tgg tgc aaa ccc gag cag gac gcg gcc gcc gcc gcg gcg cac agc ctg    1632
Trp Cys Lys Pro Glu Gln Asp Ala Ala Ala Ala Ala His Ser Leu
    530                 535                 540 cag gac ctc cag cag ctg cac ctc ggc agc gcg gcc cac aac ttc ttc    1680
Gln Asp Leu Gln Gln Leu His Leu Gly Ser Ala Ala His Asn Phe Phe
545                 550                 555                 560 cag gcg tcg tcg agc tcc aca gtc tac aac ggc ggc gcc ggc gcc agt    1728
Gln Ala Ser Ser Ser Ser Thr Val Tyr Asn Gly Gly Ala Gly Ala Ser
                565                 570                 575 ggt ggg tac cag ggc ctc ggt ggt ggc agc tct ttc ctc atg ccg tcg    1776
Gly Gly Tyr Gln Gly Leu Gly Gly Gly Ser Ser Phe Leu Met Pro Ser
            580                 585                 590 agc act gtc gtg gcg gcg gcc gac cag ggg cac agc agc acg gcc aac    1824
Ser Thr Val Val Ala Ala Ala Asp Gln Gly His Ser Ser Thr Ala Asn
        595                 600                 605 cag ggg agc acg tgc agc tac ggg gac gac cac cag gag ggg aag ctc    1872
Gln Gly Ser Thr Cys Ser Tyr Gly Asp Asp His Gln Glu Gly Lys Leu
    610                 615                 620 atc ggt tac gac gcc gcc atg gtg gcg acc gca gct ggt gga gac ccg    1920
Ile Gly Tyr Asp Ala Ala Met Val Ala Thr Ala Ala Gly Gly Asp Pro
625                 630                 635                 640 tac gct gcg gcg agg aac ggg tac cag ttc tcg cag ggc tcg gga tcc    1968
Tyr Ala Ala Ala Arg Asn Gly Tyr Gln Phe Ser Gln Gly Ser Gly Ser
                645                 650                 655 acg gtg agc atc gcg agg gcg aac ggg tac gct aac aac tgg agc tct    2016
Thr Val Ser Ile Ala Arg Ala Asn Gly Tyr Ala Asn Asn Trp Ser Ser
            660                 665                 670 cct ttc aac aac ggc atg ggg tga                                    2040
Pro Phe Asn Asn Gly Met Gly
        675
```

<210> SEQ ID NO 29
<211> LENGTH: 679
<212> TYPE: PRT
<213> ORGANISM: Zea mays

<400> SEQUENCE: 29

```
Met Ala Ser Ala Asn Asn Trp Leu Gly Phe Ser Leu Ser Gly Gln Asp
1               5                   10                  15

Asn Pro Gln Pro Asn Gln Asp Ser Ser Pro Ala Ala Gly Ile Asp Ile
                20                  25                  30

Ser Gly Ala Ser Asp Phe Tyr Gly Leu Pro Thr Gln Gln Gly Ser Asp
            35                  40                  45

Gly His Leu Gly Val Pro Gly Leu Arg Asp Asp His Ala Ser Tyr Gly
        50                  55                  60

Ile Met Glu Ala Tyr Asn Arg Val Pro Gln Glu Thr Gln Asp Trp Asn
65                  70                  75                  80

Met Arg Gly Leu Asp Tyr Asn Gly Gly Ser Glu Leu Ser Met Leu
            85                  90                  95

Val Gly Ser Ser Gly Gly Gly Gly Asn Gly Lys Arg Ala Val Glu
        100                 105                 110

Asp Ser Glu Pro Lys Leu Glu Asp Phe Leu Gly Gly Asn Ser Phe Val
        115                 120                 125

Ser Asp Gln Asp Gln Ser Gly Gly Tyr Leu Phe Ser Gly Val Pro Ile
130                 135                 140

Ala Ser Ser Ala Asn Ser Asn Ser Gly Ser Asn Thr Met Glu Leu Ser
145                 150                 155                 160

Met Ile Lys Thr Trp Leu Arg Asn Asn Gln Val Ala Gln Pro Gln Pro
                165                 170                 175

Pro Ala Pro His Gln Pro Gln Pro Glu Glu Met Ser Thr Asp Ala Ser
            180                 185                 190

Gly Ser Ser Phe Gly Cys Ser Asp Ser Met Gly Arg Asn Ser Met Val
            195                 200                 205

Ala Ala Gly Gly Ser Ser Gln Ser Leu Ala Leu Ser Met Ser Thr Gly
        210                 215                 220

Ser His Leu Pro Met Val Val Pro Ser Gly Ala Ala Ser Gly Ala Ala
225                 230                 235                 240

Ser Glu Ser Thr Ser Ser Glu Asn Lys Arg Ala Ser Gly Ala Met Asp
                245                 250                 255

Ser Pro Gly Ser Ala Val Glu Ala Val Pro Arg Lys Ser Ile Asp Thr
            260                 265                 270

Phe Gly Gln Arg Thr Ser Ile Tyr Arg Gly Val Thr Arg His Arg Trp
            275                 280                 285

Thr Gly Arg Tyr Glu Ala His Leu Trp Asp Asn Ser Cys Arg Arg Glu
        290                 295                 300

Gly Gln Ser Arg Lys Gly Arg Gln Val Tyr Leu Gly Gly Tyr Asp Lys
305                 310                 315                 320

Glu Asp Lys Ala Ala Arg Ala Tyr Asp Leu Ala Ala Leu Lys Tyr Trp
                325                 330                 335

Gly Thr Thr Thr Thr Thr Asn Phe Pro Ile Ser Asn Tyr Glu Lys Glu
            340                 345                 350

Leu Glu Glu Met Lys His Met Thr Arg Gln Glu Tyr Ile Ala Tyr Leu
            355                 360                 365

Arg Arg Asn Ser Ser Gly Phe Ser Arg Gly Ala Ser Lys Tyr Arg Gly
        370                 375                 380

Val Thr Arg His His Gln His Gly Arg Trp Gln Ala Arg Ile Gly Arg
385                 390                 395                 400

Val Ala Gly Asn Lys Asp Leu Tyr Leu Gly Thr Phe Ser Thr Glu Glu
                405                 410                 415
```

```
Glu Ala Ala Glu Ala Tyr Asp Ile Ala Ala Ile Lys Phe Arg Gly Leu
                420                 425                 430

Asn Ala Val Thr Asn Phe Asp Met Ser Arg Tyr Asp Val Lys Ser Ile
            435                 440                 445

Leu Glu Ser Ser Thr Leu Pro Val Gly Gly Ala Ala Arg Arg Leu Lys
        450                 455                 460

Asp Ala Val Asp His Val Glu Ala Gly Ala Thr Ile Trp Arg Ala Asp
465                 470                 475                 480

Met Asp Gly Ala Val Ile Ser Gln Leu Ala Glu Ala Gly Met Gly Gly
                485                 490                 495

Tyr Ala Ser Tyr Gly His His Gly Trp Pro Thr Ile Ala Phe Gln Gln
                500                 505                 510

Pro Ser Pro Leu Ser Val His Tyr Pro Tyr Gly Gln Pro Ser Arg Gly
            515                 520                 525

Trp Cys Lys Pro Glu Gln Asp Ala Ala Ala Ala Ala His Ser Leu
        530                 535                 540

Gln Asp Leu Gln Gln Leu His Leu Gly Ser Ala Ala His Asn Phe Phe
545                 550                 555                 560

Gln Ala Ser Ser Ser Ser Thr Val Tyr Asn Gly Gly Ala Gly Ala Ser
                565                 570                 575

Gly Gly Tyr Gln Gly Leu Gly Gly Ser Ser Phe Leu Met Pro Ser
            580                 585                 590

Ser Thr Val Val Ala Ala Ala Asp Gln Gly His Ser Ser Thr Ala Asn
                595                 600                 605

Gln Gly Ser Thr Cys Ser Tyr Gly Asp His Gln Glu Gly Lys Leu
            610                 615                 620

Ile Gly Tyr Asp Ala Ala Met Val Ala Thr Ala Gly Gly Asp Pro
625                 630                 635                 640

Tyr Ala Ala Arg Asn Gly Tyr Gln Phe Ser Gln Gly Ser Gly Ser
                645                 650                 655

Thr Val Ser Ile Ala Arg Ala Asn Gly Tyr Ala Asn Asn Trp Ser Ser
            660                 665                 670

Pro Phe Asn Asn Gly Met Gly
        675

<210> SEQ ID NO 30
<211> LENGTH: 2088
<212> TYPE: DNA
<213> ORGANISM: Oryza sativa
<220> FEATURE:
<221> NAME/KEY: CDS
<222> LOCATION: (1)...(2088)

<400> SEQUENCE: 30 atg gcc acc atg aac aac tgg ctg gcc ttc tcc ctc tcc ccg cag gat      48
Met Ala Thr Met Asn Asn Trp Leu Ala Phe Ser Leu Ser Pro Gln Asp
1               5                   10                  15 cag ctc ccg ccg tct cag acc aac tcc act ctc atc tcc gcc gcc gcc      96
Gln Leu Pro Pro Ser Gln Thr Asn Ser Thr Leu Ile Ser Ala Ala Ala
            20                  25                  30 acc acc acc acc gcc ggc gac tcc tcc acc ggc gac gtc tgc ttc aac      144
Thr Thr Thr Thr Ala Gly Asp Ser Ser Thr Gly Asp Val Cys Phe Asn
        35                  40                  45 atc ccc caa gat tgg agc atg agg gga tcg gag ctc tcg gcg ctc gtc      192
Ile Pro Gln Asp Trp Ser Met Arg Gly Ser Glu Leu Ser Ala Leu Val
    50                  55                  60 gcc gag ccg aag ctg gag gac ttc ctc ggc ggc atc tcc ttc tcg gag      240
Ala Glu Pro Lys Leu Glu Asp Phe Leu Gly Gly Ile Ser Phe Ser Glu
```

|  |  |  |  |  |  |  |  |  |  |  |  |  |  |  |
|---|---|---|---|---|---|---|---|---|---|---|---|---|---|---|
|  | Ala | Glu | Pro | Lys | Leu | Glu | Asp | Phe | Leu | Gly | Gly | Ile | Ser | Phe | Ser | Glu |
|  | 65 |  |  |  | 70 |  |  |  |  | 75 |  |  |  |  | 80 |

| cag | cag | cat | cat | cac | ggc | ggc | aag | ggc | ggc | gtg | atc | ccg | agc | agc | gcc | 288 |
|---|---|---|---|---|---|---|---|---|---|---|---|---|---|---|---|---|
| Gln | Gln | His | His | His | Gly | Gly | Lys | Gly | Gly | Val | Ile | Pro | Ser | Ser | Ala |  |
|  |  |  |  | 85 |  |  |  |  | 90 |  |  |  |  | 95 |  |  |

| gcc | gct | tgc | tac | gcg | agc | tcc | ggc | agc | agc | gtc | ggc | tac | ctg | tac | cct | 336 |
|---|---|---|---|---|---|---|---|---|---|---|---|---|---|---|---|---|
| Ala | Ala | Cys | Tyr | Ala | Ser | Ser | Gly | Ser | Ser | Val | Gly | Tyr | Leu | Tyr | Pro |  |
|  |  |  | 100 |  |  |  |  | 105 |  |  |  |  | 110 |  |  |  |

| cct | cca | agc | tca | tcc | tcg | ctc | cag | ttc | gcc | gac | tcc | gtc | atg | gtg | gcc | 384 |
|---|---|---|---|---|---|---|---|---|---|---|---|---|---|---|---|---|
| Pro | Pro | Ser | Ser | Ser | Ser | Leu | Gln | Phe | Ala | Asp | Ser | Val | Met | Val | Ala |  |
|  |  |  | 115 |  |  |  |  | 120 |  |  |  |  | 125 |  |  |  |

| acc | tcc | tcg | ccc | gtc | gtc | gcc | cac | gac | ggc | gtc | agc | ggc | ggc | ggc | atg | 432 |
|---|---|---|---|---|---|---|---|---|---|---|---|---|---|---|---|---|
| Thr | Ser | Ser | Pro | Val | Val | Ala | His | Asp | Gly | Val | Ser | Gly | Gly | Gly | Met |  |
|  | 130 |  |  |  |  | 135 |  |  |  |  | 140 |  |  |  |  |  |

| gtg | agc | gcc | gcc | gcc | gcc | gcg | gcg | gcc | agt | ggc | aac | ggc | ggc | att | ggc | 480 |
|---|---|---|---|---|---|---|---|---|---|---|---|---|---|---|---|---|
| Val | Ser | Ala | Ala | Ala | Ala | Ala | Ala | Ala | Ser | Gly | Asn | Gly | Gly | Ile | Gly |  |
| 145 |  |  |  |  | 150 |  |  |  |  | 155 |  |  |  |  | 160 |  |

| ctg | tcc | atg | atc | aag | aac | tgg | ctc | cgg | agc | cag | ccg | gcg | ccg | cag | ccg | 528 |
|---|---|---|---|---|---|---|---|---|---|---|---|---|---|---|---|---|
| Leu | Ser | Met | Ile | Lys | Asn | Trp | Leu | Arg | Ser | Gln | Pro | Ala | Pro | Gln | Pro |  |
|  |  |  |  | 165 |  |  |  |  | 170 |  |  |  |  | 175 |  |  |

| gcg | cag | gcg | ctg | tct | ctg | tcc | atg | aac | atg | gcg | ggg | acg | acg | acg | gcg | 576 |
|---|---|---|---|---|---|---|---|---|---|---|---|---|---|---|---|---|
| Ala | Gln | Ala | Leu | Ser | Leu | Ser | Met | Asn | Met | Ala | Gly | Thr | Thr | Thr | Ala |  |
|  |  |  | 180 |  |  |  |  | 185 |  |  |  |  | 190 |  |  |  |

| cag | ggc | ggc | ggc | gcc | atg | gcg | ctc | ctc | gcc | ggc | gca | ggg | gag | cga | ggc | 624 |
|---|---|---|---|---|---|---|---|---|---|---|---|---|---|---|---|---|
| Gln | Gly | Gly | Gly | Ala | Met | Ala | Leu | Leu | Ala | Gly | Ala | Gly | Glu | Arg | Gly |  |
|  |  | 195 |  |  |  |  | 200 |  |  |  |  | 205 |  |  |  |  |

| cgg | acg | acg | ccc | gcg | tca | gag | agc | ctg | tcc | acg | tcg | gcg | cac | gga | gcg | 672 |
|---|---|---|---|---|---|---|---|---|---|---|---|---|---|---|---|---|
| Arg | Thr | Thr | Pro | Ala | Ser | Glu | Ser | Leu | Ser | Thr | Ser | Ala | His | Gly | Ala |  |
|  | 210 |  |  |  |  | 215 |  |  |  |  | 220 |  |  |  |  |  |

| acg | acg | gcg | acg | atg | gct | ggt | ggt | cgc | aag | gag | att | aac | gag | gaa | ggc | 720 |
|---|---|---|---|---|---|---|---|---|---|---|---|---|---|---|---|---|
| Thr | Thr | Ala | Thr | Met | Ala | Gly | Gly | Arg | Lys | Glu | Ile | Asn | Glu | Glu | Gly |  |
| 225 |  |  |  | 230 |  |  |  |  | 235 |  |  |  |  | 240 |  |  |

| agc | ggc | agc | gcc | ggc | gcc | gtg | gtt | gcc | gtc | ggc | tcg | gag | tca | ggc | ggc | 768 |
|---|---|---|---|---|---|---|---|---|---|---|---|---|---|---|---|---|
| Ser | Gly | Ser | Ala | Gly | Ala | Val | Val | Ala | Val | Gly | Ser | Glu | Ser | Gly | Gly |  |
|  |  |  | 245 |  |  |  |  | 250 |  |  |  |  | 255 |  |  |  |

| agc | ggc | gcc | gtg | gtg | gag | gcc | ggc | gcg | gcg | gcg | gcg | gcg | gcg | agg | aag | 816 |
|---|---|---|---|---|---|---|---|---|---|---|---|---|---|---|---|---|
| Ser | Gly | Ala | Val | Val | Glu | Ala | Gly | Ala | Ala | Ala | Ala | Ala | Ala | Arg | Lys |  |
|  |  | 260 |  |  |  |  | 265 |  |  |  |  | 270 |  |  |  |  |

| tcc | gtc | gac | acg | ttc | ggc | cag | aga | aca | tcg | atc | tac | cgc | ggc | gtg | aca | 864 |
|---|---|---|---|---|---|---|---|---|---|---|---|---|---|---|---|---|
| Ser | Val | Asp | Thr | Phe | Gly | Gln | Arg | Thr | Ser | Ile | Tyr | Arg | Gly | Val | Thr |  |
|  | 275 |  |  |  |  | 280 |  |  |  |  | 285 |  |  |  |  |  |

| agg | cat | aga | tgg | aca | ggg | agg | tat | gag | gct | cat | ctt | tgg | gac | aac | agc | 912 |
|---|---|---|---|---|---|---|---|---|---|---|---|---|---|---|---|---|
| Arg | His | Arg | Trp | Thr | Gly | Arg | Tyr | Glu | Ala | His | Leu | Trp | Asp | Asn | Ser |  |
|  | 290 |  |  |  |  | 295 |  |  |  |  | 300 |  |  |  |  |  |

| tgc | aga | aga | gag | ggc | caa | act | cgc | aag | ggt | cgt | caa | gtc | tat | cta | ggt | 960 |
|---|---|---|---|---|---|---|---|---|---|---|---|---|---|---|---|---|
| Cys | Arg | Arg | Glu | Gly | Gln | Thr | Arg | Lys | Gly | Arg | Gln | Val | Tyr | Leu | Gly |  |
| 305 |  |  |  | 310 |  |  |  |  | 315 |  |  |  |  | 320 |  |  |

| ggt | tat | gac | aaa | gag | gaa | aaa | gct | gct | aga | gct | tat | gat | ttg | gct | gct | 1008 |
|---|---|---|---|---|---|---|---|---|---|---|---|---|---|---|---|---|
| Gly | Tyr | Asp | Lys | Glu | Glu | Lys | Ala | Ala | Arg | Ala | Tyr | Asp | Leu | Ala | Ala |  |
|  |  |  | 325 |  |  |  |  | 330 |  |  |  |  | 335 |  |  |  |

| ctc | aaa | tac | tgg | ggc | ccg | acg | acg | aca | aat | ttt | ccg | gta | aat | aac | | 1056 |
|---|---|---|---|---|---|---|---|---|---|---|---|---|---|---|---|---|
| Leu | Lys | Tyr | Trp | Gly | Pro | Thr | Thr | Thr | Asn | Phe | Pro | Val | Asn | Asn |  |  |
|  |  | 340 |  |  |  |  | 345 |  |  |  |  | 350 |  |  |  |  |

| tat | gaa | aag | gag | ctg | gag | gag | atg | aag | cac | atg | aca | agg | cag | gag | ttc | 1104 |
|---|---|---|---|---|---|---|---|---|---|---|---|---|---|---|---|---|
| Tyr | Glu | Lys | Glu | Leu | Glu | Glu | Met | Lys | His | Met | Thr | Arg | Gln | Glu | Phe |  |
|  | 355 |  |  |  |  | 360 |  |  |  |  | 365 |  |  |  |  |  |

| gta | gcc | tct | ttg | aga | agg | aag | agc | agt | ggt | ttc | tcc | aga | ggt | gca | tcc | 1152 |
|---|---|---|---|---|---|---|---|---|---|---|---|---|---|---|---|---|
| Val | Ala | Ser | Leu | Arg | Arg | Lys | Ser | Ser | Gly | Phe | Ser | Arg | Gly | Ala | Ser |  |
| 370 |  |  |  |  | 375 |  |  |  |  | 380 |  |  |  |  |  |  |

```
att tac cgt gga gta act agg cat cac cag cat ggg aga tgg caa gca    1200
Ile Tyr Arg Gly Val Thr Arg His His Gln His Gly Arg Trp Gln Ala
385                 390                 395                 400 agg ata gga aga gtt gca ggg aac aag gac ctc tac ttg ggc acc ttc    1248
Arg Ile Gly Arg Val Ala Gly Asn Lys Asp Leu Tyr Leu Gly Thr Phe
            405                 410                 415 agc acg cag gag gag gcg gcg gag gcg tac gac atc gcg gcg atc aag    1296
Ser Thr Gln Glu Glu Ala Ala Glu Ala Tyr Asp Ile Ala Ala Ile Lys
        420                 425                 430 ttc cgg ggg ctc aac gcc gtc acc aac ttc gac atg agc cgc tac gac    1344
Phe Arg Gly Leu Asn Ala Val Thr Asn Phe Asp Met Ser Arg Tyr Asp
    435                 440                 445 gtc aag agc atc ctc gac agc gct gcc ctc ccc gtc ggc acc gcc gcc    1392
Val Lys Ser Ile Leu Asp Ser Ala Ala Leu Pro Val Gly Thr Ala Ala
450                 455                 460 aag cgc ctc aag gac gcc gag gcc gcc gcc gcc tac gac gtc ggc cgc    1440
Lys Arg Leu Lys Asp Ala Glu Ala Ala Ala Ala Tyr Asp Val Gly Arg
465                 470                 475                 480 atc gcc tcg cac ctc ggc ggc gac ggc gcc tac gcc gcg cat tac ggc    1488
Ile Ala Ser His Leu Gly Gly Asp Gly Ala Tyr Ala Ala His Tyr Gly
            485                 490                 495 cac cac cac cac tcg gcc gcc gcc gcc tgg ccg acc atc gcg ttc cag    1536
His His His His Ser Ala Ala Ala Ala Trp Pro Thr Ile Ala Phe Gln
        500                 505                 510 gcg gcg gcg gcg ccg ccg ccg cac gcc gcc ggg ctt tac cac ccg tac    1584
Ala Ala Ala Ala Pro Pro Pro His Ala Ala Gly Leu Tyr His Pro Tyr
    515                 520                 525 gcg cag ccg ctg cgt ggg tgg tgc aag cag gag cag gac cac gcc gtg    1632
Ala Gln Pro Leu Arg Gly Trp Cys Lys Gln Glu Gln Asp His Ala Val
530                 535                 540 atc gcg gcg gcg cac agc ctg cag gat ctc cac cac ctc aac ctc ggc    1680
Ile Ala Ala Ala His Ser Leu Gln Asp Leu His His Leu Asn Leu Gly
545                 550                 555                 560 gcc gcc gcc gcc gcg cat gac ttc ttc tcg cag gcg atg cag cag cag    1728
Ala Ala Ala Ala Ala His Asp Phe Phe Ser Gln Ala Met Gln Gln Gln
            565                 570                 575 cac ggc ctc ggc agc atc gac aac gcg tcg ctc gag cac agc acc ggc    1776
His Gly Leu Gly Ser Ile Asp Asn Ala Ser Leu Glu His Ser Thr Gly
        580                 585                 590 tcc aac tcc gtc gtc tac aac ggc gac aat ggc ggc gga ggc ggc ggc    1824
Ser Asn Ser Val Val Tyr Asn Gly Asp Asn Gly Gly Gly Gly Gly Gly
    595                 600                 605 tac atc atg gcg ccg atg agc gcc gtg tcg gcc acg gcc acc gcg gtg    1872
Tyr Ile Met Ala Pro Met Ser Ala Val Ser Ala Thr Ala Thr Ala Val
610                 615                 620 gcg agc agc cac gat cac ggc ggc gac ggc ggg aag cag gtg cag atg    1920
Ala Ser Ser His Asp His Gly Gly Asp Gly Gly Lys Gln Val Gln Met
625                 630                 635                 640 ggg tac gac agc tac ctc gtc ggc gca gac gcc tac ggc ggc ggc ggc    1968
Gly Tyr Asp Ser Tyr Leu Val Gly Ala Asp Ala Tyr Gly Gly Gly Gly
            645                 650                 655 gcc ggg agg atg cca tcc tgg gcg atg acg ccg gcg tcg gcg ccg gcc    2016
Ala Gly Arg Met Pro Ser Trp Ala Met Thr Pro Ala Ser Ala Pro Ala
        660                 665                 670 gcc acg agc agc agc gac atg acc gga gtc tgc cat ggc gca cag ctc    2064
Ala Thr Ser Ser Ser Asp Met Thr Gly Val Cys His Gly Ala Gln Leu
    675                 680                 685 ttc agc gtc tgg aac gac aca taa                                    2088
Phe Ser Val Trp Asn Asp Thr
690                 695
```

<210> SEQ ID NO 31
<211> LENGTH: 695
<212> TYPE: PRT
<213> ORGANISM: Oryza sativa

<400> SEQUENCE: 31

Met Ala Thr Met Asn Asn Trp Leu Ala Phe Ser Leu Ser Pro Gln Asp
1               5                   10                  15

Gln Leu Pro Pro Ser Gln Thr Asn Ser Thr Leu Ile Ser Ala Ala Ala
            20                  25                  30

Thr Thr Thr Thr Ala Gly Asp Ser Ser Thr Gly Asp Val Cys Phe Asn
        35                  40                  45

Ile Pro Gln Asp Trp Ser Met Arg Gly Ser Glu Leu Ser Ala Leu Val
50                  55                  60

Ala Glu Pro Lys Leu Glu Asp Phe Leu Gly Gly Ile Ser Phe Ser Glu
65                  70                  75                  80

Gln Gln His His His Gly Gly Lys Gly Gly Val Ile Pro Ser Ser Ala
                85                  90                  95

Ala Ala Cys Tyr Ala Ser Ser Gly Ser Ser Val Gly Tyr Leu Tyr Pro
            100                 105                 110

Pro Pro Ser Ser Ser Ser Leu Gln Phe Ala Asp Ser Val Met Val Ala
        115                 120                 125

Thr Ser Ser Pro Val Val Ala His Asp Gly Val Ser Gly Gly Gly Met
130                 135                 140

Val Ser Ala Ala Ala Ala Ala Ala Ser Gly Asn Gly Gly Ile Gly
145                 150                 155                 160

Leu Ser Met Ile Lys Asn Trp Leu Arg Ser Gln Pro Ala Pro Gln Pro
                165                 170                 175

Ala Gln Ala Leu Ser Leu Ser Met Asn Met Ala Gly Thr Thr Thr Ala
            180                 185                 190

Gln Gly Gly Gly Ala Met Ala Leu Leu Ala Gly Ala Gly Glu Arg Gly
        195                 200                 205

Arg Thr Thr Pro Ala Ser Glu Ser Leu Ser Thr Ser Ala His Gly Ala
210                 215                 220

Thr Thr Ala Thr Met Ala Gly Gly Arg Lys Glu Ile Asn Glu Glu Gly
225                 230                 235                 240

Ser Gly Ser Ala Gly Ala Val Val Ala Val Gly Ser Glu Ser Gly Gly
                245                 250                 255

Ser Gly Ala Val Val Glu Ala Gly Ala Ala Ala Ala Ala Arg Lys
            260                 265                 270

Ser Val Asp Thr Phe Gly Gln Arg Thr Ser Ile Tyr Arg Gly Val Thr
        275                 280                 285

Arg His Arg Trp Thr Gly Arg Tyr Glu Ala His Leu Trp Asp Asn Ser
290                 295                 300

Cys Arg Arg Glu Gly Gln Thr Arg Lys Gly Arg Gln Val Tyr Leu Gly
305                 310                 315                 320

Gly Tyr Asp Lys Glu Glu Lys Ala Ala Arg Ala Tyr Asp Leu Ala Ala
                325                 330                 335

Leu Lys Tyr Trp Gly Pro Thr Thr Thr Thr Asn Phe Pro Val Asn Asn
            340                 345                 350

Tyr Glu Lys Glu Leu Glu Glu Met Lys His Met Thr Arg Gln Glu Phe
        355                 360                 365

Val Ala Ser Leu Arg Arg Lys Ser Ser Gly Phe Ser Arg Gly Ala Ser

```
        370                 375                 380
Ile Tyr Arg Gly Val Thr Arg His Gln His Gly Arg Trp Gln Ala
385                 390                 395                 400

Arg Ile Gly Arg Val Ala Gly Asn Lys Asp Leu Tyr Leu Gly Thr Phe
                405                 410                 415

Ser Thr Gln Glu Glu Ala Ala Glu Ala Tyr Asp Ile Ala Ala Ile Lys
                420                 425                 430

Phe Arg Gly Leu Asn Ala Val Thr Asn Phe Asp Met Ser Arg Tyr Asp
            435                 440                 445

Val Lys Ser Ile Leu Asp Ser Ala Ala Leu Pro Val Gly Thr Ala Ala
        450                 455                 460

Lys Arg Leu Lys Asp Ala Glu Ala Ala Ala Tyr Asp Val Gly Arg
465                 470                 475                 480

Ile Ala Ser His Leu Gly Gly Asp Gly Ala Tyr Ala Ala His Tyr Gly
                485                 490                 495

His His His His Ser Ala Ala Ala Ala Trp Pro Thr Ile Ala Phe Gln
                500                 505                 510

Ala Ala Ala Ala Pro Pro His Ala Gly Leu Tyr His Pro Tyr
            515                 520                 525

Ala Gln Pro Leu Arg Gly Trp Cys Lys Gln Glu Gln Asp His Ala Val
        530                 535                 540

Ile Ala Ala Ala His Ser Leu Gln Asp Leu His His Leu Asn Leu Gly
545                 550                 555                 560

Ala Ala Ala Ala His Asp Phe Phe Ser Gln Ala Met Gln Gln Gln
                565                 570                 575

His Gly Leu Gly Ser Ile Asp Asn Ala Ser Leu Glu His Ser Thr Gly
            580                 585                 590

Ser Asn Ser Val Val Tyr Asn Gly Asp Asn Gly Gly Gly Gly
        595                 600                 605

Tyr Ile Met Ala Pro Met Ser Ala Val Ser Ala Thr Ala Thr Ala Val
                610                 615                 620

Ala Ser Ser His Asp His Gly Asp Gly Gly Lys Gln Val Gln Met
625                 630                 635                 640

Gly Tyr Asp Ser Tyr Leu Val Gly Ala Asp Ala Tyr Gly Gly Gly
                645                 650                 655

Ala Gly Arg Met Pro Ser Trp Ala Met Thr Pro Ala Ser Ala Pro Ala
            660                 665                 670

Ala Thr Ser Ser Ser Asp Met Thr Gly Val Cys His Gly Ala Gln Leu
        675                 680                 685

Phe Ser Val Trp Asn Asp Thr
690                 695

<210> SEQ ID NO 32
<211> LENGTH: 1680
<212> TYPE: DNA
<213> ORGANISM: Oryza sativa
<220> FEATURE:
<221> NAME/KEY: CDS
<222> LOCATION: (1)...(1680)

<400> SEQUENCE: 32 atg gcc tcc atc acc aac tgg ctc ggc ttc tcc tcc tcc ttc tcc        48
Met Ala Ser Ile Thr Asn Trp Leu Gly Phe Ser Ser Ser Phe Ser
1               5                   10                  15 ggc gcc ggc gcc gac ccc gtc ctg ccc cac ccg ccg ctg caa gag tgg    96
Gly Ala Gly Ala Asp Pro Val Leu Pro His Pro Pro Leu Gln Glu Trp
```

-continued

|     |     |     |     | 20  |     |     |     |     | 25  |     |     |     |     | 30  |     |     |      |
|-----|-----|-----|-----|-----|-----|-----|-----|-----|-----|-----|-----|-----|-----|-----|-----|-----|------|
| ggg | agc | gct | tat | gag | ggc | ggc | ggc | acg | gtg | gcg | gcc | gcc | ggc | ggg | gag |     | 144  |
| Gly | Ser | Ala | Tyr | Glu | Gly | Gly | Gly | Thr | Val | Ala | Ala | Ala | Gly | Gly | Glu |     |      |
|     | 35  |     |     |     | 40  |     |     |     |     | 45  |     |     |     |     |     |     |      |
| gag | acg | gcg | gcg | ccg | aag | ctg | gag | gac | ttc | ctc | ggc | atg | cag | gtg | cag |     | 192  |
| Glu | Thr | Ala | Ala | Pro | Lys | Leu | Glu | Asp | Phe | Leu | Gly | Met | Gln | Val | Gln |     |      |
| 50  |     |     |     |     | 55  |     |     |     |     | 60  |     |     |     |     |     |     |      |
| cag | gag | acg | gcc | gcc | gcg | gcg | gcg | ggg | cac | ggc | cgt | gga | ggc | agc | tcg |     | 240  |
| Gln | Glu | Thr | Ala | Ala | Ala | Ala | Ala | Gly | His | Gly | Arg | Gly | Gly | Ser | Ser |     |      |
| 65  |     |     |     |     | 70  |     |     |     |     | 75  |     |     |     |     | 80  |     |      |
| tcg | gtc | gtt | ggg | ctg | tcc | atg | atc | aag | aac | tgg | cta | cgc | agc | cag | ccg |     | 288  |
| Ser | Val | Val | Gly | Leu | Ser | Met | Ile | Lys | Asn | Trp | Leu | Arg | Ser | Gln | Pro |     |      |
|     |     |     |     | 85  |     |     |     |     | 90  |     |     |     |     | 95  |     |     |      |
| ccg | ccc | gcg | gtg | gtt | ggg | gga | gaa | gac | gct | atg | atg | gcg | ctc | gcg | gtg |     | 336  |
| Pro | Pro | Ala | Val | Val | Gly | Gly | Glu | Asp | Ala | Met | Met | Ala | Leu | Ala | Val |     |      |
|     |     | 100 |     |     |     |     | 105 |     |     |     |     | 110 |     |     |     |     |      |
| tcg | acg | tcg | gcg | tcc | ccg | ccg | gtg | gac | gcg | acg | gtg | ccg | gcc | tgc | att |     | 384  |
| Ser | Thr | Ser | Ala | Ser | Pro | Pro | Val | Asp | Ala | Thr | Val | Pro | Ala | Cys | Ile |     |      |
|     |     | 115 |     |     |     |     | 120 |     |     |     |     | 125 |     |     |     |     |      |
| tcg | ccg | gat | ggg | atg | ggg | tcg | aag | gcg | gcc | gac | ggc | ggc | ggc | gcg | gcc |     | 432  |
| Ser | Pro | Asp | Gly | Met | Gly | Ser | Lys | Ala | Ala | Asp | Gly | Gly | Gly | Ala | Ala |     |      |
|     | 130 |     |     |     |     | 135 |     |     |     |     | 140 |     |     |     |     |     |      |
| gag | gcg | gcg | gcg | gcg | gcg | gcg | gcg | cag | agg | atg | aag | gcg | gcc | atg | gac |     | 480  |
| Glu | Ala | Ala | Ala | Ala | Ala | Ala | Ala | Gln | Arg | Met | Lys | Ala | Ala | Met | Asp |     |      |
| 145 |     |     |     |     | 150 |     |     |     |     | 155 |     |     |     |     | 160 |     |      |
| acg | ttc | ggg | cag | cgg | acg | tcc | atc | tac | cgg | ggt | gtc | acc | aag | cac | agg |     | 528  |
| Thr | Phe | Gly | Gln | Arg | Thr | Ser | Ile | Tyr | Arg | Gly | Val | Thr | Lys | His | Arg |     |      |
|     |     |     |     | 165 |     |     |     |     | 170 |     |     |     |     | 175 |     |     |      |
| tgg | aca | gga | agg | tat | gaa | gcc | cat | ctt | tgg | gat | aac | agc | tgc | aga | aga |     | 576  |
| Trp | Thr | Gly | Arg | Tyr | Glu | Ala | His | Leu | Trp | Asp | Asn | Ser | Cys | Arg | Arg |     |      |
|     |     |     | 180 |     |     |     |     | 185 |     |     |     |     | 190 |     |     |     |      |
| gaa | ggt | cag | act | cgc | aaa | ggc | aga | caa | gta | tat | ctt | gga | gga | tat | gat |     | 624  |
| Glu | Gly | Gln | Thr | Arg | Lys | Gly | Arg | Gln | Val | Tyr | Leu | Gly | Gly | Tyr | Asp |     |      |
|     |     |     | 195 |     |     |     |     | 200 |     |     |     |     | 205 |     |     |     |      |
| aag | gaa | gaa | aaa | gct | gct | agg | gct | tat | gat | ttg | gct | gcc | ctt | aaa | tac |     | 672  |
| Lys | Glu | Glu | Lys | Ala | Ala | Arg | Ala | Tyr | Asp | Leu | Ala | Ala | Leu | Lys | Tyr |     |      |
|     | 210 |     |     |     |     | 215 |     |     |     |     | 220 |     |     |     |     |     |      |
| tgg | ggc | act | aca | acg | acg | acg | aat | ttt | ccg | gta | agc | aac | tac | gaa | aaa |     | 720  |
| Trp | Gly | Thr | Thr | Thr | Thr | Thr | Asn | Phe | Pro | Val | Ser | Asn | Tyr | Glu | Lys |     |      |
| 225 |     |     |     |     | 230 |     |     |     |     | 235 |     |     |     |     | 240 |     |      |
| gag | ttg | gat | gaa | atg | aag | cac | atg | aat | agg | cag | gaa | ttt | gtt | gca | tcc |     | 768  |
| Glu | Leu | Asp | Glu | Met | Lys | His | Met | Asn | Arg | Gln | Glu | Phe | Val | Ala | Ser |     |      |
|     |     |     |     | 245 |     |     |     |     | 250 |     |     |     |     | 255 |     |     |      |
| ctt | aga | aga | aaa | agc | agt | gga | ttt | tca | cgt | ggt | gct | tcc | ata | tat | cgt |     | 816  |
| Leu | Arg | Arg | Lys | Ser | Ser | Gly | Phe | Ser | Arg | Gly | Ala | Ser | Ile | Tyr | Arg |     |      |
|     |     |     | 260 |     |     |     |     | 265 |     |     |     |     | 270 |     |     |     |      |
| ggt | gtt | aca | aga | cac | cat | cag | cat | gga | agg | tgg | caa | gca | agg | ata | gga |     | 864  |
| Gly | Val | Thr | Arg | His | His | Gln | His | Gly | Arg | Trp | Gln | Ala | Arg | Ile | Gly |     |      |
|     |     | 275 |     |     |     |     | 280 |     |     |     |     | 285 |     |     |     |     |      |
| cgg | gtg | gca | gga | aac | aag | gat | ctg | tat | ttg | ggc | aca | ttt | ggc | acc | caa |     | 912  |
| Arg | Val | Ala | Gly | Asn | Lys | Asp | Leu | Tyr | Leu | Gly | Thr | Phe | Gly | Thr | Gln |     |      |
|     | 290 |     |     |     |     | 295 |     |     |     |     | 300 |     |     |     |     |     |      |
| gag | gaa | gct | gca | gag | gca | tat | gat | atc | gct | gca | atc | aaa | ttc | cgt | ggt |     | 960  |
| Glu | Glu | Ala | Ala | Glu | Ala | Tyr | Asp | Ile | Ala | Ala | Ile | Lys | Phe | Arg | Gly |     |      |
| 305 |     |     |     |     | 310 |     |     |     |     | 315 |     |     |     |     | 320 |     |      |
| ctc | aat | gct | gtg | aca | aac | ttt | gac | atg | agc | cgg | tac | gat | gtc | aag | agc |     | 1008 |
| Leu | Asn | Ala | Val | Thr | Asn | Phe | Asp | Met | Ser | Arg | Tyr | Asp | Val | Lys | Ser |     |      |
|     |     |     |     | 325 |     |     |     |     | 330 |     |     |     |     | 335 |     |     |      |
| atc | att | gaa | agc | agc | aat | ctc | cca | att | ggt | act | gga | acc | acc | cgg | cga |     | 1056 |

```
Ile Ile Glu Ser Ser Asn Leu Pro Ile Gly Thr Gly Thr Thr Arg Arg
                340                 345                 350 ttg aag gac tcc tct gat cac act gat aat gtc atg gac atc aat gtc       1104
Leu Lys Asp Ser Ser Asp His Thr Asp Asn Val Met Asp Ile Asn Val
        355                 360                 365 aat acc gaa ccc aat aat gtg gta tca tcc cac ttc acc aat ggg gtt       1152
Asn Thr Glu Pro Asn Asn Val Val Ser Ser His Phe Thr Asn Gly Val
370                 375                 380 ggc aac tat ggt tcg cag cat tat ggt tac aat gga tgg tcg cca att       1200
Gly Asn Tyr Gly Ser Gln His Tyr Gly Tyr Asn Gly Trp Ser Pro Ile
385                 390                 395                 400 agc atg cag ccg atc ccc tcg cag tac gcc aac ggc cag ccc agg gca       1248
Ser Met Gln Pro Ile Pro Ser Gln Tyr Ala Asn Gly Gln Pro Arg Ala
                405                 410                 415 tgg ttg aaa caa gag cag gac agc tct gtg gtt aca gcg gcg cag aac       1296
Trp Leu Lys Gln Glu Gln Asp Ser Ser Val Val Thr Ala Ala Gln Asn
            420                 425                 430 ctg cac aat cta cat cat ttt agt tcc ttg ggc tac acc cac aac ttc       1344
Leu His Asn Leu His His Phe Ser Ser Leu Gly Tyr Thr His Asn Phe
        435                 440                 445 ttc cag caa tct gat gtt cca gac gtc aca ggt ttc gtt gat gcg cct       1392
Phe Gln Gln Ser Asp Val Pro Asp Val Thr Gly Phe Val Asp Ala Pro
450                 455                 460 tcg agg tcc agt gac tca tac tcc ttc agg tac aat gga aca aat ggc       1440
Ser Arg Ser Ser Asp Ser Tyr Ser Phe Arg Tyr Asn Gly Thr Asn Gly
465                 470                 475                 480 ttt cat ggt ctc ccg ggt gga atc agc tat gct atg ccg gtt gcg aca       1488
Phe His Gly Leu Pro Gly Gly Ile Ser Tyr Ala Met Pro Val Ala Thr
                485                 490                 495 gcg gtg gac caa ggt cag ggc atc cat ggc tat gga gaa gat ggt gtg       1536
Ala Val Asp Gln Gly Gln Gly Ile His Gly Tyr Gly Glu Asp Gly Val
            500                 505                 510 gca ggc att gac acc aca cat gac ctg tat ggc agc cgt aat gtg tac       1584
Ala Gly Ile Asp Thr Thr His Asp Leu Tyr Gly Ser Arg Asn Val Tyr
        515                 520                 525 tac ctt tcc gag ggt tcg ctt ctt gcc gat gtc gaa aaa gaa ggc gac       1632
Tyr Leu Ser Glu Gly Ser Leu Leu Ala Asp Val Glu Lys Glu Gly Asp
530                 535                 540 tat ggc caa tct gtg ggg ggc aac agc tgg gtt ttg ccg aca ccg tag       1680
Tyr Gly Gln Ser Val Gly Gly Asn Ser Trp Val Leu Pro Thr Pro
545                 550                 555

<210> SEQ ID NO 33
<211> LENGTH: 559
<212> TYPE: PRT
<213> ORGANISM: Oryza sativa

<400> SEQUENCE: 33

Met Ala Ser Ile Thr Asn Trp Leu Gly Phe Ser Ser Ser Ser Phe Ser
1               5                   10                  15

Gly Ala Gly Ala Asp Pro Val Leu Pro His Pro Pro Leu Gln Glu Trp
                20                  25                  30

Gly Ser Ala Tyr Glu Gly Gly Gly Thr Val Ala Ala Ala Gly Gly Glu
            35                  40                  45

Glu Thr Ala Ala Pro Lys Leu Glu Asp Phe Leu Gly Met Gln Val Gln
        50                  55                  60

Gln Glu Thr Ala Ala Ala Ala Ala Gly His Gly Arg Gly Gly Ser Ser
65                  70                  75                  80

Ser Val Val Gly Leu Ser Met Ile Lys Asn Trp Leu Arg Ser Gln Pro
```

```
                      85                  90                  95
Pro Pro Ala Val Val Gly Gly Glu Asp Ala Met Met Ala Leu Ala Val
                100                 105                 110

Ser Thr Ser Ala Ser Pro Pro Val Asp Ala Thr Val Pro Ala Cys Ile
                115                 120                 125

Ser Pro Asp Gly Met Gly Ser Lys Ala Ala Asp Gly Gly Ala Ala
            130                 135                 140

Glu Ala Ala Ala Ala Ala Ala Gln Arg Met Lys Ala Ala Met Asp
145                 150                 155                 160

Thr Phe Gly Gln Arg Thr Ser Ile Tyr Arg Gly Val Thr Lys His Arg
                165                 170                 175

Trp Thr Gly Arg Tyr Glu Ala His Leu Trp Asp Asn Ser Cys Arg Arg
                180                 185                 190

Glu Gly Gln Thr Arg Lys Gly Arg Gln Val Tyr Leu Gly Gly Tyr Asp
                195                 200                 205

Lys Glu Glu Lys Ala Ala Arg Ala Tyr Asp Leu Ala Ala Leu Lys Tyr
            210                 215                 220

Trp Gly Thr Thr Thr Thr Thr Asn Phe Pro Val Ser Asn Tyr Glu Lys
225                 230                 235                 240

Glu Leu Asp Glu Met Lys His Met Asn Arg Gln Glu Phe Val Ala Ser
                245                 250                 255

Leu Arg Arg Lys Ser Ser Gly Phe Ser Arg Gly Ala Ser Ile Tyr Arg
                260                 265                 270

Gly Val Thr Arg His His Gln His Gly Arg Trp Gln Ala Arg Ile Gly
                275                 280                 285

Arg Val Ala Gly Asn Lys Asp Leu Tyr Leu Gly Thr Phe Gly Thr Gln
                290                 295                 300

Glu Glu Ala Ala Glu Ala Tyr Asp Ile Ala Ala Ile Lys Phe Arg Gly
305                 310                 315                 320

Leu Asn Ala Val Thr Asn Phe Asp Met Ser Arg Tyr Asp Val Lys Ser
                325                 330                 335

Ile Ile Glu Ser Ser Asn Leu Pro Ile Gly Thr Gly Thr Thr Arg Arg
                340                 345                 350

Leu Lys Asp Ser Ser Asp His Thr Asp Asn Val Met Asp Ile Asn Val
                355                 360                 365

Asn Thr Glu Pro Asn Asn Val Val Ser Ser His Phe Thr Asn Gly Val
                370                 375                 380

Gly Asn Tyr Gly Ser Gln His Tyr Gly Tyr Asn Gly Trp Ser Pro Ile
385                 390                 395                 400

Ser Met Gln Pro Ile Pro Ser Gln Tyr Ala Asn Gly Gln Pro Arg Ala
                405                 410                 415

Trp Leu Lys Gln Glu Gln Asp Ser Ser Val Val Thr Ala Ala Gln Asn
                420                 425                 430

Leu His Asn Leu His His Phe Ser Ser Leu Gly Tyr Thr His Asn Phe
                435                 440                 445

Phe Gln Gln Ser Asp Val Pro Asp Val Thr Gly Phe Val Asp Ala Pro
                450                 455                 460

Ser Arg Ser Ser Asp Ser Tyr Ser Phe Arg Tyr Asn Gly Thr Asn Gly
465                 470                 475                 480

Phe His Gly Leu Pro Gly Gly Ile Ser Tyr Ala Met Pro Val Ala Thr
                485                 490                 495

Ala Val Asp Gln Gly Gln Gly Ile His Gly Tyr Gly Glu Asp Gly Val
                500                 505                 510
```

```
                Ala Gly Ile Asp Thr Thr His Asp Leu Tyr Gly Ser Arg Asn Val Tyr
                        515                 520                 525

Tyr Leu Ser Glu Gly Ser Leu Leu Ala Asp Val Glu Lys Glu Gly Asp
                530                 535                 540

Tyr Gly Gln Ser Val Gly Gly Asn Ser Trp Val Leu Pro Thr Pro
                545                 550                 555

<210> SEQ ID NO 34
                <211> LENGTH: 2112
                <212> TYPE: DNA
                <213> ORGANISM: Oryza sativa
                <220> FEATURE:
                <221> NAME/KEY: CDS
                <222> LOCATION: (1)...(2112)

<400> SEQUENCE: 34 atg gct tct gca aac aac tgg ctg ggc ttc tcg ctc tcc ggc caa gag    48
                Met Ala Ser Ala Asn Asn Trp Leu Gly Phe Ser Leu Ser Gly Gln Glu
                1               5                   10                  15 aat ccg cag cct cac cag gat agc tcg cct ccg gca gcc atc gac gtc    96
                Asn Pro Gln Pro His Gln Asp Ser Ser Pro Pro Ala Ala Ile Asp Val
                                20                  25                  30 tcc ggc gcc ggc gac ttc tat ggc ctg ccg acg tcg cag ccg acg gcg    144
                Ser Gly Ala Gly Asp Phe Tyr Gly Leu Pro Thr Ser Gln Pro Thr Ala
                            35                  40                  45 gcc gac gcg cac ctc ggc gtg gcg ggg cat cat cac aac gcc tcg tat    192
                Ala Asp Ala His Leu Gly Val Ala Gly His His His Asn Ala Ser Tyr
                        50                  55                  60 ggc atc atg gag gcc ttc aat agg gga gct caa gag gca caa gat tgg    240
                Gly Ile Met Glu Ala Phe Asn Arg Gly Ala Gln Glu Ala Gln Asp Trp
                65                  70                  75                  80 aac atg agg ggg ctg gac tac aac ggc ggc gcc tcg gag ctg tcg atg    288
                Asn Met Arg Gly Leu Asp Tyr Asn Gly Gly Ala Ser Glu Leu Ser Met
                                85                  90                  95 ctc gtc ggc tcc agc ggc ggc aag agg gcg gcg gcg gtg gag gag acc    336
                Leu Val Gly Ser Ser Gly Gly Lys Arg Ala Ala Ala Val Glu Glu Thr
                            100                 105                 110 gag ccg aag ctg gag gac ttc ctc ggc ggc aac tcg ttc gtc tcc gag    384
                Glu Pro Lys Leu Glu Asp Phe Leu Gly Gly Asn Ser Phe Val Ser Glu
                        115                 120                 125 caa gat cat cac gcg gcg ggg ggc ttc ctc ttc tcc ggc gtc ccg atg    432
                Gln Asp His His Ala Ala Gly Gly Phe Leu Phe Ser Gly Val Pro Met
                    130                 135                 140 gcc agc agc acc aac agc aac agc ggg agc aac act atg gag ctc tcc    480
                Ala Ser Ser Thr Asn Ser Asn Ser Gly Ser Asn Thr Met Glu Leu Ser
                145                 150                 155                 160 atg atc aag acc tgg ctc cgg aac aac ggc cag gtg ccc gcc ggc cac    528
                Met Ile Lys Thr Trp Leu Arg Asn Asn Gly Gln Val Pro Ala Gly His
                                165                 170                 175 cag ccg cag cag cag cag ccg gcg gcc gcg gcc gcc gcg cag cag         576
                Gln Pro Gln Gln Gln Gln Pro Ala Ala Ala Ala Ala Ala Gln Gln
                            180                 185                 190 cag gcg cac gag gcg gcg gag atg agc acc gac gcg agc gcg agc agc    624
                Gln Ala His Glu Ala Ala Glu Met Ser Thr Asp Ala Ser Ala Ser Ser
                        195                 200                 205 ttc ggg tgc tcc tcc gac gcg atg ggg agg agt aac aac ggc ggc gcg    672
                Phe Gly Cys Ser Ser Asp Ala Met Gly Arg Ser Asn Asn Gly Gly Ala
                    210                 215                 220 gtc tcg gcg gcg gcc ggc ggg acg agc tcg cag agc ctg gcg ctc tcg    720
                Val Ser Ala Ala Ala Gly Gly Thr Ser Ser Gln Ser Leu Ala Leu Ser
```

```
                225                 230                 235                 240
atg agc acg ggc tcg cac tcg cac ctg cct atc gtc gtc gcc ggc ggc        768
Met Ser Thr Gly Ser His Ser His Leu Pro Ile Val Val Ala Gly Gly
                    245                 250                 255 ggg aac gcc agc ggc gga gcg gcc gag agc aca tcg tcg gag aac aag        816
Gly Asn Ala Ser Gly Gly Ala Ala Glu Ser Thr Ser Ser Glu Asn Lys
                260                 265                 270 cgg gcc agc ggc gcc atg gat tcg ccg ggc ggt ggc gcg ata gag gcc        864
Arg Ala Ser Gly Ala Met Asp Ser Pro Gly Gly Gly Ala Ile Glu Ala
            275                 280                 285 gtg ccg agg aag tcc atc gac acg ttc ggg caa agg acc tcg ata tat        912
Val Pro Arg Lys Ser Ile Asp Thr Phe Gly Gln Arg Thr Ser Ile Tyr
        290                 295                 300 cga ggt gta aca agg cat aga tgg aca ggg cga tat gag gct cat ctc        960
Arg Gly Val Thr Arg His Arg Trp Thr Gly Arg Tyr Glu Ala His Leu
305                 310                 315                 320 tgg gat aat agc tgt aga aga gaa ggg cag agt cgc aag ggt agg caa       1008
Trp Asp Asn Ser Cys Arg Arg Glu Gly Gln Ser Arg Lys Gly Arg Gln
                325                 330                 335 gtt tat ctt ggt ggc tat gac aag gag gat aaa gca gcg aga gct tat       1056
Val Tyr Leu Gly Gly Tyr Asp Lys Glu Asp Lys Ala Ala Arg Ala Tyr
                340                 345                 350 gat ttg gca gct ctg aag tat tgg ggc aca aca aca aca aat ttc           1104
Asp Leu Ala Ala Leu Lys Tyr Trp Gly Thr Thr Thr Thr Asn Phe
            355                 360                 365 cca ata agt aac tat gaa aaa gag cta gat gaa atg aaa cat atg acc       1152
Pro Ile Ser Asn Tyr Glu Lys Glu Leu Asp Glu Met Lys His Met Thr
        370                 375                 380 agg cag gag tat att gca tac cta aga agg aat agc agt gga ttt tct       1200
Arg Gln Glu Tyr Ile Ala Tyr Leu Arg Arg Asn Ser Ser Gly Phe Ser
385                 390                 395                 400 cgt ggt gca tcg aaa tat cgt ggt gta acc agg cac cat cag cat ggg       1248
Arg Gly Ala Ser Lys Tyr Arg Gly Val Thr Arg His His Gln His Gly
                405                 410                 415 aga tgg caa gca agg ata ggg agg gtt gca gga aac aag gac ctc tac       1296
Arg Trp Gln Ala Arg Ile Gly Arg Val Ala Gly Asn Lys Asp Leu Tyr
                420                 425                 430 tta ggc acc ttc agc acc gag gag gag gcg gcg gag gcg tac gac atc       1344
Leu Gly Thr Phe Ser Thr Glu Glu Glu Ala Ala Glu Ala Tyr Asp Ile
            435                 440                 445 gcg gcg atc aag ttc cgg ggg ctc aac gcc gtc acc aac ttt gac atg       1392
Ala Ala Ile Lys Phe Arg Gly Leu Asn Ala Val Thr Asn Phe Asp Met
        450                 455                 460 agc cgc tac gac gtc aag agc atc ctg gag agc agc acg ctg ccg gtg       1440
Ser Arg Tyr Asp Val Lys Ser Ile Leu Glu Ser Ser Thr Leu Pro Val
465                 470                 475                 480 ggc ggc gcg gcg agg cgg ctg aag gag gcg gcg gac cac gcg gag gcg       1488
Gly Gly Ala Ala Arg Arg Leu Lys Glu Ala Ala Asp His Ala Glu Ala
                485                 490                 495 gcc ggc gcc acc atc tgg cgc gcc gcc gac atg gac ggc gcc ggc gtc       1536
Ala Gly Ala Thr Ile Trp Arg Ala Ala Asp Met Asp Gly Ala Gly Val
                500                 505                 510 atc tcc ggc ctg gcc gac gtc ggg atg ggc gcc tac gcc gcc tcg tac       1584
Ile Ser Gly Leu Ala Asp Val Gly Met Gly Ala Tyr Ala Ala Ser Tyr
            515                 520                 525 cac cac cac cac cac cac ggc tgg ccg acc atc gcg ttc cag cag ccg       1632
His His His His His His Gly Trp Pro Thr Ile Ala Phe Gln Gln Pro
        530                 535                 540 ccg ccg ctc gcc gtg cac tac ccg tac ggc cag gcg ccg gcg gcg ccg       1680
```

| | | | | | | | | | | | | | | | |
|---|---|---|---|---|---|---|---|---|---|---|---|---|---|---|---|
|Pro|Pro|Leu|Ala|Val|His|Tyr|Pro|Tyr|Gly|Gln|Ala|Pro|Ala|Ala|Pro|
|545| | | |550| | | |555| | | |560| | | |

| | | | | | | | | | | | | | |
|---|---|---|---|---|---|---|---|---|---|---|---|---|---|
|tcg|cgc|ggg|tgg|tgc|aag|ccc|gag|cag|gac|gcc|gcc|gtc|gct gcc gcc|
|Ser|Arg|Gly|Trp|Cys|Lys|Pro|Glu|Gln|Asp|Ala|Ala|Val|Ala Ala Ala|
| | | | |565| | | |570| | | |575| |

1728 gcg cac agc ctc cag gac ctc cag cag ctg cac ctc ggc agc gcc gcc
Ala His Ser Leu Gln Asp Leu Gln Gln Leu His Leu Gly Ser Ala Ala
              580                  585                  590

1776 gcc cac aac ttc ttc cag gcg tcg tcg agc tcg acg gtc tac aac ggc
Ala His Asn Phe Phe Gln Ala Ser Ser Ser Ser Thr Val Tyr Asn Gly
              595                  600                  605

1824 ggc ggc ggc ggg tac cag ggc ctc ggt ggc aac gcc ttc ttg atg ccg
Gly Gly Gly Gly Tyr Gln Gly Leu Gly Gly Asn Ala Phe Leu Met Pro
610                  615                  620

1872 gcg agc acc gtc gtg gcc gac cag ggg cac agc agc acg gcc acc aac
Ala Ser Thr Val Val Ala Asp Gln Gly His Ser Ser Thr Ala Thr Asn
625                  630                  635                  640

1920 cat gga aac acc tgc agc tac ggc aac gag gag cag ggg aag ctc atc
His Gly Asn Thr Cys Ser Tyr Gly Asn Glu Glu Gln Gly Lys Leu Ile
              645                  650                  655

1968 ggg tac gac gcc atg gcg atg gcg agc ggc gcc gcc ggc ggg ggg tac
Gly Tyr Asp Ala Met Ala Met Ala Ser Gly Ala Ala Gly Gly Gly Tyr
              660                  665                  670

2016 cag ctg tcg cag ggc tcg gcg tcg acg gtg agc atc gcg agg gcg aac
Gln Leu Ser Gln Gly Ser Ala Ser Thr Val Ser Ile Ala Arg Ala Asn
              675                  680                  685

2064 ggc tac tcg gcc aac tgg agc tcg cct ttc aat ggc gcc atg gga tga
Gly Tyr Ser Ala Asn Trp Ser Ser Pro Phe Asn Gly Ala Met Gly
690                  695                  700

2112

<210> SEQ ID NO 35
<211> LENGTH: 703
<212> TYPE: PRT
<213> ORGANISM: Oryza sativa

<400> SEQUENCE: 35

Met Ala Ser Ala Asn Asn Trp Leu Gly Phe Ser Leu Ser Gly Gln Glu
1               5                   10                  15

Asn Pro Gln Pro His Gln Asp Ser Ser Pro Ala Ala Ile Asp Val
            20                  25                  30

Ser Gly Ala Gly Asp Phe Tyr Gly Leu Pro Thr Ser Gln Pro Thr Ala
        35                  40                  45

Ala Asp Ala His Leu Gly Val Ala Gly His His His Asn Ala Ser Tyr
50                  55                  60

Gly Ile Met Glu Ala Phe Asn Arg Gly Ala Gln Glu Ala Gln Asp Trp
65                  70                  75                  80

Asn Met Arg Gly Leu Asp Tyr Asn Gly Gly Ala Ser Glu Leu Ser Met
                85                  90                  95

Leu Val Gly Ser Ser Gly Gly Lys Arg Ala Ala Ala Val Glu Glu Thr
            100                 105                 110

Glu Pro Lys Leu Glu Asp Phe Leu Gly Gly Asn Ser Phe Val Ser Glu
        115                 120                 125

Gln Asp His His Ala Ala Gly Gly Phe Leu Phe Ser Gly Val Pro Met
    130                 135                 140

Ala Ser Ser Thr Asn Ser Asn Ser Gly Ser Asn Thr Met Glu Leu Ser
145                 150                 155                 160

Met Ile Lys Thr Trp Leu Arg Asn Asn Gly Gln Val Pro Ala Gly His
                165                 170                 175

```
Gln Pro Gln Gln Gln Gln Pro Ala Ala Ala Ala Ala Ala Gln Gln
            180                 185                 190

Gln Ala His Glu Ala Ala Glu Met Ser Thr Asp Ala Ser Ala Ser Ser
        195                 200                 205

Phe Gly Cys Ser Ser Asp Ala Met Gly Arg Ser Asn Asn Gly Gly Ala
    210                 215                 220

Val Ser Ala Ala Ala Gly Gly Thr Ser Ser Gln Ser Leu Ala Leu Ser
225                 230                 235                 240

Met Ser Thr Gly Ser His Ser His Leu Pro Ile Val Val Ala Gly Gly
                245                 250                 255

Gly Asn Ala Ser Gly Gly Ala Ala Glu Ser Thr Ser Ser Glu Asn Lys
            260                 265                 270

Arg Ala Ser Gly Ala Met Asp Ser Pro Gly Gly Gly Ala Ile Glu Ala
        275                 280                 285

Val Pro Arg Lys Ser Ile Asp Thr Phe Gly Gln Arg Thr Ser Ile Tyr
    290                 295                 300

Arg Gly Val Thr Arg His Arg Trp Thr Gly Arg Tyr Glu Ala His Leu
305                 310                 315                 320

Trp Asp Asn Ser Cys Arg Arg Glu Gly Gln Ser Arg Lys Gly Arg Gln
                325                 330                 335

Val Tyr Leu Gly Gly Tyr Asp Lys Glu Asp Lys Ala Ala Arg Ala Tyr
            340                 345                 350

Asp Leu Ala Ala Leu Lys Tyr Trp Gly Thr Thr Thr Thr Asn Phe
        355                 360                 365

Pro Ile Ser Asn Tyr Glu Lys Glu Leu Asp Glu Met Lys His Met Thr
    370                 375                 380

Arg Gln Glu Tyr Ile Ala Tyr Leu Arg Arg Asn Ser Ser Gly Phe Ser
385                 390                 395                 400

Arg Gly Ala Ser Lys Tyr Arg Gly Val Thr Arg His His Gln His Gly
                405                 410                 415

Arg Trp Gln Ala Arg Ile Gly Arg Val Ala Gly Asn Lys Asp Leu Tyr
            420                 425                 430

Leu Gly Thr Phe Ser Thr Glu Glu Glu Ala Ala Glu Ala Tyr Asp Ile
        435                 440                 445

Ala Ala Ile Lys Phe Arg Gly Leu Asn Ala Val Thr Asn Phe Asp Met
    450                 455                 460

Ser Arg Tyr Asp Val Lys Ser Ile Leu Glu Ser Ser Thr Leu Pro Val
465                 470                 475                 480

Gly Gly Ala Ala Arg Arg Leu Lys Glu Ala Ala Asp His Ala Glu Ala
                485                 490                 495

Ala Gly Ala Thr Ile Trp Arg Ala Ala Asp Met Asp Gly Ala Gly Val
            500                 505                 510

Ile Ser Gly Leu Ala Asp Val Gly Met Gly Ala Tyr Ala Ala Ser Tyr
        515                 520                 525

His His His His His Gly Trp Pro Thr Ile Ala Phe Gln Gln Pro
    530                 535                 540

Pro Pro Leu Ala Val His Tyr Pro Tyr Gly Gln Ala Pro Ala Ala Pro
545                 550                 555                 560

Ser Arg Gly Trp Cys Lys Pro Glu Gln Asp Ala Ala Val Ala Ala Ala
                565                 570                 575

Ala His Ser Leu Gln Asp Leu Gln Leu His Leu Gly Ser Ala Ala
            580                 585                 590
```

-continued

```
Ala His Asn Phe Phe Gln Ala Ser Ser Ser Thr Val Tyr Asn Gly
    595                 600                 605
Gly Gly Gly Gly Tyr Gln Gly Leu Gly Gly Asn Ala Phe Leu Met Pro
610                 615                 620
Ala Ser Thr Val Val Ala Asp Gln Gly His Ser Ser Thr Ala Thr Asn
625                 630                 635                 640
His Gly Asn Thr Cys Ser Tyr Gly Asn Glu Glu Gln Gly Lys Leu Ile
            645                 650                 655
Gly Tyr Asp Ala Met Ala Met Ala Ser Gly Ala Ala Gly Gly Tyr
            660                 665                 670
Gln Leu Ser Gln Gly Ser Ala Ser Thr Val Ser Ile Ala Arg Ala Asn
            675                 680                 685
Gly Tyr Ser Ala Asn Trp Ser Ser Pro Phe Asn Gly Ala Met Gly
            690                 695                 700

<210> SEQ ID NO 36
<211> LENGTH: 1977
<212> TYPE: DNA
<213> ORGANISM: Oryza sativa
<220> FEATURE:
<221> NAME/KEY: CDS
<222> LOCATION: (1)...(1977)

<400> SEQUENCE: 36 atg gct tct gca gat aac tgg cta ggc ttc tcg ctc tcc ggc caa ggc      48
Met Ala Ser Ala Asp Asn Trp Leu Gly Phe Ser Leu Ser Gly Gln Gly
  1               5                  10                  15 aac cca cag cat cac cag aac ggc tcg ccg tct gcc gcc ggc gac gcc      96
Asn Pro Gln His His Gln Asn Gly Ser Pro Ser Ala Ala Gly Asp Ala
             20                  25                  30 gcc atc gac atc tcc ggc tca ggc gac ttc tat ggt ctg cca acg ccg     144
Ala Ile Asp Ile Ser Gly Ser Gly Asp Phe Tyr Gly Leu Pro Thr Pro
         35                  40                  45 gac gca cac cac atc ggc atg gcg ggc gaa gac gcg ccc tat ggc gtc     192
Asp Ala His His Ile Gly Met Ala Gly Glu Asp Ala Pro Tyr Gly Val
     50                  55                  60 atg gat gct ttc aac aga ggc acc cat gaa acc caa gat tgg gcg atg     240
Met Asp Ala Phe Asn Arg Gly Thr His Glu Thr Gln Asp Trp Ala Met
 65                  70                  75                  80 agg ggt ttg gac tac ggc ggc ggc tcc tcc gac ctc tcg atg ctc gtc     288
Arg Gly Leu Asp Tyr Gly Gly Gly Ser Ser Asp Leu Ser Met Leu Val
                 85                  90                  95 ggc tcg agc ggc ggc ggg agg agg acg gtg gcc ggc gac ggc gtc ggc     336
Gly Ser Ser Gly Gly Gly Arg Arg Thr Val Ala Gly Asp Gly Val Gly
            100                 105                 110 gag gcg ccg aag ctg gag aac ttc ctc gac ggc aac tca ttc tcc gac     384
Glu Ala Pro Lys Leu Glu Asn Phe Leu Asp Gly Asn Ser Phe Ser Asp
        115                 120                 125 gtg cac ggc caa gcc gcc ggg ggg tac ctc tac tcc gga agc gct gtc     432
Val His Gly Gln Ala Ala Gly Gly Tyr Leu Tyr Ser Gly Ser Ala Val
    130                 135                 140 ggc ggc gcc ggt ggt tac agt aac ggc gga tgc ggc ggc gga acc ata     480
Gly Gly Ala Gly Gly Tyr Ser Asn Gly Gly Cys Gly Gly Gly Thr Ile
145                 150                 155                 160 gag ctg tcc atg atc aag acg tgg ctc cgg agc aac cag tcg cag cag     528
Glu Leu Ser Met Ile Lys Thr Trp Leu Arg Ser Asn Gln Ser Gln Gln
                165                 170                 175 cag cca tcg ccg ccg cag cac gct gat cag ggc atg agc acc gac gcc     576
Gln Pro Ser Pro Pro Gln His Ala Asp Gln Gly Met Ser Thr Asp Ala
            180                 185                 190
```

```
agc gcg agc agc tac gcg tgc tcc gac gtg ctg gtg ggg agc tgc ggc    624
Ser Ala Ser Ser Tyr Ala Cys Ser Asp Val Leu Val Gly Ser Cys Gly
        195                 200                 205 ggc ggc ggc gcc ggg ggc acg gcg agc tcg cat ggg cag ggc ctg gcg    672
Gly Gly Gly Ala Gly Gly Thr Ala Ser Ser His Gly Gln Gly Leu Ala
    210                 215                 220 ctg tcg atg agc acg ggg tcg gtg gcc gcc gcc gga ggg ggc ggc gcc    720
Leu Ser Met Ser Thr Gly Ser Val Ala Ala Ala Gly Gly Gly Gly Ala
225                 230                 235                 240 gtc gtc gcg gcc gag agc tcg tcg tcg gag aac aag cgg gtg gat tcg    768
Val Val Ala Ala Glu Ser Ser Ser Ser Glu Asn Lys Arg Val Asp Ser
                245                 250                 255 ccg ggc ggc gcc gtg gac ggc gcc gtc ccg agg aaa tcc atc gac acc    816
Pro Gly Gly Ala Val Asp Gly Ala Val Pro Arg Lys Ser Ile Asp Thr
            260                 265                 270 ttc ggg caa agg acg tct ata tac cga ggt gta aca agg cat aga tgg    864
Phe Gly Gln Arg Thr Ser Ile Tyr Arg Gly Val Thr Arg His Arg Trp
        275                 280                 285 aca gga aga tat gaa gct cat ctg tgg gat aat agc tgt agg aga gaa    912
Thr Gly Arg Tyr Glu Ala His Leu Trp Asp Asn Ser Cys Arg Arg Glu
    290                 295                 300 ggc caa agt cgc aag ggg aga cag gtt tat ttg ggc ggt tat gac aaa    960
Gly Gln Ser Arg Lys Gly Arg Gln Val Tyr Leu Gly Gly Tyr Asp Lys
305                 310                 315                 320 gaa gat aag gcg gct cgg gct tat gat ttg gca gct cta aaa tac tgg   1008
Glu Asp Lys Ala Ala Arg Ala Tyr Asp Leu Ala Ala Leu Lys Tyr Trp
                325                 330                 335 ggc acg acc aca aca aca aat ttc cca atg agt aat tat gaa aag gag   1056
Gly Thr Thr Thr Thr Thr Asn Phe Pro Met Ser Asn Tyr Glu Lys Glu
            340                 345                 350 cta gag gaa atg aaa cac atg acc agg cag gag tac att gca cat ctt   1104
Leu Glu Glu Met Lys His Met Thr Arg Gln Glu Tyr Ile Ala His Leu
        355                 360                 365 aga agg aat agc agt gga ttt tct cgt ggt gca tcc aaa tat cgt ggt   1152
Arg Arg Asn Ser Ser Gly Phe Ser Arg Gly Ala Ser Lys Tyr Arg Gly
    370                 375                 380 gtt act agg cat cat cag cat ggg aga tgg cag gca agg ata ggg cga   1200
Val Thr Arg His His Gln His Gly Arg Trp Gln Ala Arg Ile Gly Arg
385                 390                 395                 400 gtt gca ggc aac aag gat atc tac cta ggc acc ttc agc acc gag gag   1248
Val Ala Gly Asn Lys Asp Ile Tyr Leu Gly Thr Phe Ser Thr Glu Glu
                405                 410                 415 gag gcc gcc gag gcg tac gac atc gcc gcc atc aag ttc cgc ggg ctc   1296
Glu Ala Ala Glu Ala Tyr Asp Ile Ala Ala Ile Lys Phe Arg Gly Leu
            420                 425                 430 aac gcc gtc acc aac ttc gac atg agc cgg tac gac gtc aag agc atc   1344
Asn Ala Val Thr Asn Phe Asp Met Ser Arg Tyr Asp Val Lys Ser Ile
        435                 440                 445 ctg gac agc agc acg ctg ccg gtc ggc ggc gcg gcg cgg cgg ctc aag   1392
Leu Asp Ser Ser Thr Leu Pro Val Gly Gly Ala Ala Arg Arg Leu Lys
    450                 455                 460 gag gcg gag gtc gcc gcc gcc gcc gcg ggc ggc ggc gtg atc gtc tcc   1440
Glu Ala Glu Val Ala Ala Ala Ala Ala Gly Gly Gly Val Ile Val Ser
465                 470                 475                 480 cac ctg gcc gac ggc ggt gtg ggt ggg tac tac tac ggg tgc ggc ccg   1488
His Leu Ala Asp Gly Gly Val Gly Gly Tyr Tyr Tyr Gly Cys Gly Pro
                485                 490                 495 acc atc gcg ttc ggc ggc ggc cag cag ccg gcg ccg ctc gcc gtg       1536
Thr Ile Ala Phe Gly Gly Gly Gln Gln Pro Ala Pro Leu Ala Val
```

```
                           500                 505                 510
cac tac ccg tcg tac ggc cag gcc agc ggg tgg tgc aag ccg gag cag      1584
His Tyr Pro Ser Tyr Gly Gln Ala Ser Gly Trp Cys Lys Pro Glu Gln
            515                 520                 525 gac gcg gtg atc gcg gcc ggg cac tgc gcg acg gac ctc cag cac ctg      1632
Asp Ala Val Ile Ala Ala Gly His Cys Ala Thr Asp Leu Gln His Leu
        530                 535                 540 cac ctc ggg agc ggc ggc gcc gcc gcc acc cac aac ttc ttc cag cag      1680
His Leu Gly Ser Gly Gly Ala Ala Ala Thr His Asn Phe Phe Gln Gln
545                 550                 555                 560 ccg gcg tca agc tcg gcc gtc tac ggc aac ggc ggc ggc ggc ggc          1728
Pro Ala Ser Ser Ser Ala Val Tyr Gly Asn Gly Gly Gly Gly Gly
                565                 570                 575 aac gcg ttc atg atg ccg atg ggc gcc gtg gtg gcc gcc gcc gat cac      1776
Asn Ala Phe Met Met Pro Met Gly Ala Val Val Ala Ala Ala Asp His
            580                 585                 590 ggc ggg cag agc agc gcc tac ggc ggt ggc gac gag agc ggg agg ctc      1824
Gly Gly Gln Ser Ser Ala Tyr Gly Gly Gly Asp Glu Ser Gly Arg Leu
        595                 600                 605 gtc gtg ggg tac gac ggc gtc gtc gac ccg tac gcg gcc atg aga agc      1872
Val Val Gly Tyr Asp Gly Val Val Asp Pro Tyr Ala Ala Met Arg Ser
610                 615                 620 gcg tac gag ctc tcg cag ggc tcg tcg tcg tcg gtg agc gtc gcg          1920
Ala Tyr Glu Leu Ser Gln Gly Ser Ser Ser Ser Val Ser Val Ala
625                 630                 635                 640 aag gcg gcg aac ggg tac ccg gac aac tgg agc tcg ccg ttc aac ggc      1968
Lys Ala Ala Asn Gly Tyr Pro Asp Asn Trp Ser Ser Pro Phe Asn Gly
            645                 650                 655 atg gga tga                                                          1977
Met Gly <210> SEQ ID NO 37
<211> LENGTH: 658
<212> TYPE: PRT
<213> ORGANISM: Oryza sativa

<400> SEQUENCE: 37

Met Ala Ser Ala Asp Asn Trp Leu Gly Phe Ser Leu Ser Gly Gln Gly
1               5                   10                  15

Asn Pro Gln His His Gln Asn Gly Ser Pro Ser Ala Ala Gly Asp Ala
            20                  25                  30

Ala Ile Asp Ile Ser Gly Ser Gly Asp Phe Tyr Gly Leu Pro Thr Pro
        35                  40                  45

Asp Ala His His Ile Gly Met Ala Gly Glu Asp Ala Pro Tyr Gly Val
    50                  55                  60

Met Asp Ala Phe Asn Arg Gly Thr His Glu Thr Gln Asp Trp Ala Met
65                  70                  75                  80

Arg Gly Leu Asp Tyr Gly Gly Gly Ser Ser Asp Leu Ser Met Leu Val
                85                  90                  95

Gly Ser Ser Gly Gly Gly Arg Arg Thr Val Ala Gly Asp Gly Val Gly
            100                 105                 110

Glu Ala Pro Lys Leu Glu Asn Phe Leu Asp Gly Asn Ser Phe Ser Asp
        115                 120                 125

Val His Gly Gln Ala Ala Gly Gly Tyr Leu Tyr Ser Gly Ser Ala Val
    130                 135                 140

Gly Gly Ala Gly Gly Tyr Ser Asn Gly Gly Cys Gly Gly Gly Thr Ile
145                 150                 155                 160
```

-continued

```
Glu Leu Ser Met Ile Lys Thr Trp Leu Arg Ser Asn Gln Ser Gln Gln
                165                 170                 175

Gln Pro Ser Pro Pro Gln His Ala Asp Gln Gly Met Ser Thr Asp Ala
            180                 185                 190

Ser Ala Ser Ser Tyr Ala Cys Ser Asp Val Leu Val Gly Ser Cys Gly
        195                 200                 205

Gly Gly Gly Ala Gly Gly Thr Ala Ser Ser His Gly Gln Gly Leu Ala
    210                 215                 220

Leu Ser Met Ser Thr Gly Ser Val Ala Ala Gly Gly Gly Gly Gly Ala
225                 230                 235                 240

Val Val Ala Ala Glu Ser Ser Ser Glu Asn Lys Arg Val Asp Ser
                245                 250                 255

Pro Gly Gly Ala Val Asp Gly Ala Val Pro Arg Lys Ser Ile Asp Thr
            260                 265                 270

Phe Gly Gln Arg Thr Ser Ile Tyr Arg Gly Val Thr Arg His Arg Trp
        275                 280                 285

Thr Gly Arg Tyr Glu Ala His Leu Trp Asp Asn Ser Cys Arg Arg Glu
    290                 295                 300

Gly Gln Ser Arg Lys Gly Arg Gln Val Tyr Leu Gly Gly Tyr Asp Lys
305                 310                 315                 320

Glu Asp Lys Ala Ala Arg Ala Tyr Asp Leu Ala Ala Leu Lys Tyr Trp
                325                 330                 335

Gly Thr Thr Thr Thr Thr Asn Phe Pro Met Ser Asn Tyr Glu Lys Glu
            340                 345                 350

Leu Glu Glu Met Lys His Met Thr Arg Gln Glu Tyr Ile Ala His Leu
        355                 360                 365

Arg Arg Asn Ser Ser Gly Phe Ser Arg Gly Ala Ser Lys Tyr Arg Gly
    370                 375                 380

Val Thr Arg His His Gln His Gly Arg Trp Gln Ala Arg Ile Gly Arg
385                 390                 395                 400

Val Ala Gly Asn Lys Asp Ile Tyr Leu Gly Thr Phe Ser Thr Glu Glu
                405                 410                 415

Glu Ala Ala Glu Ala Tyr Asp Ile Ala Ala Ile Lys Phe Arg Gly Leu
            420                 425                 430

Asn Ala Val Thr Asn Phe Asp Met Ser Arg Tyr Asp Val Lys Ser Ile
        435                 440                 445

Leu Asp Ser Ser Thr Leu Pro Val Gly Gly Ala Ala Arg Arg Leu Lys
    450                 455                 460

Glu Ala Glu Val Ala Ala Ala Ala Gly Gly Gly Val Ile Val Ser
465                 470                 475                 480

His Leu Ala Asp Gly Gly Val Gly Gly Tyr Tyr Tyr Gly Cys Gly Pro
                485                 490                 495

Thr Ile Ala Phe Gly Gly Gly Gln Gln Pro Ala Pro Leu Ala Val
            500                 505                 510

His Tyr Pro Ser Tyr Gly Gln Ala Ser Gly Trp Cys Lys Pro Glu Gln
        515                 520                 525

Asp Ala Val Ile Ala Ala Gly His Cys Ala Thr Asp Leu Gln His Leu
    530                 535                 540

His Leu Gly Ser Gly Gly Ala Ala Thr His Asn Phe Phe Gln Gln
545                 550                 555                 560

Pro Ala Ser Ser Ser Ala Val Tyr Gly Asn Gly Gly Gly Gly Gly
                565                 570                 575

Asn Ala Phe Met Met Pro Met Gly Ala Val Val Ala Ala Ala Asp His
```

```
                580             585              590
Gly Gly Gln Ser Ser Ala Tyr Gly Gly Asp Glu Ser Gly Arg Leu
            595             600             605

Val Val Gly Tyr Asp Gly Val Asp Pro Tyr Ala Ala Met Arg Ser
610             615             620

Ala Tyr Glu Leu Ser Gln Gly Ser Ser Ser Ser Val Ser Val Ala
625             630             635             640

Lys Ala Ala Asn Gly Tyr Pro Asp Asn Trp Ser Ser Pro Phe Asn Gly
                645             650             655

Met Gly

<210> SEQ ID NO 38
<211> LENGTH: 2112
<212> TYPE: DNA
<213> ORGANISM: Sorghum bicolor
<220> FEATURE:
<221> NAME/KEY: CDS
<222> LOCATION: (1)...(2112)

<400> SEQUENCE: 38 atg gct act gtg aac aac tgg ctc gct ttc tcc ctc tcc ccg cag gag    48
Met Ala Thr Val Asn Asn Trp Leu Ala Phe Ser Leu Ser Pro Gln Glu
1               5                   10                  15 ctg ccg ccc acc cag acg gac tcc acc ctc atc tct gcc gcc acc acc    96
Leu Pro Pro Thr Gln Thr Asp Ser Thr Leu Ile Ser Ala Ala Thr Thr
            20                  25                  30 gac gat gtc tcc ggc gat gtc tgc ttc aac atc ccc caa gat tgg agc   144
Asp Asp Val Ser Gly Asp Val Cys Phe Asn Ile Pro Gln Asp Trp Ser
        35                  40                  45 atg agg gga tcc gag ctt tcg gcg ctc gtc gcc gag ccg aag ctg gag   192
Met Arg Gly Ser Glu Leu Ser Ala Leu Val Ala Glu Pro Lys Leu Glu
    50                  55                  60 gac ttc ctc ggc gga atc tcc ttc tcc gag cag cac cac aag gcc aac   240
Asp Phe Leu Gly Gly Ile Ser Phe Ser Glu Gln His His Lys Ala Asn
65                  70                  75                  80 tgc aac atg atc ccc agc act agc agc aca gct tgc tac gcg agc tcg   288
Cys Asn Met Ile Pro Ser Thr Ser Ser Thr Ala Cys Tyr Ala Ser Ser
                85                  90                  95 ggt gct acc gcc ggc tac cat cac cag ctg tac cac cag ccc acc agc   336
Gly Ala Thr Ala Gly Tyr His His Gln Leu Tyr His Gln Pro Thr Ser
            100                 105                 110 tcc gcg ctc cac ttc gct gac tcc gtc atg gtg gcc tcc tcg gcc ggc   384
Ser Ala Leu His Phe Ala Asp Ser Val Met Val Ala Ser Ser Ala Gly
        115                 120                 125 ggc gtc cac gac gga ggt gcc atg ctc agc gcg gcc agc gct aat ggt   432
Gly Val His Asp Gly Gly Ala Met Leu Ser Ala Ala Ser Ala Asn Gly
    130                 135                 140 agc gct ggc gct ggc gct gcc agt gcc aat ggc agc ggc agc atc ggg   480
Ser Ala Gly Ala Gly Ala Ala Ser Ala Asn Gly Ser Gly Ser Ile Gly
145                 150                 155                 160 ctg tcc atg atc aag aac tgg ctg cgg agc caa cca gct ccc atg cag   528
Leu Ser Met Ile Lys Asn Trp Leu Arg Ser Gln Pro Ala Pro Met Gln
                165                 170                 175 ccg agg gtg gcg gcg gct gag agc gtg cag ggg ctc tct ttg tcc atg   576
Pro Arg Val Ala Ala Ala Glu Ser Val Gln Gly Leu Ser Leu Ser Met
            180                 185                 190 aac atg gcg ggg gcg acg caa ggc gcc gct ggc atg cca ctt ctt gct   624
Asn Met Ala Gly Ala Thr Gln Gly Ala Ala Gly Met Pro Leu Leu Ala
        195                 200                 205
```

```
gga gag cgc ggc cgg gcg ccc gag agt gtc tcg acg tcg gca cag ggt      672
Gly Glu Arg Gly Arg Ala Pro Glu Ser Val Ser Thr Ser Ala Gln Gly
        210                 215                 220 gga gcc gtc gtc acg gct cca aag gag gat agc ggt ggc agc ggt gtt      720
Gly Ala Val Val Thr Ala Pro Lys Glu Asp Ser Gly Gly Ser Gly Val
225                 230                 235                 240 gcc gcc acc ggc gcc cta gta gcc gtg agc acg gac acg ggt ggc agc      768
Ala Ala Thr Gly Ala Leu Val Ala Val Ser Thr Asp Thr Gly Gly Ser
                245                 250                 255 ggc gcg tcg gct gac aac acg gca agg aag acg gtg gac acg ttc ggg      816
Gly Ala Ser Ala Asp Asn Thr Ala Arg Lys Thr Val Asp Thr Phe Gly
            260                 265                 270 cag cgc acg tcg att tac cgt ggc gtg aca agg cat aga tgg act ggg      864
Gln Arg Thr Ser Ile Tyr Arg Gly Val Thr Arg His Arg Trp Thr Gly
        275                 280                 285 aga tat gaa gca cat ctg tgg gac aac agt tgc aga agg gaa gga caa      912
Arg Tyr Glu Ala His Leu Trp Asp Asn Ser Cys Arg Arg Glu Gly Gln
    290                 295                 300 act cgc aag ggt cgt caa gtc tat tta ggt ggc tat gat aaa gag gag      960
Thr Arg Lys Gly Arg Gln Val Tyr Leu Gly Gly Tyr Asp Lys Glu Glu
305                 310                 315                 320 aaa gct gct agg gct tat gat ctg gct gct ctt aag tac tgg ggt ccc     1008
Lys Ala Ala Arg Ala Tyr Asp Leu Ala Ala Leu Lys Tyr Trp Gly Pro
                325                 330                 335 acg aca aca aca aat ttt cca gtg aat aac tac gaa aag gag ctg gag     1056
Thr Thr Thr Thr Asn Phe Pro Val Asn Asn Tyr Glu Lys Glu Leu Glu
            340                 345                 350 gat atg aag cac atg aca agg cag gag ttt gta gcg tct ctg aga agg     1104
Asp Met Lys His Met Thr Arg Gln Glu Phe Val Ala Ser Leu Arg Arg
        355                 360                 365 aag agc agt ggt ttc tcc aga ggt gca tcc att tac agg gga gtg act     1152
Lys Ser Ser Gly Phe Ser Arg Gly Ala Ser Ile Tyr Arg Gly Val Thr
    370                 375                 380 agg cat cac cag cat gga aga tgg caa gca cgg att gga cga gtt gca     1200
Arg His His Gln His Gly Arg Trp Gln Ala Arg Ile Gly Arg Val Ala
385                 390                 395                 400 ggg aac aag gat ctc tac ttg ggc acc ttc agc acg cag gag gag gca     1248
Gly Asn Lys Asp Leu Tyr Leu Gly Thr Phe Ser Thr Gln Glu Glu Ala
                405                 410                 415 gcg gag gca tac gac att gcg gcg atc aag ttc cgc ggc ctc aac gcc     1296
Ala Glu Ala Tyr Asp Ile Ala Ala Ile Lys Phe Arg Gly Leu Asn Ala
            420                 425                 430 gtc aca aac ttc gac atg agc cgc tac gac gtc aag agc atc ctg gac     1344
Val Thr Asn Phe Asp Met Ser Arg Tyr Asp Val Lys Ser Ile Leu Asp
        435                 440                 445 agc agt gcg ctc ccc atc ggc agc gcc gcc aag cgt ctc aag gag gcc     1392
Ser Ser Ala Leu Pro Ile Gly Ser Ala Ala Lys Arg Leu Lys Glu Ala
    450                 455                 460 gag gcc gcc gcg tcc gca cag cac cat gcc ggc gtg gtg agc tac gac     1440
Glu Ala Ala Ala Ser Ala Gln His His Ala Gly Val Val Ser Tyr Asp
465                 470                 475                 480 gtc ggc cgc ata gcc tca cag ctc ggc gac ggc ggc gcc ctg gcg gcg     1488
Val Gly Arg Ile Ala Ser Gln Leu Gly Asp Gly Gly Ala Leu Ala Ala
                485                 490                 495 gcg tac ggc gcg cac tac cat ggc gcc tgg ccg acc atc gcg ttc cag     1536
Ala Tyr Gly Ala His Tyr His Gly Ala Trp Pro Thr Ile Ala Phe Gln
            500                 505                 510 ccg agc gcg gcc acg ggc ctg tac cac ccg tac gcg cag ccg atg cgc     1584
Pro Ser Ala Ala Thr Gly Leu Tyr His Pro Tyr Ala Gln Pro Met Arg
        515                 520                 525
```

```
ggg tgg tgc aag cag gag cag gac cac gcg gtg atc gcg gcc gcg cac      1632
Gly Trp Cys Lys Gln Glu Gln Asp His Ala Val Ile Ala Ala Ala His
530                 535                 540 agc ctg cag gag ctc cac cac ctg aac ctg ggt gct gcc gcc ggc gcg      1680
Ser Leu Gln Glu Leu His His Leu Asn Leu Gly Ala Ala Ala Gly Ala
545                 550                 555                 560 cac gac ttc ttc tcg gcg ggg cag cag gcg gcg atg cac ggc ctg ggt      1728
His Asp Phe Phe Ser Ala Gly Gln Gln Ala Ala Met His Gly Leu Gly
                565                 570                 575 agc atg gac aat gca tca ctc gag cac agc acc ggc tcc aac tcc gtc      1776
Ser Met Asp Asn Ala Ser Leu Glu His Ser Thr Gly Ser Asn Ser Val
            580                 585                 590 gtg tac aac ggt gtt ggt gat agc aac ggc agc acc gtc gtc ggc agt      1824
Val Tyr Asn Gly Val Gly Asp Ser Asn Gly Ser Thr Val Val Gly Ser
        595                 600                 605 ggt ggc tac atg atg cct atg agc gct gcc acg gcg acg gct acc acg      1872
Gly Gly Tyr Met Met Pro Met Ser Ala Ala Thr Ala Thr Ala Thr Thr
610                 615                 620 gca atg gtg agc cac gag cag gtg cat gca cgg gca cag ggt gat cac      1920
Ala Met Val Ser His Glu Gln Val His Ala Arg Ala Gln Gly Asp His
625                 630                 635                 640 cac gac gaa gcc aag cag gct gct cag atg ggg tac gag agc tac ctg      1968
His Asp Glu Ala Lys Gln Ala Ala Gln Met Gly Tyr Glu Ser Tyr Leu
                645                 650                 655 gtg aac gca gag aac tat ggc ggc ggg agg atg tct gcg gcc tgg gcg      2016
Val Asn Ala Glu Asn Tyr Gly Gly Gly Arg Met Ser Ala Ala Trp Ala
            660                 665                 670 act gtc tca gcg cca ccg gcg gca agc agc aac gat aac atg gcg gac      2064
Thr Val Ser Ala Pro Pro Ala Ala Ser Ser Asn Asp Asn Met Ala Asp
        675                 680                 685 gtc ggc cat ggc ggc gca cag ctc ttc agt gtc tgg aac gat act taa      2112
Val Gly His Gly Gly Ala Gln Leu Phe Ser Val Trp Asn Asp Thr
690                 695                 700

<210> SEQ ID NO 39
<211> LENGTH: 703
<212> TYPE: PRT
<213> ORGANISM: Sorghum bicolor

<400> SEQUENCE: 39

Met Ala Thr Val Asn Asn Trp Leu Ala Phe Ser Leu Ser Pro Gln Glu
1               5                   10                  15

Leu Pro Pro Thr Gln Thr Asp Ser Thr Leu Ile Ser Ala Ala Thr Thr
            20                  25                  30

Asp Asp Val Ser Gly Asp Val Cys Phe Asn Ile Pro Gln Asp Trp Ser
        35                  40                  45

Met Arg Gly Ser Glu Leu Ser Ala Leu Val Ala Glu Pro Lys Leu Glu
    50                  55                  60

Asp Phe Leu Gly Gly Ile Ser Phe Ser Glu Gln His His Lys Ala Asn
65                  70                  75                  80

Cys Asn Met Ile Pro Ser Thr Ser Ser Thr Ala Cys Tyr Ala Ser Ser
                85                  90                  95

Gly Ala Thr Ala Gly Tyr His His Gln Leu Tyr His Gln Pro Thr Ser
            100                 105                 110

Ser Ala Leu His Phe Ala Asp Ser Val Met Val Ala Ser Ser Ala Gly
        115                 120                 125

Gly Val His Asp Gly Gly Ala Met Leu Ser Ala Ala Ser Ala Asn Gly
    130                 135                 140
```

```
Ser Ala Gly Ala Gly Ala Ala Ser Ala Asn Gly Ser Gly Ser Ile Gly
145                 150                 155                 160

Leu Ser Met Ile Lys Asn Trp Leu Arg Ser Gln Pro Ala Pro Met Gln
                165                 170                 175

Pro Arg Val Ala Ala Glu Ser Val Gln Gly Leu Ser Leu Ser Met
            180                 185                 190

Asn Met Ala Gly Ala Thr Gln Gly Ala Gly Met Pro Leu Leu Ala
            195                 200                 205

Gly Glu Arg Gly Arg Ala Pro Glu Ser Val Ser Thr Ser Ala Gln Gly
210                 215                 220

Gly Ala Val Val Thr Ala Pro Lys Glu Asp Ser Gly Ser Gly Val
225                 230                 235                 240

Ala Ala Thr Gly Ala Leu Val Ala Val Ser Thr Asp Thr Gly Gly Ser
                245                 250                 255

Gly Ala Ser Ala Asp Asn Thr Ala Arg Lys Thr Val Asp Thr Phe Gly
            260                 265                 270

Gln Arg Thr Ser Ile Tyr Arg Gly Val Thr Arg His Arg Trp Thr Gly
            275                 280                 285

Arg Tyr Glu Ala His Leu Trp Asp Asn Ser Cys Arg Arg Glu Gly Gln
290                 295                 300

Thr Arg Lys Gly Arg Gln Val Tyr Leu Gly Gly Tyr Asp Lys Glu Glu
305                 310                 315                 320

Lys Ala Ala Arg Ala Tyr Asp Leu Ala Ala Leu Lys Tyr Trp Gly Pro
                325                 330                 335

Thr Thr Thr Thr Asn Phe Pro Val Asn Asn Tyr Glu Lys Glu Leu Glu
            340                 345                 350

Asp Met Lys His Met Thr Arg Gln Glu Phe Val Ala Ser Leu Arg Arg
            355                 360                 365

Lys Ser Ser Gly Phe Ser Arg Gly Ala Ser Ile Tyr Arg Gly Val Thr
370                 375                 380

Arg His His Gln His Gly Arg Trp Gln Ala Arg Ile Gly Arg Val Ala
385                 390                 395                 400

Gly Asn Lys Asp Leu Tyr Leu Gly Thr Phe Ser Thr Gln Glu Glu Ala
                405                 410                 415

Ala Glu Ala Tyr Asp Ile Ala Ala Ile Lys Phe Arg Gly Leu Asn Ala
            420                 425                 430

Val Thr Asn Phe Asp Met Ser Arg Tyr Asp Val Lys Ser Ile Leu Asp
            435                 440                 445

Ser Ser Ala Leu Pro Ile Gly Ser Ala Ala Lys Arg Leu Lys Glu Ala
450                 455                 460

Glu Ala Ala Ala Ser Ala Gln His His Ala Gly Val Val Ser Tyr Asp
465                 470                 475                 480

Val Gly Arg Ile Ala Ser Gln Leu Gly Asp Gly Gly Ala Leu Ala Ala
                485                 490                 495

Ala Tyr Gly Ala His Tyr His Gly Ala Trp Pro Thr Ile Ala Phe Gln
            500                 505                 510

Pro Ser Ala Ala Thr Gly Leu Tyr His Pro Tyr Ala Gln Pro Met Arg
            515                 520                 525

Gly Trp Cys Lys Gln Glu Gln Asp His Ala Val Ile Ala Ala His
530                 535                 540

Ser Leu Gln Glu Leu His His Leu Asn Leu Gly Ala Ala Ala Gly Ala
545                 550                 555                 560
```

```
His Asp Phe Phe Ser Ala Gly Gln Gln Ala Met His Gly Leu Gly
                565                 570                 575

Ser Met Asp Asn Ala Ser Leu Glu His Ser Thr Gly Ser Asn Ser Val
                580                 585                 590

Val Tyr Asn Gly Val Gly Asp Ser Asn Gly Ser Thr Val Val Gly Ser
                595                 600                 605

Gly Gly Tyr Met Met Pro Met Ser Ala Ala Thr Ala Thr Ala Thr Thr
                610                 615                 620

Ala Met Val Ser His Glu Gln Val His Ala Arg Ala Gln Gly Asp His
625                 630                 635                 640

His Asp Glu Ala Lys Gln Ala Ala Gln Met Gly Tyr Glu Ser Tyr Leu
                645                 650                 655

Val Asn Ala Glu Asn Tyr Gly Gly Arg Met Ser Ala Ala Trp Ala
                660                 665                 670

Thr Val Ser Ala Pro Pro Ala Ala Ser Ser Asn Asp Asn Met Ala Asp
                675                 680                 685

Val Gly His Gly Gly Ala Gln Leu Phe Ser Val Trp Asn Asp Thr
690                 695                 700

<210> SEQ ID NO 40
<211> LENGTH: 2082
<212> TYPE: DNA
<213> ORGANISM: Sorghum bicolor
<220> FEATURE:
<221> NAME/KEY: CDS
<222> LOCATION: (1)...(2082)

<400> SEQUENCE: 40
```

| | | | | | | | | | | | | | | | | |
|---|---|---|---|---|---|---|---|---|---|---|---|---|---|---|---|---|
| atg | gct | tcg | acg | aac | aac | cac | tgg | ctg | ggt | ttc | tcg | ctc | tcg | ggc | cag | 48 |
| Met | Ala | Ser | Thr | Asn | Asn | His | Trp | Leu | Gly | Phe | Ser | Leu | Ser | Gly | Gln | |
| 1 | | | | 5 | | | | | 10 | | | | | 15 | | |
| gat | aac | ccg | cag | cct | aat | cat | cag | gac | agc | tcg | cct | gcc | gcc | gcc | ggc | 96 |
| Asp | Asn | Pro | Gln | Pro | Asn | His | Gln | Asp | Ser | Ser | Pro | Ala | Ala | Ala | Gly | |
| | | 20 | | | | | 25 | | | | | 30 | | | | |
| atc | gac | atc | tcc | ggc | gcc | agc | gac | ttc | tat | ggc | ttg | ccc | acg | cag | cag | 144 |
| Ile | Asp | Ile | Ser | Gly | Ala | Ser | Asp | Phe | Tyr | Gly | Leu | Pro | Thr | Gln | Gln | |
| | 35 | | | | | 40 | | | | | 45 | | | | | |
| ggc | tcc | gac | ggg | aat | ctc | ggc | gtg | ccg | ggc | ctg | cgg | gac | gat | cac | gct | 192 |
| Gly | Ser | Asp | Gly | Asn | Leu | Gly | Val | Pro | Gly | Leu | Arg | Asp | Asp | His | Ala | |
| 50 | | | | | 55 | | | | | 60 | | | | | | |
| tct | tat | ggc | atc | atg | gag | gcc | ttc | aac | agg | gtt | cct | caa | gaa | acc | caa | 240 |
| Ser | Tyr | Gly | Ile | Met | Glu | Ala | Phe | Asn | Arg | Val | Pro | Gln | Glu | Thr | Gln | |
| 65 | | | | 70 | | | | | 75 | | | | | 80 | | |
| gat | tgg | aac | atg | agg | gga | ttg | gac | tac | aac | ggc | ggt | ggc | tcg | gaa | ctc | 288 |
| Asp | Trp | Asn | Met | Arg | Gly | Leu | Asp | Tyr | Asn | Gly | Gly | Gly | Ser | Glu | Leu | |
| | | | | 85 | | | | | 90 | | | | | 95 | | |
| tcg | atg | ctt | gtg | ggg | tcc | agc | ggc | ggc | ggg | ggc | ggc | ggc | aag | agg | | 336 |
| Ser | Met | Leu | Val | Gly | Ser | Ser | Gly | Gly | Gly | Gly | Gly | Gly | Lys | Arg | | |
| | | | 100 | | | | | 105 | | | | | 110 | | | |
| gcc | gtg | gaa | gac | agc | gag | ccc | aag | ctc | gaa | gat | ttc | ctc | ggc | ggc | aac | 384 |
| Ala | Val | Glu | Asp | Ser | Glu | Pro | Lys | Leu | Glu | Asp | Phe | Leu | Gly | Gly | Asn | |
| | | 115 | | | | | 120 | | | | | 125 | | | | |
| tcg | ttc | gtc | tcc | gag | cat | gat | cag | tcc | ggc | ggt | tac | ctg | ttc | tct | gga | 432 |
| Ser | Phe | Val | Ser | Glu | His | Asp | Gln | Ser | Gly | Gly | Tyr | Leu | Phe | Ser | Gly | |
| | 130 | | | | | 135 | | | | | 140 | | | | | |
| gtc | ccg | atg | gcc | agc | agc | acc | aac | agc | aac | agc | ggg | agc | aac | acc | atg | 480 |
| Val | Pro | Met | Ala | Ser | Ser | Thr | Asn | Ser | Asn | Ser | Gly | Ser | Asn | Thr | Met | |
| 145 | | | | | 150 | | | | | 155 | | | | | 160 | |
| gag | ctc | tcc | atg | atc | aag | acc | tgg | ctc | cgg | aac | aac | cag | gtg | ccc | cag | 528 |

```
                 Glu Leu Ser Met Ile Lys Thr Trp Leu Arg Asn Asn Gln Val Pro Gln
                                 165                 170                 175 ccg cag ccg cca gca gct ccg cat cag gcg ccg cag act gag gag atg                576
Pro Gln Pro Pro Ala Ala Pro His Gln Ala Pro Gln Thr Glu Glu Met
            180                 185                 190 agc acc gac gcc aac gcc agc gcc agc agc ttt ggc tgc tcg gat tcg                624
Ser Thr Asp Ala Asn Ala Ser Ala Ser Ser Phe Gly Cys Ser Asp Ser
        195                 200                 205 atg ggg agg aac ggc acg gtg gcg gct gct ggg agc tcc cag agc ctg                672
Met Gly Arg Asn Gly Thr Val Ala Ala Ala Gly Ser Ser Gln Ser Leu
    210                 215                 220 gcg ctc tcg atg agc acg ggc tcg cac ctg ccg atg gtt gtg gcc ggc                720
Ala Leu Ser Met Ser Thr Gly Ser His Leu Pro Met Val Val Ala Gly
225                 230                 235                 240 ggc ggc gcc agc gga gcg gcc tcg gag agc acg tca tcg gag aac aag                768
Gly Gly Ala Ser Gly Ala Ala Ser Glu Ser Thr Ser Ser Glu Asn Lys
                245                 250                 255 cga gcg agc ggc gcc atg gat tcg ccc ggc agc gcg gta gaa gcc gtc                816
Arg Ala Ser Gly Ala Met Asp Ser Pro Gly Ser Ala Val Glu Ala Val
            260                 265                 270 ccg agg aag tcc atc gac acg ttc ggg caa agg acc tct ata tat cga                864
Pro Arg Lys Ser Ile Asp Thr Phe Gly Gln Arg Thr Ser Ile Tyr Arg
        275                 280                 285 ggt gta aca aga cat aga tgg aca ggg cga tat gag gct cat cta tgg                912
Gly Val Thr Arg His Arg Trp Thr Gly Arg Tyr Glu Ala His Leu Trp
    290                 295                 300 gat aat agt tgt aga aga gaa ggg cag agt cgc aag ggt agg caa gtt                960
Asp Asn Ser Cys Arg Arg Glu Gly Gln Ser Arg Lys Gly Arg Gln Val
305                 310                 315                 320 tac ctt ggt ggc tat gac aag gaa gac aag gca gca agg gct tat gat               1008
Tyr Leu Gly Gly Tyr Asp Lys Glu Asp Lys Ala Ala Arg Ala Tyr Asp
                325                 330                 335 ttg gca gct ctc aag tat tgg ggc act act aca aca aca aat ttc cct               1056
Leu Ala Ala Leu Lys Tyr Trp Gly Thr Thr Thr Thr Thr Asn Phe Pro
            340                 345                 350 ata agc aac tat gaa aag gag cta gag gaa atg aaa cat atg act agg               1104
Ile Ser Asn Tyr Glu Lys Glu Leu Glu Glu Met Lys His Met Thr Arg
        355                 360                 365 cag gag tat att gca tac cta aga aga aat agc agt gga ttt tct cgt               1152
Gln Glu Tyr Ile Ala Tyr Leu Arg Arg Asn Ser Ser Gly Phe Ser Arg
    370                 375                 380 ggc gca tca aaa tat cgt gga gta act aga cat cat cag cat ggg aga               1200
Gly Ala Ser Lys Tyr Arg Gly Val Thr Arg His His Gln His Gly Arg
385                 390                 395                 400 tgg caa gca agg ata ggg aga gtt gca gga aac aag gat ctc tac ttg               1248
Trp Gln Ala Arg Ile Gly Arg Val Ala Gly Asn Lys Asp Leu Tyr Leu
                405                 410                 415 ggc aca ttc agc acc gag gag gag gcg gcg gag gcc tac gac atc gcc               1296
Gly Thr Phe Ser Thr Glu Glu Glu Ala Ala Glu Ala Tyr Asp Ile Ala
            420                 425                 430 gcg atc aag ttc cgc ggt ctg aac gcc gtc acc aac ttc gac atg agc               1344
Ala Ile Lys Phe Arg Gly Leu Asn Ala Val Thr Asn Phe Asp Met Ser
        435                 440                 445 cgc tac gac gtc aag agc atc ctc gag agc agc acg ctg cct gtc ggc               1392
Arg Tyr Asp Val Lys Ser Ile Leu Glu Ser Ser Thr Leu Pro Val Gly
    450                 455                 460 ggc gcg gcc agg cgc ctc aag gat gcc gtg gac cac gtg gag gcc ggc               1440
Gly Ala Ala Arg Arg Leu Lys Asp Ala Val Asp His Val Glu Ala Gly
465                 470                 475                 480
```

| | | |
|---|---|---|
| gcc acc atc tgg cgc gcc gac atg gac ggc ggc gtg atc tcc cag ctc<br>Ala Thr Ile Trp Arg Ala Asp Met Asp Gly Gly Val Ile Ser Gln Leu<br>485 490 495 | | 1488 |
| gcc gaa gcc ggg atg ggc ggc tac gcc tcg tac ggg cac cac gcc tgg<br>Ala Glu Ala Gly Met Gly Gly Tyr Ala Ser Tyr Gly His His Ala Trp<br>500 505 510 | | 1536 |
| ccg acc atc gcg ttc cag cag ccg tcg ccg ctc tcc gtc cac tac ccg<br>Pro Thr Ile Ala Phe Gln Gln Pro Ser Pro Leu Ser Val His Tyr Pro<br>515 520 525 | | 1584 |
| tac ggg cag ccg ccg tcc cgc ggg tgg tgc aag ccc gag cag gac gcg<br>Tyr Gly Gln Pro Pro Ser Arg Gly Trp Cys Lys Pro Glu Gln Asp Ala<br>530 535 540 | | 1632 |
| gcc gtc gcc gcc gcc gcg cac agc ctg cag gac ctc cag cag ctg cac<br>Ala Val Ala Ala Ala Ala His Ser Leu Gln Asp Leu Gln Gln Leu His<br>545 550 555 560 | | 1680 |
| ctc ggc agc gcg gca cac aac ttc ttc cag gcg tcg tcg agc tcg gca<br>Leu Gly Ser Ala Ala His Asn Phe Phe Gln Ala Ser Ser Ser Ser Ala<br>565 570 575 | | 1728 |
| gtc tac aac agc ggc ggc ggc gct agc ggc ggg tac cac cag ggc<br>Val Tyr Asn Ser Gly Gly Gly Ala Ser Gly Gly Tyr His Gln Gly<br>580 585 590 | | 1776 |
| ctc ggt ggc ggc agc agc tcc ttc ctc atg ccg tcg agc act gtc gtg<br>Leu Gly Gly Gly Ser Ser Ser Phe Leu Met Pro Ser Ser Thr Val Val<br>595 600 605 | | 1824 |
| gcg ggg gcc gac cag ggg cac agc agc agc acg gcc aac cag ggg agc<br>Ala Gly Ala Asp Gln Gly His Ser Ser Ser Thr Ala Asn Gln Gly Ser<br>610 615 620 | | 1872 |
| acg tgc agc tac ggg gac gat cac cag gaa ggg aag ctc atc ggg tac<br>Thr Cys Ser Tyr Gly Asp Asp His Gln Glu Gly Lys Leu Ile Gly Tyr<br>625 630 635 640 | | 1920 |
| gac gcc atg gtg gcg gcg acc gca gcc ggc ggg gac ccg tac gcc gcg<br>Asp Ala Met Val Ala Ala Thr Ala Ala Gly Gly Asp Pro Tyr Ala Ala<br>645 650 655 | | 1968 |
| gcg agg agc ggg tac cag ttc tcg tcg cag ggc tcg gga tcc acg gtg<br>Ala Arg Ser Gly Tyr Gln Phe Ser Ser Gln Gly Ser Gly Ser Thr Val<br>660 665 670 | | 2016 |
| agc atc gcg agg gcg aac ggg tac tct aac aac tgg agc tct cct ttc<br>Ser Ile Ala Arg Ala Asn Gly Tyr Ser Asn Asn Trp Ser Ser Pro Phe<br>675 680 685 | | 2064 |
| aac ggc ggc atg ggg tga<br>Asn Gly Gly Met Gly<br>690 | | 2082 |

<210> SEQ ID NO 41
<211> LENGTH: 693
<212> TYPE: PRT
<213> ORGANISM: Sorghum bicolor

<400> SEQUENCE: 41

Met Ala Ser Thr Asn Asn His Trp Leu Gly Phe Ser Leu Ser Gly Gln
1               5                   10                  15

Asp Asn Pro Gln Pro Asn His Gln Asp Ser Ser Pro Ala Ala Ala Gly
                20                  25                  30

Ile Asp Ile Ser Gly Ala Ser Asp Phe Tyr Gly Leu Pro Thr Gln Gln
            35                  40                  45

Gly Ser Asp Gly Asn Leu Gly Val Pro Gly Leu Arg Asp Asp His Ala
        50                  55                  60

Ser Tyr Gly Ile Met Glu Ala Phe Asn Arg Val Pro Gln Glu Thr Gln
65                  70                  75                  80

-continued

```
Asp Trp Asn Met Arg Gly Leu Asp Tyr Asn Gly Gly Gly Ser Glu Leu
                 85                  90                  95
Ser Met Leu Val Gly Ser Ser Gly Gly Gly Gly Gly Lys Arg
            100                 105                 110
Ala Val Glu Asp Ser Glu Pro Lys Leu Glu Asp Phe Leu Gly Gly Asn
            115                 120                 125
Ser Phe Val Ser Glu His Asp Gln Ser Gly Gly Tyr Leu Phe Ser Gly
            130                 135                 140
Val Pro Met Ala Ser Ser Thr Asn Ser Asn Ser Gly Ser Asn Thr Met
145                 150                 155                 160
Glu Leu Ser Met Ile Lys Thr Trp Leu Arg Asn Asn Gln Val Pro Gln
                165                 170                 175
Pro Gln Pro Pro Ala Ala Pro His Gln Ala Pro Gln Thr Glu Glu Met
                180                 185                 190
Ser Thr Asp Ala Asn Ala Ser Ala Ser Ser Phe Gly Cys Ser Asp Ser
            195                 200                 205
Met Gly Arg Asn Gly Thr Val Ala Ala Ala Gly Ser Ser Gln Ser Leu
            210                 215                 220
Ala Leu Ser Met Ser Thr Gly Ser His Leu Pro Met Val Val Ala Gly
225                 230                 235                 240
Gly Gly Ala Ser Gly Ala Ala Ser Glu Ser Thr Ser Ser Glu Asn Lys
                245                 250                 255
Arg Ala Ser Gly Ala Met Asp Ser Pro Gly Ser Ala Val Glu Ala Val
                260                 265                 270
Pro Arg Lys Ser Ile Asp Thr Phe Gly Gln Arg Thr Ser Ile Tyr Arg
                275                 280                 285
Gly Val Thr Arg His Arg Trp Thr Gly Arg Tyr Glu Ala His Leu Trp
            290                 295                 300
Asp Asn Ser Cys Arg Arg Glu Gly Gln Ser Arg Lys Gly Arg Gln Val
305                 310                 315                 320
Tyr Leu Gly Gly Tyr Asp Lys Glu Asp Lys Ala Ala Arg Ala Tyr Asp
                325                 330                 335
Leu Ala Ala Leu Lys Tyr Trp Gly Thr Thr Thr Thr Thr Asn Phe Pro
            340                 345                 350
Ile Ser Asn Tyr Glu Lys Glu Leu Glu Glu Met Lys His Met Thr Arg
            355                 360                 365
Gln Glu Tyr Ile Ala Tyr Leu Arg Arg Asn Ser Ser Gly Phe Ser Arg
            370                 375                 380
Gly Ala Ser Lys Tyr Arg Gly Val Thr Arg His His Gln His Gly Arg
385                 390                 395                 400
Trp Gln Ala Arg Ile Gly Arg Val Ala Gly Asn Lys Asp Leu Tyr Leu
                405                 410                 415
Gly Thr Phe Ser Thr Glu Glu Glu Ala Ala Glu Ala Tyr Asp Ile Ala
            420                 425                 430
Ala Ile Lys Phe Arg Gly Leu Asn Ala Val Thr Asn Phe Asp Met Ser
            435                 440                 445
Arg Tyr Asp Val Lys Ser Ile Leu Glu Ser Ser Thr Leu Pro Val Gly
            450                 455                 460
Gly Ala Ala Arg Arg Leu Lys Asp Ala Val Asp His Val Glu Ala Gly
465                 470                 475                 480
Ala Thr Ile Trp Arg Ala Asp Met Asp Gly Gly Val Ile Ser Gln Leu
                485                 490                 495
Ala Glu Ala Gly Met Gly Gly Tyr Ala Ser Tyr Gly His His Ala Trp
```

```
              500                 505                 510
Pro Thr Ile Ala Phe Gln Gln Pro Ser Pro Leu Ser Val His Tyr Pro
            515                 520                 525

Tyr Gly Gln Pro Pro Ser Arg Gly Trp Cys Lys Pro Glu Gln Asp Ala
            530                 535                 540

Ala Val Ala Ala Ala Ala His Ser Leu Gln Asp Leu Gln Gln Leu His
545                 550                 555                 560

Leu Gly Ser Ala Ala His Asn Phe Phe Gln Ala Ser Ser Ser Ser Ala
                565                 570                 575

Val Tyr Asn Ser Gly Gly Gly Ala Ser Gly Gly Tyr His Gln Gly
            580                 585                 590

Leu Gly Gly Gly Ser Ser Phe Leu Met Pro Ser Ser Thr Val Val
            595                 600                 605

Ala Gly Ala Asp Gln Gly His Ser Ser Ser Thr Ala Asn Gln Gly Ser
            610                 615                 620

Thr Cys Ser Tyr Gly Asp Asp His Gln Glu Gly Lys Leu Ile Gly Tyr
625                 630                 635                 640

Asp Ala Met Val Ala Ala Thr Ala Ala Gly Gly Asp Pro Tyr Ala Ala
                645                 650                 655

Ala Arg Ser Gly Tyr Gln Phe Ser Ser Gln Gly Ser Gly Ser Thr Val
            660                 665                 670

Ser Ile Ala Arg Ala Asn Gly Tyr Ser Asn Asn Trp Ser Ser Pro Phe
            675                 680                 685

Asn Gly Gly Met Gly
    690

<210> SEQ ID NO 42
<211> LENGTH: 1272
<212> TYPE: DNA
<213> ORGANISM: Artificial Sequence
<220> FEATURE:
<223> OTHER INFORMATION: Maize optimized FLP coding sequence
<220> FEATURE:
<221> NAME/KEY: CDS
<222> LOCATION: (1)...(1272)

<400> SEQUENCE: 42 atg ccc cag ttc gac atc ctc tgc aag acc ccc ccc aag gtg ctc gtg     48
Met Pro Gln Phe Asp Ile Leu Cys Lys Thr Pro Pro Lys Val Leu Val
1               5                   10                  15 agg cag ttc gtg gag agg ttc gag agg ccc tcc ggc gag aag atc gcc     96
Arg Gln Phe Val Glu Arg Phe Glu Arg Pro Ser Gly Glu Lys Ile Ala
            20                  25                  30 ctc tgc gcc gcc gag ctc acc tac ctc tgc tgg atg atc acc cac aac    144
Leu Cys Ala Ala Glu Leu Thr Tyr Leu Cys Trp Met Ile Thr His Asn
        35                  40                  45 ggc acc gcc att aag agg gcc acc ttc atg tca tac aac acc atc atc    192
Gly Thr Ala Ile Lys Arg Ala Thr Phe Met Ser Tyr Asn Thr Ile Ile
    50                  55                  60 tcc aac tcc ctc tcc ttc gac atc gtg aac aag tcc ctc cag ttc aaa    240
Ser Asn Ser Leu Ser Phe Asp Ile Val Asn Lys Ser Leu Gln Phe Lys
65                  70                  75                  80 tac aag acc cag aag gcc acc atc ctc gag gcc tcc ctc aag aag ctc    288
Tyr Lys Thr Gln Lys Ala Thr Ile Leu Glu Ala Ser Leu Lys Lys Leu
                85                  90                  95 atc ccc gcc tgg gag ttc acc atc atc ccc tac tac ggc cag aag cac    336
Ile Pro Ala Trp Glu Phe Thr Ile Ile Pro Tyr Tyr Gly Gln Lys His
            100                 105                 110
```

-continued

| | |
|---|---|
| cag tcc gac atc acc gac atc gtg tca tcc ctc cag ctt cag ttc gag<br>Gln Ser Asp Ile Thr Asp Ile Val Ser Ser Leu Gln Leu Gln Phe Glu<br>115                 120                 125 | 384 |
| tcc tcc gag gag gct gac aag ggc aac tcc cac tcc aag aag atg ctg<br>Ser Ser Glu Glu Ala Asp Lys Gly Asn Ser His Ser Lys Lys Met Leu<br>130                 135                 140 | 432 |
| aag gcc ctc ctc tcc gag ggc gag tcc atc tgg gag atc acc gag aag<br>Lys Ala Leu Leu Ser Glu Gly Glu Ser Ile Trp Glu Ile Thr Glu Lys<br>145                 150                 155                 160 | 480 |
| atc ctc aac tcc ttc gag tac acc tcc agg ttc act aag acc aag acc<br>Ile Leu Asn Ser Phe Glu Tyr Thr Ser Arg Phe Thr Lys Thr Lys Thr<br>                165                 170                 175 | 528 |
| ctc tac cag ttc ctc ttc ctc gcc acc ttc atc aac tgc ggc agg ttc<br>Leu Tyr Gln Phe Leu Phe Leu Ala Thr Phe Ile Asn Cys Gly Arg Phe<br>                180                 185                 190 | 576 |
| tca gac atc aag aac gtg gac ccc aag tcc ttc aag ctc gtg cag aac<br>Ser Asp Ile Lys Asn Val Asp Pro Lys Ser Phe Lys Leu Val Gln Asn<br>                195                 200                 205 | 624 |
| aag tac ctc ggc gtg atc atc cag tgc ctc gtg acc gag acc aag acc<br>Lys Tyr Leu Gly Val Ile Ile Gln Cys Leu Val Thr Glu Thr Lys Thr<br>210                 215                 220 | 672 |
| tcc gtg tcc agg cac atc tac ttc ttc tcc gct cgc ggc agg atc gac<br>Ser Val Ser Arg His Ile Tyr Phe Phe Ser Ala Arg Gly Arg Ile Asp<br>225                 230                 235                 240 | 720 |
| ccc ctc gtg tac ctc gac gag ttc ctc agg aac tca gag ccc gtg ctc<br>Pro Leu Val Tyr Leu Asp Glu Phe Leu Arg Asn Ser Glu Pro Val Leu<br>                245                 250                 255 | 768 |
| aag agg gtg aac agg acc ggc aac tcc tcc tcc aac aag cag gag tac<br>Lys Arg Val Asn Arg Thr Gly Asn Ser Ser Ser Asn Lys Gln Glu Tyr<br>                260                 265                 270 | 816 |
| cag ctc ctc aag gac aac ctc gtg agg tcc tac aac aag gcc ctc aag<br>Gln Leu Leu Lys Asp Asn Leu Val Arg Ser Tyr Asn Lys Ala Leu Lys<br>                275                 280                 285 | 864 |
| aag aac gcc ccc tac tcc atc ttc gcc atc aag aac ggc ccc aag tcc<br>Lys Asn Ala Pro Tyr Ser Ile Phe Ala Ile Lys Asn Gly Pro Lys Ser<br>290                 295                 300 | 912 |
| cac atc ggt agg cac ctc atg acc tcc ttc ctc tca atg aag ggc ctc<br>His Ile Gly Arg His Leu Met Thr Ser Phe Leu Ser Met Lys Gly Leu<br>305                 310                 315                 320 | 960 |
| acc gag ctc acc aac gtg gtg ggc aac tgg tcc gac aag agg gcc tcc<br>Thr Glu Leu Thr Asn Val Val Gly Asn Trp Ser Asp Lys Arg Ala Ser<br>                325                 330                 335 | 1008 |
| gcc gtg gcc agg acc acc tac acc cac cag atc acc gcc atc ccc gac<br>Ala Val Ala Arg Thr Thr Tyr Thr His Gln Ile Thr Ala Ile Pro Asp<br>                340                 345                 350 | 1056 |
| cac tac ttc gcc ctc gtg tca agg tac tac gcc tac gac ccc atc tcc<br>His Tyr Phe Ala Leu Val Ser Arg Tyr Tyr Ala Tyr Asp Pro Ile Ser<br>                355                 360                 365 | 1104 |
| aag gag atg atc gcc ctc aag gac gag act aac ccc atc gag gag tgg<br>Lys Glu Met Ile Ala Leu Lys Asp Glu Thr Asn Pro Ile Glu Glu Trp<br>                370                 375                 380 | 1152 |
| cag cac atc gag cag ctc aag ggc tcc gcc gag ggc tcc atc agg tac<br>Gln His Ile Glu Gln Leu Lys Gly Ser Ala Glu Gly Ser Ile Arg Tyr<br>385                 390                 395                 400 | 1200 |
| ccc gcc tgg aac ggc atc atc tcc cag gag gtg ctc gac tac ctc tcc<br>Pro Ala Trp Asn Gly Ile Ile Ser Gln Glu Val Leu Asp Tyr Leu Ser<br>                405                 410                 415 | 1248 |
| tcc tac atc aac agg agg atc tga<br>Ser Tyr Ile Asn Arg Arg Ile<br>                420 | 1272 |

<210> SEQ ID NO 43
<211> LENGTH: 423
<212> TYPE: PRT
<213> ORGANISM: Artificial Sequence
<220> FEATURE:
<223> OTHER INFORMATION: FLP

<400> SEQUENCE: 43

```
Met Pro Gln Phe Asp Ile Leu Cys Lys Thr Pro Pro Lys Val Leu Val
1               5                   10                  15

Arg Gln Phe Val Glu Arg Phe Glu Arg Pro Ser Gly Glu Lys Ile Ala
            20                  25                  30

Leu Cys Ala Ala Glu Leu Thr Tyr Leu Cys Trp Met Ile Thr His Asn
        35                  40                  45

Gly Thr Ala Ile Lys Arg Ala Thr Phe Met Ser Tyr Asn Thr Ile Ile
50                  55                  60

Ser Asn Ser Leu Ser Phe Asp Ile Val Asn Lys Ser Leu Gln Phe Lys
65                  70                  75                  80

Tyr Lys Thr Gln Lys Ala Thr Ile Leu Glu Ala Ser Leu Lys Lys Leu
                85                  90                  95

Ile Pro Ala Trp Glu Phe Thr Ile Ile Pro Tyr Tyr Gly Gln Lys His
            100                 105                 110

Gln Ser Asp Ile Thr Asp Ile Val Ser Ser Leu Gln Leu Gln Phe Glu
        115                 120                 125

Ser Ser Glu Glu Ala Asp Lys Gly Asn Ser His Ser Lys Lys Met Leu
    130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
            180                 185                 190

Ser Asp Ile Lys Asn Val Asp Pro Lys Ser Phe Lys Leu Val Gln Asn
        195                 200                 205

Lys Tyr Leu Gly Val Ile Ile Gln Cys Leu Val Thr Glu Thr Lys Thr
    210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Ser Asn Lys Gln Glu Tyr
            260                 265                 270

Gln Leu Leu Lys Asp Asn Leu Val Arg Ser Tyr Asn Lys Ala Leu Lys
        275                 280                 285

Lys Asn Ala Pro Tyr Ser Ile Phe Ala Ile Lys Asn Gly Pro Lys Ser
    290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
                325                 330                 335

Ala Val Ala Arg Thr Thr Tyr Thr His Gln Ile Thr Ala Ile Pro Asp
            340                 345                 350

His Tyr Phe Ala Leu Val Ser Arg Tyr Tyr Ala Tyr Asp Pro Ile Ser
        355                 360                 365
```

```
Lys Glu Met Ile Ala Leu Lys Asp Glu Thr Asn Pro Ile Glu Glu Trp
        370                 375                 380

Gln His Ile Glu Gln Leu Lys Gly Ser Ala Glu Gly Ser Ile Arg Tyr
385                 390                 395                 400

Pro Ala Trp Asn Gly Ile Ile Ser Gln Glu Val Leu Asp Tyr Leu Ser
                405                 410                 415

Ser Tyr Ile Asn Arg Arg Ile
            420

<210> SEQ ID NO 44
<211> LENGTH: 1032
<212> TYPE: DNA
<213> ORGANISM: Artificial Sequence
<220> FEATURE:
<223> OTHER INFORMATION: Maize optimized Cre coding sequence
<220> FEATURE:
<221> NAME/KEY: CDS
<222> LOCATION: (1)...(1032)

<400> SEQUENCE: 44 atg tcc aac ctg ctc acg gtt cac cag aac ctt ccg gct ctt cca gtg      48
Met Ser Asn Leu Leu Thr Val His Gln Asn Leu Pro Ala Leu Pro Val
1               5                   10                  15 gac gcg acg tcc gat gaa gtc agg aag aac ctc atg gac atg ttc cgc      96
Asp Ala Thr Ser Asp Glu Val Arg Lys Asn Leu Met Asp Met Phe Arg
                20                  25                  30 gac agg caa gcg ttc agc gag cac acc tgg aag atg ctg ctc tcc gtc     144
Asp Arg Gln Ala Phe Ser Glu His Thr Trp Lys Met Leu Leu Ser Val
            35                  40                  45 tgc cgc tcc tgg gct gca tgg tgc aag ctg aac aac agg aag tgg ttc     192
Cys Arg Ser Trp Ala Ala Trp Cys Lys Leu Asn Asn Arg Lys Trp Phe
        50                  55                  60 ccc gct gag ccc gag gac gtg agg gat tac ctt ctg tac ctg caa gct     240
Pro Ala Glu Pro Glu Asp Val Arg Asp Tyr Leu Leu Tyr Leu Gln Ala
65                  70                  75                  80 cgc ggg ctg gca gtg aag acc atc cag caa cac ctt gga caa ctg aac     288
Arg Gly Leu Ala Val Lys Thr Ile Gln Gln His Leu Gly Gln Leu Asn
                85                  90                  95 atg ctt cac agg cgc tcc ggc ctc ccg cgc ccc agc gac tcg aac gcc     336
Met Leu His Arg Arg Ser Gly Leu Pro Arg Pro Ser Asp Ser Asn Ala
            100                 105                 110 gtg agc ctc gtc atg cgc cgc atc agg aag gaa aac gtc gat gcc ggc     384
Val Ser Leu Val Met Arg Arg Ile Arg Lys Glu Asn Val Asp Ala Gly
        115                 120                 125 gaa agg gca aag cag gcc ctc gcg ttc gag agg acc gat ttc gac cag     432
Glu Arg Ala Lys Gln Ala Leu Ala Phe Glu Arg Thr Asp Phe Asp Gln
130                 135                 140 gtc cgc agc ctg atg gag aac agc gac agg tgc cag gac att agg aac     480
Val Arg Ser Leu Met Glu Asn Ser Asp Arg Cys Gln Asp Ile Arg Asn
145                 150                 155                 160 ctg gcg ttc ctc gga att gca tac aac acg ctc ctc agg atc gcg gaa     528
Leu Ala Phe Leu Gly Ile Ala Tyr Asn Thr Leu Leu Arg Ile Ala Glu
                165                 170                 175 att gcc cgc att cgc gtg aag gac att agc cgc acc gac ggc ggc agg     576
Ile Ala Arg Ile Arg Val Lys Asp Ile Ser Arg Thr Asp Gly Gly Arg
            180                 185                 190 atg ctt atc cac att ggc agg acc aag acg ctc gtt tcc acc gca ggc     624
Met Leu Ile His Ile Gly Arg Thr Lys Thr Leu Val Ser Thr Ala Gly
        195                 200                 205 gtc gaa aag gcc ctc agc ctc gga gtg acc aag ctc gtc gaa cgc tgg     672
```

```
Val Glu Lys Ala Leu Ser Leu Gly Val Thr Lys Leu Val Glu Arg Trp
210                 215                 220 atc tcc gtg tcc ggc gtc gcg gac gac cca aac aac tac ctc ttc tgc    720
Ile Ser Val Ser Gly Val Ala Asp Asp Pro Asn Asn Tyr Leu Phe Cys
225                 230                 235                 240 cgc gtc cgc aag aac ggg gtg gct gcc cct agc gcc acc agc caa ctc    768
Arg Val Arg Lys Asn Gly Val Ala Ala Pro Ser Ala Thr Ser Gln Leu
                245                 250                 255 agc acg agg gcc ttg gaa ggt att ttc gag gcc acc cac cgc ctg atc    816
Ser Thr Arg Ala Leu Glu Gly Ile Phe Glu Ala Thr His Arg Leu Ile
        260                 265                 270 tac ggc gcg aag gat gac agc ggt caa cgc tac ctc gca tgg tcc ggg    864
Tyr Gly Ala Lys Asp Asp Ser Gly Gln Arg Tyr Leu Ala Trp Ser Gly
            275                 280                 285 cac tcc gcc cgc gtt gga gct gct agg gac atg gcc cgc gcc ggt gtt    912
His Ser Ala Arg Val Gly Ala Ala Arg Asp Met Ala Arg Ala Gly Val
        290                 295                 300 tcc atc ccc gaa atc atg cag gcg ggt gga tgg acg aac gtg aac att    960
Ser Ile Pro Glu Ile Met Gln Ala Gly Gly Trp Thr Asn Val Asn Ile
305                 310                 315                 320 gtc atg aac tac att cgc aac ctt gac agc gag acg ggc gca atg gtt   1008
Val Met Asn Tyr Ile Arg Asn Leu Asp Ser Glu Thr Gly Ala Met Val
                325                 330                 335 cgc ctc ctg gaa gat ggt gac tga                                   1032
Arg Leu Leu Glu Asp Gly Asp
                340
```

<210> SEQ ID NO 45
<211> LENGTH: 343
<212> TYPE: PRT
<213> ORGANISM: Artificial Sequence
<220> FEATURE:
<223> OTHER INFORMATION: Cre

<400> SEQUENCE: 45

```
Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
```

```
            180                 185                 190
Met Leu Ile His Ile Gly Arg Thr Lys Thr Leu Val Ser Thr Ala Gly
            195                 200                 205
Val Glu Lys Ala Leu Ser Leu Gly Val Thr Lys Leu Val Glu Arg Trp
            210                 215                 220
Ile Ser Val Ser Gly Val Ala Asp Asp Pro Asn Asn Tyr Leu Phe Cys
225                 230                 235                 240
Arg Val Arg Lys Asn Gly Val Ala Ala Pro Ser Ala Thr Ser Gln Leu
                245                 250                 255
Ser Thr Arg Ala Leu Glu Gly Ile Phe Glu Ala Thr His Arg Leu Ile
            260                 265                 270
Tyr Gly Ala Lys Asp Asp Ser Gly Gln Arg Tyr Leu Ala Trp Ser Gly
            275                 280                 285
His Ser Ala Arg Val Gly Ala Ala Arg Asp Met Ala Arg Ala Gly Val
            290                 295                 300
Ser Ile Pro Glu Ile Met Gln Ala Gly Gly Trp Thr Asn Val Asn Ile
305                 310                 315                 320
Val Met Asn Tyr Ile Arg Asn Leu Asp Ser Glu Thr Gly Ala Met Val
                325                 330                 335
Arg Leu Leu Glu Asp Gly Asp
            340
```

<210> SEQ ID NO 46
<211> LENGTH: 34
<212> TYPE: DNA
<213> ORGANISM: Artificial Sequence
<220> FEATURE:
<223> OTHER INFORMATION: FRT1

<400> SEQUENCE: 46
gaagttccta tactttctag agaataggaa cttc        34

<210> SEQ ID NO 47
<211> LENGTH: 34
<212> TYPE: DNA
<213> ORGANISM: Artificial Sequence
<220> FEATURE:
<223> OTHER INFORMATION: FRT5

<400> SEQUENCE: 47
gaagttccta tactcttttg agaataggaa cttc        34

<210> SEQ ID NO 48
<211> LENGTH: 34
<212> TYPE: DNA
<213> ORGANISM: Artificial Sequence
<220> FEATURE:
<223> OTHER INFORMATION: FRT6

<400> SEQUENCE: 48
gaagttccta tacttttga agaataggaa cttc         34

<210> SEQ ID NO 49
<211> LENGTH: 34
<212> TYPE: DNA
<213> ORGANISM: Artificial Sequence
<220> FEATURE:
<223> OTHER INFORMATION: FRT7

<400> SEQUENCE: 49
gaagttccta tacttattga agaataggaa cttc        34

```
<210> SEQ ID NO 50
<211> LENGTH: 34
<212> TYPE: DNA
<213> ORGANISM: Artificial Sequence
<220> FEATURE:
<223> OTHER INFORMATION: FRT87

<400> SEQUENCE: 50
gaagttccta tactttctgg agaataggaa cttc                                    34

<210> SEQ ID NO 51
<211> LENGTH: 975
<212> TYPE: DNA
<213> ORGANISM: Zea mays
<220> FEATURE:
<221> NAME/KEY: CDS
<222> LOCATION: (1)...(975)

<400> SEQUENCE: 51 atg gag acg cca cag cag caa tcc gcc gcc gcc gcc gcc gcc gcc             48
Met Glu Thr Pro Gln Gln Gln Ser Ala Ala Ala Ala Ala Ala Ala
 1               5                  10                  15 cac ggg cag gac gac ggc ggg tcg ccg ccg atg tcg ccg gcc tcc gcc         96
His Gly Gln Asp Asp Gly Gly Ser Pro Pro Met Ser Pro Ala Ser Ala
                 20                  25                  30 gcg gcg gcg gcg ctg gcg aac gcg cgg tgg aac ccg acc aag gag cag         144
Ala Ala Ala Ala Leu Ala Asn Ala Arg Trp Asn Pro Thr Lys Glu Gln
             35                  40                  45 gtg gcc gtg ctg gag ggg ctg tac gag cac ggc ctg cgc acc ccc agc         192
Val Ala Val Leu Glu Gly Leu Tyr Glu His Gly Leu Arg Thr Pro Ser
 50                  55                  60 gcg gag cag ata cag cag atc acg ggc agg ctg cgg gag cac ggc gcc         240
Ala Glu Gln Ile Gln Gln Ile Thr Gly Arg Leu Arg Glu His Gly Ala
 65                  70                  75                  80 atc gag ggc aag aac gtc ttc tac tgg ttc cag aac cac aag gcc cgc         288
Ile Glu Gly Lys Asn Val Phe Tyr Trp Phe Gln Asn His Lys Ala Arg
                 85                  90                  95 cag cgc cag agg cag aag cag gac agc ttc gcc tac ttc agc agg ctc         336
Gln Arg Gln Arg Gln Lys Gln Asp Ser Phe Ala Tyr Phe Ser Arg Leu
            100                 105                 110 ctc cgc cgg ccc ccg ccg ctg ccc gtg ctc tcc atg ccc ccc gcg cca         384
Leu Arg Arg Pro Pro Pro Leu Pro Val Leu Ser Met Pro Pro Ala Pro
            115                 120                 125 ccg tac cat cac gcc cgc gtc ccg gcg ccg ccc gcg ata ccg atg ccg         432
Pro Tyr His His Ala Arg Val Pro Ala Pro Pro Ala Ile Pro Met Pro
            130                 135                 140 atg gcg ccg ccg ccg ccc gct gca tgc aac gac aac ggc ggc gcg cgt         480
Met Ala Pro Pro Pro Pro Ala Ala Cys Asn Asp Asn Gly Gly Ala Arg
145                 150                 155                 160 gtg atc tac agg aac cca ttc tac gtg gct gcg ccg cag gcg ccc cct         528
Val Ile Tyr Arg Asn Pro Phe Tyr Val Ala Ala Pro Gln Ala Pro Pro
                165                 170                 175 gca aat gcc gcc tac tac tac cca cag cca cag cag cag cag cag cag         576
Ala Asn Ala Ala Tyr Tyr Tyr Pro Gln Pro Gln Gln Gln Gln Gln Gln
            180                 185                 190 cag gtg aca gtc atg tac cag tac ccg aga atg gag gta gcc ggc cag         624
Gln Val Thr Val Met Tyr Gln Tyr Pro Arg Met Glu Val Ala Gly Gln
            195                 200                 205 gac aag atg atg acc agg gcc gcg gcg cac cag cag cag cag cac aac         672
Asp Lys Met Met Thr Arg Ala Ala Ala His Gln Gln Gln Gln His Asn
            210                 215                 220
```

```
ggc gcc ggg caa caa ccg gga cgc gcc ggc cac ccc agc cgc gag acg       720
Gly Ala Gly Gln Gln Pro Gly Arg Ala Gly His Pro Ser Arg Glu Thr
225                 230                 235                 240 ctc cag ctg ttc ccg ctc cag ccc acc ttc gtg ctg cgg cac gac aag       768
Leu Gln Leu Phe Pro Leu Gln Pro Thr Phe Val Leu Arg His Asp Lys
                245                 250                 255 ggg cgc gcc gcc aac ggc agt aat aac gac tcc ctg acg tcg acg tcg       816
Gly Arg Ala Ala Asn Gly Ser Asn Asn Asp Ser Leu Thr Ser Thr Ser
            260                 265                 270 acg gcg act gcg aca gcg aca gcg aca gcg tcc gct tcc atc               864
Thr Ala Thr Ala Thr Ala Thr Ala Thr Ala Ser Ala Ser Ile
        275                 280                 285 tcc gag gac tcg gat ggc ctg gag agc ggc agc tcc ggc aag ggc gtc       912
Ser Glu Asp Ser Asp Gly Leu Glu Ser Gly Ser Ser Gly Lys Gly Val
290                 295                 300 gag gag gcg ccc gcg ctg ccg ttc tat gac ttc ttc ggg ctc cag tcc       960
Glu Glu Ala Pro Ala Leu Pro Phe Tyr Asp Phe Phe Gly Leu Gln Ser
305                 310                 315                 320 tcc gga ggc cgc tga                                                   975
Ser Gly Gly Arg <210> SEQ ID NO 52
<211> LENGTH: 324
<212> TYPE: PRT
<213> ORGANISM: Zea mays

<400> SEQUENCE: 52

Met Glu Thr Pro Gln Gln Gln Ser Ala Ala Ala Ala Ala Ala
1               5                   10                  15

His Gly Gln Asp Asp Gly Gly Ser Pro Pro Met Ser Pro Ala Ser Ala
            20                  25                  30

Ala Ala Ala Ala Leu Ala Asn Ala Arg Trp Asn Pro Thr Lys Glu Gln
        35                  40                  45

Val Ala Val Leu Glu Gly Leu Tyr Glu His Gly Leu Arg Thr Pro Ser
    50                  55                  60

Ala Glu Gln Ile Gln Gln Ile Thr Gly Arg Leu Arg Glu His Gly Ala
65                  70                  75                  80

Ile Glu Gly Lys Asn Val Phe Tyr Trp Phe Gln Asn His Lys Ala Arg
                85                  90                  95

Gln Arg Gln Arg Gln Lys Gln Asp Ser Phe Ala Tyr Phe Ser Arg Leu
            100                 105                 110

Leu Arg Arg Pro Pro Pro Leu Pro Val Leu Ser Met Pro Pro Ala Pro
        115                 120                 125

Pro Tyr His His Ala Arg Val Pro Ala Pro Ala Ile Pro Met Pro
    130                 135                 140

Met Ala Pro Pro Pro Ala Ala Cys Asn Asp Asn Gly Gly Ala Arg
145                 150                 155                 160

Val Ile Tyr Arg Asn Pro Phe Tyr Val Ala Ala Pro Gln Ala Pro Pro
                165                 170                 175

Ala Asn Ala Ala Tyr Tyr Tyr Pro Gln Pro Gln Gln Gln Gln Gln
            180                 185                 190

Gln Val Thr Val Met Tyr Gln Tyr Pro Arg Met Glu Val Ala Gly Gln
        195                 200                 205

Asp Lys Met Met Thr Arg Ala Ala Ala His Gln Gln Gln His Asn
    210                 215                 220

Gly Ala Gly Gln Gln Pro Gly Arg Ala Gly His Pro Ser Arg Glu Thr
```

```
            225                 230                 235                 240
Leu Gln Leu Phe Pro Leu Gln Pro Thr Phe Val Leu Arg His Asp Lys
                    245                 250                 255

Gly Arg Ala Ala Asn Gly Ser Asn Asn Asp Ser Leu Thr Ser Thr Ser
                260                 265                 270

Thr Ala Thr Ala Thr Ala Thr Ala Thr Ala Thr Ala Ser Ala Ser Ile
            275                 280                 285

Ser Glu Asp Ser Asp Gly Leu Glu Ser Gly Ser Ser Gly Lys Gly Val
        290                 295                 300

Glu Glu Ala Pro Ala Leu Pro Phe Tyr Asp Phe Phe Gly Leu Gln Ser
305                 310                 315                 320

Ser Gly Gly Arg

<210> SEQ ID NO 53
<211> LENGTH: 30
<212> TYPE: DNA
<213> ORGANISM: Artificial Sequence
<220> FEATURE:
<223> OTHER INFORMATION: FRT12

<400> SEQUENCE: 53
agttcctata ctctatgtag aataggaact                                          30

<210> SEQ ID NO 54
<211> LENGTH: 665
<212> TYPE: DNA
<213> ORGANISM: Artificial Sequence
<220> FEATURE:
<223> OTHER INFORMATION: Promoter construct comprising Zea mays rab17
      promoter and attB1 site

<400> SEQUENCE: 54
ctatagtatt ttaaaattgc attaacaaac atgtcctaat tggtactcct gagatactat         60
accctcctgt tttaaaatag ttggcattat cgaattatca ttttactttt taatgttttc        120
tcttctttta atatatttta tgaattttaa tgtattttaa aatgttatgc agttcgctct        180 ggactttttct gctgcgccta cacttgggtg tactgggcct aaattcagcc tgaccgaccg       240
cctgcattga ataatggatg agcaccggta aaatccgcgt acccaacttt cgagaagaac        300
cgagacgtgg cgggccgggc caccgacgca cggcaccagc gactgcacac gtcccgccgg        360
cgtacgtgta cgtgctgttc cctcactggc cgcccaatcc actcatgcat gcccacgtac        420 accccctgccg tggcgcgccc agatcctaat cctttcgccg ttctgcactt ctgctgccta      480
taaatggcgg catcgaccgt cacctgcttc accaccggcg agccacatcg agaacacgat       540
cgagcacaca agcacgaaga ctcgtttagg agaaaccaca aaccaccaag ccgtgcaagc       600
accaagcttg gtcacccggt ccgggcctag aaggccagct tcaagtttgt acaaaaaagc       660
aggct                                                                     665

<210> SEQ ID NO 55
<211> LENGTH: 961
<212> TYPE: DNA
<213> ORGANISM: Zea mays

<400> SEQUENCE: 55
gatccgattg actatctcat tcctccaaac ccaaacacct caaatatatc tgctatcggg         60
attggcattc ctgtatccct acgcccgtgt acccctgtt tagagaacct cccaaggtat        120
aagatggcga agattattgt tgtcttgtct ttcatcatat atcgagtctt tccctaggat        180
```

-continued

```
attattattg gcaatgagca ttacacggtt aatcgattga gagaacatgc atctcacctt      240
cagcaaataa ttacgataat ccatatttta cgcttcgtaa cttctcatga gtttcgatat      300
acaaatttgt tttctggaca ccctaccatt catcctcttc ggagaagaga ggaagtgtcc      360
tcaatttaaa tatgttgtca tgctgtagtt cttcacccaa tctcaacagg taccaagcac      420
attgtttcca caattatat tttagtcaca ataaatctat attattatta atatactaaa       480
actatactga cgctcagatg cttttactag ttccttgctag tatgtgatgt aggtctacgt     540
ggaccagaaa atagtgagac acggaagaca aaagaagtaa agaggcccg gactacggcc       600 cacatgagat tcggccccgc cacctccggc aaccagcggc cgatccaacg gaagtgcgcg     660
cacacacaca acctcgtata tatcgccgcg cggaagcggc gcgaccgagg aagccttgtc    720
ctcgacaccc cctacacagg tgtcgcgctg cccccgacac gagtcccgca tgcgtcccac    780
gcggccgcgc cagatcccgc ctccgcgcgt tgccacgccc tctataaaca cccagctctc    840
cctcgccctc atctacctca ctcgtagtcg tagctcaagc atcagcggca gcggcagcgg    900
caggagctct gggcagcgtg cgcacgtggg gtacctagct cgctctgcta gcctacctta    960
a                                                                      961
```

<210> SEQ ID NO 56
<211> LENGTH: 22
<212> TYPE: DNA
<213> ORGANISM: Artificial Sequence
<220> FEATURE:
<223> OTHER INFORMATION: Homing endonuclease target site

<400> SEQUENCE: 56
atatacctca cacgtacgcg ta                                               22

<210> SEQ ID NO 57
<211> LENGTH: 909
<212> TYPE: DNA
<213> ORGANISM: Zea mays
<220> FEATURE:
<221> NAME/KEY: CDS
<222> LOCATION: (1)...(909)

<400> SEQUENCE: 57

```
atg gcg gcc aat gcg ggc ggc ggt gga gcg gga gga ggc agc ggc agc       48
Met Ala Ala Asn Ala Gly Gly Gly Gly Ala Gly Gly Gly Ser Gly Ser
 1               5                  10                  15 ggc agc gtg gct gcg ccg gcg gtg tgc cgc ccc agc ggc tcg cgg tgg       96
Gly Ser Val Ala Ala Pro Ala Val Cys Arg Pro Ser Gly Ser Arg Trp
             20                  25                  30 acg ccg acg ccg gag cag atc agg atg ctg aag gag ctc tac tac ggc      144
Thr Pro Thr Pro Glu Gln Ile Arg Met Leu Lys Glu Leu Tyr Tyr Gly
         35                  40                  45 tgc ggc atc cgg tcg ccc agc tcg gag cag atc cag cgc atc acc gcc      192
Cys Gly Ile Arg Ser Pro Ser Ser Glu Gln Ile Gln Arg Ile Thr Ala
     50                  55                  60 atg ctg cgg cag cac ggc aag atc gag ggc aag aac gtc ttc tac tgg      240
Met Leu Arg Gln His Gly Lys Ile Glu Gly Lys Asn Val Phe Tyr Trp
 65                  70                  75                  80 ttc cag aac cac aag gcc cgc gag cgc cag aag cgc cgc ctc acc agc      288
Phe Gln Asn His Lys Ala Arg Glu Arg Gln Lys Arg Arg Leu Thr Ser
                 85                  90                  95 ctc gac gtc aac gtg ccc gcc gcc ggc gcg gcc gac gcc acc acc agc      336
Leu Asp Val Asn Val Pro Ala Ala Gly Ala Ala Asp Ala Thr Thr Ser
            100                 105                 110
```

```
caa ctc ggc gtc ctc tcg ctg tcg tcg ccg ccg cct tca ggc gcg gcg     384
Gln Leu Gly Val Leu Ser Leu Ser Ser Pro Pro Pro Ser Gly Ala Ala
        115                 120                 125 cct ccc tcg ccc acc ctc ggc ttc tac gcc gcc ggc aat ggc ggc gga     432
Pro Pro Ser Pro Thr Leu Gly Phe Tyr Ala Ala Gly Asn Gly Gly Gly
    130                 135                 140 tcg gct gtg ctg ctg gac acg agt tcc gac tgg ggc agc agc ggc gct     480
Ser Ala Val Leu Leu Asp Thr Ser Ser Asp Trp Gly Ser Ser Gly Ala
145                 150                 155                 160 gcc atg gcc acc gag aca tgc ttc ctg cag gac tac atg ggc gtg acg     528
Ala Met Ala Thr Glu Thr Cys Phe Leu Gln Asp Tyr Met Gly Val Thr
                165                 170                 175 gac acg ggc agc tcg tcg cag tgg cca cgc ttc tcg tcg tcg gac acg     576
Asp Thr Gly Ser Ser Ser Gln Trp Pro Arg Phe Ser Ser Ser Asp Thr
            180                 185                 190 ata atg gcg gcg gcc gcg gcg cgg gcg gcg acg acg cgg gcg ccc gag     624
Ile Met Ala Ala Ala Ala Arg Ala Ala Thr Thr Arg Ala Pro Glu
        195                 200                 205 acg ctc cct ctc ttc ccg acc tgc ggc gac gac ggc ggc agc ggt agc     672
Thr Leu Pro Leu Phe Pro Thr Cys Gly Asp Asp Gly Gly Ser Gly Ser
    210                 215                 220 agc agc tac ttg ccg ttc tgg ggt gcc gcg tcc aca act gcc ggc gcc     720
Ser Ser Tyr Leu Pro Phe Trp Gly Ala Ala Ser Thr Thr Ala Gly Ala
225                 230                 235                 240 act tct tcc gtt gcg atc cag cag caa cac cag ctg cag gag cag tac     768
Thr Ser Ser Val Ala Ile Gln Gln Gln His Gln Leu Gln Glu Gln Tyr
                245                 250                 255 agc ttt tac agc aac agc aac agc acc cag ctg gcc ggc acc ggc aac     816
Ser Phe Tyr Ser Asn Ser Asn Ser Thr Gln Leu Ala Gly Thr Gly Asn
            260                 265                 270 caa gac gta tcg gca aca gca gca gcc gcc gcc ctg gag ctg agc         864
Gln Asp Val Ser Ala Thr Ala Ala Ala Ala Leu Glu Leu Ser
        275                 280                 285 ctc agc tca tgg tgc tcc cct tac cct gct gca ggg agt atg tga         909
Leu Ser Ser Trp Cys Ser Pro Tyr Pro Ala Ala Gly Ser Met
    290                 295                 300
```

<210> SEQ ID NO 58
<211> LENGTH: 302
<212> TYPE: PRT
<213> ORGANISM: Zea mays

<400> SEQUENCE: 58

```
Met Ala Ala Asn Ala Gly Gly Gly Gly Ala Gly Gly Ser Gly Ser
1               5                   10                  15

Gly Ser Val Ala Ala Pro Ala Val Cys Arg Pro Ser Gly Ser Arg Trp
                20                  25                  30

Thr Pro Thr Pro Glu Gln Ile Arg Met Leu Lys Glu Leu Tyr Tyr Gly
            35                  40                  45

Cys Gly Ile Arg Ser Pro Ser Ser Glu Gln Ile Gln Arg Ile Thr Ala
        50                  55                  60

Met Leu Arg Gln His Gly Lys Ile Glu Gly Lys Asn Val Phe Tyr Trp
65                  70                  75                  80

Phe Gln Asn His Lys Ala Arg Glu Arg Gln Lys Arg Arg Leu Thr Ser
                85                  90                  95

Leu Asp Val Asn Val Pro Ala Ala Gly Ala Ala Asp Ala Thr Thr Ser
            100                 105                 110

Gln Leu Gly Val Leu Ser Leu Ser Ser Pro Pro Pro Ser Gly Ala Ala
```

```
            115                 120                 125
Pro Pro Ser Pro Thr Leu Gly Phe Tyr Ala Ala Gly Asn Gly Gly Gly
        130                 135                 140

Ser Ala Val Leu Leu Asp Thr Ser Ser Asp Trp Gly Ser Ser Gly Ala
145                 150                 155                 160

Ala Met Ala Thr Glu Thr Cys Phe Leu Gln Asp Tyr Met Gly Val Thr
                165                 170                 175

Asp Thr Gly Ser Ser Ser Gln Trp Pro Arg Phe Ser Ser Ser Asp Thr
            180                 185                 190

Ile Met Ala Ala Ala Ala Arg Ala Ala Thr Thr Arg Ala Pro Glu
        195                 200                 205

Thr Leu Pro Leu Phe Pro Thr Cys Gly Asp Asp Gly Gly Ser Gly Ser
210                 215                 220

Ser Ser Tyr Leu Pro Phe Trp Gly Ala Ala Ser Thr Thr Ala Gly Ala
225                 230                 235                 240

Thr Ser Ser Val Ala Ile Gln Gln Gln His Gln Leu Gln Glu Gln Tyr
                245                 250                 255

Ser Phe Tyr Ser Asn Ser Asn Ser Thr Gln Leu Ala Gly Thr Gly Asn
            260                 265                 270

Gln Asp Val Ser Ala Thr Ala Ala Ala Ala Ala Leu Glu Leu Ser
        275                 280                 285

Leu Ser Ser Trp Cys Ser Pro Tyr Pro Ala Ala Gly Ser Met
290                 295                 300
```

<210> SEQ ID NO 59
<211> LENGTH: 2260
<212> TYPE: DNA
<213> ORGANISM: Zea mays

<400> SEQUENCE: 59

```
cttccctaac ctttgcactg tccaaaatgg cttcctgatc ccctcacttc ctcgaatcaa      60
tctaagaaga aactcaagcc gcaaccatta ggggcagatt aattgctgca ctttcagata     120
atcaaccatg ccactgtga caactggct cgctttctcc ctctcccgc aggagctgcc      180
gccctcccag acgacggact ccacactcat ctcggccgcc accgccgacc atgtctccgg     240
cgatgtctgc ttcaacatcc cccaagattg gagcatgagg ggatcagagc tttcggcgct     300
cgtcgcggag ccgaagctgg aggacttcct cggcggcatc tccttctccg agcagcatca     360
caaggccaac tgcaacatga tacccagcac tagcagcaca gtttgctacg cgagctcagg     420
tgctagcacc ggctaccatc accagctgta ccaccagccc accagctcag cgctccactt     480
cgcggactcc gtaatggtgg cctcctcggc cggtgtccac gacggcggtg ccatgctcag     540
cgcggccgcc gctaacggtg tcgctggcgc tgccagtgcc aacggcggcg catcgggct     600
gtccatgatt aagaactggc tgcggagcca accggcgccc atgcagccga gggtggcggc     660
ggctgagggc gcgcagggc tctctttgtc catgaacatg gcggggacga cccaaggcgc     720
tgctggcatg ccacttctcg ctggagagcg cgcacgggcg cccgagagtg tatcgacgtc     780
agcacagggt ggagccgtcg tcgtcacggc gccgaaggag gatagcggtg cagcggtgt     840
tgccggcgct ctagtagccg tgagcacgga cacgggtgg agcggcggcg cgtcggctga     900
caacacggca aggaagacgg tggacacgtt cgggcagcgc acgtcgattt accgtggcgt     960
gacaaggcat agatggactg ggagatatga ggcacatctt tgggataaca gttgcagaag    1020
ggaagggcaa actcgtaagg gtcgtcaagt ctatttaggt ggctatgata agaggagaa    1080
```

```
agctgctagg gcttatgatc ttgctgctct gaagtactgg ggtgccacaa caacaacaaa    1140
ttttccagtg agtaactacg aaaaggagct cgaggacatg aagcacatga caaggcagga    1200
gtttgtagcg tctctgagaa ggaagagcag tggtttctcc agaggtgcat ccatttacag    1260
gggagtgact aggcatcacc aacatggaag atggcaagca cggattggac gagttgcagg    1320
gaacaaggat ctttacttgg gcaccttcag cacccaggag gaggcagcgg aggcgtacga    1380
catcgcggcg atcaagttcc gcggcctcaa cgccgtcacc aacttcgaca tgagccgcta    1440
cgacgtgaag agcatcctgg acagcagcgc cctccccatc ggcagcgccg ccaagcgcct    1500
caaggaggcc gaggccgcag cgtccgcgca gcaccaccac gccggcgtgg tgagctacga    1560
cgtcggccgc atcgcctcgc agctcggcga cggcggagcc ctggcggcgg cgtacggcgc    1620
gcactaccac ggcgccgcct ggccgaccat cgcgttccag ccgggcgccg ccagcacagg    1680
cctgtaccac ccgtacgcgc agcagccaat gcgcggcggc gggtggtgca agcaggagca    1740
ggaccacgcg gtgatcgcgg ccgcgcacag cctgcaggac ctccaccacc tgaacctggg    1800
cgcggccggc gcgcacgact ttttctcggc agggcagcag gccgccgccg ctgcgatgca    1860
cggcctgggt agcatcgaca gtgcgtcgct cgagcacagc accggctcca actccgtcgt    1920
ctacaacggc gggtcggcg acagcaacgg cgccagcgcc gtcggcggca gtggcggtgg    1980
ctacatgatg ccgatgagcg ctgccggagc aaccactaca tcggcaatgg tgagccacga    2040
gcaggtgcat gcacgggcct acgacgaagc caagcaggct gctcagatgg ggtacgagag    2100
ctacctggtg aacgcggaga caatggtgg cggaaggatg tctgcatggg ggactgtcgt    2160
gtctgcagcc gcggcggcag cagcaagcag caacgacaac atggccgccg acgtcggcca    2220
tggcggcgcg cagctcttca gtgtctggaa cgacacttaa                          2260
```

<210> SEQ ID NO 60
<211> LENGTH: 3766
<212> TYPE: DNA
<213> ORGANISM: Sorghum bicolor

<400> SEQUENCE: 60

```
atggctactg tgaacaactg gctcgctttc tccctctccc cgcaggagct gccgcccacc      60
cagacggact ccaccctcat ctctgccgcc accaccgacg atgtctccgg cgatgtctgc     120
ttcaacatcc cccaaggtat gcatctatcg atcgatatat gtacgtacag tgcgcatata     180
tatatatatc tgcagtttgt ggtacgaata ctgattgaag ctagcatgaa atgtcgtttg     240 ttcttttcaga ttggagcatg agggatccg agctttcggc gctcgtcgcc gagccgaagc     300
tggaggactt cctcggcgga atctccttct ccgagcagca ccacaaggcc aactgcaaca     360
tgatccccag cactagcagc acagcttgct acgcgagctc gggtgctacc gccggctacc     420
atcaccagct gtaccaccag cccaccagct ccgcgctcca cttcgctgac tccgtcatgg     480
tggcctcctc ggccgcggc gtccacgacg gaggtgccat gctcagcgcg ccagcgcta     540 atggtagcgc tggcgctggc gctgccagtg ccaatggcag cggcagcatc gggctgtcca     600
tgatcaagaa ctggctgcgg agccaaccag ctcccatgca gccgagggtg gcggcggctg     660
agagcgtgca ggggctctct ttgtccatga acatggcggg ggcgacgcaa ggcgccgctg     720
gcatgccact tcttgctgga gagcgcggcc gggcgcccga gagtgtctcg acgtcggcac     780
agggtggagc cgtcgtcacg gctccaaagg aggatagcgg tggcagcggt gttgccgcca     840 ccggcgcct agtagccgtg agcacggaca cgggtggcag cggcgcgtcg gctgacaaca     900
cggcaaggaa gacggtggac acgttcgggc agcgcacgtc gatttaccgt ggcgtgacaa     960
```

```
ggtaataagg gtccggtatt acaatgaatc gtcacttcgt cagagaacta aactagcaca    1020
aatcagcaat gaatcaagta atatcatgaa atttagaaaa gccgttagca atgcaaggag    1080
ctatcattat agatttgatt gcatctagac agttctgaat taaatgagta gggcaatgtg    1140
tagcctttga tgatctcgct gattattagg agtgccattt gtattggcta tgattgtggt    1200
atatacagca gtagacaatt aacaaaaggc taccactttc gaattatttt aggcatagat    1260
ggactgggag atatgaagca catctgtggg acaacagttg cagaagggaa ggacaaactc    1320
gcaagggtcg tcaaggtacc aatataatgc aatacaccgt atttaaatat atatgctttt    1380
ctgtaattaa gtttatactt tcacaaaact gacattactt cgcattatca tttttggatt    1440
gtcgtcgtca tgattggcgg gattgaaatg aactattgaa tctacagtct atttaggtaa    1500
gcgatttcac ttggttatta atttgggacc aactacttaa tccagtttgt ttttccccta    1560
taaccattat ttttcatct gtgttctcaa ctcttacttt tccatcttgt tccactgata    1620
ggtggctatg ataaagagga gaaagctgct agggcttatg atctggctgc tcttaagtac    1680
tggggtccca cgacaacaac aaattttcca gtatgtatat gtagaatgca gttttacttc    1740
actgaagatc ataccttgc tatgtctcaa atgccgttca ttagttagtg gatctgaagt    1800
gaaggttctg taattttgt taactatgta cattgctgga attgtactta aagtcatttg    1860
tttttgtata tctaggtgaa taactacgaa aaggagctgg aggatatgaa gcacatgaca    1920
aggcaggagt ttgtagcgtc tctgagaagg tcggtcgaac agcattgatt aatcaatgcc    1980
aactctattg aataaacatc tactctgtta attgttaaag tttgagagaa agatctgcat    2040
gttagatctt aatagaccac tgtatatgaa tgcaggaaga gcagtggttt ctccagaggt    2100
gcatccattt acaggggagt gactaggtat gaattcatat aatggcgtca acaaacacac    2160
atacactttg attgaggagg cgaatgcacg catggattga atgtgaatgg tgttttactt    2220
gaactatgta attataggca tcaccagcat ggaagatggc aagcacggat tggacgagtt    2280
gcagggaaca aggatctcta cttgggcacc ttcagtaagt atcagagatg ttttctcatt    2340
gtatatagag gagtacttct atatgtatat atacattcag ttattcacca cacaaaagca    2400
aattgcagtc aactaataac aatctcaacg caatgagaag caagtgttac agctgatagt    2460
acacatttgt agaccttctg catatggatg ttatatatga tgactattaa aaatgtgacc    2520
attgcatcaa gtcatgcaaa gttgcattgc agtagtacat acattactta gtgcatgctc    2580
ctcaagtggc ttttcaaac ctgatcccat gtctggcgct attgttgtct cccattcacc    2640
cgtgcatcag gtcaaaatag tactatgcct caataagaaa cacatgagca tgcactggca    2700
gcagcagact aatcaagttc tatcatttac taataaacta attaggctac agcatccaaa    2760
agattctacc cattaagcca caactgttca tgcatgcatt cataaccag gataccacca    2820 tgcatgcgtg caccgtgttc gtgcttggaa tattgagctg agccgagtgc accttgcgt    2880 ggatgcaggc acgcaggagg aggcagcgga ggcatacgac attgcggcga tcaagttccg    2940
cggcctcaac gccgtcacaa acttcgacat gagccgctac gacgtcaaga gcatcctgga    3000
cagcagtgcg ctccccatcg gcagcgccgc caagcgtctc aaggaggccg aggccgccgc    3060
gtccgcacag caccatgccg gcgtggtgag ctacgacgtc ggccgcatag cctcacagct    3120
cggcgacggc ggcgccctgg cggcggcgta cggcgcgcac taccatggcg cctggccgac    3180
catcgcgttc cagccgagcg cggccacggg cctgtaccac ccgtacgcgc agccgatgcg    3240
cgggtggtgc aagcaggagc aggaccacgc ggtgatcgcg gccgcgcaca gcctgcagga    3300
```

```
gctccaccac ctgaacctgg gtgctgccgc cggcgcgcac gacttcttct cggcggggca    3360
gcaggcggcg atgcacggcc tgggtagcat ggacaatgca tcactcgagc acagcaccgg    3420
ctccaactcc gtcgtgtaca acggtgttgg tgatagcaac ggcagcaccg tcgtcggcag    3480
tggtggctac atgatgccta tgagcgctgc cacggcgacg gctaccacgg caatggtgag    3540
ccacgagcag gtgcatgcac gggcacaggg tgatcaccac gacgaagcca agcaggctgc    3600
tcagatgggg tacgagagct acctggtgaa cgcagagaac tatggcggcg ggaggatgtc    3660
tgcggcctgg gcgactgtct cagcgccacc ggcggcaagc agcaacgata acatggcgga    3720
cgtcggccat ggcggcgcac agctcttcag tgtctggaac gatact                  3766
```

<210> SEQ ID NO 61
<211> LENGTH: 530
<212> TYPE: PRT
<213> ORGANISM: Glycine max

<400> SEQUENCE: 61

```
Met Asp Ser Ser Ser Ser Pro Pro Asn Ser Thr Asn Asn Asn Ser
1               5                   10                  15

Leu Ala Phe Ser Leu Ser Asn His Phe Pro Asn Pro Ser Ser Ser Pro
                20                  25                  30

Leu Ser Leu Phe His Ser Phe Thr Tyr Pro Ser Leu Ser Leu Thr Gly
            35                  40                  45

Ser Asn Thr Val Asp Ala Pro Pro Glu Pro Thr Ala Gly Ala Gly Pro
        50                  55                  60

Thr Asn Leu Ser Ile Phe Thr Gly Gly Pro Lys Phe Glu Asp Phe Leu
65                  70                  75                  80

Gly Gly Ser Ala Ala Thr Ala Thr Thr Val Ala Cys Ala Pro Pro Gln
                85                  90                  95

Leu Pro Gln Phe Ser Thr Asp Asn Asn Asn His Leu Tyr Asp Ser Glu
            100                 105                 110

Leu Lys Ser Thr Ile Ala Ala Cys Phe Pro Arg Ala Leu Ala Ala Glu
        115                 120                 125

Gln Ser Thr Glu Pro Gln Lys Pro Ser Pro Lys Lys Thr Val Asp Thr
130                 135                 140

Phe Gly Gln Arg Thr Ser Ile Tyr Arg Gly Val Thr Arg His Arg Trp
145                 150                 155                 160

Thr Gly Arg Tyr Glu Ala His Leu Trp Asp Asn Ser Cys Arg Arg Glu
                165                 170                 175

Gly Gln Ser Arg Lys Gly Arg Gln Val Tyr Leu Gly Gly Tyr Asp Lys
            180                 185                 190

Glu Asp Lys Ala Ala Arg Ala Tyr Asp Leu Ala Ala Leu Lys Tyr Trp
        195                 200                 205

Gly Pro Thr Thr Thr Thr Asn Phe Pro Ile Ser Asn Tyr Glu Lys Glu
210                 215                 220

Leu Glu Glu Met Lys Asn Met Thr Arg Gln Glu Phe Val Ala Ser Leu
225                 230                 235                 240

Arg Arg Lys Ser Ser Gly Phe Ser Arg Gly Ala Ser Ile Tyr Arg Gly
                245                 250                 255

Val Thr Arg His His Gln His Gly Arg Trp Gln Ala Arg Ile Gly Arg
            260                 265                 270

Val Ala Gly Asn Lys Asp Leu Tyr Leu Gly Thr Phe Ser Thr Gln Glu
        275                 280                 285

Glu Ala Ala Glu Ala Tyr Asp Ile Ala Ala Ile Lys Phe Arg Gly Leu
```

```
                    290                 295                 300
Asn Ala Val Thr Asn Phe Asp Met Ser Arg Tyr Asp Val Lys Ser Ile
305                 310                 315                 320

Ala Asn Ser Thr Leu Pro Ile Gly Gly Leu Ser Gly Lys Asn Lys Asn
                325                 330                 335

Ser Thr Asp Ser Ala Ser Glu Ser Lys Ser His Glu Pro Ser Gln Ser
            340                 345                 350

Asp Gly Asp Pro Ser Ser Ala Ser Ser Val Thr Phe Ala Ser Gln Gln
        355                 360                 365

Gln Pro Ser Ser Ser Asn Leu Ser Phe Ala Ile Pro Ile Lys Gln Asp
    370                 375                 380

Pro Ser Asp Tyr Trp Ser Ile Leu Gly Tyr His Asn Thr Pro Leu Asp
385                 390                 395                 400

Asn Ser Gly Ile Arg Asn Thr Thr Ser Thr Val Thr Thr Thr Thr Phe
                405                 410                 415

Pro Ser Ser Asn Asn Gly Thr Ala Ser Ser Leu Thr Pro Phe Asn Met
            420                 425                 430

Glu Phe Ser Ser Ala Pro Ser Ser Thr Gly Ser Asp Asn Asn Ala Ala
        435                 440                 445

Phe Phe Ser Gly Gly Gly Ile Phe Val Gln Gln Gln Thr Ser His Gly
    450                 455                 460

His Gly Asn Ala Ser Ser Gly Ser Ser Ser Ser Leu Ser Cys Ser
465                 470                 475                 480

Ile Pro Phe Ala Thr Pro Ile Phe Ser Leu Asn Ser Asn Thr Ser Tyr
                485                 490                 495

Glu Ser Ser Ala Gly Tyr Gly Asn Trp Ile Gly Pro Thr Leu His Thr
            500                 505                 510

Phe Gln Ser His Ala Lys Pro Ser Leu Phe Gln Thr Pro Ile Phe Gly
        515                 520                 525

Met Glu
530

<210> SEQ ID NO 62
<211> LENGTH: 528
<212> TYPE: PRT
<213> ORGANISM: Glycine max

<400> SEQUENCE: 62

Met Asp Ser Cys Ser Ser Pro Pro Asn Asn Asn Ser Leu Ala Phe Ser
1               5                   10                  15

Leu Ser Asn His Phe Pro Asn Pro Ser Ser Ser Pro Leu Ser Leu Phe
                20                  25                  30

His Ser Phe Thr Tyr Pro Ser Leu Ser Leu Thr Gly Ser His Thr Ala
            35                  40                  45

Asp Ala Pro Pro Glu Pro Ile Ala Gly Gly Gly Ala Thr Asn Leu Ser
        50                  55                  60

Ile Phe Thr Gly Ala Pro Lys Phe Glu Asp Phe Leu Gly Gly Ser Ser
65                  70                  75                  80

Ala Thr Ala Thr Ala Thr Thr Cys Ala Pro Pro Gln Leu Pro Gln Phe
                85                  90                  95

Ser Thr Asp Asn Asn Asn His Leu Tyr Asp Ser Glu Leu Lys Thr Thr
            100                 105                 110

Ile Ala Ala Cys Phe Pro Arg Ala Phe Ala Ala Glu Pro Thr Thr Glu
        115                 120                 125
```

Pro Gln Lys Pro Ser Pro Lys Lys Thr Val Asp Thr Phe Gly Gln Arg
130                 135                 140

Thr Ser Ile Tyr Arg Gly Val Thr Arg His Arg Trp Thr Gly Arg Tyr
145                 150                 155                 160

Glu Ala His Leu Trp Asp Asn Ser Cys Arg Arg Glu Gly Gln Ser Arg
                165                 170                 175

Lys Gly Arg Gln Val Tyr Leu Gly Gly Tyr Asp Lys Glu Asp Lys Ala
            180                 185                 190

Ala Arg Ala Tyr Asp Leu Ala Ala Leu Lys Tyr Trp Gly Pro Thr Thr
        195                 200                 205

Thr Thr Asn Phe Pro Ile Ser Asn Tyr Glu Lys Glu Leu Glu Glu Met
210                 215                 220

Lys Asn Met Thr Arg Gln Glu Phe Val Ala Ser Leu Arg Arg Lys Ser
225                 230                 235                 240

Ser Gly Phe Ser Arg Gly Ala Ser Ile Tyr Arg Gly Val Thr Arg His
                245                 250                 255

His Gln His Gly Arg Trp Gln Ala Arg Ile Gly Arg Val Ala Gly Asn
            260                 265                 270

Lys Asp Leu Tyr Leu Gly Thr Phe Ser Thr Gln Glu Glu Ala Ala Glu
        275                 280                 285

Ala Tyr Asp Ile Ala Ala Ile Lys Phe Arg Gly Leu Asn Ala Val Thr
290                 295                 300

Asn Phe Asp Met Ser Arg Tyr Asp Val Lys Ser Ile Ala Asn Ser Thr
305                 310                 315                 320

Leu Pro Ile Gly Gly Leu Ser Gly Lys Asn Lys Asn Ser Thr Asp Ser
                325                 330                 335

Ala Ser Glu Ser Lys Ser His Glu Ala Ser Arg Ser Asp Glu Arg Asp
            340                 345                 350

Pro Ser Ala Ala Ser Ser Val Thr Phe Ala Ser Gln Gln Gln Pro Ser
        355                 360                 365

Ser Ser Thr Leu Ser Phe Ala Ile Pro Ile Lys Gln Asp Pro Ser Asp
370                 375                 380

Tyr Trp Ser Ile Leu Gly Tyr His Asn Ser Pro Leu Asp Asn Thr Gly
385                 390                 395                 400

Ile Arg Asn Thr Thr Ser Val Thr Ala Thr Ser Phe Pro Ser Ser Asn
                405                 410                 415

Asn Gly Thr Thr Ser Ser Leu Thr Pro Phe His Met Glu Phe Ser Asn
            420                 425                 430

Ala Pro Thr Ser Thr Gly Ser Asp Asn Asp Ala Ala Phe Phe Ser Gly
        435                 440                 445

Gly Gly Ile Phe Val Gln Gln Ser Gly His Gly Asn Gly His Gly
450                 455                 460

Ser Gly Ser Ser Gly Ser Ser Ser Leu Ser Cys Ser Ile Pro
465                 470                 475                 480

Phe Ala Thr Pro Ile Phe Ser Leu Asn Ser Thr Ser Tyr Glu Asn
                485                 490                 495

Ser Ala Gly Tyr Gly Asn Trp Ile Gly Pro Thr Leu His Thr Phe Gln
            500                 505                 510

Ser His Ala Lys Pro Ser Leu Phe Gln Thr Pro Ile Phe Gly Met Glu
        515                 520                 525

<210> SEQ ID NO 63
<211> LENGTH: 488
<212> TYPE: PRT

<213> ORGANISM: Zea mays

<400> SEQUENCE: 63

```
Met Asp Met Asp Met Ser Ser Ala Tyr Pro His His Trp Leu Ser Phe
1               5                   10                  15
Ser Leu Ser Asn Asn Tyr His His Gly Leu Leu Glu Ala Phe Ser Asn
            20                  25                  30
Ser Ser Gly Thr Pro Leu Gly Asp Glu Gln Gly Ala Val Glu Glu Ser
        35                  40                  45
Pro Arg Thr Val Glu Asp Phe Leu Gly Gly Val Gly Gly Ala Gly Ala
    50                  55                  60
Pro Pro Gln Pro Ala Ala Ala Asp Gln Asp His Gln Leu Val Cys
65                  70                  75                  80
Gly Glu Leu Gly Ser Ile Thr Ala Arg Phe Leu Arg His Tyr Pro Ala
                85                  90                  95
Ala Pro Ala Gly Thr Thr Val Glu Asn Pro Gly Ala Val Thr Val Ala
            100                 105                 110
Ala Met Ser Ser Thr Asp Val Ala Gly Ala Glu Ser Asp Gln Ala Arg
        115                 120                 125
Arg Pro Ala Glu Thr Phe Gly Gln Arg Thr Ser Ile Tyr Arg Gly Val
    130                 135                 140
Thr Arg His Arg Trp Thr Gly Arg Tyr Glu Ala His Leu Trp Asp Asn
145                 150                 155                 160
Ser Cys Arg Arg Glu Gly Gln Ser Arg Lys Gly Arg Gln Val Tyr Leu
                165                 170                 175
Gly Gly Tyr Asp Lys Glu Glu Lys Ala Ala Arg Ala Tyr Asp Leu Ala
            180                 185                 190
Ala Leu Lys Tyr Trp Gly Pro Thr Thr Thr Thr Asn Phe Pro Val Ser
        195                 200                 205
Asn Tyr Glu Lys Glu Leu Glu Glu Met Lys Ser Met Thr Arg Gln Glu
    210                 215                 220
Phe Ile Ala Ser Leu Arg Arg Lys Ser Ser Gly Phe Ser Arg Gly Ala
225                 230                 235                 240
Ser Ile Tyr Arg Gly Val Thr Arg His His Gln His Gly Arg Trp Gln
                245                 250                 255
Ala Arg Ile Gly Arg Val Ala Gly Asn Lys Asp Leu Tyr Leu Gly Thr
            260                 265                 270
Phe Ser Thr Gln Glu Glu Ala Ala Glu Ala Tyr Asp Ile Ala Ala Ile
        275                 280                 285
Lys Phe Arg Gly Leu Asn Ala Val Thr Asn Phe Asp Met Ser Arg Tyr
    290                 295                 300
Asp Val Glu Ser Ile Leu Ser Ser Asp Leu Pro Val Gly Gly Gly Ala
305                 310                 315                 320
Ser Gly Arg Ala Pro Ala Lys Phe Pro Leu Asp Ser Leu Gln Pro Gly
                325                 330                 335
Ser Ala Ala Ala Met Met Leu Ala Gly Ala Ala Ala Ser Gln Ala
            340                 345                 350
Thr Met Pro Pro Ser Glu Lys Asp Tyr Trp Ser Leu Leu Ala Leu His
        355                 360                 365
Tyr Gln Gln Gln Gln Glu Gln Glu Arg Gln Phe Pro Ala Ser Ala Tyr
    370                 375                 380
Glu Ala Tyr Gly Ser Gly Gly Val Asn Val Asp Phe Thr Met Gly Thr
385                 390                 395                 400
```

```
Ser Ser Gly Asn Asn Asn Asn Thr Gly Ser Gly Val Met Trp Gly
                405                 410                 415

Ala Thr Thr Gly Ala Val Val Gly Gln Gln Asp Ser Ser Gly Lys
            420                 425                 430

Gln Gly Asn Gly Tyr Ala Ser Asn Ile Pro Tyr Ala Ala Ala Met
        435                 440                 445

Val Ser Gly Ser Ala Gly Tyr Glu Gly Ser Thr Gly Asp Asn Gly Thr
450                 455                 460

Trp Val Thr Thr Thr Ser Ser Asn Thr Gly Thr Ala Pro His Tyr
465                 470                 475                 480

Tyr Asn Tyr Leu Phe Gly Met Glu
                485
```

<210> SEQ ID NO 64
<211> LENGTH: 495
<212> TYPE: PRT
<213> ORGANISM: Oryza sativa

<400> SEQUENCE: 64

```
Met Asp Met Asp Thr Ser His His Tyr Pro Trp Leu Asn Phe Ser Leu
1               5                   10                  15

Ala His His Cys Glu Met Glu Glu Glu Arg Gly Ala Ala Ala Glu
            20                  25                  30

Leu Ala Ala Ile Ala Gly Ala Ala Pro Pro Lys Leu Glu Asp Phe
        35                  40                  45

Leu Gly Gly Gly Cys Asn Gly Gly Ser Ser Gly Gly Ala Cys Pro Pro
    50                  55                  60

Val Gln Thr Thr Ala Pro Thr Ala Ala Glu Leu Tyr Glu Ser Glu Leu
65                  70                  75                  80

Lys Phe Leu Ala Ala Gly Phe Gln Leu Ser Gly Ala Ala Gly Ala Ala
                85                  90                  95

Pro Pro Val Pro Ala Leu Leu Pro Ala Ala Ala Leu Glu Gln Thr Asp
            100                 105                 110

Glu Thr Lys Gln Leu Ala Leu Pro Pro Gln Ala Ala Val Ala Pro Pro
        115                 120                 125

Pro Glu Gln Lys Lys Ala Val Asp Ser Phe Gly Gln Arg Thr Ser Ile
    130                 135                 140

Tyr Arg Gly Val Thr Arg His Arg Trp Thr Gly Arg Tyr Glu Ala His
145                 150                 155                 160

Leu Trp Asp Asn Ser Cys Arg Arg Glu Gly Gln Ser Arg Lys Gly Arg
                165                 170                 175

Gln Val Tyr Leu Gly Gly Tyr Asp Lys Glu Glu Lys Ala Ala Arg Ala
            180                 185                 190

Tyr Asp Leu Ala Ala Leu Lys Tyr Trp Gly Pro Ser Thr Thr Thr Asn
        195                 200                 205

Phe Pro Val Ala Glu Tyr Glu Lys Glu Leu Glu Met Lys His Met
    210                 215                 220

Thr Arg Gln Glu Phe Val Ala Ser Leu Arg Arg Lys Ser Ser Gly Phe
225                 230                 235                 240

Ser Arg Gly Ala Ser Ile Tyr Arg Gly Val Thr Arg His His Gln His
                245                 250                 255

Gly Arg Trp Gln Ala Arg Ile Gly Arg Val Ala Gly Asn Lys Asp Leu
            260                 265                 270

Tyr Leu Gly Thr Phe Gly Thr Glu Glu Glu Ala Ala Glu Ala Tyr Asp
        275                 280                 285
```

-continued

```
Ile Ala Ala Ile Lys Phe Arg Gly Leu Asn Ala Val Thr Asn Phe Glu
        290                 295                 300

Ile Gly Arg Tyr Asn Val Glu Ser Ile Ile Ser Asn Leu Pro Ile
305                 310                 315                 320

Gly Ser Met Ala Gly Asn Arg Ser Thr Lys Ala Gly Leu Glu Leu Ala
                325                 330                 335

Pro Ser Ser Ala Asp Ala Ile Ala Ala Thr Glu Ala Asn His Thr
                340                 345                 350

Gly Val Ala Pro Pro Ser Thr Leu Ala Phe Thr Ala Leu Pro Met Lys
                355                 360                 365

Tyr Asp Gln Ala Asp Tyr Leu Ser Tyr Leu Ala Leu Gln His His Gln
        370                 375                 380

Gln Gly Asn Leu Gln Gly Leu Gly Phe Gly Leu Tyr Ser Ser Gly Val
385                 390                 395                 400

Asn Leu Asp Phe Ala Asn Ala Asn Gly Asn Gly Ala Met Ser Asn Cys
                405                 410                 415

Tyr Thr Asn Val Ser Leu His Glu Gln Gln Gln His Gln His Gln
                420                 425                 430

His Gln Gln Glu Gln Gln Gln Asp Gln Gln Asp Asp Gln Ser Gln Ser
        435                 440                 445

Ser Asn Asn Ser Cys Gly Ser Ile Pro Phe Ala Thr Pro Ile Ala Phe
        450                 455                 460

Ser Gly Ser Tyr Glu Ser Ser Met Thr Ala Ala Gly Thr Phe Gly Tyr
465                 470                 475                 480

Tyr Pro Asn Val Ala Ala Phe Gln Thr Pro Ile Phe Gly Met Glu
                485                 490                 495

<210> SEQ ID NO 65
<211> LENGTH: 558
<212> TYPE: PRT
<213> ORGANISM: Arabidopsis thaliana

<400> SEQUENCE: 65

Met Lys Asn Asn Asn Lys Ser Ser Ser Ser Ser Ser Tyr Asp Ser
1               5                   10                  15

Ser Leu Ser Pro Ser Ser Ser Ser Ser His Gln Asn Trp Leu Ser
                20                  25                  30

Phe Ser Leu Ser Asn Asn Asn Asn Phe Asn Ser Ser Ser Asn Pro
                35                  40                  45

Asn Leu Thr Ser Ser Thr Ser Asp His His Pro His Pro Ser His
        50                  55                  60

Leu Ser Leu Phe Gln Ala Phe Ser Thr Ser Pro Val Glu Arg Gln Asp
65                  70                  75                  80

Gly Ser Pro Gly Val Ser Pro Ser Asp Ala Thr Ala Val Leu Ser Val
                85                  90                  95

Tyr Pro Gly Gly Pro Lys Leu Glu Asn Phe Leu Gly Gly Gly Ala Ser
                100                 105                 110

Thr Thr Thr Thr Arg Pro Met Gln Gln Val Gln Ser Leu Gly Gly Val
                115                 120                 125

Val Phe Ser Ser Asp Leu Gln Pro Pro Leu His Pro Pro Ser Ala Ala
                130                 135                 140

Glu Ile Tyr Asp Ser Glu Leu Lys Ser Ile Ala Ala Ser Phe Leu Gly
145                 150                 155                 160

Asn Tyr Ser Gly Gly His Ser Ser Glu Val Ser Ser Val His Lys Gln
```

```
                165                 170                 175
Gln Pro Asn Pro Leu Ala Val Ser Glu Ala Ser Pro Thr Pro Lys Lys
            180                 185                 190

Asn Val Glu Ser Phe Gly Gln Arg Thr Ser Ile Tyr Arg Gly Val Thr
            195                 200                 205

Arg His Arg Trp Thr Gly Arg Tyr Glu Ala His Leu Trp Asp Asn Ser
        210                 215                 220

Cys Arg Arg Glu Gly Gln Ser Arg Lys Gly Arg Gln Val Tyr Leu Gly
225                 230                 235                 240

Gly Tyr Asp Lys Glu Asp Lys Ala Ala Arg Ala Tyr Asp Leu Ala Ala
                245                 250                 255

Leu Lys Tyr Trp Gly Pro Thr Thr Thr Thr Asn Phe Pro Ile Ser Asn
            260                 265                 270

Tyr Glu Ser Glu Leu Glu Glu Met Lys His Met Thr Arg Gln Glu Phe
            275                 280                 285

Val Ala Ser Leu Arg Arg Lys Ser Ser Gly Phe Ser Arg Gly Ala Ser
            290                 295                 300

Met Tyr Arg Gly Val Thr Arg His His Gln His Gly Arg Trp Gln Ala
305                 310                 315                 320

Arg Ile Gly Arg Val Ala Gly Asn Lys Asp Leu Tyr Leu Gly Thr Phe
                325                 330                 335

Ser Thr Gln Glu Glu Ala Ala Glu Ala Tyr Asp Ile Ala Ala Ile Lys
            340                 345                 350

Phe Arg Gly Leu Asn Ala Val Thr Asn Phe Asp Ile Ser Arg Tyr Asp
            355                 360                 365

Val Lys Ser Ile Ala Ser Cys Asn Leu Pro Val Gly Gly Leu Met Pro
370                 375                 380

Lys Pro Ser Pro Ala Thr Ala Ala Asp Lys Thr Val Asp Leu Ser
385                 390                 395                 400

Pro Ser Asp Ser Pro Ser Leu Thr Thr Pro Ser Leu Thr Phe Asn Val
                405                 410                 415

Ala Thr Pro Val Asn Asp His Gly Gly Thr Phe Tyr His Thr Gly Ile
            420                 425                 430

Pro Ile Lys Pro Asp Pro Ala Asp His Tyr Trp Ser Asn Ile Phe Gly
        435                 440                 445

Phe Gln Ala Asn Pro Lys Ala Glu Met Arg Pro Leu Ala Asn Phe Gly
    450                 455                 460

Ser Asp Leu His Asn Pro Ser Pro Gly Tyr Ala Ile Met Pro Val Met
465                 470                 475                 480

Gln Glu Gly Glu Asn Asn Phe Gly Gly Ser Phe Val Gly Ser Asp Gly
                485                 490                 495

Tyr Asn Asn His Ser Ala Ala Ser Asn Pro Val Ser Ala Ile Pro Leu
            500                 505                 510

Ser Ser Thr Thr Thr Met Ser Asn Gly Asn Glu Gly Tyr Gly Gly Asn
            515                 520                 525

Ile Asn Trp Ile Asn Asn Asn Ile Ser Ser Ser Tyr Gln Thr Ala Lys
        530                 535                 540

Ser Asn Leu Ser Val Leu His Thr Pro Val Phe Gly Leu Glu
545                 550                 555

<210> SEQ ID NO 66
<211> LENGTH: 568
<212> TYPE: PRT
<213> ORGANISM: Arabidopsis thaliana
```

<400> SEQUENCE: 66

```
Met Asn Ser Asn Asn Trp Leu Ala Phe Pro Leu Ser Pro Thr His Ser
1               5                   10                  15

Ser Leu Pro Pro His Ile His Ser Ser Gln Asn Ser His Phe Asn Leu
            20                  25                  30

Gly Leu Val Asn Asp Asn Ile Asp Asn Pro Phe Gln Asn Gln Gly Trp
        35                  40                  45

Asn Met Ile Asn Pro His Gly Gly Gly Glu Gly Gly Glu Val Pro
    50                  55                  60

Lys Val Ala Asp Phe Leu Gly Val Ser Lys Ser Gly Asp His His Thr
65                  70                  75                  80

Asp His Asn Leu Val Pro Tyr Asn Asp Ile His Gln Thr Asn Ala Ser
                85                  90                  95

Asp Tyr Tyr Phe Gln Thr Asn Ser Leu Leu Pro Thr Val Val Thr Cys
            100                 105                 110

Ala Ser Asn Ala Pro Asn Asn Tyr Glu Leu Gln Glu Ser Ala His Asn
        115                 120                 125

Leu Gln Ser Leu Thr Leu Ser Met Gly Ser Thr Gly Ala Ala Ala
    130                 135                 140

Glu Val Ala Thr Val Lys Ala Ser Pro Ala Glu Thr Ser Ala Asp Asn
145                 150                 155                 160

Ser Ser Ser Thr Thr Asn Thr Ser Gly Gly Ala Ile Val Glu Ala Thr
                165                 170                 175

Pro Arg Arg Thr Leu Glu Thr Phe Gly Gln Arg Thr Ser Ile Tyr Arg
            180                 185                 190

Gly Val Thr Arg His Arg Trp Thr Gly Arg Tyr Glu Ala His Leu Trp
        195                 200                 205

Asp Asn Ser Cys Arg Arg Glu Gly Gln Ser Arg Lys Gly Arg Gln Val
    210                 215                 220

Tyr Leu Gly Gly Tyr Asp Lys Glu Glu Lys Ala Ala Arg Ala Tyr Asp
225                 230                 235                 240

Leu Ala Ala Leu Lys Tyr Trp Gly Pro Ser Thr Thr Thr Asn Phe Pro
                245                 250                 255

Ile Thr Asn Tyr Glu Lys Glu Val Glu Glu Met Lys Asn Met Thr Arg
            260                 265                 270

Gln Glu Phe Val Ala Ser Ile Arg Arg Lys Ser Ser Gly Phe Ser Arg
        275                 280                 285

Gly Ala Ser Met Tyr Arg Gly Val Thr Arg His His Gln His Gly Arg
    290                 295                 300

Trp Gln Ala Arg Ile Gly Arg Val Ala Gly Asn Lys Asp Leu Tyr Leu
305                 310                 315                 320

Gly Thr Phe Ser Thr Glu Glu Glu Ala Ala Glu Ala Tyr Asp Ile Ala
                325                 330                 335

Ala Ile Lys Phe Arg Gly Leu Asn Ala Val Thr Asn Phe Glu Ile Asn
            340                 345                 350

Arg Tyr Asp Val Lys Ala Ile Leu Glu Ser Asn Thr Leu Pro Ile Gly
        355                 360                 365

Gly Gly Ala Ala Lys Arg Leu Lys Glu Ala Gln Ala Leu Glu Ser Ser
    370                 375                 380

Arg Lys Arg Glu Glu Met Ile Ala Leu Gly Ser Asn Phe His Gln Tyr
385                 390                 395                 400

Gly Ala Ala Ser Gly Ser Ser Ser Val Ala Ser Ser Ser Arg Leu Gln
```

-continued

```
                        405                 410                 415
Leu Gln Pro Tyr Pro Leu Ser Ile Gln Gln Pro Phe Glu His Leu His
                420                 425                 430

His His Gln Pro Leu Leu Thr Leu Gln Asn Asn Asn Asp Ile Ser Gln
            435                 440                 445

Tyr His Asp Ser Phe Ser Tyr Ile Gln Thr Gln Leu His Leu His Gln
        450                 455                 460

Gln Gln Thr Asn Asn Tyr Leu Gln Ser Ser His Thr Ser Gln Leu
465                 470                 475                 480

Tyr Asn Ala Tyr Leu Gln Ser Asn Pro Gly Leu Leu His Gly Phe Val
                485                 490                 495

Ser Asp Asn Asn Asn Thr Ser Gly Phe Leu Gly Asn Asn Gly Ile Gly
            500                 505                 510

Ile Gly Ser Ser Ser Thr Val Gly Ser Ser Ala Glu Glu Phe Pro
        515                 520                 525

Ala Val Lys Val Asp Tyr Asp Met Pro Pro Ser Gly Gly Ala Thr Gly
                530                 535                 540

Tyr Gly Gly Trp Asn Ser Gly Glu Ser Ala Gln Gly Ser Asn Pro Gly
545                 550                 555                 560

Gly Val Phe Thr Met Trp Asn Glu
                565

<210> SEQ ID NO 67
<211> LENGTH: 474
<212> TYPE: PRT
<213> ORGANISM: Sorghum bicolor

<400> SEQUENCE: 67

Met Asp Met Asp Met Ser Ser Ala Tyr Pro His His Trp Leu Ser Phe
1               5                   10                  15

Ser Leu Ser Asn Asn Tyr His His Gly Leu Leu Glu Ala Phe Ser Asn
                20                  25                  30

Ser Ser Ser Ala Ala Pro Leu Gly Asp Glu Gln Gly Thr Val Glu Glu
            35                  40                  45

Ser Pro Lys Met Val Glu Asp Phe Leu Gly Gly Val Gly Gly Ala Gly
        50                  55                  60

Ala Pro Pro Ala Ala Ala Thr Ala Ala Glu Asp His Gln Leu Val Cys
65                  70                  75                  80

Gly Glu Leu Gly Ser Ile Thr Ala Gly Phe Leu Arg His Tyr Pro Ala
                85                  90                  95

Pro Gly Thr Thr Val Glu Asn Pro Gly Ala Val Thr Val Ala Ala Met
            100                 105                 110

Ser Thr Asp Val Ala Glu Ser Asp Gln Ala Arg Arg Pro Ala Glu Thr
        115                 120                 125

Phe Gly Gln Arg Thr Ser Ile Tyr Arg Gly Val Thr Arg His Arg Trp
    130                 135                 140

Thr Gly Arg Tyr Glu Ala His Leu Trp Asp Asn Ser Cys Arg Arg Glu
145                 150                 155                 160

Gly Gln Ser Arg Lys Gly Arg Gln Val Tyr Leu Gly Gly Tyr Asp Lys
                165                 170                 175

Glu Glu Lys Ala Ala Arg Ala Tyr Asp Leu Ala Ala Leu Lys Tyr Trp
            180                 185                 190

Gly Ala Thr Thr Thr Thr Asn Phe Pro Val Ser Asn Tyr Glu Lys Glu
        195                 200                 205
```

Leu Glu Glu Met Lys Ser Met Thr Arg Gln Glu Phe Ile Ala Ser Leu
210                 215                 220

Arg Arg Lys Ser Ser Gly Phe Ser Arg Gly Ala Ser Ile Tyr Arg Gly
225                 230                 235                 240

Val Thr Arg His His Gln His Gly Arg Trp Gln Ala Arg Ile Gly Arg
                245                 250                 255

Val Ala Gly Asn Lys Asp Leu Tyr Leu Gly Thr Phe Ser Thr Gln Glu
            260                 265                 270

Glu Ala Ala Glu Ala Tyr Asp Ile Ala Ile Lys Phe Arg Gly Leu
        275                 280                 285

Asn Ala Val Thr Asn Phe Asp Met Ser Arg Tyr Asp Val Asp Ser Ile
290                 295                 300

Leu Asn Ser Asp Leu Pro Val Gly Gly Ala Ala Gly Arg Ala Ser
305                 310                 315                 320

Lys Phe Pro Leu Asp Ser Leu Gln Pro Gly Ser Ala Ala Met Ile
                325                 330                 335

Ala Gly Ala Ala Ser Gln Ala Met Pro Pro Ser Glu Lys Asp Tyr Trp
            340                 345                 350

Ser Leu Leu Ala Leu His Tyr Gln Gln Gln Gln Gln Gln Gln Phe
        355                 360                 365

Pro Ala Ser Ala Tyr Glu Ala Tyr Gly Ser Gly Val Asn Val Asp Phe
    370                 375                 380

Thr Met Gly Thr Ser Ser His Ser Ser Ser Asn Thr Gly Ser Gly Val
385                 390                 395                 400

Met Trp Gly Thr Thr Thr Gly Ala Met Gly Gln Gln Asp Ser Ser Ser
                405                 410                 415

Ser Lys Gln Gly Asn Gly Tyr Ala Ser Asn Ile Pro Tyr Ala Ala Ala
            420                 425                 430

Ala Ala Ala Met Val Ser Gly Ser Ala Gly Tyr Glu Gly Ser Thr Gly
        435                 440                 445

Asn Asn Gly Thr Trp Val Thr Ser Ser Thr Ser Thr Thr Ala Pro
    450                 455                 460

Gln Tyr Tyr Asn Tyr Leu Phe Gly Met Glu
465                 470

<210> SEQ ID NO 68
<211> LENGTH: 549
<212> TYPE: PRT
<213> ORGANISM: Oryza sativa

<400> SEQUENCE: 68

Met Asp Met Asn Ser Gly Trp Leu Gly Phe Ser Leu Ser Ser Ser Ser
1               5                   10                  15

Ala Arg Gly Tyr Gly Asp Gly Cys Gly Glu Gly Asn Gly Gly Gly Asp
                20                  25                  30

Gly Asp Gly Ser Cys Ser Ser Pro Val Ala Ala Ser Pro Leu Val Ala
            35                  40                  45

Met Pro Leu His Ser Asp Gly Ser Val His Tyr Asp Ala Pro Asp Trp
    50                  55                  60

Arg His Ala Glu Ala Lys Asp Pro Lys Leu Glu Asp Phe Met Ser Val
65                  70                  75                  80

Ser Tyr Ser Asn Lys Ser Ser Ser Asn Leu Tyr Gly Ser Ser Ser Ser
                85                  90                  95

Ser Ser Cys Gly His Ala Asp Gln Ile Lys Tyr His His Val His Asp
            100                 105                 110

```
Val Gln Ala Phe Ser Thr Pro Tyr Phe Tyr Gly His Gly Gly Ser Gly
        115                 120                 125

Val Gly Ile Asp Ile Asn Met Asn Ala Pro Pro Ala Gly Cys Thr Gly
    130                 135                 140

Val Leu Pro Asp His Arg Pro Pro Pro Gln Gln Asp His Ile Phe
145                 150                 155                 160

Leu Pro Pro His Gly Gln Tyr Phe Leu Gly Pro Pro Asn Pro Met Ala
            165                 170                 175

Pro Ala Pro Met Tyr Asn Ala Gly Gly Gly Gly Val Val Asp
            180                 185                 190

Gly Ser Met Ser Ile Ser Gly Ile Lys Ser Trp Leu Arg Gln Ala Met
        195                 200                 205

Tyr Val Pro Glu Arg Ser Ala Ala Leu Ser Leu Ser Val Pro Ala
    210                 215                 220

Ala Pro Pro Ser Glu Ala Pro Leu Pro Pro Ala Ala Met Pro Val Val
225                 230                 235                 240

Arg Lys Pro Ala Gln Thr Phe Gly Gln Arg Thr Ser Gln Phe Arg Gly
                245                 250                 255

Val Thr Arg His Arg Trp Thr Gly Arg Tyr Glu Ala His Leu Trp Asp
        260                 265                 270

Asn Thr Cys Arg Lys Glu Gly Gln Thr Arg Lys Gly Arg Gln Val Tyr
    275                 280                 285

Leu Gly Gly Tyr Asp Lys Glu Glu Lys Ala Ala Arg Ala Tyr Asp Leu
    290                 295                 300

Ala Ala Leu Lys Tyr Trp Gly Pro Thr Thr His Ile Asn Phe Pro Leu
305                 310                 315                 320

Ser Thr Tyr Glu Lys Glu Leu Glu Glu Met Lys His Met Thr Arg Gln
                325                 330                 335

Glu Phe Ile Ala His Leu Arg Arg Asn Ser Ser Gly Phe Ser Arg Gly
            340                 345                 350

Ala Ser Met Tyr Arg Gly Val Thr Arg His His Gln His Gly Arg Trp
        355                 360                 365

Gln Ala Arg Ile Gly Arg Val Ala Gly Asn Lys Asp Leu Tyr Leu Gly
    370                 375                 380

Thr Phe Ser Thr Gln Glu Glu Ala Ala Glu Ala Tyr Asp Ile Ala Ala
385                 390                 395                 400

Ile Lys Phe Arg Gly Leu Asn Ala Val Thr Asn Phe Asp Ile Ser Lys
                405                 410                 415

Tyr Asp Val Lys Arg Ile Cys Ser Ser Thr His Leu Ile Gly Gly Asp
            420                 425                 430

Leu Ala Cys Arg Arg Ser Pro Thr Arg Met Leu Pro Pro Asp Ala Pro
        435                 440                 445

Ala Gly Ala Ala Gly Val Asp Val Val Ala Pro Gly Asp His Gln
    450                 455                 460

Gln Ile Ser Ala Gly Gly Gly Ala Ser Asp Asn Ser Asp Thr Ala
465                 470                 475                 480

Ser Asp Gly His Arg Gly Ala His Leu Leu His Gly Leu Gln Tyr Ala
                485                 490                 495

His Ala Met Lys Phe Glu Ala Gly Glu Ser Ser Gly Gly Gly Gly
            500                 505                 510

Asp Gly Ala Thr Thr Asn Trp Met Ala Ala Ala Ala Ala Ala Arg
        515                 520                 525
```

-continued

```
Pro Val Ala Gly Ile Pro Thr Val His His Gln Leu Pro Val Phe
        530                 535                 540
Ala Leu Trp Asn Asp
545

<210> SEQ ID NO 69
<211> LENGTH: 553
<212> TYPE: PRT
<213> ORGANISM: Glycine max

<400> SEQUENCE: 69

Met Asn Asn Asn Trp Leu Ser Phe Pro Leu Ser Pro Thr His Ser Ser
1               5                   10                  15
Leu Pro Ala His Asp Leu Gln Ala Thr Gln Tyr His Gln Phe Ser Leu
            20                  25                  30
Gly Leu Val Asn Glu Asn Met Asp Asn Pro Phe Gln Asn His Asp Trp
        35                  40                  45
Asn Leu Ile Asn Thr His Ser Ser Asn Glu Ile Pro Lys Val Ala Asp
    50                  55                  60
Phe Leu Gly Val Ser Lys Ser Glu Asn Gln Ser Asp Leu Ala Ala Leu
65                  70                  75                  80
Asn Glu Ile His Ser Asn Asp Ser Asp Tyr Leu Phe Thr Asn Asn Ser
                85                  90                  95
Leu Val Pro Met Gln Asn Pro Val Leu Asp Thr Pro Ser Asn Glu Tyr
            100                 105                 110
Gln Glu Asn Ala Asn Ser Asn Leu Gln Ser Leu Thr Leu Ser Met Gly
        115                 120                 125
Ser Gly Lys Asp Ser Thr Cys Glu Thr Ser Gly Glu Asn Ser Thr Asn
    130                 135                 140
Thr Thr Val Glu Val Ala Pro Arg Arg Thr Leu Asp Thr Phe Gly Gln
145                 150                 155                 160
Arg Thr Ser Ile Tyr Arg Gly Val Thr Arg His Arg Trp Thr Gly Arg
                165                 170                 175
Tyr Glu Ala His Leu Trp Asp Asn Ser Cys Arg Arg Glu Gly Gln Ser
            180                 185                 190
Arg Lys Gly Arg Gln Val Tyr Leu Gly Gly Tyr Asp Lys Glu Glu Lys
        195                 200                 205
Ala Ala Arg Ala Tyr Asp Leu Ala Ala Leu Lys Tyr Trp Gly Thr Ser
    210                 215                 220
Thr Thr Thr Asn Phe Pro Ile Ser Asn Tyr Glu Lys Glu Leu Asp Glu
225                 230                 235                 240
Met Lys His Met Thr Arg Gln Glu Phe Val Ala Ala Ile Arg Arg Lys
                245                 250                 255
Ser Ser Gly Phe Ser Arg Gly Ala Ser Met Tyr Arg Gly Val Thr Arg
            260                 265                 270
His His Gln His Gly Arg Trp Gln Ala Arg Ile Gly Arg Val Ala Gly
        275                 280                 285
Asn Lys Asp Leu Tyr Leu Gly Thr Phe Ser Thr Glu Glu Glu Ala Ala
    290                 295                 300
Glu Ala Tyr Asp Ile Ala Ala Ile Lys Phe Arg Gly Leu Asn Ala Val
305                 310                 315                 320
Thr Asn Phe Asp Met Ser Arg Tyr Asp Val Lys Ala Ile Leu Glu Ser
                325                 330                 335
Asn Thr Leu Pro Ile Gly Gly Gly Ala Ala Lys Arg Leu Lys Glu Ala
            340                 345                 350
```

```
Gln Ala Leu Glu Ser Ser Arg Lys Arg Glu Glu Met Ile Ala Leu Gly
            355                 360                 365

Ser Ser Ser Thr Phe Gln Tyr Gly Thr Ser Ala Ser Ser Arg Leu
    370                 375                 380

His Ala Tyr Pro Leu Met Gln His His Gln Phe Glu Gln Pro Gln
385                 390                 395                 400

Pro Leu Leu Thr Leu Gln Asn His Asp Ile Ser Ser His Phe Ser
                405                 410                 415

His Gln Gln Asp Pro Leu His His Gln Gly Tyr Ile Gln Thr Gln Leu
                420                 425                 430

Gln Leu His Gln Gln Ser Gly Ala Ser Ser Tyr Ser Phe Gln Asn Asn
            435                 440                 445

Ala Gln Phe Tyr Asn Gly Tyr Leu Gln Asn His Pro Ala Leu Leu Gln
            450                 455                 460

Gly Met Met Asn Met Gly Ser Ser Ser Ser Ser Ser Val Leu Glu
465                 470                 475                 480

Asn Asn Asn Ser Asn Asn Asn Asn Asn Val Gly Gly Phe Val Gly
                485                 490                 495

Ser Gly Phe Gly Met Ala Ser Asn Ala Thr Ala Gly Asn Thr Val Gly
                500                 505                 510

Thr Ala Glu Glu Leu Gly Leu Val Lys Val Asp Tyr Asp Met Pro Ala
            515                 520                 525

Gly Gly Tyr Gly Gly Trp Ser Ala Ala Asp Ser Met Gln Thr Ser Asn
            530                 535                 540

Gly Gly Val Phe Thr Met Trp Asn Asp
545                 550

<210> SEQ ID NO 70
<211> LENGTH: 509
<212> TYPE: PRT
<213> ORGANISM: Medicago truncatula

<400> SEQUENCE: 70

Met Asp Lys Ser Ser Ser Ser Pro Pro Thr Asn Thr Asn Asn Thr Ser
1               5                   10                  15

Leu Ala Phe Ser Leu Ser Asn Asn Asn Phe Pro Asn Pro Ser His Ser
                20                  25                  30

Ser Ser Ser His Leu Ser Leu Phe His Ser Phe Thr Pro Tyr Pro Ser
            35                  40                  45

Ser Ile Ile Pro Pro Ser Leu Thr Leu Thr Gly Ser Asn Asn Pro Val
        50                  55                  60

Glu Ala Ser Pro Glu Ala Thr Asp Gly Gly Thr Thr Asn Leu Ser Ile
65                  70                  75                  80

Phe Thr Gly Gly His Lys Phe Glu Asp Phe Leu Gly Ser Ser Val Ala
                85                  90                  95

Pro Thr Arg Thr Ala Ala Ala Thr Cys Ala Pro Thr Gln Leu Gln Gln
            100                 105                 110

Phe Ser Thr Asp Asn Asp Val Tyr Asn Ser Glu Leu Lys Lys Thr Ile
        115                 120                 125

Ala Ala Cys Phe Pro Gly Gly Tyr Pro Thr Glu Pro Asn Ser Glu Pro
    130                 135                 140

Gln Lys Pro Ser Pro Lys Lys Thr Val Asp Thr Phe Gly Gln Arg Thr
145                 150                 155                 160

Ser Ile Tyr Arg Gly Val Thr Arg His Arg Trp Thr Gly Arg Tyr Glu
```

```
                165                 170                 175
Ala His Leu Trp Asp Asn Ser Cys Arg Arg Glu Gly Gln Ser Arg Lys
            180                 185                 190

Gly Arg Gln Gly Gly Tyr Asp Lys Glu Glu Lys Ala Ala Arg Ala Tyr
        195                 200                 205

Asp Leu Ala Ala Leu Lys Tyr Trp Gly Pro Thr Thr Thr Thr Asn Phe
    210                 215                 220

Pro Ile Ser Asn Tyr Glu Lys Glu Ile Asp Asp Met Lys Asn Met Thr
225                 230                 235                 240

Arg Gln Glu Phe Val Ala Ser Leu Arg Arg Lys Ser Ser Gly Phe Ser
                245                 250                 255

Arg Gly Ala Ser Ile Tyr Arg Gly Val Thr Arg His His Gln His Gly
            260                 265                 270

Arg Trp Gln Ala Arg Ile Gly Arg Val Ala Gly Asn Lys Asp Leu Tyr
        275                 280                 285

Leu Gly Thr Phe Ser Thr Gln Glu Glu Ala Ala Glu Ala Tyr Asp Ile
    290                 295                 300

Ala Ala Ile Lys Phe Arg Gly Leu Asn Ala Val Thr Asn Phe Asp Met
305                 310                 315                 320

Ser Arg Tyr Asp Val Lys Ser Ile Ala Asn Cys Ser Leu Pro Ile Gly
                325                 330                 335

Gly Leu Ser Asn Lys Asn Asn Lys Asn Ser Thr Asp Cys Val Ser Glu
            340                 345                 350

Thr Lys Ile Asn Glu Pro Ile Gln Ser Asp Glu Ile Asp His Pro Ser
        355                 360                 365

Ser Thr Ser Ser Ala Thr Thr Leu Ser Phe Ala Leu Pro Ile Lys Gln
    370                 375                 380

Asp Pro Ser Thr Asp Tyr Trp Ser Asn Ile Leu Gly Phe His Asn Asn
385                 390                 395                 400

Pro Ser Ala Val Thr Thr Thr Ile Pro Phe Asn Met Asp Phe Ser
                405                 410                 415

Ala His Val Pro Ser Asn Thr Asn Ser Asp Asn Pro His Asn Ala Ala
            420                 425                 430

Phe Phe Ser Gly Ser Gly Ile Phe Val Gln Gln Gln Asn Met Asn Gly
        435                 440                 445

Ser Ser Gly Ser Asn Ser Ser Ser Ser Ser Ala Ser Thr Ser Ser
    450                 455                 460

Ile Pro Phe Ala Thr Pro Ile Phe Ser Leu Asn Ser Asn Ser Ser Ser
465                 470                 475                 480

Tyr Gly Asn Gly Asn Asn Trp Ile Gly His Thr Phe Gln Thr His Ala
                485                 490                 495

Lys Pro Ser Leu Phe Gln Thr Pro Ile Phe Gly Met Glu
            500                 505

<210> SEQ ID NO 71
<211> LENGTH: 492
<212> TYPE: PRT
<213> ORGANISM: Zea mays

<400> SEQUENCE: 71

Met Asp Thr Ser His His Tyr His Pro Trp Leu Asn Phe Ser Leu Ala
1               5                   10                  15

His His Cys Asp Leu Glu Glu Glu Arg Gly Ala Ala Ala Glu Leu
            20                  25                  30
```

-continued

```
Ala Ala Ile Ala Gly Ala Ala Pro Pro Lys Leu Glu Asp Phe Leu
         35                  40                  45
Gly Gly Gly Val Ala Thr Gly Gly Pro Glu Ala Val Ala Pro Ala Glu
 50                  55                  60
Met Tyr Asp Ser Asp Leu Lys Phe Ile Ala Ala Gly Phe Leu Gly
 65                  70                  75                  80
Gly Ser Ala Ala Ala Ala Thr Ser Pro Leu Ser Ser Leu Asp Gln
                 85                  90                  95
Ala Gly Ser Lys Leu Ala Leu Pro Ala Ala Ala Pro Ala Pro
            100                 105                 110
Glu Gln Arg Lys Ala Val Asp Ser Phe Gly Gln Arg Thr Ser Ile Tyr
            115                 120                 125
Arg Gly Val Thr Arg His Arg Trp Thr Gly Arg Tyr Glu Ala His Leu
130                 135                 140
Trp Asp Asn Ser Cys Arg Arg Glu Gly Gln Ser Arg Lys Gly Arg Gln
145                 150                 155                 160
Val Tyr Leu Gly Gly Tyr Asp Lys Glu Glu Lys Ala Ala Arg Ala Tyr
                165                 170                 175
Asp Leu Ala Ala Leu Lys Tyr Trp Gly Ser Ser Thr Thr Thr Asn Phe
            180                 185                 190
Pro Val Ala Glu Tyr Glu Lys Glu Val Glu Glu Met Lys Asn Met Thr
            195                 200                 205
Arg Gln Glu Phe Val Ala Ser Leu Arg Arg Lys Ser Ser Gly Phe Ser
            210                 215                 220
Arg Gly Ala Ser Ile Tyr Arg Gly Val Thr Arg His His Gln His Gly
225                 230                 235                 240
Arg Trp Gln Ala Arg Ile Gly Arg Val Ala Gly Asn Lys Asp Leu Tyr
                245                 250                 255
Leu Gly Thr Phe Ser Thr Glu Glu Ala Ala Glu Ala Tyr Asp Ile
            260                 265                 270
Ala Ala Ile Lys Phe Arg Gly Leu Asn Ala Val Thr Asn Phe Glu Ile
            275                 280                 285
Ser Arg Tyr Asn Val Glu Thr Ile Met Ser Ser Asn Leu Pro Val Ala
            290                 295                 300
Ser Met Ser Ser Ser Ala Ala Ala Ala Gly Gly Arg Ser Ser Lys
305                 310                 315                 320
Ala Leu Glu Ser Pro Ser Gly Ser Leu Asp Gly Gly Gly Met
                325                 330                 335
Pro Val Val Glu Ala Ser Thr Ala Pro Pro Leu Phe Ile Pro Val Lys
            340                 345                 350
Tyr Asp Gln Gln Gln Glu Tyr Leu Ser Met Leu Ala Leu Gln Gln
            355                 360                 365
His His Gln Gln Gln Ala Gly Asn Leu Leu Gln Gly Pro Leu Val
            370                 375                 380
Gly Phe Gly Gly Leu Tyr Ser Ser Gly Val Asn Leu Asp Phe Ala Asn
385                 390                 395                 400
Ser His Gly Thr Ala Pro Ser Ser Met Ala His Cys Tyr Ala
                405                 410                 415
Asn Gly Thr Ala Ser Ala Ser His Glu His Gln His Met Gln Gln
            420                 425                 430
Gly Gly Glu Asn Glu Thr Gln Pro Gln Pro Gln Gln Ser Ser Ser Ser
            435                 440                 445
Cys Ser Ser Leu Pro Phe Ala Thr Pro Val Ala Phe Asn Gly Ser Tyr
```

```
            450                 455                 460
Glu Ser Ser Ile Thr Ala Ala Gly Pro Phe Gly Tyr Ser Tyr Pro Asn
465                 470                 475                 480

Val Ala Ala Phe Gln Thr Pro Ile Tyr Gly Met Glu
                    485                 490

<210> SEQ ID NO 72
<211> LENGTH: 469
<212> TYPE: PRT
<213> ORGANISM: Oryza sativa

<400> SEQUENCE: 72

Met Asp Met Asp Met Ser Ser Ala Tyr Pro His His Trp Leu Ser Phe
1               5                   10                  15

Ser Leu Ser Asn Asn Tyr His His Gly Leu Leu Glu Ala Leu Ser Thr
                20                  25                  30

Thr Ser Ala Pro Pro Leu Gly Glu Glu Gly Pro Ala Glu Gly Ala Pro
            35                  40                  45

Lys Met Glu Asp Phe Leu Gly Leu Gly Gly Gly Gly Ala Val
50                  55                  60

Ala Ala Ala Pro Ala Ala Ala Pro Glu Asp Gln Leu Ser Cys Gly Glu
65                  70                  75                  80

Leu Gly Ser Ile Ala Ala Gly Phe Leu Arg Arg Tyr Pro Ala Pro Glu
                85                  90                  95

Asn Ala Gly Gly Val Thr Ile Ala Met Ala Thr Asp Ala Ala Ala Glu
                100                 105                 110

Leu Ala Asp Pro Ala Arg Arg Thr Ala Glu Thr Phe Gly Gln Arg Thr
            115                 120                 125

Ser Ile Tyr Arg Gly Val Thr Arg His Arg Trp Thr Gly Arg Tyr Glu
130                 135                 140

Ala His Leu Trp Asp Asn Ser Cys Arg Arg Glu Gly Gln Ser Arg Lys
145                 150                 155                 160

Gly Arg Gln Val Tyr Leu Gly Gly Tyr Asp Lys Glu Glu Lys Ala Ala
                165                 170                 175

Arg Ala Tyr Asp Leu Ala Ala Leu Lys Tyr Trp Gly Pro Thr Thr Thr
            180                 185                 190

Thr Asn Phe Pro Val Ala Asn Tyr Glu Thr Glu Leu Glu Glu Met Lys
            195                 200                 205

Ser Met Thr Arg Gln Glu Phe Ile Ala Ser Leu Arg Arg Lys Ser Ser
210                 215                 220

Gly Phe Ser Arg Gly Ala Ser Ile Tyr Arg Gly Val Thr Arg His His
225                 230                 235                 240

Gln His Gly Arg Trp Gln Ala Arg Ile Gly Arg Val Ala Gly Asn Lys
                245                 250                 255

Asp Leu Tyr Leu Gly Thr Phe Ser Thr Gln Glu Glu Ala Ala Glu Ala
            260                 265                 270

Tyr Asp Ile Ala Ala Ile Lys Phe Arg Gly Leu Asn Ala Val Thr Asn
            275                 280                 285

Phe Asp Met Ser Arg Tyr Asp Val Asp Ser Ile Leu Asn Ser Asp Leu
290                 295                 300

Pro Val Gly Gly Gly Ala Ala Thr Arg Ala Ser Lys Phe Pro Ser Asp
305                 310                 315                 320

Pro Ser Leu Pro Leu Pro Ser Pro Ala Met Pro Pro Ser Glu Lys Asp
                325                 330                 335
```

```
Tyr Trp Ser Leu Leu Ala Leu His Tyr His His Gln Gln Gln
                340                 345                 350

Gln Gln Gln Gln Phe Pro Ala Ser Ala Phe Asp Thr Tyr Gly Cys Ser
            355                 360                 365

Ser Gly Val Asn Val Asp Phe Thr Met Gly Thr Ser Ser His Ser Gly
        370                 375                 380

Ser Asn Ser Asn Ser Ser Ser Ser Ala Ile Trp Gly Thr Ala Ala
385                 390                 395                 400

Gly Ala Ala Met Gly Arg Gln Gln Asn Gly Ser Ser Asn Lys Gln
                405                 410                 415

Ser Asn Ser Tyr Ser Gly Asn Asn Ile Pro Tyr Ala Ala Ala Ala
            420                 425                 430

Met Thr Ser Gly Ser Ala Leu Tyr Gly Gly Ser Thr Gly Ser Asn Gly
                435                 440                 445

Thr Trp Val Ala Ser Asn Thr Ser Thr Ala Pro His Phe Tyr Asn Tyr
            450                 455                 460

Leu Phe Gly Met Glu
465

<210> SEQ ID NO 73
<211> LENGTH: 562
<212> TYPE: PRT
<213> ORGANISM: Glycine max

<400> SEQUENCE: 73

Met Asn Asn Asn Trp Leu Ser Phe Pro Leu Ser Pro Thr His Ser Ser
1               5                   10                  15

Leu Pro Ala His Asp Leu Gln Ala Thr Gln Tyr His Gln Phe Ser Leu
                20                  25                  30

Gly Leu Val Asn Glu Asn Met Glu Asn Pro Phe Gln Asn His Asp Trp
            35                  40                  45

Ser Leu Ile Asn Thr His Ser Ser Ser Glu Val Pro Lys Val Ala Asp
    50                  55                  60

Phe Leu Gly Val Ser Lys Ser Glu Asn Glu Ser Asp Leu Ala Ala Ser
65                  70                  75                  80

Leu Asn Glu Ile Gln Ser Asn Asp Ser Asp Tyr Leu Phe Thr Asn Asn
                85                  90                  95

Ser Leu Val Pro Met Gln Asn Pro Ala Val Asp Thr Pro Ser Asn Glu
            100                 105                 110

Tyr Gln Glu Asn Ala Asn Ser Ser Leu Gln Ser Leu Thr Leu Ser Met
        115                 120                 125

Gly Ser Gly Lys Asp Ser Thr Cys Glu Thr Ser Gly Asp Asn Ser Thr
    130                 135                 140

Asn Thr Thr Thr Thr Thr Val Glu Ala Pro Arg Arg Thr Leu
145                 150                 155                 160

Asp Thr Phe Gly Gln Arg Thr Ser Ile Tyr Arg Gly Val Thr Arg His
                165                 170                 175

Arg Trp Thr Gly Arg Tyr Glu Ala His Leu Trp Asp Asn Ser Cys Arg
            180                 185                 190

Arg Glu Gly Gln Ser Arg Lys Gly Arg Gln Val Tyr Leu Gly Gly Tyr
        195                 200                 205

Asp Lys Glu Glu Lys Ala Ala Arg Ser Tyr Asp Leu Ala Ala Leu Lys
    210                 215                 220

Tyr Trp Gly Thr Ser Thr Thr Thr Asn Phe Pro Ile Ser Asn Tyr Glu
225                 230                 235                 240
```

```
Lys Glu Leu Asp Glu Met Lys His Met Thr Arg Gln Glu Phe Val Ala
                245                 250                 255

Ala Ile Arg Arg Lys Ser Ser Gly Phe Ser Arg Gly Ala Ser Met Tyr
            260                 265                 270

Arg Gly Val Thr Arg His His Gln His Gly Arg Trp Gln Ala Arg Ile
            275                 280                 285

Gly Arg Val Ala Gly Asn Lys Asp Leu Tyr Leu Gly Thr Phe Ser Thr
290                 295                 300

Glu Glu Glu Ala Ala Glu Ala Tyr Asp Ile Ala Ala Ile Lys Phe Arg
305                 310                 315                 320

Gly Leu Asn Ala Val Thr Asn Phe Asp Met Ser Arg Tyr Asp Val Lys
                325                 330                 335

Ala Ile Leu Glu Ser Asn Thr Leu Pro Ile Gly Gly Ala Ala Lys
                340                 345                 350

Arg Leu Lys Glu Ala Gln Ala Leu Glu Ser Ser Arg Lys Arg Glu Glu
                355                 360                 365

Met Ile Ala Leu Gly Ser Ser Thr Phe Gln Tyr Gly Thr Thr Ser Ser
370                 375                 380

Asn Ser Arg Leu His Ala Tyr Pro Leu Met Gln His His His Gln Phe
385                 390                 395                 400

Glu Gln Pro Gln Pro Leu Leu Thr Leu Gln Asn His Asp Ile Ser Ser
                405                 410                 415

His Phe Ser His Gln Gln Asp Pro Leu His Gln Gly Tyr Ile Gln Thr
                420                 425                 430

Gln Leu Gln Leu His Gln Gln Gln Ser Gly Gly Ser Ser Ser Tyr Ser
                435                 440                 445

Phe Gln Asn Asn Ile Asn Asn Ala Gln Phe Tyr Asn Gly Tyr Asn
450                 455                 460

Leu Gln Asn His Pro Ala Leu Leu Gln Gly Met Ile Asn Met Gly Ser
465                 470                 475                 480

Ser Ser Ser Ser Val Leu Glu Asn Asn Ser Asn Asn Asn Asn
                485                 490                 495

Val Gly Gly Phe Val Gly Ser Gly Phe Gly Met Ala Ser Asn Ala Thr
                500                 505                 510

Ser Gly Asn Thr Val Gly Thr Ala Glu Glu Leu Gly Leu Val Lys Val
                515                 520                 525

Asp Tyr Asp Met Pro Thr Gly Gly Tyr Gly Gly Trp Ser Ala Ala Ala
                530                 535                 540

Ala Ala Glu Ser Met Gln Thr Ser Asn Ser Gly Val Phe Thr Met Trp
545                 550                 555                 560

Asn Asp
```

<210> SEQ ID NO 74
<211> LENGTH: 574
<212> TYPE: PRT
<213> ORGANISM: Arabidopsis thaliana

<400> SEQUENCE: 74

```
Met Asn Ser Asn Asn Trp Leu Gly Phe Pro Leu Ser Pro Asn Asn Ser
1               5                   10                  15

Ser Leu Pro Pro His Glu Tyr Asn Leu Gly Leu Val Ser Asp His Met
                20                  25                  30

Asp Asn Pro Phe Gln Thr Gln Glu Trp Asn Met Ile Asn Pro His Gly
            35                  40                  45
```

```
Gly Gly Gly Asp Glu Gly Gly Glu Val Pro Lys Val Ala Asp Phe Leu
 50              55              60

Gly Val Ser Lys Pro Asp Glu Asn Gln Ser Asn His Leu Val Ala Tyr
 65              70              75              80

Asn Asp Ser Asp Tyr Tyr Phe His Thr Asn Ser Leu Met Pro Ser Val
                 85              90              95

Gln Ser Asn Asp Val Val Val Ala Ala Cys Asp Ser Asn Thr Pro Asn
            100             105             110

Asn Ser Ser Tyr His Glu Leu Gln Glu Ser Ala His Asn Leu Gln Ser
        115             120             125

Leu Thr Leu Ser Met Gly Thr Thr Ala Gly Asn Val Val Asp Lys
130             135             140

Ala Ser Pro Ser Glu Thr Thr Gly Asp Asn Ala Ser Gly Gly Ala Leu
145             150             155             160

Ala Val Val Glu Thr Ala Thr Pro Arg Arg Ala Leu Asp Thr Phe Gly
                165             170             175

Gln Arg Thr Ser Ile Tyr Arg Gly Val Thr Arg His Arg Trp Thr Gly
            180             185             190

Arg Tyr Glu Ala His Leu Trp Asp Asn Ser Cys Arg Arg Glu Gly Gln
        195             200             205

Ser Arg Lys Gly Arg Gln Val Tyr Leu Gly Gly Tyr Asp Lys Glu Asp
210             215             220

Lys Ala Ala Arg Ser Tyr Asp Leu Ala Ala Leu Lys Tyr Trp Gly Pro
225             230             235             240

Ser Thr Thr Thr Asn Phe Pro Ile Thr Asn Tyr Glu Lys Glu Val Glu
                245             250             255

Glu Met Lys His Met Thr Arg Gln Glu Phe Val Ala Ala Ile Arg Arg
            260             265             270

Lys Ser Ser Gly Phe Ser Arg Gly Ala Ser Met Tyr Arg Gly Val Thr
        275             280             285

Arg His His Gln His Gly Arg Trp Gln Ala Arg Ile Gly Arg Val Ala
290             295             300

Gly Asn Lys Asp Leu Tyr Leu Gly Thr Phe Ser Thr Glu Glu Glu Ala
305             310             315             320

Ala Glu Ala Tyr Asp Ile Ala Ala Ile Lys Phe Arg Gly Leu Asn Ala
                325             330             335

Val Thr Asn Phe Glu Ile Asn Arg Tyr Asp Val Lys Ala Ile Leu Glu
            340             345             350

Ser Ser Thr Leu Pro Ile Gly Gly Ala Ala Lys Arg Leu Lys Glu
        355             360             365

Ala Gln Ala Leu Glu Ser Ser Arg Lys Arg Glu Ala Glu Met Ile Ala
370             375             380

Leu Gly Ser Ser Phe Gln Tyr Gly Gly Gly Ser Ser Thr Gly Ser Gly
385             390             395             400

Ser Thr Ser Ser Arg Leu Gln Leu Gln Pro Tyr Pro Leu Ser Ile Gln
                405             410             415

Gln Pro Leu Glu Pro Phe Leu Ser Leu Gln Asn Asn Asp Ile Ser His
            420             425             430

Tyr Asn Asn Asn Asn Ala His Asp Ser Ser Ser Phe Asn His His Ser
        435             440             445

Tyr Ile Gln Thr Gln Leu His Leu His Gln Gln Thr Asn Asn Tyr Leu
450             455             460
```

```
Gln Gln Gln Ser Ser Gln Asn Ser Gln Gln Leu Tyr Asn Ala Tyr Leu
465                 470                 475                 480

His Ser Asn Pro Ala Leu Leu His Gly Leu Val Ser Thr Ser Ile Val
            485                 490                 495

Asp Asn Asn Asn Asn Gly Gly Ser Ser Gly Ser Tyr Asn Thr Ala
        500                 505                 510

Ala Phe Leu Gly Asn His Gly Ile Gly Ile Gly Ser Ser Thr Val
            515                 520                 525

Gly Ser Thr Glu Glu Phe Pro Thr Val Lys Thr Asp Tyr Asp Met Pro
        530                 535                 540

Ser Ser Asp Gly Thr Gly Gly Tyr Ser Gly Trp Thr Ser Glu Ser Val
545                 550                 555                 560

Gln Gly Ser Asn Pro Gly Gly Val Phe Thr Met Trp Asn Glu
            565                 570
```

<210> SEQ ID NO 75
<211> LENGTH: 543
<212> TYPE: PRT
<213> ORGANISM: Medicago truncatula

<400> SEQUENCE: 75

```
Met Asn Asn Asn Trp Leu Ser Phe Pro Leu Ser Pro Ser His Ser Ser
1               5                   10                  15

Leu Pro Ser Asn Asp Leu Gln Ala Thr Gln Tyr His His Phe Pro Leu
            20                  25                  30

Gly Leu Val Asn Asp Asn Met Glu Asn Pro Phe Gln Asn His Asp Trp
        35                  40                  45

Asn Leu Met Asn Thr His Asn Ser Asn Glu Val Pro Lys Val Ala Asp
50                  55                  60

Phe Leu Gly Val Cys Lys Ser Glu Asn His Ser Asp Leu Ala Thr Pro
65                  70                  75                  80

Asn Glu Ile Gln Ser Asn Asp Ser Asp Tyr Leu Phe Thr Asn Asn Asn
                85                  90                  95

Thr Leu Met Pro Met Gln Asn Gln Met Val Thr Thr Cys Thr Asn Glu
            100                 105                 110

Tyr Gln Glu Lys Ala Ser Asn Ser Asn Leu Gln Ser Leu Thr Leu Ser
        115                 120                 125

Met Gly Ser Gly Lys Asp Ser Thr Cys Glu Thr Ser Gly Glu Asn Ser
    130                 135                 140

Thr Asn Thr Val Glu Val Ala Val Pro Lys Arg Thr Ser Glu Thr Phe
145                 150                 155                 160

Gly Gln Arg Thr Ser Ile Tyr Arg Gly Val Thr Lys His Arg Trp Thr
                165                 170                 175

Gly Arg Tyr Glu Ala His Leu Trp Asp Asn Ser Cys Arg Arg Glu Gly
            180                 185                 190

Gln Ser Arg Lys Gly Arg Gln Gly Gly Tyr Asp Lys Glu Glu Lys Ala
        195                 200                 205

Ala Arg Ser Tyr Asp Leu Ala Ala Leu Lys Tyr Trp Gly Thr Ser Thr
    210                 215                 220

Thr Thr Asn Phe Pro Val Ser Asn Tyr Glu Lys Glu Ile Asp Glu Met
225                 230                 235                 240

Lys His Met Thr Arg Gln Glu Phe Val Ala Ser Ile Arg Arg Lys Ser
                245                 250                 255

Ser Gly Phe Ser Arg Gly Ala Ser Met Tyr Arg Gly Val Thr Arg His
            260                 265                 270
```

```
His Gln His Gly Arg Trp Gln Ala Arg Ile Gly Arg Val Ala Gly Asn
            275                 280                 285
Lys Asp Leu Tyr Leu Gly Thr Phe Ser Thr Glu Glu Ala Ala Glu
    290                 295                 300
Ala Tyr Asp Ile Ala Ala Ile Lys Phe Arg Gly Leu Asn Ala Val Thr
305                 310                 315                 320
Asn Phe Asp Met Thr Arg Tyr Asp Val Lys Ala Ile Leu Glu Ser Asn
                325                 330                 335
Thr Leu Pro Ile Gly Gly Ala Ala Lys Arg Leu Lys Glu Ala Gln
            340                 345                 350
Ala Leu Glu Thr Ser Arg Lys Arg Glu Glu Met Leu Ala Leu Asn Ser
            355                 360                 365
Ser Ser Phe Gln Tyr Gly Thr Ser Ser Ser Asn Thr Arg Leu Gln
    370                 375                 380
Pro Tyr Pro Leu Met Gln Tyr His Gln Phe Glu Gln Pro Gln Pro
385                 390                 395                 400
Leu Leu Thr Leu Gln Asn Asn His Glu Ser Leu Asn Ser Gln Gln Phe
                405                 410                 415
Ser Gln His Gln Gly Gly Gly Tyr Phe Gln Thr Gln Leu Glu Leu Cys
            420                 425                 430
Gln Gln Gln Asn Gln Gln Pro Ser Gln Asn Ser Asn Ile Gly Ser Phe
            435                 440                 445
Tyr Asn Gly Tyr Tyr Gln Asn His Pro Gly Leu Phe Gln Met Asn Asn
450                 455                 460
Ile Gly Ser Ser Ser Ser Ser Val Met Gly Asn Asn Gly Gly Gly
465                 470                 475                 480
Ser Ser Gly Ile Tyr Ser Asn Ser Gly Gly Leu Ile Ser Asn Asn Ala
            485                 490                 495
Val Glu Glu Phe Val Pro Val Lys Val Asp Tyr Asp Met Gln Gly Asp
                500                 505                 510
Gly Ser Gly Phe Gly Gly Trp Ser Ala Ala Gly Glu Asn Met Gln Thr
    515                 520                 525
Ala Asp Leu Phe Thr Met Trp Asn Asp Tyr Glu Thr Arg Glu Asn
530                 535                 540

<210> SEQ ID NO 76
<211> LENGTH: 543
<212> TYPE: PRT
<213> ORGANISM: Zea mays

<400> SEQUENCE: 76

Met Asp Met Asn Asn Gly Trp Leu Gly Phe Ser Leu Ser Pro Ser Ala
1               5                   10                  15
Ala Ser Arg Gly Gly Tyr Gly Tyr Gly Asp Gly Gly Gly Ala Ser
            20                  25                  30
Ala Ser Ala Cys Gly Asp Gly Glu Gly Ser Cys Pro Ser Pro Ala Ala
            35                  40                  45
Ala Ala Ser Pro Leu Pro Leu Val Ala Met Pro Leu Asp Asp Ser Leu
            50                  55                  60
His Tyr Ser Ser Ala Pro Asp Trp Arg His Gly Ala Ala Glu Ala Lys
65                  70                  75                  80
Gly Pro Lys Leu Glu Asp Phe Met Ser Ile Thr Cys Ser Asn Lys Ser
                85                  90                  95
Ser Gly Arg Ser Leu Tyr Asp Ser Cys Gly His His Asp Asp Glu Gln
```

```
                100                 105                 110
Ala Ser Lys Tyr His Glu Val His Gly Ile His Pro Leu Ser Cys Gly
            115                 120                 125
Ser Tyr Tyr His Gly Cys Ile Ser Ser Gly Gly Gly Gly Gly Gly Gly
            130                 135                 140
Ile Gly Leu Gly Ile Asn Met Asn Ala Pro Pro Cys Thr Gly Gly Phe
145                 150                 155                 160
Pro Asp His Gln His His Gln Phe Val Pro Ser Ser His His Gly Gln
                165                 170                 175
Tyr Phe Leu Gly Ala Pro Ala Ala Ser Ala Gly Pro Pro Ala Gly Ala
            180                 185                 190
Ala Met Pro Met Tyr Asn Ala Gly Gly Ser Val Val Gly Gly Ser
            195                 200                 205
Met Ser Ile Ser Gly Ile Lys Ser Trp Leu Arg Glu Ala Met Tyr Val
            210                 215                 220
Pro Pro Glu Arg Pro Ala Ala Ala Leu Ser Leu Ala Val Thr Asp
225                 230                 235                 240
Asp Val Pro Pro Ala Glu Pro Pro Gln Leu Leu Pro Ala Pro Leu Pro
                245                 250                 255
Val His Arg Lys Pro Ala Gln Thr Phe Gly Gln Arg Thr Ser Gln Phe
            260                 265                 270
Arg Gly Val Thr Arg His Arg Trp Thr Gly Arg Tyr Glu Ala His Leu
            275                 280                 285
Trp Asp Asn Thr Cys Arg Lys Glu Gly Gln Thr Arg Lys Gly Arg Gln
            290                 295                 300
Val Tyr Leu Gly Gly Tyr Asp Arg Glu Glu Lys Ala Ala Arg Ala Tyr
305                 310                 315                 320
Asp Leu Ala Ala Leu Lys Tyr Trp Gly Pro Ser Thr His Ile Asn Phe
                325                 330                 335
Pro Leu Ser His Tyr Glu Lys Glu Leu Glu Glu Met Lys His Met Ser
            340                 345                 350
Arg Gln Glu Phe Ile Ala His Leu Arg Arg Asn Ser Ser Gly Phe Ser
            355                 360                 365
Arg Gly Ala Ser Met Tyr Arg Gly Val Thr Arg His His Gln His Gly
            370                 375                 380
Arg Trp Gln Ala Arg Ile Gly Arg Val Ala Gly Asn Lys Asp Leu Tyr
385                 390                 395                 400
Leu Gly Thr Phe Ser Thr Gln Glu Glu Ala Ala Glu Ala Tyr Asp Ile
                405                 410                 415
Ala Ala Ile Lys Phe Arg Gly Leu Asn Ala Val Thr Asn Phe Asp Ile
            420                 425                 430
Ser Lys Tyr Asp Val Lys Arg Ile Cys Ala Ser Thr His Leu Ile Gly
            435                 440                 445
Gly Gly Asp Ala Cys Arg Arg Ser Pro Thr Arg Pro Pro Asp Ala Ala
            450                 455                 460
Pro Ala Leu Ala Gly Gly Ala Asp Arg Ser Ser Asp Ala Pro Gly Asp
465                 470                 475                 480
Gln Ala Ala Ser Asp Asn Ser Asp Thr Ser Asp Gly His Arg Gly Ala
                485                 490                 495
His Leu Leu His Gly Leu Gln Tyr Gly His Pro Met Lys Leu Glu Ala
            500                 505                 510
Gly Glu Gly Ser Ser Trp Met Ala Ala Ala Ala Ala Arg Pro Val
            515                 520                 525
```

Pro Gly Val His Gln Leu Pro Met Phe Ala Leu Trp Asn Asp Cys
            530                 535                 540

<210> SEQ ID NO 77
<211> LENGTH: 512
<212> TYPE: PRT
<213> ORGANISM: Glycine max

<400> SEQUENCE: 77

Met Ser Asn Trp Leu Gly Phe Ser Leu Thr Pro His Leu Arg Ile Asp
1               5                   10                  15

Glu Glu Phe Glu Arg Glu Asn Gln Arg Gly Gly Gly Ile Ile Leu
            20                  25                  30

Phe Glu Lys Lys Lys Thr Lys Trp Arg Tyr Asp Ser Ala Ile Gly Gly
            35                  40                  45

Gly Asn Ser Asn Glu Glu Gly Pro Lys Leu Glu Asp Phe Leu Gly Cys
        50                  55                  60

Tyr Ser Asn Ser Pro Ala Lys Val Phe Cys Gln Asp Ser Gln Pro Asp
65                  70                  75                  80

Gln Asn Gln Ser Gln Asn Asn Val Ser Lys Ile Asn Ile Glu Thr Gly
                85                  90                  95

Asp Asn Leu Thr Asn Pro Ser Ser Leu Leu His Ser Phe His Ala Tyr
            100                 105                 110

Asn Asp Asn Ser His Ala Leu Ile Pro Thr Asn Gly Met Tyr Lys Ser
            115                 120                 125

Trp Leu Ala Gln Thr Gln Phe Ser Ser Asp Gly Lys Pro Ser Asn Glu
        130                 135                 140

Ala Asn Gly Cys Asn Phe Gln Ser Leu Ser Leu Thr Met Ser Pro Ser
145                 150                 155                 160

Val Gln Asn Gly Val Gly Ala Ile Ser Ser Val Gln Val Asn Glu Asp
                165                 170                 175

Ser Arg Lys Arg Val Met Ala Lys Ser His Ala Arg Glu Pro Val Pro
            180                 185                 190

Arg Lys Ser Ile Asp Thr Phe Gly Gln Arg Thr Ser Gln Tyr Arg Gly
            195                 200                 205

Val Thr Arg His Arg Trp Thr Gly Arg Tyr Glu Ala His Leu Trp Asp
        210                 215                 220

Asn Ser Cys Arg Lys Glu Gly Gln Thr Arg Lys Gly Arg Gln Gly Gly
225                 230                 235                 240

Tyr Asp Lys Glu Glu Lys Ala Ala Lys Ala Tyr Asp Leu Ala Ala Leu
                245                 250                 255

Lys Tyr Trp Gly Pro Thr Thr His Ile Asn Phe Pro Leu Ser Thr Tyr
            260                 265                 270

Glu Lys Glu Leu Glu Glu Met Lys His Met Thr Arg Gln Glu Phe Val
            275                 280                 285

Ala Asn Leu Arg Arg Lys Ser Ser Gly Phe Ser Arg Gly Ala Ser Val
        290                 295                 300

Tyr Arg Gly Val Thr Arg His His Gln His Gly Arg Trp Gln Ala Arg
305                 310                 315                 320

Ile Gly Arg Val Ala Gly Asn Lys Asp Leu Tyr Leu Gly Thr Phe Ser
                325                 330                 335

Thr Gln Glu Glu Ala Ala Glu Ala Tyr Asp Ile Ala Ala Ile Lys Phe
            340                 345                 350

Arg Gly Thr Ser Ala Val Thr Asn Phe Asp Ile Ser Arg Tyr Asp Val

```
            355                 360                 365
Lys Arg Ile Cys Ser Ser Thr Leu Ile Ala Gly Asp Leu Ala Lys
    370                 375                 380

Arg Ser Pro Lys Glu Ser Pro Ala Pro Pro Pro Leu Ala Ile Thr
385                 390                 395                 400

Asp Gly Glu His Ser Asp Glu Leu Ser Asn Met Met Trp Asn Ala Asn
                405                 410                 415

Asn Ser Asp Glu Gln Ala Gln Asn Glu Ser Gly Gly Ala Glu Phe Asn
            420                 425                 430

Asn Asn Val Thr Glu Ser Ser Ser Gln Gln Val Ser Pro Ser Ser
                435                 440                 445

Asn Lys Asp Ala Leu Asn Pro Gln Ser Pro Asn Glu Phe Gly Val Ser
    450                 455                 460

Gly Ala Asp Tyr Gly His Gly Tyr Phe Thr Leu Asp Gly Pro Lys Tyr
465                 470                 475                 480

Asp Asp Gly Asn Asn Glu Asn Asp His Met Ser Thr Asn Arg Leu Gly
                485                 490                 495

Asn Leu Gly Leu Val Asn Gln Val Pro Met Phe Ala Leu Trp Asn Glu
            500                 505                 510

<210> SEQ ID NO 78
<211> LENGTH: 485
<212> TYPE: PRT
<213> ORGANISM: Sorghum bicolor

<400> SEQUENCE: 78

Met Asp Thr Ser His His Tyr Pro Trp Leu Asn Phe Ser Leu Ala His
1               5                   10                  15

His Gly Asp Leu Glu Glu Glu Arg Gly Ala Ala Ala Glu Leu Ala
            20                  25                  30

Ala Ile Ala Gly Ala Ala Pro Pro Lys Leu Glu Asp Phe Leu Gly
        35                  40                  45

Gly Gly Val Ile Asn Gly Glu Ser Ala Arg Ser Gly Gly Val Pro
    50                  55                  60

Val Ala Ala Pro Glu Val Ser Ala Pro Ala Glu Met Tyr Asp Ser Asp
65                  70                  75                  80

Leu Lys Phe Ile Ala Ala Gly Phe Leu Gly Gly Ser Ala Ala
            85                  90                  95

Gly Pro Val Ala Thr Ser Pro Leu Ser Ser Leu Asp Gln Ala Asp Pro
                100                 105                 110

Lys Leu Ala Leu Pro Ala Ala Ala Ala Pro Ala Pro Glu Gln
        115                 120                 125

Arg Lys Ala Val Asp Ser Phe Gly Gln Arg Thr Ser Ile Tyr Arg Gly
    130                 135                 140

Val Thr Arg His Arg Trp Thr Gly Arg Tyr Glu Ala His Leu Trp Asp
145                 150                 155                 160

Asn Ser Cys Arg Arg Glu Gly Gln Ser Arg Lys Gly Arg Gln Gly Gly
                165                 170                 175

Tyr Asp Lys Glu Glu Lys Ala Ala Arg Ala Tyr Asp Leu Ala Ala Leu
            180                 185                 190

Lys Tyr Trp Gly Ser Ser Thr Thr Thr Asn Phe Pro Val Ala Glu Tyr
        195                 200                 205

Glu Lys Glu Leu Glu Glu Met Lys Thr Met Thr Arg Gln Glu Phe Val
    210                 215                 220
```

```
Ala Ser Leu Arg Arg Lys Ser Ser Gly Phe Ser Arg Gly Ala Ser Ile
225                 230                 235                 240

Tyr Arg Gly Val Thr Arg His His Gln His Gly Arg Trp Gln Ala Arg
            245                 250                 255

Ile Gly Arg Val Ala Gly Asn Lys Asp Leu Tyr Leu Gly Thr Phe Ser
            260                 265                 270

Thr Glu Glu Glu Ala Ala Glu Ala Tyr Asp Ile Ala Ala Ile Lys Phe
        275                 280                 285

Arg Gly Leu Asn Ala Val Thr Asn Phe Glu Ile Ser Arg Tyr Asn Val
        290                 295                 300

Glu Ser Ile Met Asn Ser Asn Ile Pro Met Gly Ser Met Ser Ala Gly
305                 310                 315                 320

Gly Arg Ser Asn Lys Ala Leu Glu Ser Pro Pro Ser Gly Ser Pro Asp
            325                 330                 335

Ala Met Pro Val Glu Ala Ser Thr Ala Pro Leu Phe Ala Ala Leu Pro
            340                 345                 350

Val Lys Tyr Asp Gln Gln Gln Asp Tyr Leu Ser Met Leu Ala Leu
        355                 360                 365

Gln His His Gln Gln Gly Asn Leu Gln Gly Leu Gly Phe Gly Leu Tyr
370                 375                 380

Ser Ser Gly Val Asn Leu Asp Phe Ala Asn Ser His Ser Thr Ala Ser
385                 390                 395                 400

Ser Met Thr His Cys Tyr Val Asn Gly Gly Thr Val Ser Ser His Glu
            405                 410                 415

Gln His Gln His His Gln Gln Leu Gln Asp His Gln Gln Gly Glu
        420                 425                 430

Ser Glu Thr Gln Gln Ser Ser Asn Ser Cys Ser Ser Leu Pro Phe Ala
            435                 440                 445

Thr Pro Ile Ala Phe Asn Gly Ser Tyr Glu Ser Ser Met Thr Ala Ala
            450                 455                 460

Gly Pro Phe Gly Tyr Ser Tyr Pro Asn Val Ala Ala Phe Gln Thr Pro
465                 470                 475                 480

Ile Tyr Gly Met Glu
                485

<210> SEQ ID NO 79
<211> LENGTH: 507
<212> TYPE: PRT
<213> ORGANISM: Glycine max

<400> SEQUENCE: 79

Met Ala Arg Ala Thr Asn Trp Leu Ser Phe Ser Leu Ser Pro Met Glu
1               5                   10                  15

Met Leu Arg Thr Ser Glu Pro Gln Phe Leu Gln Tyr Asp Ala Ala Ser
            20                  25                  30

Ala Thr Ser Ser His His Tyr Tyr Leu Asp Asn Leu Tyr Thr Asn Gly
        35                  40                  45

Trp Gly Asn Gly Ser Leu Lys Phe Glu Gln Asn Leu Asn His Ser Asp
    50                  55                  60

Val Ser Phe Val Glu Ser Ser Gln Ser Val Gly His Val Pro Pro
65                  70                  75                  80

Pro Pro Pro Lys Leu Glu Asp Phe Leu Gly Asp Ser Ser Ala Val Met
            85                  90                  95

Arg Tyr Ser Asp Ser Gln Thr Glu Thr Gln Asp Ser Ser Leu Thr His
        100                 105                 110
```

Ile Tyr Asp His His His His His His His Gly Ser Thr Ser
115                 120                 125

Tyr Phe Gly Gly Asp Gln Gln Asp Leu Lys Ala Ile Thr Gly Phe Gln
130                 135                 140

Ala Phe Ser Thr Asn Ser Gly Ser Glu Val Asp Asp Ser Ala Ser Ile
145                 150                 155                 160

Gly Lys Ala Gln Ala Ser Glu Phe Gly Thr His Ser Ile Glu Ser Ser
                165                 170                 175

Gly Asn Glu Phe Ala Ala Phe Ser Gly Gly Thr Thr Gly Thr Leu Ser
                180                 185                 190

Leu Ala Val Ala Leu Ser Ser Glu Lys Ala Val Val Ala Glu Ser
            195                 200                 205

Asn Ser Ser Lys Lys Ile Val Asp Thr Phe Gly Gln Arg Thr Ser Ile
        210                 215                 220

Tyr Arg Gly Val Thr Arg His Arg Trp Thr Gly Arg Tyr Glu Ala His
225                 230                 235                 240

Leu Trp Asp Asn Ser Cys Arg Arg Glu Gly Gln Ala Arg Lys Gly Arg
                245                 250                 255

Gln Gly Gly Tyr Asp Lys Glu Glu Lys Ala Ala Arg Ala Tyr Asp Leu
                260                 265                 270

Ala Ala Leu Lys Tyr Trp Gly Pro Thr Ala Thr Asn Phe Pro Val
            275                 280                 285

Ser Asn Tyr Ser Lys Glu Val Glu Glu Met Lys His Val Thr Lys Gln
        290                 295                 300

Glu Phe Ile Ala Ser Leu Arg Arg Lys Ser Ser Gly Phe Ser Arg Gly
305                 310                 315                 320

Ala Ser Ile Tyr Arg Gly Val Thr Arg His His Gln Gln Gly Arg Trp
                325                 330                 335

Gln Ala Arg Ile Gly Arg Val Ala Gly Asn Lys Asp Leu Tyr Leu Gly
                340                 345                 350

Thr Phe Ala Thr Glu Glu Ala Ala Glu Ala Tyr Asp Ile Ala Ala
            355                 360                 365

Ile Lys Phe Arg Gly Ala Asn Ala Val Thr Asn Phe Glu Met Asn Arg
        370                 375                 380

Tyr Asp Val Glu Ala Ile Met Lys Ser Ser Leu Pro Val Gly Gly Ala
385                 390                 395                 400

Ala Lys Arg Leu Arg Leu Ser Leu Glu Ser Glu Gln Lys Ala Pro Pro
                405                 410                 415

Val Asn Ser Ser Ser Gln Gln Asn Pro Gln Cys Gly Asn Val Ser
            420                 425                 430

Gly Ser Ile Asn Phe Ser Ala Ile His Gln Pro Ile Ala Ser Ile Pro
        435                 440                 445

Cys Gly Ile Pro Phe Asp Ser Thr Thr Ala Tyr Tyr Pro His Asn Leu
450                 455                 460

Phe Gln His Phe His Pro Thr Asn Ala Gly Ala Ala Ala Ser Ala Val
465                 470                 475                 480

Thr Ser Ala Asn Ala Thr Ala Leu Thr Ala Leu Pro Ala Ser Ala Ala
                485                 490                 495

Thr Glu Phe Phe Ile Trp Pro His Gln Ser Tyr
                500                 505

<210> SEQ ID NO 80
<211> LENGTH: 569

```
<212> TYPE: PRT
<213> ORGANISM: Arabidopsis thaliana

<400> SEQUENCE: 80

Met Glu Met Leu Arg Ser Ser Asp Gln Ser Gln Phe Val Ser Tyr Asp
1               5                   10                  15

Ala Ser Ser Ala Ala Ser Ser Pro Tyr Leu Leu Asp Asn Phe Tyr
            20                  25                  30

Gly Trp Ser Asn Gln Lys Pro Gln Glu Phe Phe Lys Glu Glu Ala Gln
            35                  40                  45

Leu Ala Ala Ala Ala Ser Met Ala Asp Ser Thr Ile Leu Thr Thr Phe
    50                  55                  60

Val Asp Pro Gln Ser His His Ser Gln Asn His Ile Pro Lys Leu Glu
65                  70                  75                  80

Asp Phe Leu Gly Asp Ser Ser Ile Val Arg Tyr Ser Asp Asn Ser
            85                  90                  95

Gln Thr Asp Thr Gln Asp Ser Ser Leu Thr Gln Ile Tyr Asp Pro Arg
            100                 105                 110

His His His Asn Gln Thr Gly Phe Tyr Ser Asp His His Asp Phe Lys
            115                 120                 125

Thr Met Ala Gly Phe Gln Ser Ala Phe Ser Thr Asn Ser Gly Ser Glu
    130                 135                 140

Val Asp Asp Ser Ala Ser Ile Gly Arg Thr His Leu Ala Gly Asp Tyr
145                 150                 155                 160

Leu Gly His Val Val Glu Ser Ser Gly Pro Glu Leu Gly Phe His Gly
            165                 170                 175

Gly Ser Thr Gly Ala Leu Ser Leu Gly Val Asn Val Asn Asn Asn Thr
            180                 185                 190

Asn His Arg Asn Asp Asn Asp Asn His Tyr Arg Gly Asn Asn Gly
            195                 200                 205

Glu Arg Ile Asn Asn Asn Asn Asn Asp Asn Glu Lys Thr Asp Ser
    210                 215                 220

Glu Lys Glu Lys Ala Val Val Ala Val Glu Thr Ser Asp Cys Ser Asn
225                 230                 235                 240

Lys Lys Ile Ala Asp Thr Phe Gly Gln Arg Thr Ser Ile Tyr Arg Gly
            245                 250                 255

Val Thr Arg His Arg Trp Thr Gly Arg Tyr Glu Ala His Leu Trp Asp
            260                 265                 270

Asn Ser Cys Arg Arg Glu Gly Gln Ala Arg Lys Gly Arg Gln Val Tyr
            275                 280                 285

Leu Gly Gly Tyr Asp Lys Glu Asp Lys Ala Ala Arg Ala Tyr Asp Leu
    290                 295                 300

Ala Ala Leu Lys Tyr Trp Asn Ala Thr Ala Thr Asn Phe Pro Ile
305                 310                 315                 320

Thr Asn Tyr Ser Lys Glu Val Glu Glu Met Lys His Met Thr Lys Gln
            325                 330                 335

Glu Phe Ile Ala Ser Leu Arg Arg Lys Ser Ser Gly Phe Ser Arg Gly
            340                 345                 350

Ala Ser Ile Tyr Arg Gly Val Thr Arg His His Gln Gln Gly Arg Trp
            355                 360                 365

Gln Ala Arg Ile Gly Arg Val Ala Gly Asn Lys Asp Leu Tyr Leu Gly
    370                 375                 380

Thr Phe Ala Thr Glu Glu Glu Ala Ala Glu Ala Tyr Asp Ile Ala Ala
385                 390                 395                 400
```

```
Ile Lys Phe Arg Gly Ile Asn Ala Val Thr Asn Phe Glu Met Asn Arg
                405                 410                 415

Tyr Asp Val Glu Ala Ile Met Lys Ser Ala Leu Pro Ile Gly Gly Ala
            420                 425                 430

Ala Lys Arg Leu Lys Leu Ser Leu Glu Ala Ala Ser Ser Glu Gln
        435                 440                 445

Lys Pro Ile Leu Gly His His Gln Leu His His Phe Gln Gln Gln Gln
    450                 455                 460

Gln Gln Gln Gln Leu Gln Leu Gln Ser Ser Pro Asn His Ser Ser Ile
465                 470                 475                 480

Asn Phe Ala Leu Cys Pro Asn Ser Ala Val Gln Ser Gln Ile Ile
                485                 490                 495

Pro Cys Gly Ile Pro Phe Glu Ala Ala Ala Leu Tyr His His His Gln
            500                 505                 510

Gln Gln Gln Gln His Gln Gln Gln Gln Gln Gln Asn Phe Phe Gln
        515                 520                 525

His Phe Pro Ala Asn Ala Ala Ser Asp Ser Thr Gly Ser Asn Asn Asn
    530                 535                 540

Ser Asn Val Gln Gly Thr Met Gly Leu Met Ala Pro Asn Pro Ala Glu
545                 550                 555                 560

Phe Phe Leu Trp Pro Asn Gln Ser Tyr
                565
```

<210> SEQ ID NO 81
<211> LENGTH: 574
<212> TYPE: PRT
<213> ORGANISM: Medicago truncatula

<400> SEQUENCE: 81

```
Met Ser Asn Trp Leu Gly Phe Ser Leu Thr Pro His Leu Arg Ile Asp
1               5                   10                  15

Glu Glu Phe Gly Thr Glu Asn Gln Asn Gln Asn Gln Asn His Val Ala
            20                  25                  30

Glu Gly Ser Glu Ile Gly Arg Asn Tyr Val Thr Pro Ser Ser His Pro
        35                  40                  45

His Pro His His Leu Ser Ile Met Pro Leu Arg Ser Asp Gly Ser Leu
    50                  55                  60

Cys Val Ser Asp Ser Phe Thr Pro Gln Glu Trp Arg Tyr Glu Asn Ala
65              70                  75                  80

Ile Thr Asp Gly Asn Ser Asn Glu Glu Gly Pro Lys Leu Glu Asp Phe
                85                  90                  95

Leu Gly Cys Tyr Ser Asn Gln Asn Gln Asn Ser Thr Thr Thr Ser Thr
            100                 105                 110

Met Ser Lys Ile Asn Val Asn Val Ser Pro Ser Phe Cys Thr Asn Asn
        115                 120                 125

Asn Pro Glu Ile Asp Thr Arg Glu Asn Leu Thr Asn Gln Ser Leu Ile
    130                 135                 140

His Ser Phe His Ala Tyr Asn Asp His Ser Asn Asn His His Ala
145                 150                 155                 160

Leu Ile His Asp Asn Ser Met Tyr Lys Ser Trp Met Thr Gln Thr Gln
                165                 170                 175

Phe Ser Ser Glu Gly Lys Thr Thr Ser Ser Asp Gly Asn Gly Phe Gln
            180                 185                 190

Ser Leu Asn Leu Thr Met Ser Pro Cys Val Gln Asn Gly Val Gly Gly
```

```
              195                 200                 205
Gly Val Gly Ser Ala Ile Ser Asn Val Gln Val Asn Glu Asp Pro Arg
        210                 215                 220

Lys Arg Ser Leu Ser Lys Ser Asn Ala Arg Glu Pro Val Pro Arg Lys
225                 230                 235                 240

Ser Ile Asp Thr Phe Gly Gln Arg Thr Ser Gln Tyr Arg Gly Val Thr
                245                 250                 255

Arg His Arg Trp Thr Gly Arg Tyr Glu Ala His Leu Trp Asp Asn Ser
            260                 265                 270

Cys Arg Lys Glu Gly Gln Thr Arg Lys Gly Arg Gln Gly Gly Tyr Asp
        275                 280                 285

Lys Glu Glu Lys Ala Ala Lys Ala Tyr Asp Leu Ala Ala Leu Lys Tyr
        290                 295                 300

Trp Gly Pro Thr Thr His Ile Asn Phe Pro Leu Ser Thr Tyr Asp Lys
305                 310                 315                 320

Glu Leu Glu Glu Met Lys His Met Thr Arg Gln Glu Phe Val Ala Asn
                325                 330                 335

Leu Arg Arg Lys Ser Ser Gly Phe Ser Arg Gly Ala Ser Val Tyr Arg
            340                 345                 350

Gly Val Thr Arg His His Gln His Gly Arg Trp Gln Ala Arg Ile Gly
        355                 360                 365

Arg Val Ala Gly Asn Lys Asp Leu Tyr Leu Gly Thr Phe Ser Thr Gln
        370                 375                 380

Glu Glu Ala Ala Glu Ala Tyr Asp Ile Ala Ala Ile Lys Phe Arg Gly
385                 390                 395                 400

Thr Ser Ala Val Thr Asn Phe Asp Ile Ser Arg Tyr Asp Val Lys Arg
                405                 410                 415

Ile Cys Ser Ser Ser Thr Leu Ile Thr Gly Asp Leu Ala Lys Arg Ser
            420                 425                 430

Pro Lys Asp Ser Thr Pro Pro Ala Thr Ala Glu Asp Phe Asn Ser
        435                 440                 445

Cys Gly Ser Ser Ser Thr Leu Ser Gln Pro Pro Leu Thr Ile Thr
        450                 455                 460

Asp Gly Glu Gln His Ser Asp Glu Leu Ser Asn Met Val Trp Asn Ser
465                 470                 475                 480

Asn Asn Asp Glu Gln Lys Pro Gln Asn Gly Thr Asn Ile Thr Glu Ser
                485                 490                 495

Ser Gln His Gly Ser Pro Ser Asn Lys Asn Glu Met Asn Pro Gln Ser
            500                 505                 510

Pro Lys Cys Ser Leu Gly Leu Pro Asn Glu Phe Gly Val Ser Gly Ala
        515                 520                 525

Asp Tyr Gly His Gly Tyr Phe Thr Leu His Gly Pro Lys Phe Asp Asp
        530                 535                 540

Gly Ser Asn Glu Asn Asp His Met Asn Asn Arg Leu Gly Asn Leu
545                 550                 555                 560

Gly Leu Val Asn Gln Val Pro Met Phe Ala Leu Trp Asn Glu
                565                 570
```

<210> SEQ ID NO 82
<211> LENGTH: 541
<212> TYPE: PRT
<213> ORGANISM: Sorghum bicolor

<400> SEQUENCE: 82

```
Met Asp Met Asn Asn Gly Trp Leu Gly Phe Ser Leu Ser Pro Ser Ala
1               5                   10                  15

Gly Arg Gly Gly Tyr Gly Asp Gly Gly Ala Ser Ala Ser Gly Asp Gly
            20                  25                  30

Gly Asp Gly Ser Cys Ser Ser Pro Ala Ala Ala Ser Pro Val Pro
            35                  40                  45

Leu Val Ala Met Pro Leu Gln Pro Asp Gly Ser Leu His Tyr Thr Ser
50                  55                  60

Ala Pro Asp Trp Arg His Gly Ala Ala Glu Ala Asn Gly Pro Lys Leu
65                  70                  75                  80

Glu Asp Phe Met Ser Val Thr Cys Ser Ser Asn Asn Lys Arg Ser Ser
                85                  90                  95

Ser Ser Ser Ser Phe Tyr Asp Arg Cys Ser His Ala Glu Gln Ala Asn
            100                 105                 110

Lys Tyr His Glu Val His Asp Leu Gln Pro Leu Ser Cys Gly Ser Tyr
            115                 120                 125

Tyr His Gly Ser Ser Gly Gly Gly Asn Gly Ile Ala Leu Gly Ile
            130                 135                 140

Asn Met Asn Ala Pro Pro Cys Ser Gly Gly Phe Pro Asp His His
145                 150                 155                 160

His His His Gln Phe Val Ser Ser His His Gly Gln Tyr Phe Leu Gly
                165                 170                 175

Ala Pro Leu Asn Ala Ser Pro Pro Gly Ala Val Pro Met Tyr Ser Ala
            180                 185                 190

Gly Gly Gly Gly Val Gly Gly Ser Met Ser Ile Ser Gly Ile Lys Ser
            195                 200                 205

Trp Leu Arg Glu Ala Met Tyr Val Pro Pro Glu Arg Pro Val Ala Ala
            210                 215                 220

Ala Ala Ala Leu Ser Leu Ala Val Thr Asp Asp Val Gly Ala Glu Pro
225                 230                 235                 240

Pro Gln Leu Leu Pro Ala Ala Pro Met Pro Pro Val His Arg Lys Pro
            245                 250                 255

Ala Gln Thr Phe Gly Gln Arg Thr Ser Gln Phe Arg Gly Val Thr Arg
            260                 265                 270

His Arg Trp Thr Gly Arg Tyr Glu Ala His Leu Trp Asp Asn Thr Cys
            275                 280                 285

Arg Lys Glu Gly Gln Thr Arg Lys Gly Arg Gln Gly Gly Tyr Asp Arg
            290                 295                 300

Glu Glu Lys Ala Ala Arg Ala Tyr Asp Leu Ala Ala Leu Lys Tyr Trp
305                 310                 315                 320

Gly Pro Ser Thr His Ile Asn Phe Pro Leu Ser His Tyr Glu Lys Glu
            325                 330                 335

Leu Glu Glu Met Lys His Met Ser Arg Gln Glu Phe Ile Ala His Leu
            340                 345                 350

Arg Arg Asn Ser Ser Gly Phe Ser Arg Gly Ala Ser Met Tyr Arg Gly
            355                 360                 365

Val Thr Arg His His Gln His Gly Arg Trp Gln Ala Arg Ile Gly Arg
            370                 375                 380

Val Ala Gly Asn Lys Asp Leu Tyr Leu Gly Thr Phe Ser Thr Gln Glu
385                 390                 395                 400

Glu Ala Ala Glu Ala Tyr Asp Ile Ala Ala Ile Lys Phe Arg Gly Leu
            405                 410                 415

Asn Ala Val Thr Asn Phe Asp Ile Ser Lys Tyr Asp Val Lys Arg Ile
```

```
                    420                 425                 430
Cys Ala Ser Thr His Leu Ile Gly Gly Gly Asp Ala Cys Arg Arg Ser
                435                 440                 445

Pro Thr Gln Pro Pro Asp Ala Pro Ala Leu Ala Ile Asp Ala Ala Gly
    450                 455                 460

Ala Asp Arg Ser Ser Asp Ala Pro Gly Gly Gly Asp Gln Ala Val Ser
465                 470                 475                 480

Asp Asn Ser Asp Thr Ser Ala Gly His Arg Gly Ala His Leu Leu His
                485                 490                 495

Gly Leu Gln Tyr Gly His Pro Met Lys Leu Glu Ala Gly Glu Gly Ser
                500                 505                 510

Ser Trp Met Ala Ala Thr Ala Ala Ala Arg Pro Val Ala Gly
            515                 520                 525

Val His Gln Leu Pro Val Phe Ala Leu Trp Asn Asp Cys
    530                 535                 540
```

<210> SEQ ID NO 83
<211> LENGTH: 555
<212> TYPE: PRT
<213> ORGANISM: Arabidopsis thaliana

<400> SEQUENCE: 83

```
Met Lys Ser Phe Cys Asp Asn Asp Asn Asn His Ser Asn Thr Thr
1               5                   10                  15

Asn Leu Leu Gly Phe Ser Leu Ser Ser Asn Met Met Lys Met Gly Gly
                20                  25                  30

Arg Gly Gly Arg Glu Ala Ile Tyr Ser Ser Ser Thr Ser Ser Ala Ala
            35                  40                  45

Thr Ser Ser Ser Ser Val Pro Pro Gln Leu Val Val Gly Asp Asn Thr
50                  55                  60

Ser Asn Phe Gly Val Cys Tyr Gly Ser Asn Pro Asn Gly Gly Ile Tyr
65                  70                  75                  80

Ser His Met Ser Val Met Pro Leu Arg Ser Asp Gly Ser Leu Cys Leu
                85                  90                  95

Met Glu Ala Leu Asn Arg Ser Ser His Ser Asn His His Gln Asp Ser
                100                 105                 110

Ser Pro Lys Val Glu Asp Phe Phe Gly Thr His His Asn Asn Thr Ser
            115                 120                 125

His Lys Glu Ala Met Asp Leu Ser Leu Asp Ser Leu Phe Tyr Asn Thr
130                 135                 140

Thr His Glu Pro Asn Thr Thr Thr Asn Phe Gln Glu Phe Phe Ser Phe
145                 150                 155                 160

Pro Gln Thr Arg Asn His Glu Glu Thr Arg Asn Tyr Gly Asn Asp
                165                 170                 175

Pro Ser Leu Thr His Gly Gly Ser Phe Asn Val Gly Val Tyr Gly Glu
            180                 185                 190

Phe Gln Gln Ser Leu Ser Leu Ser Met Ser Pro Gly Ser Gln Ser Ser
            195                 200                 205

Cys Ile Thr Gly Ser His His Gln Gln Asn Gln Asn Gln Asn His
    210                 215                 220

Gln Ser Gln Asn His Gln Gln Ile Ser Glu Ala Leu Val Glu Thr Ser
225                 230                 235                 240

Val Gly Phe Glu Thr Thr Thr Met Ala Ala Ala Lys Lys Lys Arg Gly
                245                 250                 255
```

```
Gln Glu Asp Val Val Val Gly Gln Lys Gln Ile Val His Arg Lys
            260                 265                 270

Ser Ile Asp Thr Phe Gly Gln Arg Thr Ser Gln Tyr Arg Gly Val Thr
        275                 280                 285

Arg His Arg Trp Thr Gly Arg Tyr Glu Ala His Leu Trp Asp Asn Ser
    290                 295                 300

Phe Lys Lys Glu Gly His Ser Arg Lys Gly Arg Gln Val Tyr Leu Gly
305                 310                 315                 320

Gly Tyr Asp Met Glu Glu Lys Ala Ala Arg Ala Tyr Asp Leu Ala Ala
                325                 330                 335

Leu Lys Tyr Trp Gly Pro Ser Thr His Thr Asn Phe Ser Ala Glu Asn
            340                 345                 350

Tyr Gln Lys Glu Ile Glu Asp Met Lys Asn Met Thr Arg Gln Glu Tyr
        355                 360                 365

Val Ala His Leu Arg Arg Lys Ser Ser Gly Phe Ser Arg Gly Ala Ser
    370                 375                 380

Ile Tyr Arg Gly Val Thr Arg His His Gln His Gly Arg Trp Gln Ala
385                 390                 395                 400

Arg Ile Gly Arg Val Ala Gly Asn Lys Asp Leu Tyr Leu Gly Thr Phe
                405                 410                 415

Gly Thr Gln Glu Glu Ala Ala Glu Ala Tyr Asp Val Ala Ala Ile Lys
            420                 425                 430

Phe Arg Gly Thr Asn Ala Val Thr Asn Phe Asp Ile Thr Arg Tyr Asp
        435                 440                 445

Val Asp Arg Ile Met Ser Ser Asn Thr Leu Leu Ser Gly Glu Leu Ala
    450                 455                 460

Arg Arg Asn Asn Asn Ser Ile Val Val Arg Asn Thr Glu Asp Gln Thr
465                 470                 475                 480

Ala Leu Asn Ala Val Val Glu Gly Gly Ser Asn Lys Glu Val Ser Thr
                485                 490                 495

Pro Glu Arg Leu Leu Ser Phe Pro Ala Ile Phe Ala Leu Pro Gln Val
            500                 505                 510

Asn Gln Lys Met Phe Gly Ser Asn Met Gly Gly Asn Met Ser Pro Trp
        515                 520                 525

Thr Ser Asn Pro Asn Ala Glu Leu Lys Thr Val Ala Leu Thr Leu Pro
    530                 535                 540

Gln Met Pro Val Phe Ala Ala Trp Ala Asp Ser
545                 550                 555

<210> SEQ ID NO 84
<211> LENGTH: 678
<212> TYPE: PRT
<213> ORGANISM: Sorghum bicolor

<400> SEQUENCE: 84

Met Thr Asn Asn Gly Asn Gly Thr Asn Ala Ala Ser Ser Trp
1               5                   10                  15

Leu Gly Phe Ser Leu Ser Pro His Met Ala Ser Ala Met Asp Glu His
            20                  25                  30

His His Val Gln Gln Gln Gln His His His Ser Leu Phe
        35                  40                  45

Phe Pro Ser Val Thr Ala Ala Ala Ala Tyr Gly Leu Gly Gly
    50                  55                  60

Ser Asp Gly Gly Val Ala Thr Ser Ala Ser Pro Tyr Tyr Thr Pro Gln
65                  70                  75                  80
```

```
Leu Ala Ser Met Pro Leu Lys Ser Asp Gly Ser Leu Cys Ile Met Glu
                85                  90                  95

Ala Leu Arg Arg Ser Asp Gln Pro Asp His His Gly Pro Lys Leu Glu
            100                 105                 110

Asp Phe Leu Gly Ala Ala Ala Gln Ser Gln Ala Met Ala Leu Ser
        115                 120                 125

Leu Gln Asp Asn Pro Ala Ala Ala Ser Ser Phe Tyr Tyr Tyr Gly
    130                 135                 140

Asn Gly Gly Gly Gly Ser Gly His Gln His His Gly Gly Phe Leu
145                 150                 155                 160

Gln Pro Cys Ala Asp Leu Tyr Gly Gly Pro Ser Glu Ala Ser Leu Val
            165                 170                 175

Ala Asp Asp Asp Glu Ala Ala Ala Ala Thr Ala Met Ala Ser Trp
        180                 185                 190

Val Ala Ala Arg Ala Gly Glu Ser Gly Gly Val Leu Ser Ala Ala Ala
            195                 200                 205

Ala Ala Ala Gly His Gln His His His Ala Leu Ala Leu Ser Met
        210                 215                 220

Ser Ser Gly Ser Leu Ser Ser Cys Val Thr Ala His Pro Gly Ala Ala
225                 230                 235                 240

Ala Ala Asp Tyr Gly Val Val Ala Ala Thr Ala Ser Ala Ser Leu Asp
            245                 250                 255

Gly Gly Arg Lys Arg Gly Gly Ala Ala Gly Gln Lys Gln Pro Val His
            260                 265                 270

His Arg Lys Ser Ile Asp Thr Phe Gly Gln Arg Thr Ser Gln Tyr Arg
            275                 280                 285

Gly Val Thr Arg His Arg Trp Thr Gly Arg Tyr Glu Ala His Leu Trp
            290                 295                 300

Asp Asn Ser Cys Lys Lys Glu Gly Gln Thr Arg Lys Gly Arg Gln Gly
305                 310                 315                 320

Gly Tyr Asp Met Glu Glu Lys Ala Ala Arg Ala Tyr Asp Leu Ala Ala
                325                 330                 335

Leu Lys Tyr Trp Gly Pro Ser Thr His Ile Asn Phe Pro Leu Glu Asp
            340                 345                 350

Tyr Gln Glu Glu Leu Glu Glu Met Lys Asn Met Thr Arg Gln Glu Tyr
            355                 360                 365

Val Ala His Leu Arg Arg Lys Ser Ser Gly Phe Ser Arg Gly Ala Ser
            370                 375                 380

Met Tyr Arg Gly Val Thr Arg His His Gln His Gly Arg Trp Gln Ala
385                 390                 395                 400

Arg Ile Gly Arg Val Ser Gly Asn Lys Asp Leu Tyr Leu Gly Thr Phe
                405                 410                 415

Ser Thr Gln Glu Glu Ala Ala Glu Ala Tyr Asp Ile Ala Ala Ile Lys
            420                 425                 430

Phe Arg Gly Leu Asn Ala Val Thr Asn Phe Asp Ile Thr Arg Tyr Asp
        435                 440                 445

Val Asp Lys Ile Met Ala Ser Asn Thr Leu Leu Pro Gly Asp Leu Ala
    450                 455                 460

Arg Arg Arg Lys Asp Asp Pro Ala Ala Val Ile Ala Gly Ala Asp
465                 470                 475                 480

Ala Ser Asn Gly Gly Gly Val Thr Thr Ala Ala Ala Ala Ala Leu
            485                 490                 495
```

-continued

```
Val Gln Gln Ala Ala Ala Ala Ala Gly Ala Gly Gly Asn His
            500                 505             510

Ser Ala Ser Ser Ser Glu Thr Trp Ile Lys Val Ala Ala Ala Ala
        515                 520             525

Leu Gln Ala Ala Gly Ala Ala Pro Arg Asp Gly Asn His His His
        530                 535             540

His His Asp Val Leu Ser Gly Glu Ala Phe Ser Val Leu His Asp Leu
545             550                 555                 560

Val Val Thr Ala Ala Asp Gly Gly Asn Gly Asn Gly Asn Gly Gly His
                565                 570             575

His His His His Val His Asn Ser Ala Ala Thr Ala Gln His Met Ser
        580                 585                 590

Met Ser Ser Ala Ser Ser Leu Val Thr Ser Leu Gly Asn Ser Arg Glu
        595                 600             605

Gly Ser Pro Asp Arg Gly Gly Gly Leu Ser Met Leu Phe Ser Lys Pro
        610                 615             620

Pro Ala Pro Ala Pro Ala Ala Ser Ala His Ala Ala Asn Lys Pro Met
625                 630                 635             640

Ser Pro Leu Met Pro Leu Gly Ser Trp Ala Ser Thr Ala Ala Ala Ser
                645                 650             655

Ala Arg Ala Ala Ala Ala Ala Val Ser Ile Ala His Met Pro Val Phe
                660                 665             670

Ala Ala Trp Thr Asp Ala
        675

<210> SEQ ID NO 85
<211> LENGTH: 509
<212> TYPE: PRT
<213> ORGANISM: Glycine max

<400> SEQUENCE: 85

Met Ala Arg Ala Ser Thr Asn Trp Leu Ser Phe Ser Leu Ser Pro Met
1               5                   10                  15

Asp Met Leu Arg Thr Pro Glu Pro Gln Phe Val Gln Tyr Asp Ala Ala
            20                  25                  30

Ser Asp Thr Ser Ser His His Tyr Tyr Leu Asp Asn Leu Tyr Thr Asn
        35                  40                  45

Gly Trp Gly Asn Gly Ser Leu Lys Phe Glu Gln Asn Leu Asn His Ser
    50                  55                  60

Asp Val Ser Phe Val Gln Ser Ser Gln Ser Val Ser His Ala Pro
65                  70                  75                  80

Pro Lys Leu Glu Asp Phe Leu Gly Asp Ser Ser Ala Val Met Arg Tyr
            85                  90                  95

Ser Asp Ser Gln Thr Glu Thr Gln Asp Ser Ser Leu Thr His Ile Tyr
            100                 105                 110

Asp His His His His His His Gly Ser Ser Ala Tyr Phe Gly Gly
            115                 120                 125

Asp His Gln Asp Leu Lys Ala Ile Thr Gly Phe Gln Ala Phe Ser Thr
        130                 135                 140

Asn Ser Gly Ser Glu Val Asp Asp Ser Ala Ser Ile Gly Lys Ala Gln
145                 150                 155                 160

Gly Ser Glu Phe Gly Thr His Ser Ile Glu Ser Ser Val Asn Glu Phe
            165                 170                 175

Ala Ala Phe Ser Gly Gly Thr Asn Thr Gly Gly Thr Leu Ser Leu Ala
            180                 185                 190
```

Val Ala Gln Ser Ser Glu Lys Ala Val Ala Ala Ala Glu Ser Asp
            195                 200                 205

Arg Ser Lys Lys Val Val Asp Thr Phe Gly Gln Arg Thr Ser Ile Tyr
    210                 215                 220

Arg Gly Val Thr Arg His Arg Trp Thr Gly Arg Tyr Glu Ala His Leu
225                 230                 235                 240

Trp Asp Asn Ser Cys Arg Arg Glu Gly Gln Ala Arg Lys Gly Arg Gln
                245                 250                 255

Gly Gly Tyr Asp Lys Glu Glu Lys Ala Ala Arg Ser Tyr Asp Leu Ala
            260                 265                 270

Ala Leu Lys Tyr Trp Gly Pro Thr Ala Thr Thr Asn Phe Pro Val Ser
        275                 280                 285

Asn Tyr Ser Lys Glu Val Glu Glu Met Lys His Val Thr Lys Gln Glu
    290                 295                 300

Phe Ile Ala Ser Leu Arg Arg Lys Ser Ser Gly Phe Ser Arg Gly Ala
305                 310                 315                 320

Ser Ile Tyr Arg Gly Val Thr Arg His His Gln Gly Arg Trp Gln
                325                 330                 335

Ala Arg Ile Gly Arg Val Ala Gly Asn Lys Asp Leu Tyr Leu Gly Thr
            340                 345                 350

Phe Ala Thr Glu Glu Glu Ala Ala Glu Ala Tyr Asp Ile Ala Ala Ile
        355                 360                 365

Lys Phe Arg Gly Ala Asn Ala Val Thr Asn Phe Glu Met Asn Arg Tyr
    370                 375                 380

Asp Val Glu Ala Ile Met Lys Ser Ser Leu Pro Val Gly Gly Ala Ala
385                 390                 395                 400

Lys Arg Leu Lys Leu Ser Leu Glu Ser Glu Gln Lys Ala Leu Pro Val
                405                 410                 415

Ser Ser Ser Ser Ser Ser Ser Gln Gln Gln Asn Pro Gln Cys Gly Asn
            420                 425                 430

Val Ser Ala Ser Ile Asn Phe Ser Ser Ile His Gln Pro Ile Ala Ser
        435                 440                 445

Ile Pro Cys Gly Ile Pro Phe Asp Ser Thr Thr Ala Tyr Tyr His His
    450                 455                 460

Asn Leu Phe Gln His Phe His Pro Thr Asn Ala Gly Thr Ala Ala Ser
465                 470                 475                 480

Ala Val Thr Ser Ala Asn Ala Asn Ala Leu Thr Ala Leu Pro Pro Thr
                485                 490                 495

Ala Ala Ala Glu Phe Phe Ile Trp Pro His Gln Ser Tyr
            500                 505

<210> SEQ ID NO 86
<211> LENGTH: 638
<212> TYPE: PRT
<213> ORGANISM: Zea mays

<400> SEQUENCE: 86

Met Thr Ser Asn Ser Ser Gln Asn Met Ser Ser Cys Ser Thr Gly Gly
1               5                   10                  15

Ser Asp Ala Ala Val Gly Gly Ser Trp Leu Gly Phe Ser Leu Ser
            20                  25                  30

Pro His Met Ala Ala Thr Met Asp Gly Ala Ala Asp Gly Val Pro Val
        35                  40                  45

Gln His His His His Glu Gly Leu Phe Tyr Pro Pro Val Val Ser Ser

-continued

```
                50                  55                  60
Ser Pro Ala Pro Phe Cys Tyr Ala Leu Gly Gly Gly Gln Asp Gly Leu
 65                  70                  75                  80
Ala Thr Ala Ala Ala Asn Gly Gly Gly Phe Tyr Pro Gly Leu Ser
                 85                  90                  95
Ser Met Pro Leu Lys Ser Asp Gly Ser Leu Cys Ile Leu Glu Ala Leu
                    100                 105                 110
His Arg Ser Glu Gln Glu Arg His Gly Val Val Ser Ser Ser Ser
                115                 120                 125
Pro Lys Leu Glu Asp Phe Leu Gly Ala Ser Ala Ser Thr Ala Met Ala
                130                 135                 140
Leu Ser Leu Asp Ser Ser Ser Phe Tyr Tyr Gly Cys Gly His Gly His
145                 150                 155                 160
Gly His Asp Gln Gly Gly Tyr Leu Gln Pro Met Gln Cys Ala Val Met
                165                 170                 175
Pro Gly Ser Gly Gly His Asp Val Tyr Gly Gly Gly His Ala Gln Met
                180                 185                 190
Val Asp Glu Gln Ser Ala Ala Ala Met Ala Ala Ser Trp Phe Ser Ala
                195                 200                 205
Arg Gly Asn Gly Gly Tyr Asp Val Asp Gly Ala Gly Ala Gly Ala Ile
210                 215                 220
Val Pro Leu Gln Gly His Pro His Pro Leu Ala Leu Ser Met Ser Ser
225                 230                 235                 240
Gly Thr Gly Ser Gln Ser Ser Ser Val Thr Met Gln Val Gly Ser Ala
                245                 250                 255
His Ala Asp Ala Val Thr Glu Tyr Ile Ala Met Asp Gly Ser Lys Lys
                260                 265                 270
Arg Gly Ala Gly Asn Gly Ala Ser Ala Gly Gln Lys Gln Pro Thr Ile
                275                 280                 285
His Arg Lys Thr Ile Asp Thr Phe Gly Gln Arg Thr Ser Gln Tyr Arg
                290                 295                 300
Gly Val Thr Arg His Arg Trp Thr Gly Arg Tyr Glu Ala His Leu Trp
305                 310                 315                 320
Asp Asn Ser Cys Arg Lys Glu Gly Gln Thr Arg Lys Gly Arg Gln Val
                325                 330                 335
Tyr Leu Gly Gly Tyr Asp Val Glu Glu Lys Ala Ala Arg Ala Tyr Asp
                340                 345                 350
Leu Ala Ala Leu Lys Tyr Trp Gly Thr Ser Thr His Val Asn Phe Pro
                355                 360                 365
Val Glu Asp Tyr Arg Glu Glu Leu Glu Glu Met Lys Asn Met Thr Arg
                370                 375                 380
Gln Glu Tyr Val Ala His Leu Arg Arg Lys Ser Ser Gly Phe Ser Arg
385                 390                 395                 400
Gly Ala Ser Ile Tyr Arg Gly Val Thr Arg His His Gln His Gly Arg
                405                 410                 415
Trp Gln Ala Arg Ile Gly Arg Val Ser Gly Asn Lys Asp Leu Tyr Leu
                420                 425                 430
Gly Thr Phe Ser Thr Gln Glu Glu Ala Ala Glu Ala Tyr Asp Val Ala
                435                 440                 445
Ala Ile Lys Phe Arg Gly Leu Ser Ala Val Thr Asn Phe Asp Ile Thr
                450                 455                 460
Arg Tyr Asp Val Asp Lys Ile Met Glu Ser Ser Thr Leu Leu Pro Gly
465                 470                 475                 480
```

```
Glu Gln Val Arg Arg Lys Glu Gly Ala Asp Ala Val Ser Glu
            485             490             495
Ala Ala Ala Ala Leu Val Gln Ala Gly Asn Cys Met Thr Asp Thr Trp
            500             505             510
Lys Ile Gln Ala Ala Leu Pro Ala Ala Arg Ala Asp Glu Arg Gly
            515             520             525
Ala Gly Gln Gln Gln Arg Gln Asp Leu Leu Ser Ser Glu Ala Phe Ser
            530             535             540
Leu Leu His Asp Ile Val Ser Val Asp Ala Ala Gly Thr Gly Thr
545             550             555             560
Gly Gly Met Ser Asn Ala Ser Ser Leu Ala Pro Ser Val Ser Asn
            565             570             575
Ser Arg Glu Gln Ser Pro Asp Arg Gly Gly Ala Ser Leu Ala Met Leu
            580             585             590
Phe Ala Lys Pro Ala Ala Pro Lys Leu Ala Cys Pro Leu Pro Leu
            595             600             605
Gly Ser Trp Val Ser Pro Ser Ala Val Ser Ala Arg Pro Pro Gly Val
            610             615             620
Ser Ile Ala His Leu Pro Val Phe Ala Ala Trp Thr Asp Ala
625             630             635

<210> SEQ ID NO 87
<211> LENGTH: 652
<212> TYPE: PRT
<213> ORGANISM: Oryza sativa

<400> SEQUENCE: 87

Met Ala Ser Gly Asn Ser Ser Ser Ser Gly Ser Met Ala Ala Thr
1               5               10              15
Ala Gly Gly Val Gly Gly Trp Leu Gly Phe Ser Leu Ser Pro His Met
            20              25              30
Ala Thr Tyr Cys Ala Gly Gly Val Asp Asp Val Gly His His His
            35              40              45
His His Val His Gln His Gln Gln Gln His Gly Gly Gly Leu Phe Tyr
            50              55              60
Asn Pro Ala Ala Val Ala Ser Ser Phe Tyr Tyr Gly Gly Gly His Asp
65              70              75              80
Ala Val Val Thr Ser Ala Ala Gly Gly Gly Ser Tyr Tyr Gly Ala Gly
            85              90              95
Phe Ser Ser Met Pro Leu Lys Ser Asp Gly Ser Leu Cys Ile Met Glu
            100             105             110
Ala Leu Arg Gly Gly Asp Gln Glu Gln Gln Gly Val Val Val Ser Ala
            115             120             125
Ser Pro Lys Leu Glu Asp Phe Leu Gly Ala Gly Pro Ala Met Ala Leu
            130             135             140
Ser Leu Asp Asn Ser Ala Phe Tyr Tyr Gly Gly His Gly His His Gln
145             150             155             160
Gly His Ala Gln Asp Gly Gly Ala Val Gly Gly Asp Pro His His Gly
            165             170             175
Gly Gly Gly Phe Leu Gln Cys Ala Val Ile Pro Gly Ala Gly Ala Gly
            180             185             190
His Asp Ala Ala Leu Val His Asp Gln Ser Ala Ala Ala Val Ala Ala
            195             200             205
Gly Trp Ala Ala Met His Gly Gly Gly Tyr Asp Ile Ala Asn Ala Ala
```

```
              210                 215                 220
Ala Asp Asp Val Cys Ala Ala Gly Pro Ile Ile Pro Thr Gly His
225                 230                 235                 240

Leu His Pro Leu Thr Leu Ser Met Ser Ser Ala Gly Ser Gln Ser Ser
                    245                 250                 255

Cys Val Thr Val Gln Ala Ala Ala Gly Glu Pro Tyr Met Ala Met
                260                 265                 270

Asp Ala Val Ser Lys Lys Arg Gly Gly Ala Asp Arg Ala Gly Gln Lys
                275                 280                 285

Gln Pro Val His Arg Lys Ser Ile Asp Thr Phe Gly Gln Arg Thr Ser
            290                 295                 300

Gln Tyr Arg Gly Val Thr Arg His Arg Trp Thr Gly Arg Tyr Glu Ala
305                 310                 315                 320

His Leu Trp Asp Asn Ser Cys Lys Lys Glu Gly Gln Thr Arg Lys Gly
                    325                 330                 335

Arg Gln Gly Gly Tyr Asp Met Glu Glu Lys Ala Ala Arg Ala Tyr Asp
                340                 345                 350

Leu Ala Ala Leu Lys Tyr Trp Gly Pro Ser Thr His Ile Asn Phe Pro
                355                 360                 365

Leu Glu Asp Tyr Gln Glu Glu Leu Glu Glu Met Lys Asn Met Ser Arg
            370                 375                 380

Gln Glu Tyr Val Ala His Leu Arg Arg Lys Ser Ser Gly Phe Ser Arg
385                 390                 395                 400

Gly Ala Ser Ile Tyr Arg Gly Val Thr Arg His His Gln His Gly Arg
                405                 410                 415

Trp Gln Ala Arg Ile Gly Arg Val Ser Gly Asn Lys Asp Leu Tyr Leu
                420                 425                 430

Gly Thr Phe Ser Thr Gln Glu Ala Ala Glu Ala Tyr Asp Val Ala
                435                 440                 445

Ala Ile Lys Phe Arg Gly Leu Asn Ala Val Thr Asn Phe Asp Ile Thr
450                 455                 460

Arg Tyr Asp Val Asp Lys Ile Leu Glu Ser Ser Thr Leu Leu Pro Gly
465                 470                 475                 480

Glu Leu Ala Arg Arg Lys Gly Lys Val Gly Asp Gly Gly Ala Ala
                485                 490                 495

Ala Val Ala Asp Ala Ala Ala Leu Val Gln Ala Gly Asn Val Ala
                500                 505                 510

Glu Trp Lys Met Ala Thr Ala Ala Leu Pro Ala Ala Ala Arg Thr
                515                 520                 525

Glu Gln Gln Gln Gln His Gly His Gly Gly His Gln His His Asp Leu
530                 535                 540

Leu Pro Ser Asp Ala Phe Ser Val Leu Gln Asp Ile Val Ser Thr Val
545                 550                 555                 560

Asp Ala Ala Gly Ala Pro Pro Arg Ala Pro His Met Ser Met Ala Ala
                565                 570                 575

Thr Ser Leu Gly Asn Ser Arg Glu Gln Ser Pro Asp Arg Gly Val Gly
                580                 585                 590

Gly Gly Gly Gly Gly Val Leu Ala Thr Leu Phe Ala Lys Pro Ala
            595                 600                 605

Ala Ala Ser Lys Leu Tyr Ser Pro Val Pro Leu Asn Thr Trp Ala Ser
            610                 615                 620

Pro Ser Pro Ala Val Ser Ser Val Pro Ala Arg Ala Gly Val Ser Ile
625                 630                 635                 640
```

Ala His Leu Pro Met Phe Ala Ala Trp Thr Asp Ala
            645                 650

<210> SEQ ID NO 88
<211> LENGTH: 440
<212> TYPE: PRT
<213> ORGANISM: Arabidopsis thaliana

<400> SEQUENCE: 88

Met Ala Asp Ser Thr Thr Leu Ser Thr Phe Phe Asp His Ser Gln Thr
1               5                   10                  15

Gln Ile Pro Lys Leu Glu Asp Phe Leu Gly Asp Ser Phe Val Arg Tyr
            20                  25                  30

Ser Asp Asn Gln Thr Glu Thr Gln Asp Ser Ser Ser Leu Thr Pro Phe
        35                  40                  45

Tyr Asp Pro Arg His Arg Thr Val Ala Glu Gly Val Thr Gly Phe Phe
    50                  55                  60

Ser Asp His His Gln Pro Asp Phe Lys Thr Ile Asn Ser Gly Pro Glu
65                  70                  75                  80

Ile Phe Asp Asp Ser Thr Thr Ser Asn Ile Gly Gly Thr His Leu Ser
                85                  90                  95

Ser His Val Val Glu Ser Ser Thr Thr Ala Lys Leu Gly Phe Asn Gly
            100                 105                 110

Asp Cys Thr Thr Thr Gly Gly Val Leu Ser Leu Gly Val Asn Asn Thr
        115                 120                 125

Ser Asp Gln Pro Leu Ser Cys Asn Asn Gly Glu Arg Gly Gly Asn Ser
    130                 135                 140

Asn Lys Lys Lys Thr Val Ser Lys Lys Glu Thr Ser Asp Asp Ser Lys
145                 150                 155                 160

Lys Lys Ile Val Glu Thr Leu Gly Gln Arg Thr Ser Ile Tyr Arg Gly
                165                 170                 175

Val Thr Arg His Arg Trp Thr Gly Arg Tyr Glu Ala His Leu Trp Asp
            180                 185                 190

Asn Ser Cys Arg Arg Glu Gly Gln Ala Arg Lys Gly Arg Gln Val Tyr
        195                 200                 205

Leu Gly Gly Tyr Asp Lys Glu Asp Arg Ala Ala Arg Ala Tyr Asp Leu
    210                 215                 220

Ala Ala Leu Lys Tyr Trp Gly Ser Thr Ala Thr Thr Asn Phe Pro Val
225                 230                 235                 240

Ser Ser Tyr Ser Lys Glu Leu Glu Glu Met Asn His Met Thr Lys Gln
                245                 250                 255

Glu Phe Ile Ala Ser Leu Arg Arg Lys Ser Ser Gly Phe Ser Arg Gly
            260                 265                 270

Ala Ser Ile Tyr Arg Gly Val Thr Arg His His Gln Gln Gly Arg Trp
        275                 280                 285

Gln Ala Arg Ile Gly Arg Val Ala Gly Asn Lys Asp Leu Tyr Leu Gly
    290                 295                 300

Thr Phe Ala Thr Glu Glu Glu Ala Ala Glu Ala Tyr Asp Ile Ala Ala
305                 310                 315                 320

Ile Lys Phe Arg Gly Ile Asn Ala Val Thr Asn Phe Glu Met Asn Arg
                325                 330                 335

Tyr Asp Ile Glu Ala Val Met Asn Ser Ser Leu Pro Val Gly Gly Ala
            340                 345                 350

Ala Ala Lys Arg His Lys Leu Lys Leu Ala Leu Glu Ser Pro Ser Ser

```
                355                 360                 365
Ser Ser Ser Asp His Asn Leu Gln Gln Gln Leu Leu Pro Ser Ser
    370                 375                 380

Ser Pro Ser Asp Gln Asn Pro Asn Ser Ile Pro Cys Gly Ile Pro Phe
385                 390                 395                 400

Glu Pro Ser Val Leu Tyr Tyr His Gln Asn Phe Phe Gln His Tyr Pro
                405                 410                 415

Leu Val Ser Asp Ser Thr Ile Gln Ala Pro Met Asn Gln Ala Glu Phe
                420                 425                 430

Phe Leu Trp Pro Asn Gln Ser Tyr
                435                 440

<210> SEQ ID NO 89
<211> LENGTH: 651
<212> TYPE: PRT
<213> ORGANISM: Zea mays

<400> SEQUENCE: 89

Met Ala Asn Gly Ser Asn Trp Leu Gly Phe Ser Leu Ser Pro His Thr
1               5                   10                  15

Ala Met Glu Val Pro Ser Val Ser Glu Pro Ala Ser Thr His His Ala
                20                  25                  30

Pro Pro Pro Ser Ser Ser Thr Thr Ile Ser Ser Ser Ser Thr Asn
        35                  40                  45

Asn Thr Ile Ser Ser Asn Phe Leu Phe Ser Pro Met Ala Ser Pro Tyr
    50                  55                  60

Pro Gly Tyr Tyr Cys Val Gly Gly Ala Tyr Gly Asp Gly Thr Ser Ala
65                  70                  75                  80

Ala Gly Val Tyr Tyr Ser His Leu Pro Ala Met Pro Asn Lys Ser Asp
                85                  90                  95

Asp Gly Thr Leu Cys Asn Met Glu Gly Met Val Pro Ser Ser Pro Pro
            100                 105                 110

Lys Leu Glu Asp Phe Leu Gly Gly Gly Asn Gly Gly Gly Gln Glu Thr
        115                 120                 125

Ala Thr Tyr Tyr Ser His Gln Gln Gln Gly Glu Glu Gly Ala Ser
    130                 135                 140

Arg Asp Tyr Arg Gln Tyr His Tyr Gln His Gln Gln Leu Val Pro Tyr
145                 150                 155                 160

Asn Phe Gln Pro Leu Thr Glu Ala Glu Met Leu Gln Glu Gly Ala Ala
                165                 170                 175

Pro Met Glu Glu Ala Met Ala Ala Lys Asn Phe Leu Leu Ala Ser
            180                 185                 190

Tyr Gly Ala Cys Tyr Ser Asn Glu Glu Thr Arg Pro Leu Ser Leu Ser
        195                 200                 205

Met Met Ser Pro Gly Thr Gln Leu Ser Ser Cys Val Ser Ala Ala Pro
210                 215                 220

Gln Gln Gln His Gln Met Ala Ala Thr Val Ala Thr Ala Ala Thr Ala
225                 230                 235                 240

Ala Ala Ala Leu Gly Arg Ser Asn Gly Asp Gly Glu Gln Cys Val Gly
                245                 250                 255

Arg Lys Arg Ser Thr Gly Lys Gly Gly His Lys Gln Thr Val His Arg
            260                 265                 270

Lys Ser Ile Asp Thr Phe Gly Gln Arg Thr Ser Arg Tyr Arg Gly Val
        275                 280                 285
```

Thr Arg His Arg Trp Thr Gly Arg Tyr Glu Ala His Leu Trp Asp Asn
290                 295                 300

Ser Cys Arg Lys Asp Gly Gln Thr Arg Lys Gly Arg Gln Val Tyr Leu
305                 310                 315                 320

Gly Gly Tyr Asp Thr Glu Asp Lys Ala Ala Arg Ala Tyr Asp Leu Ala
            325                 330                 335

Ala Leu Lys Tyr Trp Gly Pro Ala Thr His Val Asn Phe Pro Val Glu
            340                 345                 350

Asn Tyr Arg Asp Glu Leu Glu Glu Met Lys Gly Met Thr Arg Gln Glu
            355                 360                 365

Phe Val Ala His Leu Arg Arg Arg Ser Ser Gly Phe Ser Arg Gly Ala
370                 375                 380

Ser Ile Tyr Arg Gly Val Thr Arg His His Gln Gln Gly Arg Trp Gln
385                 390                 395                 400

Ser Arg Ile Gly Arg Val Ala Gly Asn Lys Asp Leu Tyr Leu Gly Thr
            405                 410                 415

Phe Thr Thr Gln Glu Glu Ala Ala Glu Ala Tyr Asp Ile Ala Ala Ile
            420                 425                 430

Lys Phe Arg Gly Leu Asn Ala Val Thr Asn Phe Asp Ile Ala Arg Tyr
            435                 440                 445

Asp Val Asp Lys Ile Met Glu Ser Ser Thr Leu Leu Ala Val Glu Glu
450                 455                 460

Ala Arg Lys Val Lys Ala Val Glu Ala Ala Ser Ser Ala Pro Met Thr
465                 470                 475                 480

His Thr His Ser Gly Gly Lys Glu Gln Leu Asn Ala Thr Thr Ala Glu
            485                 490                 495

Glu Thr Ser Ser Ala Gly Trp Arg Met Val Leu His Gly Ser Pro His
            500                 505                 510

Gln Leu Glu Ala Ala Arg Cys Pro Glu Ala Ala Asp Leu Gln Ser Ala
            515                 520                 525

Ile Met Asn Asn Asp Ser His Pro Arg Pro Ser Leu His Gly Ile Ala
            530                 535                 540

Gly Leu Asp Ile Glu Cys Ala Val His Asp His His Asp His Leu Asp
545                 550                 555                 560

Val Pro Ala Gly Ser Arg Thr Thr Ala Ala Gly Ser Ile Asn Phe Ser
            565                 570                 575

Asn Ser Ser Ser Gln Val Thr Ser Leu Gly Asn Ser Arg Glu Gly Ser
            580                 585                 590

Pro Glu Arg Leu Gly Leu Ala Met Met Tyr Gly Lys Gln Pro Ser Ser
            595                 600                 605

Ala Val Ser Leu Ala Ala Thr Met Ser Pro Trp Thr Pro Val Ala Ala
            610                 615                 620

Gln Thr Val Ala His Val Leu Lys Gln Gln Pro Asn Val Val Val Ser
625                 630                 635                 640

His Arg Pro Val Phe Ala Ala Trp Ala Asp Ala
            645                 650

<210> SEQ ID NO 90
<211> LENGTH: 656
<212> TYPE: PRT
<213> ORGANISM: Medicago truncatula

<400> SEQUENCE: 90

Met Lys Arg Met Glu Asn Asn Asp Asp Ser Val Asp Ile Asn Asn Glu
1               5                   10                  15

```
Asn Asn Trp Leu Gly Phe Ser Leu Ser Pro Gln Met Asn Asn Ile Gly
            20                  25                  30

Val Ser Ser His Thr His His His Ser Leu Pro Ser Ala Thr Ala Thr
        35                  40                  45

Ala Ser Glu Val Val Pro Leu Gln Ala Ser Phe Tyr His Ser Ser Pro
50                      55                  60

Leu Ser Asn Phe Cys Tyr Ser Tyr Gly Leu Glu His Glu Asn Ala Gly
65                  70                  75                  80

Leu Tyr Ser Leu Leu Pro Ile Met Pro Leu Lys Ser Asp Gly Ser Leu
                85                  90                  95

Phe Glu Met Glu Ala Leu Ser Arg Ser Gln Thr Gln Ala Met Ser Thr
                100                 105                 110

Thr Ser Ala Pro Lys Leu Glu Asn Phe Leu Gly Asn Glu Ala Met Gly
            115                 120                 125

Thr Pro His Tyr Ala Cys Ser Ser Thr Val Thr Glu Thr Met Pro Leu
        130                 135                 140

Ser Leu Asp Ser Met Phe Gln Asn Gln Ile Gln Gln Asn Met Asn Met
145                 150                 155                 160

Asn Asn Gln Gln His Leu Ser Tyr Tyr Asn Ser Thr Leu Arg Asn His
                165                 170                 175

Glu Leu Met Leu Glu Gly Ser Lys Gln Ser Gln Thr Ser Ser Gly Asn
                180                 185                 190

Phe His Gln Ser Asn Met Gly Glu Asp His Gly Leu Ser Gly Leu Lys
            195                 200                 205

Asn Trp Val Leu Arg Asn Phe Pro Ala Ser His Gly His Asp Gln Ser
        210                 215                 220

Lys Met Ile Val Pro Val Glu Glu Asn Glu Gly Glu Cys Gly Ser
225                 230                 235                 240

Asn Ile Gly Ser Met Ala Tyr Gly Asp Leu His Ser Leu Ser Leu Ser
                245                 250                 255

Met Ser Pro Ser Ser Gln Ser Ser Cys Val Thr Thr Ser Gln Asn Met
                260                 265                 270

Ser Ser Ala Val Val Glu Asn Ser Val Ala Met Asp Thr Lys Lys Arg
            275                 280                 285

Gly Ser Glu Lys Phe Glu Gln Lys Gln Ile Val His Arg Lys Ser Ile
        290                 295                 300

Asp Thr Phe Gly Gln Arg Thr Ser Gln Tyr Arg Gly Val Thr Arg His
305                 310                 315                 320

Arg Trp Thr Gly Arg Tyr Glu Ala His Leu Trp Asp Asn Ser Cys Lys
                325                 330                 335

Lys Glu Gly Gln Ser Arg Lys Gly Arg Gln Gly Gly Tyr Asp Met Glu
                340                 345                 350

Glu Lys Ala Ala Arg Ala Tyr Asp Gln Ala Ala Leu Lys Tyr Trp Gly
            355                 360                 365

Pro Ser Thr His Ile Asn Phe Pro Leu Glu Asn Tyr Gln Asn Gln Leu
        370                 375                 380

Glu Glu Met Lys Asn Met Thr Arg Gln Glu Tyr Val Ala His Leu Arg
385                 390                 395                 400

Arg Lys Ser Ser Gly Phe Ser Arg Gly Ala Ser Met Tyr Arg Gly Val
                405                 410                 415

Thr Ser Arg His His Gln His Gly Arg Trp Gln Ala Ile Gly Arg
                420                 425                 430
```

Val Ala Gly Asn Lys Asp Leu Tyr Leu Gly Thr Phe Ser Thr Gln Glu
            435                 440                 445

Glu Ala Ala Glu Ala Tyr Asp Ile Ala Ala Ile Lys Phe Arg Gly Ala
        450                 455                 460

Asn Ala Val Thr Asn Phe Asp Ile Ile Lys Tyr Asp Val Lys Ile
465                 470                 475                 480

Met Ala Ser Ser Asn Leu Leu Asn Ile Glu Gln Ala Arg Arg Asn Lys
                485                 490                 495

Glu Val Val Asp Ile Ser Ser Thr Gln Tyr Ile Asp Gln Asn Lys Pro
            500                 505                 510

Ser Ser Ala Tyr Asp Asn Asn Ser Thr Gln Glu Ala Ile Ser Met Gln
        515                 520                 525

Lys Ser Met Val Leu Tyr Gln Ser Ser Gln His Gln Gln Leu Gln Gln
    530                 535                 540

Asn Gln Pro Arg Phe Glu Asn Glu Arg Thr His Gln Thr Phe Ser Ser
545                 550                 555                 560

Val Ser Leu Asp Asn Met Phe His Gln Glu Val Val Glu Glu Ala Ser
                565                 570                 575

Lys Met Arg Thr His Val Ser Asn Ala Ser Ser Leu Ala Thr Ser Leu
            580                 585                 590

Ser Ser Ser Arg Glu Gly Thr Pro Asp Arg Thr Ser Leu Gln Asn Leu
        595                 600                 605

Ser Gly Ile Met Pro Ser Thr Ala Ser Lys Leu Leu Val Thr Ser Ala
    610                 615                 620

Pro Asn Ser Asn Leu Asn Ser Trp Asp Pro Ser Gln His Leu Arg Pro
625                 630                 635                 640

Ser Leu Ser Leu Pro Gln Met Pro Val Phe Ala Ala Trp Thr Asp Ala
                645                 650                 655

<210> SEQ ID NO 91
<211> LENGTH: 546
<212> TYPE: PRT
<213> ORGANISM: Glycine max

<400> SEQUENCE: 91

Met Lys Arg Met Asn Glu Ser Asn Asn Thr Asp Asp Gly Asn Asn His
1               5                   10                  15

Asn Trp Leu Gly Phe Ser Leu Ser Pro His Met Lys Met Glu Val Thr
            20                  25                  30

Ser Ala Ala Thr Val Ser Asp Asn Asn Val Pro Thr Thr Phe Tyr Met
        35                  40                  45

Ser Pro Ser His Met Ser Asn Ser Gly Met Cys Tyr Ser Val Gly Glu
    50                  55                  60

Asn Gly Asn Phe His Ser Pro Leu Thr Val Met Pro Leu Lys Ser Asp
65                  70                  75                  80

Gly Ser Leu Gly Ile Leu Glu Ala Leu Asn Arg Ser Gln Thr Gln Val
                85                  90                  95

Met Val Pro Thr Ser Ser Pro Lys Leu Glu Asp Phe Leu Gly Gly Ala
            100                 105                 110

Thr Met Gly Thr His Glu Tyr Gly Asn His Glu Arg Gly Leu Ser Leu
        115                 120                 125

Asp Ser Ile Tyr Tyr Asn Ser Gln Asn Ala Glu Ala Gln Pro Asn Arg
    130                 135                 140

Asn Leu Leu Ser His Pro Phe Arg Gln Gln Gly His Ala Pro Ser Glu
145                 150                 155                 160

```
Glu Glu Ala Thr Lys Glu Thr His Val Ser Val Met Pro Gln Met Thr
                165                 170                 175

Gly Gly Gly Leu Gln Asn Trp Ile Leu Glu Gln Gln Met Asn Cys Gly
            180                 185                 190

Ile Trp Asn Glu Arg Ser Gly Val Ser Val Gly Thr Val Gly Cys Gly
        195                 200                 205

Glu Leu Gln Ser Leu Ser Leu Ser Met Ser Pro Gly Ser Gln Ser Ser
    210                 215                 220

Cys Val Thr Ala Pro Ser Gly Thr Asp Ser Val Ala Val Asp Ala Lys
225                 230                 235                 240

Lys Arg Gly His Ala Lys Leu Gly Gln Lys Gln Pro Val His Arg Lys
                245                 250                 255

Ser Ile Asp Thr Phe Gly Gln Arg Thr Ser Gln Tyr Arg Gly Val Thr
            260                 265                 270

Arg His Arg Trp Thr Gly Arg Tyr Glu Ala His Leu Trp Asp Asn Ser
        275                 280                 285

Cys Lys Lys Glu Gly Gln Thr Arg Lys Gly Arg Gln Gly Gly Tyr Asp
    290                 295                 300

Met Glu Glu Lys Ala Ala Arg Ala Tyr Asp Leu Ala Ala Leu Lys Tyr
305                 310                 315                 320

Trp Gly Pro Ser Thr His Ile Asn Phe Ser Ile Glu Asn Tyr Gln Val
                325                 330                 335

Gln Leu Glu Glu Met Lys Asn Met Ser Arg Gln Glu Tyr Val Ala His
            340                 345                 350

Leu Arg Arg Lys Ser Ser Gly Phe Ser Arg Gly Ala Ser Ile Tyr Arg
        355                 360                 365

Gly Val Thr Arg His His Gln His Gly Arg Trp Gln Ala Arg Ile Gly
    370                 375                 380

Arg Val Ala Gly Asn Lys Asp Leu Tyr Leu Gly Thr Phe Ser Thr Gln
385                 390                 395                 400

Glu Glu Ala Ala Glu Ala Tyr Asp Ile Ala Ala Ile Lys Phe Arg Gly
                405                 410                 415

Ala Asn Ala Val Thr Asn Phe Asp Ile Ser Arg Tyr Asp Val Glu Arg
            420                 425                 430

Ile Met Ala Ser Ser Asn Leu Leu Ala Gly Glu Leu Ala Arg Arg Asn
        435                 440                 445

Lys Asp Asn Asp Pro Arg Asn Glu Ala Ile Asp Tyr Asn Lys Ser Val
    450                 455                 460

Phe Lys Gln Glu Thr Thr Met Lys Met Ile Arg Ser Gly Arg Cys Leu
465                 470                 475                 480

Ser Ser Ser Arg Glu Ala Ser Pro Glu Lys Met Gly Pro Ser Leu Leu
                485                 490                 495

Phe Pro Lys Pro Pro Met Glu Thr Lys Ile Val Asn Pro Ile Gly
            500                 505                 510

Thr Ser Val Thr Ser Trp Leu Pro Ser Pro Thr Val Gln Met Arg Pro
        515                 520                 525

Ser Pro Ala Ile Ser Leu Ser His Leu Pro Val Phe Ala Ala Trp Thr
    530                 535                 540

Asp Thr
545

<210> SEQ ID NO 92
<211> LENGTH: 415
```

<212> TYPE: PRT
<213> ORGANISM: Arabidopsis thaliana

<400> SEQUENCE: 92

```
Met Lys Lys Trp Leu Gly Phe Ser Leu Thr Pro Pro Leu Arg Ile Cys
1               5                   10                  15

Asn Ser Glu Glu Glu Leu Arg His Asp Gly Ser Asp Val Trp Arg
            20                  25                  30

Tyr Asp Ile Asn Phe Asp His His His Asp Glu Asp Val Pro Lys
            35                  40                  45

Val Glu Asp Leu Leu Ser Asn Ser His Gln Thr Glu Tyr Pro Ile Asn
    50                  55                  60

His Asn Gln Thr Asn Val Asn Cys Thr Thr Val Val Asn Arg Leu Asn
65                  70                  75                  80

Pro Pro Gly Tyr Leu Leu His Asp Gln Thr Val Val Thr Pro His Tyr
                85                  90                  95

Pro Asn Leu Asp Pro Asn Leu Ser Asn Asp Tyr Gly Gly Phe Glu Arg
            100                 105                 110

Val Gly Ser Val Ser Val Phe Lys Ser Trp Leu Glu Gln Gly Thr Pro
        115                 120                 125

Ala Phe Pro Leu Ser Ser His Tyr Val Thr Glu Glu Ala Gly Thr Ser
    130                 135                 140

Asn Asn Ile Ser His Phe Ser Asn Glu Glu Thr Gly Tyr Asn Thr Asn
145                 150                 155                 160

Gly Ser Met Leu Ser Leu Ala Leu Ser His Gly Ala Cys Ser Asp Leu
                165                 170                 175

Ile Asn Glu Ser Asn Val Ser Ala Arg Val Glu Glu Pro Val Lys Val
            180                 185                 190

Asp Glu Lys Arg Lys Arg Leu Val Val Lys Pro Gln Val Lys Glu Ser
        195                 200                 205

Val Pro Arg Lys Ser Val Asp Ser Tyr Gly Gln Arg Thr Ser Gln Tyr
    210                 215                 220

Arg Gly Val Thr Arg His Arg Trp Thr Gly Arg Tyr Glu Ala His Leu
225                 230                 235                 240

Trp Asp Asn Ser Cys Lys Lys Glu Gly Gln Thr Arg Arg Gly Arg Gln
                245                 250                 255

Val Tyr Leu Gly Gly Tyr Asp Glu Glu Glu Lys Ala Ala Arg Ala Tyr
            260                 265                 270

Asp Leu Ala Ala Leu Lys Tyr Trp Gly Pro Thr Thr His Leu Asn Phe
        275                 280                 285

Pro Leu Ser Asn Tyr Glu Lys Glu Ile Glu Glu Leu Asn Asn Met Asn
    290                 295                 300

Arg Gln Glu Phe Val Ala Met Leu Arg Arg Asn Ser Ser Gly Phe Ser
305                 310                 315                 320

Arg Gly Ala Ser Val Tyr Arg Gly Val Thr Arg His His Gln His Gly
                325                 330                 335

Arg Trp Gln Ala Arg Ile Gly Arg Val Ala Gly Asn Lys Asp Leu Tyr
            340                 345                 350

Leu Gly Thr Phe Ser Thr Gln Glu Glu Ala Ala Glu Ala Tyr Asp Ile
        355                 360                 365

Ala Ala Ile Lys Phe Arg Gly Leu Asn Ala Val Thr Asn Phe Asp Ile
    370                 375                 380

Asn Arg Tyr Asp Val Lys Arg Ile Cys Ser Ser Ser Thr Ile Val Asp
385                 390                 395                 400
```

Ser Asp Gln Ala Lys His Ser Pro Thr Ser Ser Gly Ala Gly His
            405                 410                 415

<210> SEQ ID NO 93
<211> LENGTH: 428
<212> TYPE: PRT
<213> ORGANISM: Zea mays

<400> SEQUENCE: 93

Met Ser Pro Pro Thr Asn Gly Ala Ile Ser Leu Ala Tyr Ala Pro Ser
1               5                   10                  15

Met Met Leu Gly Ala Gly Ala Leu Thr Asn Pro Pro Leu Leu Pro Phe
            20                  25                  30

Asp Gly Phe Thr Asp Glu Asp Phe Leu Ala Ser Ala Asp Ala Ala Leu
        35                  40                  45

Leu Gly Glu Ala Gly Thr Asp Gln Thr Leu Leu Leu Pro Ser Cys
    50                  55                  60

Pro Gly Ala Asn Cys Cys Gly Ser Ser Asp Gln Gly Leu Gly
65                  70                  75                  80

Ala Leu Ala Cys Glu Val Thr Thr Ala Gly Ser Phe Ser Leu Leu Gly
                85                  90                  95

Gln Pro Ala Pro Gly Gln Val Ser Trp Glu Val Thr Ala Val Ala
            100                 105                 110

Ala Asp Arg Asn Thr Phe Ser Arg Ala Arg Asp Pro Ala Pro Ser Pro
        115                 120                 125

Pro Pro Ser Pro Ala Leu Pro Leu Val Gln Thr Thr Ser Gln Ser Gln
    130                 135                 140

Arg Thr Ser Ile Tyr Arg Gly Val Thr Arg His Arg Trp Thr Gly Arg
145                 150                 155                 160

Tyr Glu Ala His Leu Trp Asp Asn Thr Cys Arg Lys Glu Gly Gln Lys
                165                 170                 175

Arg Lys Gly Arg Gln Val Tyr Leu Gly Gly Tyr Asp Lys Glu Asp Lys
            180                 185                 190

Ala Ala Arg Ala Tyr Asp Ile Ala Ala Leu Lys Tyr Trp Gly Asp Asn
        195                 200                 205

Ala Thr Thr Asn Phe Pro Arg Glu Asn Tyr Ile Arg Glu Ile Gln Asp
    210                 215                 220

Met Gln Asn Met Asn Arg Arg Asp Val Val Ala Ser Leu Arg Arg Lys
225                 230                 235                 240

Ser Ser Gly Phe Ser Arg Gly Ala Ser Ile Tyr Arg Gly Val Thr Lys
                245                 250                 255

His His Gln His Gly Arg Trp Gln Ala Arg Ile Gly Arg Val Ala Gly
            260                 265                 270

Asn Lys Asp Leu Tyr Leu Gly Thr Phe Ala Thr Glu Gln Glu Ala Ala
        275                 280                 285

Glu Ala Tyr Asp Ile Ala Ala Leu Lys Phe Arg Gly Glu Asn Ala Val
    290                 295                 300

Thr Asn Phe Glu Pro Ser Arg Tyr Asn Leu Leu Ala Ile Ala Gln Arg
305                 310                 315                 320

Asp Ile Pro Ile Leu Gly Arg Lys Leu Ile Gln Lys Pro Ala Pro Glu
                325                 330                 335

Ala Glu Asp Gln Ala Ala Leu Ser Ala Arg Ser Phe Ser Gln Ser Gln
            340                 345                 350

Gln Ser Ser Asn Ser Leu Pro Pro Tyr Phe Leu Thr Asn Leu Leu Gln

```
            355                 360                 365
Pro Leu Pro Ser Gln His Ser Leu Ala Gln Ala Leu Pro Ser Tyr Asn
370                     375                 380

Asn Leu Gly Phe Gly Glu Pro Ser Leu Tyr Trp Pro Cys Pro Cys Gly
385                 390                 395                 400

Asp Pro Gly Glu Gln Lys Val Gln Leu Gly Ser Lys Leu Glu Ile Val
                    405                 410                 415

Asp Gly Leu Val Gln Leu Ala Asn Ser Ala Ala Asn
                420                 425

<210> SEQ ID NO 94
<211> LENGTH: 438
<212> TYPE: PRT
<213> ORGANISM: Arabidopsis thaliana

<400> SEQUENCE: 94

Met Lys Lys Arg Leu Thr Thr Ser Thr Cys Ser Ser Ser Pro Ser Ser
1               5                   10                  15

Ser Val Ser Ser Ser Thr Thr Thr Ser Ser Pro Ile Gln Ser Glu Ala
                20                  25                  30

Pro Arg Pro Lys Arg Ala Lys Arg Ala Lys Lys Ser Ser Pro Ser Gly
            35                  40                  45

Asp Lys Ser His Asn Pro Thr Ser Pro Ala Ser Thr Arg Arg Ser Ser
50                  55                  60

Ile Tyr Arg Gly Val Thr Arg His Arg Trp Thr Gly Arg Phe Glu Ala
65                  70                  75                  80

His Leu Trp Asp Lys Ser Ser Trp Asn Ser Ile Gln Asn Lys Lys Gly
                85                  90                  95

Lys Gln Val Tyr Leu Gly Ala Tyr Asp Ser Glu Glu Ala Ala Ala His
            100                 105                 110

Thr Tyr Asp Leu Ala Ala Leu Lys Tyr Trp Gly Pro Asp Thr Ile Leu
        115                 120                 125

Asn Phe Pro Ala Glu Thr Tyr Thr Lys Glu Leu Glu Glu Met Gln Arg
130                 135                 140

Val Thr Lys Glu Glu Tyr Leu Ala Ser Leu Arg Arg Gln Ser Ser Gly
145                 150                 155                 160

Phe Ser Arg Gly Val Ser Lys Tyr Arg Gly Val Ala Arg His His His
                165                 170                 175

Asn Gly Arg Trp Glu Ala Arg Ile Gly Arg Val Phe Gly Asn Lys Tyr
            180                 185                 190

Leu Tyr Leu Gly Thr Tyr Asn Thr Gln Glu Glu Ala Ala Ala Ala Tyr
        195                 200                 205

Asp Met Ala Ala Ile Glu Tyr Arg Gly Ala Asn Ala Val Thr Asn Phe
210                 215                 220

Asp Ile Ser Asn Tyr Ile Asp Arg Leu Lys Lys Lys Gly Val Phe Pro
225                 230                 235                 240

Phe Pro Val Asn Gln Ala Asn His Gln Glu Gly Ile Leu Val Glu Ala
                245                 250                 255

Lys Gln Glu Val Glu Thr Arg Glu Ala Lys Glu Glu Pro Arg Glu Glu
            260                 265                 270

Val Lys Gln Gln Tyr Val Glu Glu Pro Pro Gln Glu Glu Glu Glu Lys
        275                 280                 285

Glu Glu Glu Lys Ala Glu Gln Gln Glu Ala Glu Ile Val Gly Tyr Ser
    290                 295                 300
```

```
Glu Glu Ala Ala Val Val Asn Cys Cys Ile Asp Ser Ser Thr Ile Met
305                 310                 315                 320

Glu Met Asp Arg Cys Gly Asp Asn Asn Glu Leu Ala Trp Asn Phe Cys
            325                 330                 335

Met Met Asp Thr Gly Phe Ser Pro Phe Leu Thr Asp Gln Asn Leu Ala
            340                 345                 350

Asn Glu Asn Pro Ile Glu Tyr Pro Glu Leu Phe Asn Glu Leu Ala Phe
            355                 360                 365

Glu Asp Asn Ile Asp Phe Met Phe Asp Asp Gly Lys His Glu Cys Leu
    370                 375                 380

Asn Leu Glu Asn Leu Asp Cys Cys Val Val Gly Arg Glu Ser Pro Pro
385                 390                 395                 400

Ser Ser Ser Ser Pro Leu Ser Cys Leu Ser Thr Asp Ser Ala Ser Ser
            405                 410                 415

Thr Thr Thr Thr Thr Thr Ser Val Ser Cys Asn Tyr Leu Phe Gln Gly
            420                 425                 430

Leu Phe Val Gly Ser Glu
            435

<210> SEQ ID NO 95
<211> LENGTH: 432
<212> TYPE: PRT
<213> ORGANISM: Arabidopsis thaliana

<400> SEQUENCE: 95

Met Trp Asp Leu Asn Asp Ala Pro His Gln Thr Gln Arg Glu Glu
1               5                   10                  15

Ser Glu Glu Phe Cys Tyr Ser Ser Pro Ser Lys Arg Val Gly Ser Phe
                20                  25                  30

Ser Asn Ser Ser Ser Ala Val Val Ile Glu Asp Gly Ser Asp
            35                  40                  45

Asp Glu Leu Asn Arg Val Arg Pro Asn Asn Pro Leu Val Thr His Gln
    50                  55                  60

Phe Phe Pro Glu Met Asp Ser Asn Gly Gly Gly Val Ala Ser Gly Phe
65                  70                  75                  80

Pro Arg Ala His Trp Phe Gly Val Lys Phe Cys Gln Ser Asp Leu Ala
                85                  90                  95

Thr Gly Ser Ser Ala Gly Lys Ala Thr Asn Val Ala Ala Val Val
            100                 105                 110

Glu Pro Ala Gln Pro Leu Lys Lys Ser Arg Arg Gly Pro Arg Ser Arg
            115                 120                 125

Ser Ser Gln Tyr Arg Gly Val Thr Phe Tyr Arg Arg Thr Gly Arg Trp
130                 135                 140

Glu Ser His Ile Trp Asp Cys Gly Lys Gln Val Tyr Leu Gly Gly Phe
145                 150                 155                 160

Asp Thr Ala His Ala Ala Arg Ala Tyr Asp Arg Ala Ala Ile Lys
            165                 170                 175

Phe Arg Gly Val Glu Ala Asp Ile Asn Phe Asn Ile Asp Asp Tyr Asp
            180                 185                 190

Asp Asp Leu Lys Gln Met Thr Asn Leu Thr Lys Glu Glu Phe Val His
            195                 200                 205

Val Leu Arg Arg Gln Ser Thr Gly Phe Pro Arg Gly Ser Ser Lys Tyr
    210                 215                 220

Arg Gly Val Thr Leu His Lys Cys Gly Arg Trp Glu Ala Arg Met Gly
225                 230                 235                 240
```

```
Gln Phe Leu Gly Lys Lys Tyr Val Tyr Leu Gly Leu Phe Asp Thr Glu
                245                 250                 255

Val Glu Ala Ala Arg Ala Tyr Asp Lys Ala Ala Ile Lys Cys Asn Gly
            260                 265                 270

Lys Asp Ala Val Thr Asn Phe Asp Pro Ser Ile Tyr Asp Glu Glu Leu
        275                 280                 285

Asn Ala Glu Ser Ser Gly Asn Pro Thr Thr Pro Gln Asp His Asn Leu
    290                 295                 300

Asp Leu Ser Leu Gly Asn Ser Ala Asn Ser Lys His Lys Ser Gln Asp
305                 310                 315                 320

Met Arg Leu Arg Met Asn Gln Gln Gln Asp Ser Leu His Ser Asn
                325                 330                 335

Glu Val Leu Gly Leu Gly Gln Thr Gly Met Leu Asn His Thr Pro Asn
                340                 345                 350

Ser Asn His Gln Phe Pro Gly Ser Ser Asn Ile Gly Ser Gly Gly Gly
                355                 360                 365

Phe Ser Leu Phe Pro Ala Ala Glu Asn His Arg Phe Asp Gly Arg Ala
        370                 375                 380

Ser Thr Asn Gln Val Leu Thr Asn Ala Ala Ser Ser Gly Phe Ser
385                 390                 395                 400

Pro His His His Asn Gln Ile Phe Asn Ser Thr Ser Thr Pro His Gln
                405                 410                 415

Asn Trp Leu Gln Thr Asn Gly Phe Gln Pro Pro Leu Met Arg Pro Ser
                420                 425                 430

<210> SEQ ID NO 96
<211> LENGTH: 449
<212> TYPE: PRT
<213> ORGANISM: Arabidopsis thaliana

<400> SEQUENCE: 96

Met Leu Asp Leu Asn Leu Asn Ala Asp Ser Pro Glu Ser Thr Gln Tyr
1               5                   10                  15

Gly Gly Asp Ser Tyr Leu Asp Arg Gln Thr Ser Asp Asn Ser Ala Gly
            20                  25                  30

Asn Arg Val Glu Glu Ser Gly Thr Ser Thr Ser Val Ile Asn Ala
        35                  40                  45

Asp Gly Asp Glu Asp Ser Cys Ser Thr Arg Ala Phe Thr Leu Ser Phe
    50                  55                  60

Asp Ile Leu Lys Val Gly Ser Ser Gly Gly Asp Glu Ser Pro Ala
65                  70                  75                  80

Ala Ser Ala Ser Val Thr Lys Glu Phe Phe Pro Val Ser Gly Asp Cys
                85                  90                  95

Gly His Leu Arg Asp Val Glu Gly Ser Ser Ser Arg Asn Trp Ile
            100                 105                 110

Asp Leu Ser Phe Asp Arg Ile Gly Asp Gly Glu Thr Lys Leu Val Thr
        115                 120                 125

Pro Val Pro Thr Pro Ala Pro Val Pro Ala Gln Val Lys Lys Ser Arg
    130                 135                 140

Arg Gly Pro Arg Ser Arg Ser Ser Gln Tyr Arg Gly Val Thr Phe Tyr
145                 150                 155                 160

Arg Arg Thr Gly Arg Trp Glu Ser His Ile Trp Asp Cys Gly Lys Gln
                165                 170                 175

Val Tyr Leu Gly Gly Phe Asp Thr Ala His Ala Ala Ala Arg Ala Tyr
```

```
                180              185              190
Asp Arg Ala Ala Ile Lys Phe Arg Gly Val Asp Ala Asp Ile Asn Phe
            195                 200                 205

Thr Leu Gly Asp Tyr Glu Glu Asp Met Lys Gln Val Gln Asn Leu Ser
            210                 215                 220

Lys Glu Glu Phe Val His Ile Leu Arg Arg Gln Ser Thr Gly Phe Ser
225                 230                 235                 240

Arg Gly Ser Ser Lys Tyr Arg Gly Val Thr Leu His Lys Cys Gly Arg
                245                 250                 255

Trp Glu Ala Arg Met Gly Gln Phe Leu Gly Lys Lys Ala Tyr Asp Lys
            260                 265                 270

Ala Ala Ile Asn Thr Asn Gly Arg Glu Ala Val Thr Asn Phe Glu Met
            275                 280                 285

Ser Ser Tyr Gln Asn Glu Ile Asn Ser Glu Ser Asn Asn Ser Glu Ile
            290                 295                 300

Asp Leu Asn Leu Gly Ile Ser Leu Ser Thr Gly Asn Ala Pro Lys Gln
305                 310                 315                 320

Asn Gly Arg Leu Phe His Phe Pro Ser Asn Thr Tyr Glu Thr Gln Arg
                325                 330                 335

Gly Val Ser Leu Arg Ile Asp Asn Glu Tyr Met Gly Lys Pro Val Asn
            340                 345                 350

Thr Pro Leu Pro Tyr Gly Ser Ser Asp His Arg Leu Tyr Trp Asn Gly
            355                 360                 365

Ala Cys Pro Ser Tyr Asn Asn Pro Ala Glu Gly Arg Ala Thr Glu Lys
            370                 375                 380

Arg Ser Glu Ala Glu Gly Met Met Ser Asn Trp Gly Trp Gln Arg Pro
385                 390                 395                 400

Gly Gln Thr Ser Ala Val Arg Pro Gln Pro Gly Pro Gln Pro Pro
                405                 410                 415

Pro Leu Phe Ser Val Ala Ala Ala Ser Ser Gly Phe Ser His Phe Arg
            420                 425                 430

Pro Gln Pro Pro Asn Asp Asn Ala Thr Arg Gly Tyr Phe Tyr Pro His
                435                 440                 445

Pro

<210> SEQ ID NO 97
<211> LENGTH: 663
<212> TYPE: DNA
<213> ORGANISM: Zea mays
<220> FEATURE:
<221> NAME/KEY: CDS
<222> LOCATION: (1)...(663)

<400> SEQUENCE: 97 atg gag gcg ctg agc ggg cgg gta ggc gtc aag tgc ggg cgg tgg aac      48
Met Glu Ala Leu Ser Gly Arg Val Gly Val Lys Cys Gly Arg Trp Asn
1               5                   10                  15 cct acg gcg gag cag gtg aag gtc ctg acg gag ctc ttc cgc gcg ggg      96
Pro Thr Ala Glu Gln Val Lys Val Leu Thr Glu Leu Phe Arg Ala Gly
                20                  25                  30 ctg cgg acg ccc agc acg gag cag atc cag cgc atc tcc acc cac ctc     144
Leu Arg Thr Pro Ser Thr Glu Gln Ile Gln Arg Ile Ser Thr His Leu
            35                  40                  45 agc gcc ttc ggc aag gtg gag agc aag aac gtc ttc tac tgg ttc cag     192
Ser Ala Phe Gly Lys Val Glu Ser Lys Asn Val Phe Tyr Trp Phe Gln
        50                  55                  60
```

```
aac cac aag gcc cgc gag cgc cac cac cac aag aag cgc cgc cgc ggc      240
Asn His Lys Ala Arg Glu Arg His His His Lys Lys Arg Arg Arg Gly
 65              70                  75                  80 gcg tcg tcg tcc tcc ccc gac agc ggc agc ggc agg gga agc aac aac      288
Ala Ser Ser Ser Ser Pro Asp Ser Gly Ser Gly Arg Gly Ser Asn Asn
                 85                  90                  95 gag gaa gac ggc cgt ggt gcc gcc tcg cag tcg cac gac gcc gac gcc      336
Glu Glu Asp Gly Arg Gly Ala Ala Ser Gln Ser His Asp Ala Asp Ala
            100                 105                 110 gac gcc gac ctc gtg ctg caa ccg cca gag agc aag cgg gag gcc aga      384
Asp Ala Asp Leu Val Leu Gln Pro Pro Glu Ser Lys Arg Glu Ala Arg
        115                 120                 125 agc tat ggc cac cat cac cgg ctc gtg aca tgc tac gtc agg gac gtg      432
Ser Tyr Gly His His His Arg Leu Val Thr Cys Tyr Val Arg Asp Val
    130                 135                 140 gtg gag cag cag gag gcg tcg ccg tcg tgg gag cgg ccg acg agg gag      480
Val Glu Gln Gln Glu Ala Ser Pro Ser Trp Glu Arg Pro Thr Arg Glu
145                 150                 155                 160 gtg gag acg cta gag ctc ttc ccc ctc aag tcg tac ggc gac ctc gag      528
Val Glu Thr Leu Glu Leu Phe Pro Leu Lys Ser Tyr Gly Asp Leu Glu
                165                 170                 175 gcg gcg gag aag gtc cgg tcg tac gtc aga ggc atc gcc gcc acc agc      576
Ala Ala Glu Lys Val Arg Ser Tyr Val Arg Gly Ile Ala Ala Thr Ser
            180                 185                 190 gag cag tgc agg gag ttg tcc ttc ttc gac gtc tcc gcc ggc cgg gat      624
Glu Gln Cys Arg Glu Leu Ser Phe Phe Asp Val Ser Ala Gly Arg Asp
        195                 200                 205 ccg ccg ctc gag ctc agg ctc tgc agc ttc ggt ccc tag                  663
Pro Pro Leu Glu Leu Arg Leu Cys Ser Phe Gly Pro
    210                 215                 220

<210> SEQ ID NO 98
<211> LENGTH: 220
<212> TYPE: PRT
<213> ORGANISM: Zea mays

<400> SEQUENCE: 98

Met Glu Ala Leu Ser Gly Arg Val Gly Val Lys Cys Gly Arg Trp Asn
1               5                   10                  15

Pro Thr Ala Glu Gln Val Lys Val Leu Thr Glu Leu Phe Arg Ala Gly
            20                  25                  30

Leu Arg Thr Pro Ser Thr Glu Gln Ile Gln Arg Ile Ser Thr His Leu
        35                  40                  45

Ser Ala Phe Gly Lys Val Glu Ser Lys Asn Val Phe Tyr Trp Phe Gln
    50                  55                  60

Asn His Lys Ala Arg Glu Arg His His His Lys Lys Arg Arg Arg Gly
65                  70                  75                  80

Ala Ser Ser Ser Ser Pro Asp Ser Gly Ser Gly Arg Gly Ser Asn Asn
                85                  90                  95

Glu Glu Asp Gly Arg Gly Ala Ala Ser Gln Ser His Asp Ala Asp Ala
            100                 105                 110

Asp Ala Asp Leu Val Leu Gln Pro Pro Glu Ser Lys Arg Glu Ala Arg
        115                 120                 125

Ser Tyr Gly His His His Arg Leu Val Thr Cys Tyr Val Arg Asp Val
    130                 135                 140

Val Glu Gln Gln Glu Ala Ser Pro Ser Trp Glu Arg Pro Thr Arg Glu
145                 150                 155                 160

Val Glu Thr Leu Glu Leu Phe Pro Leu Lys Ser Tyr Gly Asp Leu Glu
```

```
                        165                 170                 175
Ala Ala Glu Lys Val Arg Ser Tyr Val Arg Gly Ile Ala Ala Thr Ser
            180                 185                 190

Glu Gln Cys Arg Glu Leu Ser Phe Phe Asp Val Ser Ala Gly Arg Asp
        195                 200                 205

Pro Pro Leu Glu Leu Arg Leu Cys Ser Phe Gly Pro
    210                 215                 220

<210> SEQ ID NO 99
<211> LENGTH: 978
<212> TYPE: DNA
<213> ORGANISM: Zea mays
<220> FEATURE:
<221> NAME/KEY: CDS
<222> LOCATION: (1)...(978)

<400> SEQUENCE: 99 atg gcg gcc aat gcg ggc ggc ggt gga gcg gga gga ggc agc ggc agc        48
Met Ala Ala Asn Ala Gly Gly Gly Gly Ala Gly Gly Gly Ser Gly Ser
 1                5                   10                  15 ggc agc gtg gct gcg ccg gcg gtg tgc cgc ccc agc ggc tcg cgg tgg        96
Gly Ser Val Ala Ala Pro Ala Val Cys Arg Pro Ser Gly Ser Arg Trp
            20                  25                  30 acg ccg acg ccg gag cag atc agg atg ctg aag gag ctc tac tac ggc       144
Thr Pro Thr Pro Glu Gln Ile Arg Met Leu Lys Glu Leu Tyr Tyr Gly
        35                  40                  45 tgc ggc atc cgg tcg ccc agc tcg gag cag atc cag cgc atc acc gcc       192
Cys Gly Ile Arg Ser Pro Ser Ser Glu Gln Ile Gln Arg Ile Thr Ala
    50                  55                  60 atg ctg cgg cag cac ggc aag atc gag ggc aag aac gtc ttc tac tgg       240
Met Leu Arg Gln His Gly Lys Ile Glu Gly Lys Asn Val Phe Tyr Trp
65                  70                  75                  80 ttc cag aac cac aag gcc cgc gag cgc cag aag cgc cgc ctc acc agc       288
Phe Gln Asn His Lys Ala Arg Glu Arg Gln Lys Arg Arg Leu Thr Ser
                85                  90                  95 ctc gac gtc aac gtg ccc gcc gcc ggc gcg gcc gac gcc acc acc agc       336
Leu Asp Val Asn Val Pro Ala Ala Gly Ala Ala Asp Ala Thr Thr Ser
            100                 105                 110 caa ctc ggc gtc ctc tcg ctg tcg tcg ccg cct tca ggc gcg gcg cct       384
Gln Leu Gly Val Leu Ser Leu Ser Ser Pro Pro Ser Gly Ala Ala Pro
        115                 120                 125 ccc tcg ccc acc ctc ggc ttc tac gcc gcc ggc aat ggc ggc gga tcg       432
Pro Ser Pro Thr Leu Gly Phe Tyr Ala Ala Gly Asn Gly Gly Gly Ser
    130                 135                 140 gct ggg ctg ctg gac acg agt tcc gac tgg ggc agc agc ggc gct gct       480
Ala Gly Leu Leu Asp Thr Ser Ser Asp Trp Gly Ser Ser Gly Ala Ala
145                 150                 155                 160 atg gcc acc gag aca tgc ttc ctg cag gac tac atg ggc gtg acg gac       528
Met Ala Thr Glu Thr Cys Phe Leu Gln Asp Tyr Met Gly Val Thr Asp
                165                 170                 175 acg ggc agc tcg tcg cag tgg cca tgc ttc tcg tcg tcg gac acg ata       576
Thr Gly Ser Ser Ser Gln Trp Pro Cys Phe Ser Ser Ser Asp Thr Ile
            180                 185                 190 atg gcg gcg gcg gcg gcc gcg gcg cgg gtg gcg acg acg cgg gcg ccc       624
Met Ala Ala Ala Ala Ala Ala Ala Arg Val Ala Thr Thr Arg Ala Pro
        195                 200                 205 gag aca ctc cct ctc ttc ccg acc tgc ggc gac gac gac gac gac gac       672
Glu Thr Leu Pro Leu Phe Pro Thr Cys Gly Asp Asp Asp Asp Asp Asp
    210                 215                 220 agc cag ccc ccg ccg cgg ccg cgg cac gca gtc cca gtc ccg gca ggc       720
```

| | | | | | | | | | | | | |
|---|---|---|---|---|---|---|---|---|---|---|---|---|
| Ser<br>225 | Gln | Pro | Pro | Pro<br>230 | Arg | Pro | Arg | His<br>235 | Ala | Val | Pro | Val Pro Ala Gly<br>240 |

| | | | | | | | | | | | | |
|---|---|---|---|---|---|---|---|---|---|---|---|---|
| gag | acc | atc | cgc | ggc | ggc | ggc | agc | agc | agc | tac | ttg | ccg ttc |
| Glu | Thr | Ile | Arg | Gly | Gly | Gly | Ser | Ser | Ser | Tyr | Leu | Pro Phe |
| | | | 245 | | | | 250 | | | | 255 | 768 |

| | | | | | | | | | | | | |
|---|---|---|---|---|---|---|---|---|---|---|---|---|
| tgg | ggt | gcc | ggt | gcc | gcg | tcc | aca | act | gcc | ggc | gcc | act tct tcc gtt |
| Trp | Gly | Ala | Gly | Ala | Ala | Ser | Thr | Thr | Ala | Gly | Ala | Thr Ser Ser Val |
| | | 260 | | | | | 265 | | | | | 270 | 816 |

| | | | | | | | | | | | | |
|---|---|---|---|---|---|---|---|---|---|---|---|---|
| gcg | atc | cag | cag | caa | cac | cag | ctg | cag | gag | cag | tac | agc ttt tac agc |
| Ala | Ile | Gln | Gln | Gln | His | Gln | Leu | Gln | Glu | Gln | Tyr | Ser Phe Tyr Ser |
| | | | 275 | | | | 280 | | | | | 285 | 864 |

| | | | | | | | | | | | | |
|---|---|---|---|---|---|---|---|---|---|---|---|---|
| aac | agc | acc | cag | ctg | gcc | ggc | acc | ggc | agc | caa | gac | gta tcg gct tca |
| Asn | Ser | Thr | Gln | Leu | Ala | Gly | Thr | Gly | Ser | Gln | Asp | Val Ser Ala Ser |
| | | 290 | | | | | 295 | | | | | 300 | 912 |

| | | | | | | | | | | | | |
|---|---|---|---|---|---|---|---|---|---|---|---|---|
| gcg | gcc | gcc | ctg | gag | ctg | agc | ctc | agc | tca | tgg | tgc | tcc cct tac cct |
| Ala | Ala | Ala | Leu | Glu | Leu | Ser | Leu | Ser | Ser | Trp | Cys | Ser Pro Tyr Pro |
| 305 | | | | 310 | | | | 315 | | | | 320 | 960 |

| | | | | |
|---|---|---|---|---|
| gct | gca | ggg | agc | atg tga |
| Ala | Ala | Gly | Ser | Met |
| | | | | 325 | 978 |

<210> SEQ ID NO 100
<211> LENGTH: 325
<212> TYPE: PRT
<213> ORGANISM: Zea mays

<400> SEQUENCE: 100

Met Ala Ala Asn Ala Gly Gly Gly Ala Gly Gly Gly Ser Gly Ser
1               5                   10                  15

Gly Ser Val Ala Ala Pro Ala Val Cys Arg Pro Ser Gly Ser Arg Trp
            20                  25                  30

Thr Pro Thr Pro Glu Gln Ile Arg Met Leu Lys Glu Leu Tyr Tyr Gly
        35                  40                  45

Cys Gly Ile Arg Ser Pro Ser Ser Glu Gln Ile Gln Arg Ile Thr Ala
    50                  55                  60

Met Leu Arg Gln His Gly Lys Ile Glu Gly Lys Asn Val Phe Tyr Trp
65              70                  75                  80

Phe Gln Asn His Lys Ala Arg Glu Arg Gln Lys Arg Arg Leu Thr Ser
            85                  90                  95

Leu Asp Val Asn Val Pro Ala Ala Gly Ala Ala Asp Ala Thr Thr Ser
        100                 105                 110

Gln Leu Gly Val Leu Ser Leu Ser Pro Ser Gly Ala Ala Pro
    115                 120                 125

Pro Ser Pro Thr Leu Gly Phe Tyr Ala Ala Gly Asn Gly Gly Ser
130                 135                 140

Ala Gly Leu Leu Asp Thr Ser Ser Asp Trp Gly Ser Ser Gly Ala Ala
145                 150                 155                 160

Met Ala Thr Glu Thr Cys Phe Leu Gln Asp Tyr Met Gly Val Thr Asp
            165                 170                 175

Thr Gly Ser Ser Ser Gln Trp Pro Cys Phe Ser Ser Ser Asp Thr Ile
        180                 185                 190

Met Ala Ala Ala Ala Ala Ala Arg Val Ala Thr Thr Arg Ala Pro
    195                 200                 205

Glu Thr Leu Pro Leu Phe Pro Thr Cys Gly Asp Asp Asp Asp Asp
    210                 215                 220

Ser Gln Pro Pro Pro Arg Pro Arg His Ala Val Pro Val Pro Ala Gly
225                 230                 235                 240

```
Glu Thr Ile Arg Gly Gly Gly Ser Ser Ser Tyr Leu Pro Phe
            245                 250                 255
Trp Gly Ala Gly Ala Ala Ser Thr Thr Ala Gly Ala Thr Ser Ser Val
        260                 265                 270
Ala Ile Gln Gln Gln His Gln Leu Gln Glu Gln Tyr Ser Phe Tyr Ser
        275                 280                 285
Asn Ser Thr Gln Leu Ala Gly Thr Gly Ser Gln Asp Val Ser Ala Ser
        290                 295                 300
Ala Ala Ala Leu Glu Leu Ser Leu Ser Ser Trp Cys Ser Pro Tyr Pro
305                 310                 315                 320
Ala Ala Gly Ser Met
            325

<210> SEQ ID NO 101
<211> LENGTH: 3727
<212> TYPE: DNA
<213> ORGANISM: Zea mays

<400> SEQUENCE: 101
atggccactg tgaacaactg gctcgctttc tccctctccc cgcaggagct gccgccctcc      60
cagacgacgg actccacact catctcggcc gccaccgccg accatgtctc cggcgatgtc     120
tgcttcaaca tccccaaga ttggagcatg agggatcag agctttcggc gctcgtcgcg      180
gagccgaagc tggaggactt cctcggcggc atctccttct ccgagcagca tcacaaggcc     240
aactgcaaca tgatacccag cactagcagc acagtttgct acgcgagctc aggtgctagc     300
accggctacc atcaccagct gtaccaccag cccaccagct cagcgctcca cttcgcggac     360
tccgtaatgg tggcctcctc ggccggtgtc cacgacggcg gtgccatgct cagcgcggcc     420
gccgctaacg tgtcgctgg cgctgccagt gccaacggcg cggcatcgg gctgtccatg      480 atcaagaact ggctgcggag ccaaccggcg cccatgcagc cgagggcggc ggcggctgag     540
ggcgcgcagg ggctctcttt gtccatgaac atggcgggga cgacccaagg cgctgctggc     600
atgccacttc tcgctggaga gcgcgcacgg gcgcccgaga gtgtatcgac gtcagcacag     660
ggtggtgccg tcgtcgtcac ggcgccgaag gaggatagcg gtggcagcgg tgttgccggt     720
gctctagtag ccgtgagcac ggacacgggt ggcagcggcg gcgcgtcggc tgacaacacg     780
gcaaggaaga cggtggacac gttcgggcag cgcacgtcga tttaccgtgg cgtgacaagg     840
taagggggtg gatgaatcaa gtaatcatga aattttgaaa agccattggt aatccaagga     900
actgtcatga tagatttgat tgcatctaga catagttccg atcgaatcaa atgagtaggc     960
caatgtttag cctttgggga tctcgctgat tattaggagt accattgtat tgggcatggt    1020
tgtggtatag tagtagacaa ttaacaaaaa agctaccact tttcaattat tttaggcata    1080
gatggactgg gagatatgag gcacatcttt gggataacag ttgcagaagg gaaggacaaa    1140
ctcgtaaggg tcgtcaaggt atacaaatat aatgcaacat actgtcatta aatatgcttt    1200
ttctgtaagt tttatatttc accaatgatg ttgttattgt taactgacat tgcttcacac    1260
tatcaatttt ggattcggcg caatgatttg tgggattgaa atcaaatctt aaatctacag    1320
tctatttagg tacgcgattt ctctccaact acttaatgca gttcgtttct ccctataacc    1380
atattctttt tcatctcaaa tctcactcga ctcttttttt ttatcttgta ccattgatag    1440
gtggctatga taaagaggag aaagctgcta gggcttatga tcttgctgct ctgaagtact    1500
ggggtcccac aacaacaaca aatttcccag tatgtatatg tagcatccag ttttactttta    1560
```

```
ctgaagttca tatctcgtta tgggctataa atatgtatca aatgatgtcc attagctagt    1620
gatctggagt gaaggttcta tagtaaagta aacgctgtgt gcggagtgca gtagcgggag    1680
gtctctcttc tattttctaa gaaaaatgga cattgctgaa attgtactta aagtcgttta    1740
ttttattttt ttgtatttcc aggtgagtaa ctacgaaaag gagctcgagg acatgaagca    1800
catgacaagg caggagtttg tagcgtctct gagaaggtcg gtctaacagc attgattaat    1860
cagtaccacc tctactgaat aaaatctgct gctatttgtt aaattttgag cgaggtcaac    1920
tgcatatttg atcttattag accactgtat atgaatgcag gaagagcagt ggtttctcca    1980
gaggtgcatc catttacagg ggagtgacta ggtatgaatt catatagcta agaacttaac    2040
atcaacaaaa acacacatac acttgggttg atgtggcaga tgcatgcatg gattgaaaat    2100
gtgtgcatgt tgttttactt gaactcgatc tctgtattta taggcatcac caacatggaa    2160
gatggcaagc acggattgga cgagttgcag ggaacaagga tctttacttg gcaccttca    2220 gtaagtagca aacaaatatg tttttgcatt gtatatagag tacccttgaa tatataaatt    2280
caccacatat acaagcaagt tacagtcaac taacacaatc tcaacgcaac gagaaagcaa    2340
gtgttccagc tgatagtaca catttgtaga ccagccgcat atggttgttt tgtatgcatg    2400
atgactatta aaaatgtgac catcgcatta agtcatgcaa agttgcattg cagtagtaca    2460
ttgcttagtg catgctcctc aagtggcttt tttcaaacct gatcccatgt ctggtgctat    2520
tgttgtctcc cattcacccg tgcatcaggt caaaatagta ccatgcctga ataagaaaaa    2580
caaaacgagc atgcactggc agcagcagac taataaacaa agttccagca tttactaata    2640
aactaattag gctacagcat ccaaaagatt cttccaatta agccacaact gttcatgcat    2700
acatgggtat gccacccagg ataccatgca tgcaccgtgc acgacgaaag cgaaacgctc    2760
gttctcggaa tattgaaact gacgaagccg agtgcaacct tctgtcgtgg atgcaggcac    2820
ccaggaggag gcagcggagg cgtacgacat cgcggcgatc aagttccgcg gcctaaacgc    2880
cgtcaccaac ttcgacatga gccgctacga cgtgaagagc atcctggaca gcagcgccct    2940
ccccatcggc agcgccgcca agcgcctcaa ggaggccgag gccgcagcgt ccgcgcagca    3000
ccaccacgcc ggcgtggtga gttacgacgt cggccgcatc gcctcgcagc tcggcgacgg    3060
cggagccctg gcggcggcgt acggcgcgca ctaccacggc gccgcctggc cgaccatcgc    3120
gttccagccg ggcgccgcca ccacaggcct gtaccacccg tacgcgcagc agccaatgcg    3180
cggcggcggg tggtgcaagc aggagcagga ccacgcggtg atcgcggccg cgcacagcct    3240
gcaggacctc caccacctga acctgggcgc ggccggcgcg cacgacttt tctcggcagg    3300 gcagcaggcc gccgccgctg cgatgcacgg cctgggtagc atcgacagtg cgtcgctcga    3360
gcacagcacc ggctccaact ccgtcgtcta caacggcggg gtcggcgaca gcaacggcgc    3420
cagcgccgtc ggcggcagtg gcggtggcta catgatgccg atgagcgctg ccggagcaac    3480
cactacatcg gcaatggtga gccacgagca ggtgcatgca cgggcctacg acgaagccaa    3540
gcaggctgct cagatggggt acgagagcta cctggtgaac gcggagaaca atggtggcgg    3600
aaggatgtct gcatggggga ctgtcgtgtc tgcagccgcg gcggcagcag caagcagcaa    3660
cgacaacatg gccgccgacg tcggccatgg cggcgcgcag ctcttcagtg tctggaacga    3720
cacttaa                                                            3727
```

<210> SEQ ID NO 102
<211> LENGTH: 4325
<212> TYPE: DNA
<213> ORGANISM: Oryza sativa

<400> SEQUENCE: 102

```
atgcatatct atcttatata aatatctacc agtgatactg ttgcttagtg ctccaaacct      60
ctcttgacct cttcttcttc ttctcagtta gcttagctta agcttcccct aaccttgagc     120
tcaccacaac aatggcgact tgatctaaca gagcttaacc aagtagcaaa tcatacatat     180
aaccatagct taattcgcat tgaatcttgt cttgttcagt gtgaatcatc aaccatggcc     240
accatgaaca actggctggc cttctccctc tccccgcagg atcagctccc gccgtctcag     300
accaactcca ctctcatctc cgccgccgcc accaccacca ccgccggcga ctcctccacc     360
ggcgacgtct gcttcaacat cccccaaggt aattaagctc accaatcgat gcatgcattc     420
atgagctaga tatagctagt gttggttggg atttgaagag acatgcatgt ttgattgatt     480
gatttgatgt gcagattgga gcatgagggg atcggagctc tcggcgctcg tcgccgagcc     540
gaagctggag gacttcctcg gcggcatctc cttctcggag cagcagcatc atcacggcgg     600
caagggcggc gtgatcccga gcagcgccgc cgcttgctac gcgagctccg gcagcagcgt     660
cggctacctg taccctcctc caagctcatc ctcgctccag ttcgccgact ccgtcatggt     720
ggccacctcc tcgcccgtcg tcgcccacga cggcgtcagc ggcggcggca tggtgagcgc     780
cgccgccgcc gcggcggcca gtggcaacgg cggcattggc ctgtccatga tcaagaactg     840
gctccggagc cagccggcgc cgcagccggc gcaggcgctg tctctgtcca tgaacatggc     900
ggggacgacg acggcgcagg gcggcggcgc catggcgctc ctcgccggcg caggggagcg     960
aggccggacg acgcccgcgt cagagagcct gtccacgtcg gcgcacggag cgacgacggc    1020
gacgatggct ggtggtcgca aggagattaa cgaggaaggc agcggcagcg ccggcgccgt    1080
ggttgccgtc ggctcggagt caggcggcag cggcgccgtg gtggaggccg gcgcggcggc    1140
ggcggcggcg aggaagtccg tcgacacgtt cggccagaga acatcgatct accgcggcgt    1200
gacaaggtat ttagggtgca attaattaat catctatcta tattttgctc aaaaaagttc    1260
atctactagc tagcttagca caaatcatca tcagtgtaat catatatatt ctttgatgat    1320
ttaactgtgt tgcatgaatt cattcctatt tgatgtttgt gatttggatc ccattttcta    1380
ggatagctat ataggtgata gattgatcat tagatttgta ggatttatca ttatgtcatt    1440
attatgtggg acatgattgt tgtgattaac aaagttgtaa tatcttttgg tttggttata    1500
ggcatagatg gacagggagg tatgaggctc atctttggga caacagctgc agaagagagg    1560
gccaaactcg caagggtcgt caaggtaggc taactagtgc catttaaatc gattaattgt    1620
ttttttatgc tccaatggcg attgatactg atcttgtttc tttttctaat gatcatttcg    1680
ggatcgaatg atcttcctct gtttgatcga acttggcttt tgaatctaca gtctatctag    1740
gtgagtgaga ttccttgaac ctagatgttc tgtttgcgat gcatgtatat attcggtaga    1800
ttgaattatt tgctgatctt tgctttcttg aagtttaatg atcttataaa ttgtaatgct    1860
gataggtggt tatgacaaag aggaaaaagc tgctagagct tatgatttgg ctgctctcaa    1920
atactgggc ccgacgacga cgacaaattt tccggtgtgt ttataattaa tatacagatt    1980
gtgtcacatt gttattttct cactctttta tttgatactg atctagtgta atgatgatta    2040
ctaaaactgt acttaaaggc aatggtttct gtatttttca ggtaaataac tatgaaaagg    2100
agctggagga gatgaagcac atgacaaggc aggagttcgt agcctctttg agaaggttgg    2160
tctctacaat caagatatcc atactatact aattaatttc cttttagatt tatagtaatt    2220
tatctatcgc attgaagtta attaattatc tgatgcttac tgatactaac aaatactgtt    2280
```

```
ccttatatgt gcaggaagag cagtggtttc tccagaggtg catccattta ccgtggagta    2340
actaggtaca tatatatatg catcattgta caattaattt ttttaatttt tttagggtaa    2400
aaaatgaaga ctgtgatata gatccattaa tttgatcttg tgtacttgta aatataggca    2460
tcaccagcat gggagatggc aagcaaggat aggaagagtt gcagggaaca aggacctcta    2520
cttgggcacc ttcagtaagt acaaatattc atatttatac tgcaaaacca tataaatcca    2580
tattaataag tatgtccttt ctcattgagt atacaaaata tcatattttc ttggcaagta    2640
caatttattc attcagggca aaatagtagt agtaagaaag aggggtgact cttcaaagaa    2700
cacagagctt acttaagcct gtaactaatt aattaaacta aaaatgtgat ctgcaagtca    2760
tgtcaagttg cattacacca ctaatatata tactctgtgc atgcttgcat gctctcctca    2820
tgtggctagc tacctttttca aaccttccat gtctggtgct actcctgtct ccattcacca    2880
ctgcacctgg tcaagatcct cactaattaa gaaacaataa tgcattattt gcagtaaata    2940
atttaactag tgttaatcac attctttgca acacaaacta atcaccaatt aagctagcta    3000
gctagccaaa atgataatct tgcttgcatg cgctaatggt gtgtgtgatg atggtggtgt    3060
cacgcatgca ggcacgcagg aggaggcggc ggaggcgtac gacatcgcgg cgatcaagtt    3120
ccgggggctc aacgccgtca ccaacttcga catgagccgc tacgacgtca agagcatcct    3180
cgacagcgct gccctccccg tcggcaccgc cgccaagcgc ctcaaggacg ccgaggccgc    3240
cgccgcctac gacgtcggcc gcatcgcctc gcacctcggc ggcgacggcg cctacgccgc    3300
gcattacggc caccaccacc actcggccgc cgccgcctgg ccgaccatcg cgttccaggc    3360
ggcggcggcg ccgccgccgc acgccgcggg gctttaccac ccgtacgcgc agccgctgcg    3420
tgggtggtgc aagcaggagc aggaccacgc cgtgatcgcg gcggcgcaca gcctgcagga    3480
tctccaccac ctcaacctcg gcgccgccgc cgccgcgcat gacttcttct cgcaggcgat    3540
gcagcagcag cacggcctcg gcagcatcga caacgcgtcg ctcgagcaca gcaccggctc    3600
caactccgtc gtctacaacg gcgacaatgg cggcggaggc ggcggctaca tcatggcgcc    3660
gatgagcgcc gtgtcggcca cggccaccgc ggtggcgagc agccacgatc acggcggcga    3720
cggcgggaag caggtgcaga tggggtacga cagctacctc gtcggcgcag acgcctacgg    3780
cggcggcggc gccgggagga tgccatcctg ggcgatgacg ccggcgtcgg cgccggccgc    3840
cacgagcagc agcgacatga ccggagtctg ccatggcgca cagctcttca gcgtctggaa    3900
cgacacataa aaaaaaaact aggttagcca gcttaattag cagggtaaac cactgacaca    3960
attaagccat acttaaatta gggttcatga gatgaccatt aagcaggtta ttatcattaa    4020
tgatgtttaa tttctcaatt agtacttagc tcaaaaggag gggatttctt ctgaaggatg    4080
gtgatggctt gtgaaattga acctggtgtt cttgccatga ttttttttttc acaagctgcc    4140
atttttgggt tcaggttcag aaggatcctg attattatta accagccata tatatataga    4200
agggtagaaa tggaggtatc ctgccttgtaa attgggcaa tggtagctag agttgatgca    4260
atgaccatgc ttcatgtgat gagaactaat tgtcttcctc tgatcaaatt aagcaggaag    4320
attaa                                                                4325
```

<210> SEQ ID NO 103
<211> LENGTH: 2088
<212> TYPE: DNA
<213> ORGANISM: Oryza sativa
<220> FEATURE:
<221> NAME/KEY: CDS
<222> LOCATION: (1)...(2088)

<400> SEQUENCE: 103

```
atg gcc act atg aac aac tgg ctc gcc ttc tcg ctc tcg ccg cag gac      48
Met Ala Thr Met Asn Asn Trp Leu Ala Phe Ser Leu Ser Pro Gln Asp
 1               5                  10                  15 caa ctc cca ccg tcg cag acc aat agc act ctc atc tcc gct gct gca      96
Gln Leu Pro Pro Ser Gln Thr Asn Ser Thr Leu Ile Ser Ala Ala Ala
             20                  25                  30 acc acc aca acc gca ggc gat tcg tca acg ggc gac gtc tgc ttc aac     144
Thr Thr Thr Thr Ala Gly Asp Ser Ser Thr Gly Asp Val Cys Phe Asn
         35                  40                  45 atc cct caa gac tgg tcc atg cgc gga agc gag ctt agc gct ctc gtc     192
Ile Pro Gln Asp Trp Ser Met Arg Gly Ser Glu Leu Ser Ala Leu Val
 50                  55                  60 gcg gag ccc aag ttg gag gat ttc ttg gga ggc atc tcc ttc tcg gag     240
Ala Glu Pro Lys Leu Glu Asp Phe Leu Gly Gly Ile Ser Phe Ser Glu
 65                  70                  75                  80 caa cag cat cat cac ggc gga aag ggc ggt gtt atc cca agc tct gct     288
Gln Gln His His His Gly Gly Lys Gly Gly Val Ile Pro Ser Ser Ala
                 85                  90                  95 gcc gca tgc tat gca agc tcc ggc tcc agc gtg ggc tac ctc tac cct     336
Ala Ala Cys Tyr Ala Ser Ser Gly Ser Ser Val Gly Tyr Leu Tyr Pro
            100                 105                 110 ccg cct tca tcc tcg tca ctt cag ttt gca gac agc gtg atg gtc gca     384
Pro Pro Ser Ser Ser Ser Leu Gln Phe Ala Asp Ser Val Met Val Ala
        115                 120                 125 acc tca tct cca gtg gtt gcg cac gat ggc gtg agc ggt ggc ggt atg     432
Thr Ser Ser Pro Val Val Ala His Asp Gly Val Ser Gly Gly Gly Met
130                 135                 140 gtc tca gca gca gcg gct gca gca gct tcg ggt aat ggc ggg att ggc     480
Val Ser Ala Ala Ala Ala Ala Ala Ala Ser Gly Asn Gly Gly Ile Gly
145                 150                 155                 160 ctc tcc atg atc aag aac tgg ctc agg agc caa ccg gct ccg caa cct     528
Leu Ser Met Ile Lys Asn Trp Leu Arg Ser Gln Pro Ala Pro Gln Pro
                165                 170                 175 gcg caa gca ctc agc ctg tcg atg aac atg gct ggt act act acc gct     576
Ala Gln Ala Leu Ser Leu Ser Met Asn Met Ala Gly Thr Thr Thr Ala
            180                 185                 190 caa ggt gga ggc gca atg gca ctt ctc gca ggc gct ggc gaa aga gga     624
Gln Gly Gly Gly Ala Met Ala Leu Leu Ala Gly Ala Gly Glu Arg Gly
        195                 200                 205 agg acc aca cca gca tcc gag agc ctc tct act tcc gcg cac gga gcc     672
Arg Thr Thr Pro Ala Ser Glu Ser Leu Ser Thr Ser Ala His Gly Ala
210                 215                 220 acc acg gct aca atg gct ggc ggg agg aaa gag atc aac gag gaa gga     720
Thr Thr Ala Thr Met Ala Gly Gly Arg Lys Glu Ile Asn Glu Glu Gly
225                 230                 235                 240 tct gga tcc gct ggt gcc gtg gtt gca gtt ggc tca gaa tca ggt gga     768
Ser Gly Ser Ala Gly Ala Val Val Ala Val Gly Ser Glu Ser Gly Gly
                245                 250                 255 tcc ggc gct gtt gtt gaa gct ggt gcc gct gcg gca gcg gct cgg aag     816
Ser Gly Ala Val Val Glu Ala Gly Ala Ala Ala Ala Ala Ala Arg Lys
            260                 265                 270 agc gtt gat act ttc ggc caa aga acg agc atc tac aga ggc gtt act     864
Ser Val Asp Thr Phe Gly Gln Arg Thr Ser Ile Tyr Arg Gly Val Thr
        275                 280                 285 cgg cac cgc tgg acc ggc agg tac gag gca cac ttg tgg gac aac agc     912
Arg His Arg Trp Thr Gly Arg Tyr Glu Ala His Leu Trp Asp Asn Ser
290                 295                 300 tgt cgc cgc gag ggc caa act agg aag gga aga cag gtc tat cta gga     960
Cys Arg Arg Glu Gly Gln Thr Arg Lys Gly Arg Gln Val Tyr Leu Gly
```

```
                Cys Arg Arg Glu Gly Gln Thr Arg Lys Gly Arg Gln Val Tyr Leu Gly
                305                 310                 315                 320 gga tat gac aaa gag gag aag gct gcc aga gcg tac gac ctg gcc gcg              1008
Gly Tyr Asp Lys Glu Glu Lys Ala Ala Arg Ala Tyr Asp Leu Ala Ala
                    325                 330                 335 ttg aag tac tgg ggt cca aca acg acg acc aac ttc ccg gtg aac aac              1056
Leu Lys Tyr Trp Gly Pro Thr Thr Thr Thr Asn Phe Pro Val Asn Asn
            340                 345                 350 tac gag aag gag ctg gaa gag atg aag cac atg acg cgg cag gag ttc              1104
Tyr Glu Lys Glu Leu Glu Glu Met Lys His Met Thr Arg Gln Glu Phe
        355                 360                 365 gtc gct tct ctc agg cgc aag tca tct ggt ttc tcc aga ggt gcg tcg              1152
Val Ala Ser Leu Arg Arg Lys Ser Ser Gly Phe Ser Arg Gly Ala Ser
    370                 375                 380 atc tat aga gga gtt acc cgc cac cac cag cac gga agg tgg cag gca              1200
Ile Tyr Arg Gly Val Thr Arg His His Gln His Gly Arg Trp Gln Ala
385                 390                 395                 400 aga atc ggg aga gtc gcc ggt aac aag gac ctg tac ttg gga acc ttc              1248
Arg Ile Gly Arg Val Ala Gly Asn Lys Asp Leu Tyr Leu Gly Thr Phe
                405                 410                 415 tcg act cag gag gag gca gcg gaa gcg tat gac att gcg gcg atc aag              1296
Ser Thr Gln Glu Glu Ala Ala Glu Ala Tyr Asp Ile Ala Ala Ile Lys
            420                 425                 430 ttc cgc ggt ctc aat gcc gtg acc aac ttc gac atg tca cgc tat gat              1344
Phe Arg Gly Leu Asn Ala Val Thr Asn Phe Asp Met Ser Arg Tyr Asp
        435                 440                 445 gtc aag tcg att ctg gat agc gct gcg ttg cct gtg gga acc gct gcc              1392
Val Lys Ser Ile Leu Asp Ser Ala Ala Leu Pro Val Gly Thr Ala Ala
    450                 455                 460 aaa cgc ctc aag gac gcg gaa gca gct gcc gcg tac gat gtt ggc agg              1440
Lys Arg Leu Lys Asp Ala Glu Ala Ala Ala Ala Tyr Asp Val Gly Arg
465                 470                 475                 480 att gcc tca cat ctc ggt gga gat gga gct tac gct gcc cac tac ggg              1488
Ile Ala Ser His Leu Gly Gly Asp Gly Ala Tyr Ala Ala His Tyr Gly
                485                 490                 495 cat cat cac cac tct gca gcc gca gct tgg cct aca ata gca ttc caa              1536
His His His His Ser Ala Ala Ala Ala Trp Pro Thr Ile Ala Phe Gln
            500                 505                 510 gcg gca gcg gct cct cct cca cac gct gct ggt ctt tac cat ccg tac              1584
Ala Ala Ala Ala Pro Pro Pro His Ala Ala Gly Leu Tyr His Pro Tyr
        515                 520                 525 gcg caa cct ctc cgc ggt tgg tgt aag cag gaa caa gat cat gcg gtg              1632
Ala Gln Pro Leu Arg Gly Trp Cys Lys Gln Glu Gln Asp His Ala Val
    530                 535                 540 att gcg gct gca cac agc ttg caa gat ctg cat cac ctc aat ctg gga              1680
Ile Ala Ala Ala His Ser Leu Gln Asp Leu His His Leu Asn Leu Gly
545                 550                 555                 560 gcc gca gca gct gcc cat gac ttc ttc tca caa gcc atg cag cag cag              1728
Ala Ala Ala Ala Ala His Asp Phe Phe Ser Gln Ala Met Gln Gln Gln
                565                 570                 575 cat ggc ctg ggc agc ata gac aat gcg tct ctg gag cac tcc acc gga              1776
His Gly Leu Gly Ser Ile Asp Asn Ala Ser Leu Glu His Ser Thr Gly
            580                 585                 590 tcg aac tcg gtg gtg tac aat gga gac aac ggc gga gga ggt gga ggt              1824
Ser Asn Ser Val Val Tyr Asn Gly Asp Asn Gly Gly Gly Gly Gly Gly
        595                 600                 605 tac atc atg gca cct atg tca gcg gtc tct gct acc gct acg gcg gtg              1872
Tyr Ile Met Ala Pro Met Ser Ala Val Ser Ala Thr Ala Thr Ala Val
    610                 615                 620
```

| | | | | | | | | | | | | | | | | |
|---|---|---|---|---|---|---|---|---|---|---|---|---|---|---|---|---|
| gcc | tca | tcc | cac | gac | cac | ggt | gga | gac | ggc | ggc | aag | cag | gtc | caa | atg | 1920 |
| Ala | Ser | Ser | His | Asp | His | Gly | Gly | Asp | Gly | Gly | Lys | Gln | Val | Gln | Met | |
| 625 | | | | 630 | | | | 635 | | | | 640 | | | | |
| ggc | tac | gac | tcc | tac | ctt | gtg | gga | gct | gac | gct | tac | ggc | gga | gga | gga | 1968 |
| Gly | Tyr | Asp | Ser | Tyr | Leu | Val | Gly | Ala | Asp | Ala | Tyr | Gly | Gly | Gly | Gly | |
| | | | | 645 | | | | 650 | | | | | 655 | | | |
| gct | ggt | cgc | atg | cct | agc | tgg | gcc | atg | acg | cct | gct | tct | gct | cct | gcg | 2016 |
| Ala | Gly | Arg | Met | Pro | Ser | Trp | Ala | Met | Thr | Pro | Ala | Ser | Ala | Pro | Ala | |
| | | 660 | | | | | 665 | | | | | 670 | | | | |
| gct | acg | agc | tcg | tcg | gat | atg | aca | gga | gtg | tgt | cat | ggc | gcc | caa | ctg | 2064 |
| Ala | Thr | Ser | Ser | Ser | Asp | Met | Thr | Gly | Val | Cys | His | Gly | Ala | Gln | Leu | |
| | | 675 | | | | 680 | | | | | 685 | | | | | |
| ttc | tcg | gtg | tgg | aat | gat | aca | tag | | | | | | | | | 2088 |
| Phe | Ser | Val | Trp | Asn | Asp | Thr | | | | | | | | | | |
| | 690 | | | | 695 | | | | | | | | | | | |

```
<210> SEQ ID NO 104
<211> LENGTH: 2133
<212> TYPE: DNA
<213> ORGANISM: Zea mays
<220> FEATURE:
<221> NAME/KEY: CDS
<222> LOCATION: (1)...(2133)

<400> SEQUENCE: 104
```

| | | | | | | | | | | | | | | | |
|---|---|---|---|---|---|---|---|---|---|---|---|---|---|---|---|
| atg | gcc | act | gtg | aac | aac | tgg | ctc | gct | ttc | tcc | ctc | tcc | ccg | cag | gag | 48 |
| Met | Ala | Thr | Val | Asn | Asn | Trp | Leu | Ala | Phe | Ser | Leu | Ser | Pro | Gln | Glu | |
| 1 | | | | 5 | | | | | 10 | | | | | 15 | | |
| ctg | ccg | ccc | tcc | cag | acg | acg | gac | tcc | aca | ctc | atc | tcg | gcc | gcc | acc | 96 |
| Leu | Pro | Pro | Ser | Gln | Thr | Thr | Asp | Ser | Thr | Leu | Ile | Ser | Ala | Ala | Thr | |
| | | | 20 | | | | | 25 | | | | | 30 | | | |
| gcc | gac | cat | gtc | tcc | ggc | gat | gtc | tgc | ttc | aac | atc | ccc | caa | gat | tgg | 144 |
| Ala | Asp | His | Val | Ser | Gly | Asp | Val | Cys | Phe | Asn | Ile | Pro | Gln | Asp | Trp | |
| | | | 35 | | | | | 40 | | | | | 45 | | | |
| agc | atg | agg | gga | tca | gag | ctt | tcg | gcg | ctc | gtc | gcg | gag | ccg | aag | ctg | 192 |
| Ser | Met | Arg | Gly | Ser | Glu | Leu | Ser | Ala | Leu | Val | Ala | Glu | Pro | Lys | Leu | |
| | 50 | | | | | 55 | | | | | 60 | | | | | |
| gag | gac | ttc | ctc | ggc | ggc | atc | tcc | ttc | tcc | gag | cag | cat | cac | aag | gcc | 240 |
| Glu | Asp | Phe | Leu | Gly | Gly | Ile | Ser | Phe | Ser | Glu | Gln | His | His | Lys | Ala | |
| 65 | | | | | 70 | | | | | 75 | | | | | 80 | |
| aac | tgc | aac | atg | ata | ccc | agc | act | agc | agc | aca | gtt | tgc | tac | gcg | agc | 288 |
| Asn | Cys | Asn | Met | Ile | Pro | Ser | Thr | Ser | Ser | Thr | Val | Cys | Tyr | Ala | Ser | |
| | | | | 85 | | | | | 90 | | | | | 95 | | |
| tca | ggt | gct | agc | acc | ggc | tac | cat | cac | cag | ctg | tac | cac | cag | ccc | acc | 336 |
| Ser | Gly | Ala | Ser | Thr | Gly | Tyr | His | His | Gln | Leu | Tyr | His | Gln | Pro | Thr | |
| | | | 100 | | | | | 105 | | | | | 110 | | | |
| agc | tca | gcg | ctc | cac | ttc | gcg | gac | tcc | gta | atg | gtg | gcc | tcc | tcg | gcc | 384 |
| Ser | Ser | Ala | Leu | His | Phe | Ala | Asp | Ser | Val | Met | Val | Ala | Ser | Ser | Ala | |
| | | 115 | | | | | 120 | | | | | 125 | | | | |
| ggt | gtc | cac | gac | ggc | ggt | gcc | atg | ctc | agc | gcg | gcc | gcc | gct | aac | ggt | 432 |
| Gly | Val | His | Asp | Gly | Gly | Ala | Met | Leu | Ser | Ala | Ala | Ala | Ala | Asn | Gly | |
| | 130 | | | | | 135 | | | | | 140 | | | | | |
| gtc | gct | ggc | gct | gcc | agt | gcc | aac | ggc | ggc | ggc | atc | ggg | ctg | tcc | atg | 480 |
| Val | Ala | Gly | Ala | Ala | Ser | Ala | Asn | Gly | Gly | Gly | Ile | Gly | Leu | Ser | Met | |
| 145 | | | | | 150 | | | | | 155 | | | | | 160 | |
| att | aag | aac | tgg | ctg | cgg | agc | caa | ccg | gcg | ccc | atg | cag | ccg | agg | gtg | 528 |
| Ile | Lys | Asn | Trp | Leu | Arg | Ser | Gln | Pro | Ala | Pro | Met | Gln | Pro | Arg | Val | |
| | | | | 165 | | | | | 170 | | | | | 175 | | |
| gcg | gcg | gct | gag | ggc | gcg | cag | ggg | ctc | tct | ttg | tcc | atg | aac | atg | gcg | 576 |
| Ala | Ala | Ala | Glu | Gly | Ala | Gln | Gly | Leu | Ser | Leu | Ser | Met | Asn | Met | Ala | |
| | | | 180 | | | | | 185 | | | | | 190 | | | |

```
ggg acg acc caa ggc gct gct ggc atg cca ctt ctc gct gga gag cgc    624
Gly Thr Thr Gln Gly Ala Ala Gly Met Pro Leu Leu Ala Gly Glu Arg
        195                 200                 205 gca cgg gcg ccc gag agt gta tcg acg tca gca cag ggt gga gcc gtc    672
Ala Arg Ala Pro Glu Ser Val Ser Thr Ser Ala Gln Gly Gly Ala Val
210                 215                 220 gtc gtc acg gcg ccg aag gag gat agc ggt ggc agc ggt gtt gcc ggc    720
Val Val Thr Ala Pro Lys Glu Asp Ser Gly Gly Ser Gly Val Ala Gly
225                 230                 235                 240 gct cta gta gcc gtg agc acg gac acg ggt ggc agc ggc ggc gcg tcg    768
Ala Leu Val Ala Val Ser Thr Asp Thr Gly Gly Ser Gly Gly Ala Ser
                245                 250                 255 gct gac aac acg gca agg aag acg gtg gac acg ttc ggg cag cgc acg    816
Ala Asp Asn Thr Ala Arg Lys Thr Val Asp Thr Phe Gly Gln Arg Thr
            260                 265                 270 tcg att tac cgt ggc gtg aca agg cat aga tgg act ggg aga tat gag    864
Ser Ile Tyr Arg Gly Val Thr Arg His Arg Trp Thr Gly Arg Tyr Glu
        275                 280                 285 gca cat ctt tgg gat aac agt tgc aga agg gaa ggg caa act cgt aag    912
Ala His Leu Trp Asp Asn Ser Cys Arg Arg Glu Gly Gln Thr Arg Lys
    290                 295                 300 ggt cgt caa gtc tat tta ggt ggc tat gat aaa gag gag aaa gct gct    960
Gly Arg Gln Val Tyr Leu Gly Gly Tyr Asp Lys Glu Glu Lys Ala Ala
305                 310                 315                 320 agg gct tat gat ctt gct gct ctg aag tac tgg ggt gcc aca aca aca   1008
Arg Ala Tyr Asp Leu Ala Ala Leu Lys Tyr Trp Gly Ala Thr Thr Thr
                325                 330                 335 aca aat ttt cca gtg agt aac tac gaa aag gag ctc gag gac atg aag   1056
Thr Asn Phe Pro Val Ser Asn Tyr Glu Lys Glu Leu Glu Asp Met Lys
            340                 345                 350 cac atg aca agg cag gag ttt gta gcg tct ctg aga agg aag agc agt   1104
His Met Thr Arg Gln Glu Phe Val Ala Ser Leu Arg Arg Lys Ser Ser
        355                 360                 365 ggt ttc tcc aga ggt gca tcc att tac agg gga gtg act agg cat cac   1152
Gly Phe Ser Arg Gly Ala Ser Ile Tyr Arg Gly Val Thr Arg His His
    370                 375                 380 caa cat gga aga tgg caa gca cgg att gga cga gtt gca ggg aac aag   1200
Gln His Gly Arg Trp Gln Ala Arg Ile Gly Arg Val Ala Gly Asn Lys
385                 390                 395                 400 gat ctt tac ttg ggc acc ttc agc acc cag gag gag gca gcg gag gcg   1248
Asp Leu Tyr Leu Gly Thr Phe Ser Thr Gln Glu Glu Ala Ala Glu Ala
                405                 410                 415 tac gac atc gcg gcg atc aag ttc cgc ggc ctc aac gcc gtc acc aac   1296
Tyr Asp Ile Ala Ala Ile Lys Phe Arg Gly Leu Asn Ala Val Thr Asn
            420                 425                 430 ttc gac atg agc cgc tac gac gtg aag agc atc ctg gac agc agc gcc   1344
Phe Asp Met Ser Arg Tyr Asp Val Lys Ser Ile Leu Asp Ser Ser Ala
        435                 440                 445 ctc ccc atc ggc agc gcc gcc aag cgc ctc aag gag gcc gag gcc gca   1392
Leu Pro Ile Gly Ser Ala Ala Lys Arg Leu Lys Glu Ala Glu Ala Ala
    450                 455                 460 gcg tcc gcg cag cac cac cac gcc ggc gtg gtg agc tac gac gtc ggc   1440
Ala Ser Ala Gln His His His Ala Gly Val Val Ser Tyr Asp Val Gly
465                 470                 475                 480 cgc atc gcc tcg cag ctc ggc gac ggc gga gcc ctg gcg gcg gcg tac   1488
Arg Ile Ala Ser Gln Leu Gly Asp Gly Gly Ala Leu Ala Ala Ala Tyr
                485                 490                 495 ggc gcg cac tac cac ggc gcc gcc tgg ccg acc atc gcg ttc cag ccg   1536
Gly Ala His Tyr His Gly Ala Ala Trp Pro Thr Ile Ala Phe Gln Pro
            500                 505                 510
```

```
ggc gcc gcc agc aca ggc ctg tac cac ccg tac gcg cag cag cca atg    1584
Gly Ala Ala Ser Thr Gly Leu Tyr His Pro Tyr Ala Gln Gln Pro Met
            515                 520                 525 cgc ggc ggc ggg tgg tgc aag cag gag cag gac cac gcg gtg atc gcg    1632
Arg Gly Gly Gly Trp Cys Lys Gln Glu Gln Asp His Ala Val Ile Ala
530                 535                 540 gcc gcg cac agc ctg cag gac ctc cac cac ctg aac ctg ggc gcg gcc    1680
Ala Ala His Ser Leu Gln Asp Leu His His Leu Asn Leu Gly Ala Ala
545                 550                 555                 560 ggc gcg cac gac ttt ttc tcg gca ggg cag cag gcc gcc gcc gct gcg    1728
Gly Ala His Asp Phe Phe Ser Ala Gly Gln Gln Ala Ala Ala Ala Ala
                565                 570                 575 atg cac ggc ctg ggt agc atc gac agt gcg tcg ctc gag cac agc acc    1776
Met His Gly Leu Gly Ser Ile Asp Ser Ala Ser Leu Glu His Ser Thr
            580                 585                 590 ggc tcc aac tcc gtc gtc tac aac ggc ggg gtc ggc gac agc aac ggc    1824
Gly Ser Asn Ser Val Val Tyr Asn Gly Gly Val Gly Asp Ser Asn Gly
        595                 600                 605 gcc agc gcc gtc ggc ggc agt ggc ggt ggc tac atg atg ccg atg agc    1872
Ala Ser Ala Val Gly Gly Ser Gly Gly Gly Tyr Met Met Pro Met Ser
610                 615                 620 gct gcc gga gca acc act aca tcg gca atg gtg agc cac gag cag gtg    1920
Ala Ala Gly Ala Thr Thr Thr Ser Ala Met Val Ser His Glu Gln Val
625                 630                 635                 640 cat gca cgg gcc tac gac gaa gcc aag cag gct gct cag atg ggg tac    1968
His Ala Arg Ala Tyr Asp Glu Ala Lys Gln Ala Ala Gln Met Gly Tyr
                645                 650                 655 gag agc tac ctg gtg aac gcg gag aac aat ggt ggc gga agg atg tct    2016
Glu Ser Tyr Leu Val Asn Ala Glu Asn Asn Gly Gly Gly Arg Met Ser
            660                 665                 670 gca tgg ggg act gtc gtg tct gca gcg gcg gca gca gca agc agc       2064
Ala Trp Gly Thr Val Val Ser Ala Ala Ala Ala Ala Ser Ser
        675                 680                 685 aac gac aac atg gcc gcc gac gtc ggc cat ggc ggc gcg cag ctc ttc    2112
Asn Asp Asn Met Ala Ala Asp Val Gly His Gly Gly Ala Gln Leu Phe
690                 695                 700 agt gtc tgg aac gac act taa                                         2133
Ser Val Trp Asn Asp Thr
705                 710

<210> SEQ ID NO 105
<211> LENGTH: 710
<212> TYPE: PRT
<213> ORGANISM: Zea mays

<400> SEQUENCE: 105

Met Ala Thr Val Asn Asn Trp Leu Ala Phe Ser Leu Ser Pro Gln Glu
1               5                   10                  15

Leu Pro Pro Ser Gln Thr Thr Asp Ser Thr Leu Ile Ser Ala Ala Thr
            20                  25                  30

Ala Asp His Val Ser Gly Asp Val Cys Phe Asn Ile Pro Gln Asp Trp
        35                  40                  45

Ser Met Arg Gly Ser Glu Leu Ser Ala Leu Val Ala Glu Pro Lys Leu
    50                  55                  60

Glu Asp Phe Leu Gly Gly Ile Ser Phe Ser Glu Gln His His Lys Ala
65                  70                  75                  80

Asn Cys Asn Met Ile Pro Ser Thr Ser Ser Thr Val Cys Tyr Ala Ser
                85                  90                  95
```

```
Ser Gly Ala Ser Thr Gly Tyr His His Gln Leu Tyr His Gln Pro Thr
            100                 105                 110

Ser Ser Ala Leu His Phe Ala Asp Ser Val Met Val Ala Ser Ser Ala
        115                 120                 125

Gly Val His Asp Gly Gly Ala Met Leu Ser Ala Ala Ala Asn Gly
    130                 135                 140

Val Ala Gly Ala Ala Ser Ala Asn Gly Gly Ile Gly Leu Ser Met
145                 150                 155                 160

Ile Lys Asn Trp Leu Arg Ser Gln Pro Ala Pro Met Gln Pro Arg Val
                165                 170                 175

Ala Ala Ala Glu Gly Ala Gln Gly Leu Ser Leu Ser Met Asn Met Ala
            180                 185                 190

Gly Thr Thr Gln Gly Ala Ala Gly Met Pro Leu Leu Ala Gly Glu Arg
        195                 200                 205

Ala Arg Ala Pro Glu Ser Val Ser Thr Ser Ala Gln Gly Gly Ala Val
    210                 215                 220

Val Val Thr Ala Pro Lys Glu Asp Ser Gly Ser Gly Val Ala Gly
225                 230                 235                 240

Ala Leu Val Ala Val Ser Thr Asp Thr Gly Gly Ser Gly Gly Ala Ser
                245                 250                 255

Ala Asp Asn Thr Ala Arg Lys Thr Val Asp Thr Phe Gly Gln Arg Thr
            260                 265                 270

Ser Ile Tyr Arg Gly Val Thr Arg His Arg Trp Thr Gly Arg Tyr Glu
        275                 280                 285

Ala His Leu Trp Asp Asn Ser Cys Arg Arg Glu Gly Gln Thr Arg Lys
    290                 295                 300

Gly Arg Gln Val Tyr Leu Gly Gly Tyr Asp Lys Glu Glu Lys Ala Ala
305                 310                 315                 320

Arg Ala Tyr Asp Leu Ala Ala Leu Lys Tyr Trp Gly Ala Thr Thr Thr
                325                 330                 335

Thr Asn Phe Pro Val Ser Asn Tyr Glu Lys Glu Leu Glu Asp Met Lys
            340                 345                 350

His Met Thr Arg Gln Glu Phe Val Ala Ser Leu Arg Arg Lys Ser Ser
        355                 360                 365

Gly Phe Ser Arg Gly Ala Ser Ile Tyr Arg Gly Val Thr Arg His His
    370                 375                 380

Gln His Gly Arg Trp Gln Ala Arg Ile Gly Arg Val Ala Gly Asn Lys
385                 390                 395                 400

Asp Leu Tyr Leu Gly Thr Phe Ser Thr Gln Glu Glu Ala Ala Glu Ala
                405                 410                 415

Tyr Asp Ile Ala Ala Ile Lys Phe Arg Gly Leu Asn Ala Val Thr Asn
            420                 425                 430

Phe Asp Met Ser Arg Tyr Asp Val Lys Ser Ile Leu Asp Ser Ser Ala
        435                 440                 445

Leu Pro Ile Gly Ser Ala Ala Lys Arg Leu Lys Glu Ala Glu Ala Ala
    450                 455                 460

Ala Ser Ala Gln His His His Ala Gly Val Val Ser Tyr Asp Val Gly
465                 470                 475                 480

Arg Ile Ala Ser Gln Leu Gly Asp Gly Gly Ala Leu Ala Ala Ala Tyr
                485                 490                 495

Gly Ala His Tyr His Gly Ala Ala Trp Pro Thr Ile Ala Phe Gln Pro
            500                 505                 510

Gly Ala Ala Ser Thr Gly Leu Tyr His Pro Tyr Ala Gln Gln Pro Met
```

-continued

```
            515                 520                 525
Arg Gly Gly Gly Trp Cys Lys Gln Glu Gln Asp His Ala Val Ile Ala
            530                 535                 540
Ala Ala His Ser Leu Gln Asp Leu His His Leu Asn Leu Gly Ala Ala
545                 550                 555                 560
Gly Ala His Asp Phe Phe Ser Ala Gly Gln Gln Ala Ala Ala Ala Ala
                565                 570                 575
Met His Gly Leu Gly Ser Ile Asp Ser Ala Ser Leu Glu His Ser Thr
            580                 585                 590
Gly Ser Asn Ser Val Val Tyr Asn Gly Gly Val Gly Asp Ser Asn Gly
            595                 600                 605
Ala Ser Ala Val Gly Gly Ser Gly Gly Gly Tyr Met Met Pro Met Ser
        610                 615                 620
Ala Ala Gly Ala Thr Thr Thr Ser Ala Met Val Ser His Glu Gln Val
625                 630                 635                 640
His Ala Arg Ala Tyr Asp Glu Ala Lys Gln Ala Ala Gln Met Gly Tyr
                645                 650                 655
Glu Ser Tyr Leu Val Asn Ala Glu Asn Asn Gly Gly Gly Arg Met Ser
                660                 665                 670
Ala Trp Gly Thr Val Val Ser Ala Ala Ala Ala Ala Ala Ala Ser Ser
            675                 680                 685
Asn Asp Asn Met Ala Ala Asp Val Gly His Gly Gly Ala Gln Leu Phe
    690                 695                 700
Ser Val Trp Asn Asp Thr
705             710
```